US011401330B2

(12) United States Patent
Eavarone et al.

(10) Patent No.: US 11,401,330 B2
(45) Date of Patent: Aug. 2, 2022

(54) GLYCAN-INTERACTING COMPOUNDS AND METHODS OF USE

(71) Applicant: Seattle Genetics, Inc., Bothell, WA (US)

(72) Inventors: David A. Eavarone, North Quincy, MA (US); Jeffrey Behrens, Newton, MA (US); Alexey Alexandrovich Lugovskoy, Woburn, MA (US)

(73) Assignee: Seagen Inc., Bothell, WA (US)

(*) Notice: Subject to any disclaimer, the term of this patent is extended or adjusted under 35 U.S.C. 154(b) by 310 days.

(21) Appl. No.: 16/462,075

(22) PCT Filed: Nov. 17, 2017

(86) PCT No.: PCT/US2017/062155
§ 371 (c)(1),
(2) Date: May 17, 2019

(87) PCT Pub. No.: WO2018/094143
PCT Pub. Date: May 24, 2018

(65) Prior Publication Data
US 2019/0276541 A1 Sep. 12, 2019

Related U.S. Application Data

(60) Provisional application No. 62/480,077, filed on Mar. 31, 2017, provisional application No. 62/443,935, filed on Jan. 9, 2017, provisional application No. 62/423,575, filed on Nov. 17, 2016.

(51) Int. Cl.
C07K 16/28 (2006.01)
C07K 16/46 (2006.01)
A61P 35/04 (2006.01)

(52) U.S. Cl.
CPC .......... C07K 16/2809 (2013.01); A61P 35/04 (2018.01); C07K 16/46 (2013.01); C07K 2317/24 (2013.01); C07K 2317/565 (2013.01)

(58) Field of Classification Search
None
See application file for complete search history.

(56) References Cited

U.S. PATENT DOCUMENTS

| 4,179,337 A | 12/1979 | Davis |
| 4,301,144 A | 11/1981 | Iwashita |
| 4,444,887 A | 4/1984 | Hoffmann |
| 4,474,893 A | 10/1984 | Reading |
| 4,485,045 A | 11/1984 | Regen |
| 4,496,689 A | 1/1985 | Mitra |
| 4,544,545 A | 10/1985 | Ryan |
| 4,640,835 A | 2/1987 | Shimizu |
| 4,670,417 A | 6/1987 | Iwasaki |
| 4,695,198 A | 9/1987 | Goodacre |
| 4,714,681 A | 12/1987 | Reading |
| 4,716,111 A | 12/1987 | Osband |
| 4,791,192 A | 12/1988 | Nakagawa |
| 4,816,397 A | 3/1989 | Boss et al. |
| 4,816,567 A | 3/1989 | Cabilly et al. |
| 4,900,727 A | 2/1990 | Kallige |
| 4,925,648 A | 5/1990 | Hansen |
| 4,946,778 A | 8/1990 | Ladner et al. |
| 4,965,198 A | 10/1990 | Yamasaki |
| 4,975,369 A | 12/1990 | Beavers et al. |
| 4,978,745 A | 12/1990 | Schoemaker et al. |
| 5,013,556 A | 5/1991 | Woodle et al. |
| 5,045,532 A | 9/1991 | Della Valle |
| 5,059,680 A | 10/1991 | Davis |
| 5,091,513 A | 2/1992 | Huston |
| 5,158,886 A | 10/1992 | Kawamura |
| 5,208,020 A | 5/1993 | Chari |
| 5,225,539 A | 7/1993 | Winter |
| 5,258,498 A | 11/1993 | Huston |
| 5,403,484 A | 4/1995 | Ladner |
| 5,413,923 A | 5/1995 | Kucherlapati |
| 5,427,908 A | 6/1995 | Dower |
| 5,475,092 A | 12/1995 | Chari |
| 5,516,637 A | 5/1996 | Huang |
| 5,530,101 A | 6/1996 | Queen et al. |
| 5,565,332 A | 10/1996 | Hoogenboom |
| 5,571,698 A | 11/1996 | Ladner |
| 5,573,920 A | 11/1996 | Randle |
| 5,580,717 A | 12/1996 | Dower |

(Continued)

FOREIGN PATENT DOCUMENTS

| EP | 0313244 A2 | 4/1989 |
| EP | 0316818 A2 | 5/1989 |

(Continued)

OTHER PUBLICATIONS

Vajdos et al. (J Mol Biol. Jul. 5, 2002;320(2):415-28). (Year: 2002).*
Bedouelle et al. (FEBS J. Jan. 2006;273(1):34-46). (Year: 2006).*
Brown et al. (J Immunol. May 1, 1996; 156(9):3285-91). (Year: 1996).*
Colman (Research in Immunology, 145:33-36, 1994). (Year: 1994).*
Hedlund et al., "N-Glycolylneuraminic Acid Deficiency in Mice: Implications for Human Biology and Evolution", Molecular and Cellular Biology, 27(12), pp. 4340-4346 (2007).
Heimburg-Molinaro et al., "Cancer vaccines and carbohydrate epitopes", Vaccine., 29(48), pp. 8802-8826 (Nov. 8, 2011).
Heiskanen et al., "N-glycolylneuraminic acid xenoantigen contamination of human embryonic and mesenchymal stem cells is substantially reversible," Stem Cells, 25 pp. 197-202 (Jan. 2007).

(Continued)

Primary Examiner — Zachary S Skelding
(74) Attorney, Agent, or Firm — McNeill Baur PLLC

(57) ABSTRACT

The present disclosure provides antibodies with T cell-interacting regions and/or glycan-interacting regions. Bispecific antibodies capable of recruiting T cells to cancer cells are also provided, including bispecific antibodies capable of recruiting T cells to cancer cells expressing sialyl Tn (STn). The present disclosure also includes methods for killing cells by targeting them with antibodies having T cell-interacting regions.

10 Claims, 8 Drawing Sheets

Specification includes a Sequence Listing.

(56) References Cited

U.S. PATENT DOCUMENTS

| | | |
|---|---|---|
| 5,585,089 A | 12/1996 | Queen |
| 5,585,499 A | 12/1996 | Chari |
| 5,601,819 A | 2/1997 | Wong |
| 5,625,126 A | 4/1997 | Lonberg |
| 5,633,425 A | 5/1997 | Lonberg |
| 5,658,727 A | 8/1997 | Barbas |
| 5,693,761 A | 12/1997 | Queen et al. |
| 5,693,762 A | 12/1997 | Queen |
| 5,698,426 A | 12/1997 | Huse |
| 5,710,038 A | 1/1998 | Mes-Masson |
| 5,733,743 A | 3/1998 | Johnson |
| 5,733,920 A | 3/1998 | Mansur |
| 5,750,753 A | 5/1998 | Kimae |
| 5,780,225 A | 7/1998 | Wigler |
| 5,786,464 A | 7/1998 | Seed |
| 5,807,715 A | 9/1998 | Morrison |
| 5,811,510 A | 9/1998 | Papisov |
| 5,821,047 A | 10/1998 | Garrard |
| 5,846,545 A | 12/1998 | Chari |
| 5,849,733 A | 12/1998 | Kim |
| 5,863,990 A | 1/1999 | Papisov |
| 5,902,725 A | 5/1999 | Robbins et al. |
| 5,919,652 A | 7/1999 | Pang |
| 5,932,448 A | 8/1999 | Tso |
| 5,939,598 A | 8/1999 | Kucherlapati et al. |
| 5,951,983 A | 9/1999 | Bazin |
| 5,958,398 A | 9/1999 | Papisov |
| 5,969,108 A | 10/1999 | McCafferty |
| 6,075,181 A | 6/2000 | Kucherlapati et al. |
| 6,114,148 A | 9/2000 | Seed |
| 6,114,598 A | 9/2000 | Kucherlapati et al. |
| 6,180,370 B1 | 1/2001 | Queen et al. |
| 6,300,129 B1 | 10/2001 | Lonberg et al. |
| 6,348,584 B1 | 2/2002 | Hodgson |
| 6,673,901 B2 | 1/2004 | Koide |
| 6,852,533 B1 | 2/2005 | Rafii |
| 6,872,868 B1 | 3/2005 | Wagner |
| 6,936,612 B2 | 8/2005 | Barvian |
| 7,119,200 B2 | 10/2006 | Guzi |
| 7,208,489 B2 | 4/2007 | Barvian |
| 7,345,171 B2 | 3/2008 | Beylin |
| 7,456,168 B2 | 11/2008 | Barvian |
| 7,569,390 B1 | 8/2009 | Eric |
| 7,608,453 B2 | 10/2009 | Cattaneo |
| 7,682,794 B2 | 3/2010 | Varki |
| 7,749,225 B2 | 7/2010 | Chappuis |
| 7,820,797 B2 | 10/2010 | Boons |
| 7,855,211 B2 | 12/2010 | Coates |
| 7,863,278 B2 | 1/2011 | Beylin |
| 7,884,054 B2 | 2/2011 | Zhou |
| 7,897,347 B2 | 3/2011 | Tse |
| 7,994,100 B2 | 8/2011 | Ventresca |
| 8,084,219 B2 | 12/2011 | Varki |
| 8,232,448 B2 | 7/2012 | Varki |
| 8,298,773 B2 | 10/2012 | Vuskovic |
| 8,399,625 B1 | 3/2013 | Escher |
| 8,440,798 B2 | 5/2013 | Clausen |
| 8,506,966 B2 | 8/2013 | Podda |
| 8,524,214 B2 | 9/2013 | Yurkovetskiy |
| 8,541,231 B2 | 9/2013 | Varki |
| 8,685,383 B2 | 4/2014 | Yurkovetskiy |
| 8,685,980 B2 | 4/2014 | Besong |
| 8,808,679 B2 | 8/2014 | Yurkovetskiy |
| 8,980,311 B2 | 3/2015 | Ingale |
| 9,193,732 B2 | 11/2015 | Calienni |
| 9,254,339 B2 | 2/2016 | Yurkovetskiy |
| 9,273,142 B2 | 3/2016 | Ghaderi |
| 9,423,401 B2 | 8/2016 | Varki |
| 9,555,112 B2 | 1/2017 | Bodyak et al. |
| 9,718,888 B2 | 8/2017 | Magliery |
| 9,879,087 B2 | 1/2018 | DeSander et al. |
| 11,028,181 B2 | 6/2021 | Eavarone et al. |
| 2002/0012660 A1 | 1/2002 | Colman |
| 2002/0192231 A1 | 12/2002 | Zhu |
| 2003/0104402 A1 | 6/2003 | Zauderer |
| 2003/0108548 A1 | 6/2003 | Bluestone et al. |
| 2003/0235850 A1 | 12/2003 | Cattaneo |
| 2004/0047891 A1 | 3/2004 | Glozman |
| 2004/0115740 A1 | 6/2004 | Benson |
| 2005/0084903 A1 | 4/2005 | Kim |
| 2005/0272107 A1 | 12/2005 | Rabbitts |
| 2005/0276800 A1 | 12/2005 | Rabbitts |
| 2005/0288492 A1 | 12/2005 | Rabbitts |
| 2006/0034834 A1 | 2/2006 | Marasco |
| 2007/0048314 A1 | 3/2007 | Dai et al. |
| 2007/0059769 A1 | 3/2007 | Blixt et al. |
| 2007/0089178 A1 | 4/2007 | Zhu |
| 2007/0116727 A1 | 5/2007 | Hakomori et al. |
| 2007/0265170 A1 | 11/2007 | Blixt et al. |
| 2007/0275409 A1 | 11/2007 | Varki et al. |
| 2008/0019968 A1 | 1/2008 | Blixt et al. |
| 2008/0166805 A1 | 7/2008 | Varki |
| 2008/0193453 A1 | 8/2008 | Monterio et al. |
| 2008/0253963 A1 | 10/2008 | Morin et al. |
| 2008/0279847 A1 | 11/2008 | Hong et al. |
| 2009/0041783 A1 | 2/2009 | Takayama |
| 2009/0099073 A1 | 4/2009 | Rosen |
| 2009/0196916 A1 | 8/2009 | Ingale |
| 2009/0221803 A1 | 9/2009 | Dall'Acqua et al. |
| 2009/0280116 A1 | 11/2009 | Smith |
| 2009/0326203 A1 | 12/2009 | Adams et al. |
| 2010/0009424 A1 | 1/2010 | Forde |
| 2010/0034825 A1 | 2/2010 | Clausen et al. |
| 2010/0075344 A1 | 3/2010 | Vuskovic et al. |
| 2010/0104572 A1 | 4/2010 | Luria |
| 2010/0143939 A1 | 6/2010 | Rabbitts |
| 2010/0178292 A1 | 7/2010 | Wang |
| 2010/0196983 A1 | 8/2010 | Yang |
| 2010/0221770 A1 | 9/2010 | Varki |
| 2010/0272707 A1 | 10/2010 | Bay |
| 2010/0278818 A1 | 11/2010 | Hubert-Haddad |
| 2010/0292095 A1 | 11/2010 | Laukkanen |
| 2010/0293624 A1 | 11/2010 | Varki |
| 2011/0081356 A1 | 4/2011 | Tahara et al. |
| 2011/0135570 A1 | 6/2011 | Janatpour |
| 2011/0143373 A1 | 6/2011 | Hirvonen et al. |
| 2011/0177614 A1 | 7/2011 | Varki et al. |
| 2011/0195921 A1 | 8/2011 | Varki |
| 2012/0027813 A1 | 2/2012 | Podda |
| 2012/0039984 A1 | 2/2012 | Boons |
| 2012/0045816 A1 | 2/2012 | Ghaderi |
| 2012/0114652 A1 | 5/2012 | Elvin et al. |
| 2012/0142903 A1 | 6/2012 | Varki |
| 2012/0164068 A1 | 6/2012 | Hudson et al. |
| 2012/0177664 A1 | 7/2012 | Yokoseki |
| 2013/0011868 A1 | 1/2013 | Hosaka |
| 2013/0017200 A1 | 1/2013 | Scheer et al. |
| 2013/0039991 A1 | 2/2013 | Varki |
| 2013/0108624 A1 | 5/2013 | Wang |
| 2013/0177579 A1 | 7/2013 | Lin et al. |
| 2013/0236486 A1 | 9/2013 | Boons |
| 2014/0005069 A1 | 1/2014 | Yang |
| 2014/0106449 A1 | 4/2014 | June |
| 2014/0113979 A1 | 4/2014 | Varki et al. |
| 2014/0178365 A1 | 6/2014 | Ghaderi et al. |
| 2015/0110789 A1* | 4/2015 | Liu .................. C07K 16/2809 424/136.1 |
| 2015/0314008 A1 | 11/2015 | Yurkovetskiy |
| 2015/0368349 A1 | 12/2015 | Gonzalez et al. |
| 2016/0022829 A1 | 1/2016 | Yurkovetskiy |
| 2016/0130356 A1 | 5/2016 | DeSander et al. |
| 2016/0168211 A1* | 6/2016 | Ahmed .............. C07K 16/468 424/134.1 |
| 2016/0220696 A1 | 8/2016 | Yurkovetskiy |
| 2017/0305950 A1 | 10/2017 | Silva et al. |
| 2017/0306046 A1 | 10/2017 | daSilva et al. |
| 2018/0037663 A1 | 2/2018 | Magliery |
| 2018/0280504 A1 | 10/2018 | Silva et al. |
| 2018/0327509 A1 | 11/2018 | Eavarone et al. |
| 2019/0031780 A1 | 1/2019 | Eavarone et al. |
| 2019/0276541 A1 | 9/2019 | Eavarone et al. |
| 2020/0000932 A1 | 1/2020 | Dransfield et al. |
| 2020/0247902 A1 | 8/2020 | Prendergast et al. |

(56) References Cited

U.S. PATENT DOCUMENTS

| | | |
|---|---|---|
| 2020/0276306 A1 | 9/2020 | Da Silva et al. |
| 2021/0011021 A1 | 1/2021 | da Silva et al. |
| 2021/0017213 A1 | 1/2021 | da Silva et al. |

FOREIGN PATENT DOCUMENTS

| | | |
|---|---|---|
| EP | 0316818 B1 | 5/1993 |
| EP | 0592106 A1 | 4/1994 |
| EP | 0239400 B1 | 8/1994 |
| EP | 0404097 B1 | 9/1996 |
| EP | 0519596 B1 | 2/2005 |
| EP | 2287202 A1 | 2/2011 |
| EP | 2422811 A2 | 2/2012 |
| EP | 2565268 A4 | 10/2013 |
| EP | 2703485 A1 | 3/2014 |
| EP | 3091032 A1 | 11/2016 |
| WO | 1990002809 A1 | 3/1990 |
| WO | 1991000360 A1 | 1/1991 |
| WO | 1991009967 A1 | 7/1991 |
| WO | 1991010737 A1 | 7/1991 |
| WO | 1991010741 A1 | 7/1991 |
| WO | 1991019739 A1 | 12/1991 |
| WO | 1992001047 A1 | 1/1992 |
| WO | 1992005793 A1 | 4/1992 |
| WO | 1992008802 A1 | 5/1992 |
| WO | 1992018619 A1 | 10/1992 |
| WO | 1993011161 A1 | 6/1993 |
| WO | 1993011236 A1 | 6/1993 |
| WO | 1993017715 A1 | 9/1993 |
| WO | 1995015982 A2 | 6/1995 |
| WO | 1995020401 A1 | 8/1995 |
| WO | 1995015982 A3 | 12/1995 |
| WO | 1996033735 A1 | 10/1996 |
| WO | 1996034096 A1 | 10/1996 |
| WO | 1998016654 A1 | 4/1998 |
| WO | 1998024893 A3 | 8/1998 |
| WO | 1998046645 A2 | 10/1998 |
| WO | 1998050433 A2 | 11/1998 |
| WO | 1998050433 A3 | 2/1999 |
| WO | 1998046645 A3 | 4/1999 |
| WO | 1999014353 A3 | 6/1999 |
| WO | 2000023573 A2 | 9/2000 |
| WO | 2000054057 A1 | 9/2000 |
| WO | 2001043778 A1 | 6/2001 |
| WO | 2001040276 A3 | 1/2002 |
| WO | 2002035237 A3 | 10/2002 |
| WO | 2002077029 A2 | 10/2002 |
| WO | 2002086096 A2 | 10/2002 |
| WO | 2002086505 A2 | 10/2002 |
| WO | 2002088351 A1 | 11/2002 |
| WO | 2003014960 A2 | 2/2003 |
| WO | 2003016329 A2 | 2/2003 |
| WO | 2003062415 A2 | 7/2003 |
| WO | 2002088334 A9 | 8/2003 |
| WO | 2003040185 A3 | 9/2003 |
| WO | 2003077945 A1 | 9/2003 |
| WO | 2003086276 A2 | 10/2003 |
| WO | 2003095641 A1 | 11/2003 |
| WO | 2003097697 A2 | 11/2003 |
| WO | 2003008451 A3 | 1/2004 |
| WO | 2003062415 A3 | 6/2004 |
| WO | 2004046187 A2 | 6/2004 |
| WO | 2004046192 A2 | 6/2004 |
| WO | 2004046186 A3 | 8/2004 |
| WO | 2004046185 A3 | 9/2004 |
| WO | 2004046188 A3 | 9/2004 |
| WO | 2004046189 A3 | 9/2004 |
| WO | 2004099775 A1 | 11/2004 |
| WO | 2003097697 A3 | 12/2004 |
| WO | 2005010485 A2 | 2/2005 |
| WO | 2003086276 A3 | 4/2005 |
| WO | 2005033303 A1 | 4/2005 |
| WO | 2005088310 A2 | 9/2005 |
| WO | 2006002382 A2 | 1/2006 |
| WO | 2006002382 A3 | 10/2006 |
| WO | 2006133356 A3 | 3/2007 |
| WO | 2008040362 A2 | 4/2008 |
| WO | 2008070363 A2 | 6/2008 |
| WO | 2007059298 B1 | 9/2008 |
| WO | 2009018438 A1 | 2/2009 |
| WO | 2008040362 A3 | 3/2009 |
| WO | 2009035494 A2 | 3/2009 |
| WO | 2009035494 A3 | 4/2009 |
| WO | 2009060129 A1 | 5/2009 |
| WO | 2009091826 A2 | 7/2009 |
| WO | 2010004432 A1 | 1/2010 |
| WO | 2010030666 A2 | 3/2010 |
| WO | 2010065818 A1 | 6/2010 |
| WO | 2011003896 A1 | 1/2011 |
| WO | 2011041093 A1 | 4/2011 |
| WO | 2011088385 A2 | 7/2011 |
| WO | 2011089004 A1 | 7/2011 |
| WO | 2012007167 A1 | 1/2012 |
| WO | 2012009474 A1 | 1/2012 |
| WO | 2012048332 A2 | 4/2012 |
| WO | 2012079000 A1 | 6/2012 |
| WO | 2012094627 A2 | 7/2012 |
| WO | 2012106465 A2 | 8/2012 |
| WO | 2013023251 A1 | 2/2013 |
| WO | 2013033420 A1 | 3/2013 |
| WO | 2013040557 A2 | 3/2013 |
| WO | 2013055404 A1 | 4/2013 |
| WO | 2013074916 A1 | 5/2013 |
| WO | 2013092001 A1 | 6/2013 |
| WO | 2013126712 A1 | 8/2013 |
| WO | 2013138795 A1 | 9/2013 |
| WO | 2013151649 A1 | 10/2013 |
| WO | 2014030780 A1 | 2/2014 |
| WO | 2014039513 A2 | 3/2014 |
| WO | 2014055771 A1 | 4/2014 |
| WO | 2014028560 A3 | 5/2014 |
| WO | 2014105810 A1 | 7/2014 |
| WO | 2014106639 A1 | 7/2014 |
| WO | 2014144357 A1 | 9/2014 |
| WO | 2014144573 A2 | 9/2014 |
| WO | 2015048748 A1 | 4/2015 |
| WO | 2015054600 A3 | 6/2015 |
| WO | 2015134488 A1 | 9/2015 |
| WO | 2015159076 A1 | 10/2015 |
| WO | 2016033284 A1 | 3/2016 |
| WO | 2016057916 A1 | 4/2016 |
| WO | 2016077526 A1 | 5/2016 |
| WO | 2016090034 A2 | 6/2016 |
| WO | 2016149368 A1 | 9/2016 |
| WO | 2016201240 A1 | 12/2016 |
| WO | 2017083582 A1 | 5/2017 |
| WO | 2018094143 A1 | 5/2018 |
| WO | 2018094144 A1 | 5/2018 |

OTHER PUBLICATIONS

Henry et al., "A prostate-specific membrane antigen-targeted monoclonal antibody-chemotherapeutic conjugate designed for the treatment of prostate cancer," Cancer Res., 64, pp. 7995-8001 (Nov. 1, 2004).

Higashi et al., "Antigen of 'serum sickness' type of heterophile antibodies in human sera: indentification as gangliosides with N-glycolylneuraminic acid", Biochem Biophys Res. Comm, vol. 79, pp. 388-395 (1977).

Higashi et al., "Characterization of N-glycolylneuraminic acid-containing gangliosides as tumor-associated Hanganutziu-Deicher antigen in human colon cancer", Cancer Res., 45(8), pp. 3796-3802 (Aug. 1985).

Higashi et al., "Detection of Gangliosides as N-Glycolylneuraminic Acid-Specific Tumor-Associated Hanganutziu-Deicher Antigen in Human Retinoblastoma Cells", Jpn J Cancer Res, 79(8), pp. 952-956 (1988).

Hinrichs , M., "Antibody Drug Conjugates: Nonclinical Safety Considerations", AAPS J. 17, 1055-1064 (2015).

Hirabayashi et al,. "Specific Expression of Unusual Gm2 Ganglioside with Hanganutziu-Deicher Antigen Activity on Human Colon Cancers" 78(3), pp. 251-260 (1987).

(56) References Cited

OTHER PUBLICATIONS

Hirabayashi et al., "A new method for purification of anti-glycosphingolipid antibody. Avian anti-hematoside (NeuGc) antibody", Journal of Biochemistry, 94(1), pp. 327-330 (Jul. 1, 1983).
Hirabayashi et al., "Occurrence of Tumor-Associated Ganglioside Antigens With Hanganutziu-Deicher Antigenic Activity on Human Melanomas" Japanese Journal of Cancer Research, Japanese Cancer Association, Tokyo, JP, 78 (6), pp. 514-620 (Jan. 1, 1987).
Hirakawa et al., "Novel Anti-carbohydrate Antibodies Reveal the Cooperative Function of Sulfated N- andO-Glycans in Lymphocyte Homing", Journal of Biological Chemistry, vol. 285, No. 52, 7,pp. 40864-40878 (Oct. 2010).
Hofmann et al., "COSMC knockdown mediated aberrant O-glycosylation promotes oncogenic properties in pancreatic cancer", Mol. Cancer 14, 1-15 (2015).
Hojman, "Basic principles and clinical advancements of muscle electrotransfer", Curr Gene Ther., 10, pp. 128-138 (2010).
Hollinger et al., "Diabodies: Small bivalent and bispecific antibody fragments", Proc. Natl. Acad. Sci. USA, 90, pp. 6444-6448 (1993).
Holm et al., "Functional mapping and single chain construction of the anti-cytokeratin 8 monoclonal antibody TS1," Mol. Immunol., 44 (6), pp. 1075-1084 (Feb. 2007).
Holmberg et al., "Vaccination with Theratope (STn-KLH) as treatment for breast cancer", Expert Rev Vaccines, 3, pp. 655-663 (2004).
Honegger et al., "Yet another numbering scheme for immunoglobulin variable domains: an automatic modeling and analysis tool," J Mol. Biol., 309(3), pp. 657-670 (2001).
Hong and Stanley, "Lec3 Chinese Hamster Ovary Mutants Lack UDP-N-Acetylglucosamine 2-Epimerase Activity Because of Mutations in the Epimerase Domain of the Gne Gene." J Biol Chem, 278(52):53045-53054 (2003).
Hossler et al., "Optimal and consistent protein glycosylation inmammalian cell culture", Glycobiology, 19(9), pp. 936-949 (2009).
Huston et al., "Protein engineering of single-chain Fv analogs and fusion proteins". Methods Enzymol. 203, pp. 46-88 (1991).
Hwang et al., "Hepatic uptake and degradation of unilamellar sphingomyelincholesterol liposomes: a kinetic study", Proc Natl Acad Sci USA, 77(7), pp. 4030-4034 (Jul. 1980).
Ibrahim et al., "Humoral immune-response to naturally occurring STn in metastatic breast cancer patients (MBC pis) reated with STn-KLH vaccine", Journal of clinical oncology: official journal of the American Society of Clinical Oncology, 22, 2547, 2 pages (2004).
Ibrahim et al., "Survival Advantage in Patients with Metastatic Breast Cancer Receiving Endocrine Therapy plus Sialyl Tn-KLH Vaccine: Post Hoc Analysis of a Large Randomized Trial," 4(7), pp. 577-584 (2013).
Ikehara et al., Cloning and expression of a human gene encoding an N-acetylgalactosamine-alpha2,6-sialyltransferase (ST6GalNAc I): a candidate for synthesis of cancer-associated sialyl-Tn antigens. Glycobiology, 9 (11), pp. 1213-1224 (Nov. 1999).
Imada et al., "Sialyl Tn antigen expression is associated with the prognosis of patients with advanced colorectal cancer", Hepatogastroenterology 46, pp. 208-214 (1999).
Imai et al. "Immunohistochemical expression of T, Tn and sialyl-Tn antigens and clinical outcome in human breast carcinoma", Anti-cancer Research, 21(2B), pp. 1327-1334 (2001).
Inoue et al., "Extensive emichment ofN-glycolylneuraminic acid in extracellular sialoglycoproteins abundantly synthesized and secreted by human cancer cells", Glycobiology, 20(6), pp. 752-762 (2010).
International Preliminary Report on Patentability in related International Application No. PCT/US2011/021387, dated Jul. 26, 2012 (6 pages).
International Search Report in related International Application No. PCT/US2011/021387, dated Oct. 6, 2011 (5 pages).
International Search Report & Written Opinion dated Apr. 14, 2017 in International Application No. PCT/US2016/061427, dated Mar. 17, 2017 (13 pages).
International Search Report and Written Opinion dated Jun. 9, 2017 in Application No. PCT/US2017/015301, dated Jun. 9, 2017 (13 pages).
International Search Report and Written Opinion for corresponding PCT Application No. PCT/US2017/062156 dated Feb. 20, 2018 (15 pages).
International Search Report and Written Opinion received in PCT/US2013/029240 dated Jun. 21, 2013 (9 pages).
International Search Report and Written Opinion received in PCT/US2014/060079 dated Mar. 27, 2015 (12 pages).
International Search Report and Written Opinion received in PCT/US2015/054877 dated Feb. 9, 2016 (10 pages).
International Search Report and Written Opinion received in PCT/US2015/060287 dated Mar. 31, 2016 (16 pages).
International Search Report and Written Opinion received in PCT/US2016/036907 dated Sep. 7, 2016 (9 pages).
International Search Report and Written Opinion received in PCT/US2018/020562 dated Jun. 27, 2018 (17 pages).
Irie et al., "The Molecular Basis for the Absence of N-Glycolylneuraminic Acid in Humans", Journal of Biological Chemistry, 273(25), pp. 15866-15871 (Jun. 19, 1998).
Ishida et al., "Mucin-induced apoptosis of monocyte-derived dendritic cells during maturation", Proteomics, 8, pp. 3342-3349 (2008).
Itzkowiiz et al., "Sialosyl-Tn. A novel mucin antigen associated with prognosis in colorectal cancer patients", Cancer, 66(9), pp. 1960-1966 (Nov. 1, 1990).
Jandus et al., "Interactions between Siglec-7/9 receptors and ligands influence NK cell-dependent tumor immunosurveillance", JCI, 124(4), 1810-1820 (Apr. 2014).
Jass et al., "Distribution of sialosyl Tn and Tn antigens within normal and malignant colorectal epithelium", J Pathol, 176(2), pp. 143-149 (Jun. 1995).
Johannes et al., "Clathrin-dependent or not: is it still the question?", Traffic, 3(7), pp. 443-451 (Jun. 1995).
Johansen et al., "A Lectin HPLC Method to Enrich Selectively-glycosylated Peptides from Complex Biological Samples", Journal of Visualized Experiments, (32), p. 1398 (2009).
Johnson et al., "Kabat Database and its applications: 30 years after the first variability plot", Nucleic Acids Res, 28 (1), pp. 214-218 (2000).
Jolles et al., "Clinical uses of intravenous immunoglobulin", Clinical & Experimental Immunology, 142(1), pp. 1-11 (2005).
Ju et al., "Human Tumor Antigens Tn and Sialyl Tn Arise from Mutations in Cosmc", Cancer Research, 68(6), pp. 1636-1646(2008).
Ju et al., "Protein glycosylation: chaperone mutation in Tn syndrome", Nature, 437(7063), p. 1252 (Oct. 27, 2005).
Von Mensdorff-Pouilly et al., "Reactivity of natural and induced human antibodies to MUC1 mucin with MUC1 peptides and n-acetylgalactosamine (GalNAc) peptides", Int J Cancer, 86(5), pp. 702-712 (Jun. 1, 2000).
Wang et al., "Concentration and distribution of sialic acid in human milk and infant formulas", American Journal of Clinical Nutrition, 74&4), pp. 510-515 (2001).
Wang et al., "Dietary sialic acid supplementation improves learning and memory in piglets", American Journal of Clinical Nutrition, 85(2), pp. 561-569 (2007).
Wang, D., "N-glycan Cryptic Antigens as Active Immunological Targets in Prostate Cancer Patients", J Proteomics Bioinform, 5(4), pp. 090-095 (2012).
Warren, L., "The Distribution of Sialic Acids in Nature", Comp. Biochem. Physiol. 10, pp. 153-171 (1963).
Weiss et al., "Immunotherapy of Cancer by IL-12-based Cytokine Combinations", Expert Opinion on Biological Therapy, 7(11), pp. 1705-1721 (2007).
Welinder et al., "A new murine IgG1 anti-Tn monoclonal antibody with in vivo anti-tumor activity", Glycobiology, 21(8), pp. 1097-1107 (Aug. 2011).
Wheeler et al., "Intrabody-based strategies for inhibition of vascular endothelial growth factor receptor-2: effects on apoptosis, cell growth, and angiogenesis," FASEB J. 17, pp. 1733-1735 (2003).

(56) References Cited

OTHER PUBLICATIONS

Winkler et al., "Changing the antigen binding specificity by single point mutations of an anti-p24 (HIV-1) antibody," J. Immunol., 165(8), pp. 4505-4514 (Oct. 15, 2000).
Wirtz et al., "Intrabody construction and expression III: engineering hyperstable V(H) domains," Protein Sci. 8, pp. 2245-2250 (1999).
Wong et al., "An Investigation of Intracellular Glycosylation Activities in CHO Cells: Effects of Nucleotide Sugar Precursor Feeding", Biotechnology and Bioengineering, 107(2), pp. 321-336 (2010).
Wood et al., "Targeted genome editing across species using ZFNs and TALENs", Science, 333(6040), p. 307 (Jul. 15, 2011).
Wright, et al., "Piscine Islet Xenotransplantation." ILAR J, 45(3):314-323 (2004).
Written Opinion in related International Application No. PCT/US2011/021387, dated Oct. 6, 2011 (5 pages).
Wu et al., "An analysis of the sequences of the variable regions of Bence Jones proteins and myeloma light chains and their implications for antibody complementarity," J Exp Med, 132(2), pp. 211-250 (1970).
Wu et al., "New development of glycan arrays", Organic & Biomolecular Chemistry, 7(11), pp. 2247-2254 (2009).
Wu, X. et al. (2004) "A New Homobifunctional p-Nitro Phenyl Ester Coupling Reagent for the Preparation of Neoglycoproteins," Organic Letters 6(24), 4407-4410.
Yin et al., "Hypoxic culture induces expression of sialin, a sialic acid transporter, and cancer-associated gangliosides containing non-human sialic acid on human cancer cells", Cancer Res., 66(6), pp. 2937-2945 (Mar. 15, 2006).
Yonezawa et al., "Sialosyl-Tn antigen. Its distribution in normal human tissues and expression in adenocarcinomas. ", American Journal of Clinical Pathology, 98(2), pp. 167-174 (1992).
Yu et al., "A Multifunctional Pasteurella multocida Sialyltransferase: A Powerful Powerful Tool for the Synthesis of Sialoside Libraries", Journal of the American Chemical Society, 127(50), pp. 17618-17619 (2005).
Yu et al., "Efficient chemoenzymatic synthesis of biotinylated human serum albumin-sialoglycoside conjugates containing 0-acetylated sialic acids", Organic & Biomolecular Chemistry, 5(15), pp. 2458-2463 (2007).
Yu et al., "Highly Efficient Chemoenzymatic Synthesis of Naturally Occurring and Non-Natural α-2,6-Linked Sialosides: A P. damsela α-2,6-Sialyltransferase with Extremely Flexible Donor-Substrate Specificity", Angewandte Chemie International Edition, 45(24), pp. 3938-3944 (2006).
Chang et al., "Non-invasive phenotyping and drug testing in single cardiomyocytes or beta-cells by calcium imaging and optogenetics," PLoS One 7 (3): e33340; pp. 1-15 (2012).
Yu et al., "One-pot three-enzyme chemoenzymatic approach to the synthesis of sialosides containing natural and non-natural functionalities", Nature Protocols, 1 (5), pp. 2485-2492 (2006).
Yu et al., "Silencing of ST6GalNAc I suppresses the proliferation, migration and invasion of hepatocarcinoma cells though PI3K/AKT/NF-κB pathway", Tumor Biology, vol. 37(9), pp. 12213-12221 (May 27, 2016).
Zhang et al., "An overview of biomarkers for the ovarian cancer diagnosis", Eur. J. Obstet. Gynecol. Reprod. Biol. 158, pp. 119-123 (2011).
Zhang et al., "Immune sera and monoclonal antibodies define two configurations for the sialyl Tn tumor antigen", Cancer Res., 55, pp. 3364-3368 (1995).
Zhang et al., "Proteomics, pathway array and signaling network-based medicine in cancer", Cell Division 4(1):20 16 pages (2009).
Zhang et al.,"Identification and characterization of ovarian cancer-initiating cells from primary human tumors," Cancer Research, 68(11), pp. 4311-4320 (2008).
Zhu et al., Anti-N-glycolylneuraminic acid antibodies identified in healthy human serum:, Xenotransplantation, vol. 9, pp. 376-381 (2002).

Zhu et al., "Extended half-life and elevated steady-state level of a single-chain Fv intrabody are critical for specific intracellular retargeting of its antigen, caspase-7", J Immunol. Methods, 231, pp. 207-222 (1999).
Zoller, "CD44: can a cancer-initiating cell profit from an abundantly expressed molecule?," Nat Rev Cancer, 11(4), pp. 254-267 (2011).
Gao et al., "Identification of Cancer Stem-like Side Population Cells in Ovarian Cancer Cell Line OVCAR-3," Ultrastructual Pathology, 33, pp. 175-181 (2009).
Han et al., "A2780 human ovarian cancer cells with acquired paclitaxel resistance display cancer stem cell properties," Oneology Letters 6; pp. 1295-1298 (2013).
Ota et al., "Antitumor effect of monoclonal antibody-carboplatin conjugates in nude mice bearing human ovarian cancer cells," Int J Clin Oncol, 4, pp. 236-240 (1999).
Quiles et al., "Synthesis and Preliminary Biological Evaluation of High-Drug-Load-Paclitaxel-Antibody Conjugates for Tumor-Targeted Chemotherapy," J. Med. Chem. 53, pp. 586-594 (2010).
Negi et al., "Role of CD44 in tumour progression and strategies for targeting," Journal of drug targeting, 20, pp. 561-573 (2012).
Nelson et al., "Population screening and early detection of ovarian cancer in asymptomatic women", Australian & New Zealand Journal of Obstetrics & Gynaecology, 49(5), pp. 448-450 (2009).
Nelson et al., "Screening for Breast Cancer: An Update for the U.S. Preventive Services Task Force", Annals of Internal Medicine, 151(10), pp. 727-737 (2009).
Nelson, A. L., "Antibody fragments: hope and hype," Mabs, 2(1), pp. 77-83 (Jan.-Feb. 2010).
Newman et al., "Gene therapy progress and prospects: ultrasound for gene transfer", Gene Ther., 14, pp. 465-475 (2007).
Newsom-Davis et al., "Enhanced Immune Recognition of Cryptic Glycan Markers in Human Tumors", Cancer Res, 69, pp. 2018-2025 (2009).
Nguyen et al., "Effects of Natural Human Antibodies against a Nonhuman Sialic Acid That Metabolically Incorporates into Activated and Malignant Immune Cells", The Journal of Immunology, 175(1), pp. 228-236 (2005).
Nikoloudis et al., "Complete, multi-level conformational clustering of antibody complementarity-determining regions", PeerJ. 2, e456 40 pages (2014).
Nogueira et al., Prostatic specific antigen for prostate cancer detection, International Braz j urol, 35(5), pp. 521-529 (2009).
Porteus et al., "Chimeric nucleases stimulate gene targeting in human cells", Science, 300(5620), p. 763 (May 2, 2003).
Nohle et al., "Uptake, Metabolism and Excretion of Orally and Intravenously Administered, Double-labeled N-Glycoloylneuraminic Acid and Single-Labeled 2-Deoxy-2,3-dehydro-N-acetylneuraminic Acid in Mouse and Rat", European Journal of Biochemistry, 126(3), pp. 543-548 (1982).
Nollau et al., "Protein domain histochemistry (PDH): binding of the carbohydrate recognition domain (CRD) of recombinant human glycoreceptor CLEC10A (CD301) to formalin-fixed, paraffin-embedded breast cancer tissues," J Histochem Cytochem, 61(3), pp. 199-205 (2013).
Nossov et al., "The early detection of ovarian cancer: from traditional methods to proteomics. Can we really do better than serum CA-125?", American Journal of Obstetrics and Gynecology, 199(3), pp. 215-223 (2008).
O'Boyle et al., "Immunization of Colorectal Cancer Patients with Modified Ovine Submaxillary Gland Mucin and Adjuvants Induces IgM and IgG Antibodies to Sialylated Tn[1]", Cancer Resarch, 52, pp. 5663-5667 (1992).
Oetke et al., "Evidence for efficient uptake and incorporation of sialic acid by eukaryotic cells", Eur. J Biochem, 265, pp. 4553-4561 (2001).
Ogata et al., "Different modes of sialyl-Tn expression during malignant transformation of human colonic mucosa", Glycoconjugate Journal, 15(1), 29-35 (1998).
Ogata et al., "Tumor-associated sialylated antigens are constitutively expressed in normal human colonic mucosa", Cancer Research, 55(9), pp. 1869-1874 (May 1, 1995).

(56) References Cited

OTHER PUBLICATIONS

Ohage et al., "Intrabody construction and expression. I. The critical role of VL domain stability," J. Mol. Biol., 291(5), pp. 1119-1128 (1999).
Ohage et al.,"Intrabody construction and expression. II. A synthetic catalytic Fv fragment," J. Mol. Biol., 291(5), pp. 1129-1134 (1999).
Ohno et al., "Expression of Tn and sialyl-Tn antigens in endometrial cancer: its relationship with tumor-produced cyclooxygenase-2, tumor-infiltrated lymphocytes and patient prognosis", Anticancer Res., (6A), pp. 4047-4053 (Nov.-Dec. 2006).
Blixt,O., "Glycan Microarray Analysis of Tumor-Associates Antibodies" In: Paul Kosma (edit.): "Anticharbohydrate Antibodies", Springer-Verlag, Wien, pp. 290-293 (Nov. 27, 2011).
Oppmann et al., "Novel p19 Protein Engages IL-12p40 to Form a Cytokine, IL-23, with Biological Activities Similar as Well as Distinct from IL-12", Immunity, 13(5), pp. 715-725 (2000).
Ostrand-Rosenberg, S., "Immune surveillance: a balance between protumor and antitumor immunity", Current Opinion in Genetics & Development, 18(1), pp. 11-18 (2008).
Oyelaran et al., "Profiling Human Serum Antibodies with a Carbohydrate Antigen Microarray", Journal of Proteome Research, 8(9), pp. 4301-4310 (2009).
Ozaki et al., "Enhancement of metastatic ability by ectopic expression of ST6GalNAcl on a gastric cancer cell line in a mouse model", Clin Exp. Metastasis 29, pp. 229-238 (2012).
Ozga et al., "A systematic review of ovarian cancer and fear of recurrence", Palliat Support Care, 13(6), pp. 1771-1780 (2015).
Ozols et al., "Phase III trial of carboplatin and paclitaxel compared with cisplatin and paclitaxel in patients with optimally resected stage III ovarian cancer: a Gynecologic Oncology Group study", J Clin Oncol 21(17), pp. 3194-3200 (2003).
Padlan, E.A., "A possible procedure for reducing the immunogenicity of antibody variable domains while preserving their ligand-binding properties", Mol Immunol, 28(4-5), pp. 489-498 (Apr.-May 1991).
Padler-Karavani et al. Cross-comparison of protein recognition of sialic acid diversity on two novel sialoglycan microarrays. J BC 2012, vol. 287, No. 27, pp. 22593-22608 (2012).
Padler-Karavani et al., "Diversity in specificity, abundance, and composition of anti-Neu5Gc antibodies in normal humans: Potential implications for disease", Glycobiology, 18(10), pp. 818-830 (2008).
Padler-Karavani et al., "Human Xeno-Autoantibodies against a Non-Human Sialic Acid Serve as Novel Serum Biomarkers and Immunotherapeutics in Cancer", Cancer Research, 71, pp. 3352-3363 (Apr. 19, 2011).
Padler-Karavani, V., "Aiming at the sweet side of cancer: aberrant glycosylation as possible target for personalized-medicine," Cancer Lett., 352(1), pp. 102-112 (Sep. 28, 2014).
Panowski et al., "Site-specific antibody drug conjugates for cancer therapy," mAbs 6:1, pp. 34-45 (2014).
Pant et al., "Immunohistochemical examination of anti-STn monoclonal antibodies LLU9B4, B72.3, and B35.2 for their potential use as tumor markers", Dig Dis Sci, 53(8), pp. 2189-2194 (Aug. 2008).
Park et al., Characteristics of cell lines established from human gastric carcinoma, Cancer Res., 50, pp. 2773-2780 (1990).
Parkin et al., "Cancer burden in the year 2000. The global picture", European Journal of Cancer 37, Supplement 8 (0), pp. 4-66 (2001).
Partial Supplementary European Search Report for corresponding European Application No. 15848503.7 dated Apr. 10, 2018 (16 pages).
Partial Supplementary European Search Report for corresponding European Application No. 16865044.8 dated May 3, 2019 (11 pages).
Partial Supplementary European Search Report dated May 7, 2018 in corresponding European Application No. 15859152.9 (23 pages).
Pearce et al., "Chemo-enzymatic synthesis of the carbohydrate antigen N-glycolylneuraminic acid from glucose", Carbohydrate Research, 345(9), pp. 1225-1229 (2010).

Perez et al., "Antibody-drug conjugates: current status and future directions", Drug Discov. Today, 19, pp. 869-881 (2014).
Pershad et al., "Generating a panel of highly specific antibodies to 20 human SH2 domains by phage display," Protein Engineering Design and Selection, 23, pp. 279-288 (2010).
Persic et al., "An integrated vector system for the eukaryotic expression of antibodies or or their fragments after selection from phage display libraries", Gene., 187(1), pp. 9-18 (Mar. 10, 1997).
Petterson et al., "CD47 signals T cell death," J. Immunol., 162(12), pp. 7031-7040 (Jun. 15, 1999).
Phelps et al., "Production of Alpha 1,3-Galactosyltransferase-Deficient Pigs", Science, 299(5605), pp. 411-414 (2003).
Pinato et al., "Evolving concepts in the management of drug resistant ovarian cancer: dose dense chemotherapy and the reversal of clinical platinum resistance", Cancer Treat Rev, 39, pp. 153-160 (2013).
Pinho et al., "Biological significance of cancer-associated sialyl-Tn antigen: modulation of malignant phenotype in gastric carcinoma cells", Cancer Lett., 249(2), pp. 157-170 (May 8, 2007).
Pitot, H. C., "The Language of Oncology", Fundamentals of Oncology (Dekker, M., Ed.), pp. 15-28, New York, (1978).
Porter et al., "Chimeric Antigen Receptor-Modified T Cells in Chronic Lymphoid Leukemia", The New England Journal of Medicine, pp. 725-733 (Aug. 25, 2011).
International Search Report and Written Opinion for corresponding PCT Application No. PCT/US2017/062155 entitled "Glycan-Interacting Compounds and Methods of Use" dated Apr. 17, 2018.
An et al., "A Novel Anti-STn Monoclonal Antibody 3P9 Inhibits Human Xenografted Colorectal Carcinomas," J Immunother, vol. 36, No. 1 pp. 20-28 (2013).
Eavarone et al., "Novel Humanized anti-Sialyl-Tn, anti-CD3 bispecific antibodies demostrate tumor and T-cell specificity for immune activation at the tumor site," Cancer Research, vol. 77, No. Suppl. 13, p. 3640, Jul. 2017, and Annual Meeting of the AACR, Washington DC on Apr. 1-5, 2017.
Eaverone et al., "Abstract LB-221: Novel anti-Sialyl-Tn monoclonal antibodies and antibody-drug conjugates (ADCs) demonstrate tumor specificity, unique sequence homology and in vitro and in vivo antitumor efficacy," AACR 107 Annual Meeting 2016, Apr. 16-20, 2016, New Orleans, LA, AACR; Cancer Res 2016, vol. 76, 14 Suppl (4 pages).
Extended European Search Report for European Application No. 17871763.3, dated May 29, 2020 (9 pages).
Extended European Search Report in European Application No. 17872341.7, dated May 27, 2020 (8 pages).
Numa et al., "Tissue Expression of Siayl Tn Antigen in Gynecologic Tumors," J. Obstet. Gynacol. vol 21, No. 4 pp. 385-389 (1995).
Prendergast et al: "Abstract 36: Novel anti-Sialyl-Tn monoclonal antibodies and antibody-drug conjugates (ADCs) demonstrate tumor specificity in vitro and in vivo antitumor efficacy," AACR Annual Meeting 2017, Apr. 1-5, 2017, Washington, DC., AACR, vol. 77, Issue 13 Supplement (4 pages).
Shi et al., "Sialyl-Tn 1 Polysaccharide A1 as an Entirely Carbohydrate Immunogen: Synthesis and Immunological Evaluation," Journal of American Chemical Society, vol. 138, No. 43, pp. 14264-14272 (Oct. 21, 2016).
Acres et al., "MUC1 as a target antigen for cancer immunotherapy," Expert review of vaccines, 4, pp. 493-502 (2005).
Adams et al., "Monoclonal antibody therapy of cancer", Nature Biotechnology, 23(9), pp. 1147-1157 (2005).
Alderson et al., "Clinical cancer therapy by NK cells via antibody-dependent cell-mediated cytotoxicity," J Biomed Biotechnol., 2011, p. 379123 (2011).
Allavena et al., "Engagement of the mannose receptor by tumoral mucins activates an immune suppressive phenotype in human tumor-associated macrophages," Clin Dev Immunol, 2010, p. 547179 (2010).
Al-Lazikani et al., "Standard conformations for the canonical structures of immunoglobulins," J. Mol. Biol., 273(4), pp. 927-948 (1997).
Ames et al., "Conversion of murine Fabs isolated from a combinatorial phage display library to full length, immunoglobulins", J Immunol Methods, 184(2), pp. 177-186 (Aug. 18, 1995).

(56) References Cited

OTHER PUBLICATIONS

An et al., "Glycomics and disease markers", Current Opinion in Chemical Biology, 13(5-6), pp. 601-607 (2009).

Andergassen et al. "Glycosyltransferases as Markers for Early Tumorigenesis", Biomed Res. Int. 792672, 12 pages (2015).

Andreu et al., "FcRy Activation Regulates Inflammation-Associated Squamous Carcinogenesis", Cancer Cell, 17(2), pp. 121-134 (2010).

Ang et al., "Efficacy of chemotherapy in BRCA1/2 mutation carrier ovarian cancer in the setting of PARP inhibitor resistance: a multi-institutional study", Clin Cancer Res; 19, pp. 5485-5493 (2013).

Angata et al., "Chemical Diversity in the Sialic Acids and Related α-Keto Acids: An Evolutionary Perspective", Chemical Review, 102(2), pp. 439-470 (2002).

Arafat et al., "Antineoplastic effect of anti-erbB-2 intrabody is not correlated with scFv affinity for its target.," Cancer Gene Ther., 7, pp. 1250-1256 (2000).

Armstrong et al., "Intraperitoneal cisplatin and paclitaxel in ovarian cancer", N Engl J Med. 354(1), 34-43 (2006).

Asaoka et al., "Two chicken monoclonal antibodies specific for heterophil Hanganutziu-Deicher antigens", Immunol Lett, vol. 32, pp. 91-96 (1992).

Bapat, S. A., "Human ovarian cancer stem cells", Reproduction 140, 33-41 (2010).

Bardor et al., "Mechanism of Uptake and Incorporation of the Non-human Sialic Acid Nglycolylneuraminic Acid into Human Cells", Journal of Biological Chemistry, 280(6), pp. 4228-4237 (2005).

Barrow et al., "Suppression of Core 1 Gal-Transferase Is Associated with Reduction of TF and Reciprocal Increase of Tn, sialyl-Tn and Core 3 Glycans in Human Colon Cancer Cells," PLoS One, 8(3), e59792, p. 106 (Mar. 25, 2013).

Beatson et al., "The Breast Cancer-Associated Glycoforms of MUC1, MUC1-Tn and sialyl-Tn, Are Expressed in COSMC Wild-Type Cells and Bind the C-Type Leclin MGL", PLoS One 10, e0125994, 21 pages (2015).

Benoit et al., "Synthesis of folate-functionalized RAFT polymers for targeted siRNA delivery Biomacromolecules", 12, pp. 2708-2714 (2011).

Bergfeld et al., "Metabolism of Vertebrate Amino Sugars with N-Glycolyl Groups: Elucidating the Intracellular Fate of the Non-Human Sialic Acid N-Glycolylneuraminic Acid", Journal of Biological Chemistry, 287(34), pp. 28865-28881 (2012).

Bernard et al., "A unique epitope on the CD2 molecule defined by the monoclonal antibody 9-1: epitope-specific modulation of the E-rosette receptor and effects on T-cell functions," Human Immunol., 17, pp. 388-405 (1986).

Berns et al., "The changing view of high-grade serous ovarian cancer", Cancer Res. 72, pp. 2701-2704 (2012).

Bibkova et al., "Enhancing gene targeting with designed zinc finger nucleases", Science, 300(5620), p. 764 (May 2, 2003).

Biocca et al., "Expression and targeting of intracellular antibodies in mammalian cells," EMBO J. 9:101-108, 1990.

Blixt et al. Analysis of Tn antigenicity with a panel of new IgM and IgG1 monoclonal antibodies raised against leukemic cells. Glicobiology 2012, vol. 22, No. 4, pp. 529-542 (2012).

Bork et al., "Increasing the Sialylation of Therapeutic Glycoproteins: The Potential of the Sialic Acid Biosynthetic Pathway", Journal of Pharmaceutical Sciences, 98(10), pp. 3499-3508 (2009).

Bradbury et al., "Beyond natural antibodies: the power of in vitro display technologies", Nat Biotechnol., 29(3), pp. 245-254 (2011).

Braun et a., "Aromatase inhibitors increase the sensitivity of human tumor cells to monocyte-mediated, antibody-: lependenl cellular cytotoxicily", American Journal of Surgery, vol. 190, No. 4, pp. 570-571 (Oct. 1, 2005).

Brinkmann et al., "Phage display of disulfide-stabilized Fv fragments", J Immunol Methods, 182(1), pp. 41-50 (May 11, 1995).

Brinkman-Van Der Linden et al., "Loss of N-Glycolylneuraminic Acid in Human Evolution", J Biol Chem., 275 (12), pp. 8633-8640 (Mar. 24, 2000).

Brinkman-Van Der Linden et al., "New aspects of siglec binding specificities, including the significance of fucosylation and of the sialyl-Tn epitope Sialic acid-binding immunoglobulin superfamily lectins," J Biol Chem., 275(12), pp. 8625-8632 (Mar. 24, 2000).

Brockhausen et al., "Pathways of mucin O-glycosylation in normal and malignant rat colonic epithelial cells reveal a mechanism for cancer-associated Sialyl-Tn antigen expression", Biol Chem., 382(2), pp. 219-232 (Feb. 2001).

Bull et al., "Sialic acids sweeten a tumor's life". Cancer Res, 74(12), pp. 3199-3204 (2014).

Burger et al., "Incorporation of bevacizumab in the primary treatment of ovarian cancer", N Engl J Med, 365, pp. 2473-2483 (2011).

Burgos-Ojeda et al., "Ovarian cancer stem cell markers: prognostic and therapeutic implications," Cancer letters, 322, pp. 1-7 (2012).

Caldas et al., "Humanization of the anti-CD18 antibody 6.7: an unexpected effect of a framework residue in binding to antigen," Mol. Immunol., 39(15), pp. 941-952 (May 2003).

Campbell et al. High-throughput profiling of anti-glycan humoral responses to SIV vaccination and challenge. Plos One, 2013, vol. 8, Issue. 9, pp. 1-12 (2013).

Candefjord et al., "Technologies for localization and diagnosis of prostate cancer", Journal of Medical, Engineering & Technology, 33(8), pp. 585-603 (2009).

Cao et al., "Expression of CD175 (Tn), CD175s (sialosyl-Tn) and CD176 (Thomsen-Friedenreich antigen) on malignant human hematopoietic cells", Int J Cancer., 123(1):89-99 (Jul. 1, 2008).

Cao et al., "Immunodetection of epithelial mucin (MUC1, MUC3) and mucin-associated glycotopes (TF, Tn, and sialosyl-Tn) ialosyl-Tn) in benign and malignant lesions of colonic epithelium: apolar localization corresponds to malignant transformation", Virchows Arch, 431(3), pp. 159-166 (Sep. 1997).

Cao et al., "Thomsen-Friedenreich-related carbohydrate antigens in normal adult human tissues: a systematic and comparative study", Histochemistry and Cell Biology, 106(2), pp. 197-207 (1996).

Carlson et al., "Structures and Immunochemical Properties of Oligosaccharides Isolated from Pig Submaxillary Mucins", Journal of Biological Chemistry, 243(3), pp. 616-626 (1968).

Caron et al., "Intracellular delivery of a Tat-eGFP fusion protein into muscle cells", Mol. Ther., 3(3), pp. 310-318 (2001).

Carr et al. "A Mouse IgG1 Monoclonal Antibody Specific for N-Glycolyl Gm3 Ganglioside Recognized Breast and Melanoma Tumors", Hybridoma, 19(3), pp. 241-247 (2000).

Carrascal et al., "Sialyl Tn-expressing bladder cancer cells induce a tolerogenic phenotype in innate and adaptive immune cells", Molecular Oncology, 8(3), pp. 753-765 (2014).

Carroll, D., "Progress and prospects: zinc-finger nucleases as gene therapy agents", Gene Ther., 15(22), pp. 1463-1468 (Nov. 2008).

Casadesus et al., "A shift from N-glycolyl- to N-acetyl-sialic acid in the GM3 ganglioside impairs tumor development in mouse lymphocytic leukemia cells," Glycoconj J., 30(7), pp. 687-699 (2013).

Casset et al. "A peptide mimetic of an anti-CD4 monoclonal antibody by rational design," Biochem. Biophys. Res. Commun., 307(1), pp. 198-205 (Jul. 18, 2003).

Cathomen et al., "Zinc-finger nucleases: the next generation emerges,". Mol Ther., 16(7), pp. 1200-1207 (Jul. 2008).

Cavadas et al. "Prostate Cancer Prevention Trial and European Randomized Study of Screening for Prostate Cancer Risk Calculators: A Performance Comparison in a Contemporary Screened Cohort", European Urology, 58(4), pp. 551-558(2010).

Yu et al., "Rationalization and Design of the Complementarity Determining Region Sequences in an Antibody-Antigen Recognition Interface," PLoS ONE 7(3): e33340 doi:10.1371/journal.pone. 0033340, Mar. 22, 2012(15 pages).

Steplewski et al., "Biological activity of human-mouse IgGI, IgG2, IgG3, and IgG4 chimeric monoclonal antibodies with antitumor specificity," Proc Natl Acad Sci USA 85: 4852-4856 (1988).

Ju et al., "The Cosme connection to the Tn antigen in cancer", Cancer Biomark, 14, pp. 63-81 (2014).

Ju et al., "Tn and SialylTn antigens, Aberrant O-glycomics as Human Disease Markers", Proteomics Clin Appl, 7 pp. 618-631 (2013).

(56) References Cited

OTHER PUBLICATIONS

Ju, et al., "A unique molecular chaperone Cosme required for activity of the mammalian core β3-galactosyltransferase", Proceedings of the National Academy of Sciences, 99(26), pp. 16613-16618 (2002).

Julien et al., "Expression of Sialyl-Tn antigen in breast cancer cells transfected with the human CMP-Neu5Ac: GalNAc a2,6-sialyltransferase (ST6GalNAc 1) cDNA," Glycoconjugate Journal, 18, pp. 883-893 (2001).

Julien et al., "Sialyl-Tn in Cancer: (How) Did We Miss the Target?", Biomolecules, 2, pp. 435-166 (2012).

Julien et al., "Sialyl-Tn vaccine induces antibody-mediated tumour protection in a relevant murine model", Br J Cancer, 100(11), pp. 1746-1754 (Jun. 2, 2009).

Julien et al., "ST6GalNAc I expression in MDA-MB-231 breast cancer cells greatly modifies their O-glycosylation pattern and enhances their tumourigenicity," Glycobiology, 16, pp. 54-64 (2006).

Julien et al., "Stable expression of sialyl-Tn antigen in T47-D cells induces a decrease of cell adhesion and an increase of cell migration", Breast Cancer Research and Treatment, 90, pp. 77-84 (2005).

Juneja et al., "Large-scale preparation of sialic acid from chalaza and egg-yolk membrane", Carbohydr. Res., vol. 214, pp. 179-186 (1991).

Karim et al., "Is sialic acid in milk food for the brain?" CAB Reviews: Perspectives in Agriculture, Veterinary Science, Nutrition, and Natural Resources, 1 (018), pp. 1-11 (2006).

Karlen et al., "Sialyl-Tn antigen as a marker of colon cancer risk in ulcerative colitis: relation to dysplasia and DNA aneuploidy", Gastroenterology, 115(6), pp. 1395-1404 (1998).

Karsten et al., "What makes cancer stem cell markers different?," SpringerPlus, 2, pp. 301 (2013).

Kasai et al., "Preparation and specificity of avian anti-GM2(NeuGc) ganglioside antiserum", Biochemical and Biophysical Research Communications, Academic Press Inc. Orlando, FL, US, vol. 129, No. 2, pp. 334-341 (Jun. 14, 1985).

Katari et al., "Characterization of the shed form of the human tumor-associated glycoprotein (TAG-72) from serous effusions of patients with different types of carcinomas", Cancer Res. 50, pp. 4885-4890 (1990).

Kawachi et al., "Heterophile Hanganutziu-Deicher Antigen in Ganglioside Fractions of Human Melanoma Tissues", International Archives of Allergy and Immunology, 85(3), pp. 381-383 (1988).

Kawai T et al., "Quantitative determination of N-glycolylneuraminic acid expression in human cancerous tissues and avian lymphoma cell lines as a tumor-associated sialic acid by gas chromatography-mass spectrometry", Cancer Res, vol. 51, pp. 1242-1246 (1991).

Kawano et al., "Molecular Cloning of Cylidine Monophospho-N-Acetylneuraminic Acid Hydroxylase. Regulation of Species- and Tissue-Specific Expression of N-Glycolylneuraminic Acid", Journal of Biological Chemistry, 270(27), pp. 16458-16463 (1995).

Kayser et al., "Biosynthesis of a nonphysiological sialic acid in different rat organs, using N-propanoyl-D-hexosamines as precursors", J Biol. Chem., vol. 267, pp. 16934-16938 (1992).

Kettleborough et al., "Isolation of tumor cell-specific single-chain Fv from immunized mice using phage-antibody libraries and the re-construction of whole antibodies from these antibody fragments", Eur J Immunol, pp. 952-958 (Apr. 24, 1994).

Kilgore et al., "Comparability and monitoring immunogenic N-linked oligosaccharides from recombinant monoclonal antibodies from two different cell lines using HPLC with fluoresence detection and mass spectrometry", Methods Mol Biol., 446, pp. 333-346 (2008).

Kim et al., "Aberrant expression of MUC5AC and MUC6 gastric mucins and sialyl Tn antigen in intraepithelial neoplasms of the pancreas", Gastroenterology, 123(4), pp. 1052-1060 (2002).

Kim et al., "Hybrid restriction enzymes: zinc finger fusions to Fok I cleavage domain", Proc Natl Acad Sci USA, 93(3), pp. 1156-1160 (Feb. 6, 1996).

Kim et al., "Implication of Aberrant Glycosylation in Cancer and Use of Lectin for Cancer Biomarker Discovery", Protein & Peptide Letters, 16(5), pp. 499-507 (2009).

Kim et al., "Perspectives on the significance of altered glycosylation of glycoproteins in cancer", Glycoconjugate Journal, 14(5), pp. 569-576 (1997).

Kinney et al., "The prognostic significance of sialyl-Tn antigen in women treated with breast carcinoma treated with adjuvant chemotherapy," Cancer, 80, pp. 2240-2249 (1997).

Kirkeby et al., "MUC1 and the simple mucin-type antigens: Tn and Sialyl-Tn are differently expressed in salivary gland acini and ducts from the submandibular gland, the vestibular folds, and the soft palate", Archives of Oral Biology, 55(11), pp. 830-841 (Nov. 1, 2010).

Kjeldsen et al., "Preparation and Characterization of Monoclonal Antibodies Directed to the Tumorassociated O-linked Sialosyl-2→6 α-N-Acetylgalactosaminyl (Sialosyl-Tn) Epitope", Cancer Research, 48(8), pp. 2214-2220 (1988).

Klein et al., "New sialic acids from biological sources identified by a comprehensive and sensitive approach: liquid chromatography-electrospray ionization-mass spectrometry (LC-ESI-MS) of SIA quinoxalinones", Glycobiology, vol. 7, pp. 421-432 (1997).

Kobata et al., "Altered glycosylation of proteins produced by malignant cells, and application for the diagnosis and immunotherapy of tumours", Immunology & Cell Biology, 83(4), pp. 429-439 (2005).

Kobayashi et al., "Serum sialyl Tn as an independent predictor of poor prognosis in patients with epithelial ovarian cancer", Journal of Clinical Oncology, 10(1), pp. 95-101 (1992).

Kobayashi et al., Clinical Evaluation of Circulating Serum Sialyl Tn Antigen Levels in Patients with Epithelial Ovarian Cancer, Journal of clinical oncology: official journal of the American Society of Clinical Oncology, 9:983-987, (1991).

Koda et al., "Application of Tyramide Signal Amplification for Detection of N-Glycolylneuraminic Acid in Human Hepatocellular Carcinoma", Int J Clin Oneal, 8(5), pp. 317-321 (2003).

Kohler et al., "Continuous cultures of fused cells secreting antibody of predefined specificity", Nature, 256(5517), pp. 495-497 (Aug. 7, 1975).

Kostelny et al., "Formation of a bispecific antibody by the use of leucine zippers", J Immunol., 148(5), pp. 1547-1553 (Mar. 1, 1992).

Kozbor et al., "A human hybrid myeloma for production of human monoclonal antibodies", J Immunol., 133(6), pp. 3001-3005 (Dec. 1984).

Kozutsumi et al., "Participation of cytochrome b5 in CMP-N-acetylneuraminic acid hydroxylation in mouse liver cytosol", J Biochem., vol. 108, pp. 704-706 (1990).

Krishn et al., "Mucins and associated O-glycans based immunoprofile for stratification of colorectal polyps: clinical implication for improved colon surveillance", Oncolarget vol. 8, No. 4 pp. 7025-7038 (2017).

Kulkarni-Datar et al., "Ovarian tumor initiating cell populations persist following paclitaxel and carboplatin chemotherapy treatment in vivo", Cancer Lett, 339, pp. 237-246 (2013).

Lee et al., "Production of N-acetylneuraminic acid from N-acetylglucosamine and pyruvate using recombinant human renin binding protein and sialic acid aldolase in one pot", Enzyme and Microbial Technology, 35(2-3), pp. 121-125 (2004).

Lefranc et al., "IMGT, the international ImMunoGeneTics information system: a standardized approach for immunogenetics and immunoinformatics," Immunome Res. 1:3 11 pages, (2005).

Leth-Larsen et al."Functional heterogeneity within the CD44 high human breast cancer stem cell-like compartment reveals a gene signature predictive of distant metastasis," Molecular medicine, 18, pp. 1109-1121 (2012).

Lewartowska Aleksandra et al., "Ganglioside reactive antibodies of IgG and IgM class in sera of patients with differentiated thyroid cancer", Immunology Letters, 80(2), pp. 129-132 (Feb. 1, 2002).

Li et al., "Pancreatic Cancer Serum Detection Using a Lectin/Glyco-Antibody Array Method", Journal of Proteome Research, 8(2), pp. 483-492 (2008).

Li et al., "Prognostic value of cancer stem cell marker CD133 expression in pancreatic ductal adenocarcinoma (PDAC): a systematic review and meta-analysis", Int J Clin Exp Pathol, 8, pp. 12084-12092 (2015).

Liang et al., "The hypoxic microenvironment upgrades stem-like properties of ovarian cancer cells," BMC Cancer, 12, p. 201 (2012).

(56) References Cited

OTHER PUBLICATIONS

Liu et al., "Integrative disease classification based on cross-platform microarray data", BMC Bioinformatics, 10 Suppl 1, S25 8 pages (2009).
Liu et al., "PARP inhibitors in ovarian cancer: current status and future promise", Gynecol Oncol, 133, pp. 362-369 (2014).
Lobo et al., "The biology of cancer stem cells," 23, pp. 675-699 (2007).
Prehn et al., "The flip side of immune surveillance: immune dependency", Immunological Reviews, 222(1), pp. 341-356 (2008).
Prendergast et al., "Novel anti-Sialyl-Tn monoclonal antibodies and antibody-drig conjugates demonstrate umor specificity and anti-tumor activity", MABS, pp. 1-13 (Feb. 22, 2017).
Proba et al., "Antibody scFv fragments without disulfide bonds made by molecular evolution," J. Mol. Biol. 275, pp. 245-253 (1998).
Rabu et al., "Glycans as targets for therapeutic antitumor antibodies," Future oncology, 8, pp. 943-960 (2012).
Raedle et al., "Clinical evaluation of autoantibodies to p53 protein in patients with chronic liver disease and hepatocellular carcinoma", European Journal of Cancer, 34(8), pp. 1198-1203 (1998).
Ransohoff, D. F., "Rules of evidence for cancer molecular-marker discovery and validation", Nature Reviews Cancer, 4(4), pp. 309-314 (2004).
Reddish et al., "Specificities of anti-sialyl-Tn and anti-Tn monoclonal antibodies generated using novel clustered synthetic glycopeptide epitopes", Glycoconj. J., 14, pp. 549-560 (1997).
Reis et al., "Intestinal metaplasia of human stomach displays distinct patterns of mucin (MUC1, MUC2, MUC5AC, and MUC6) expression", Cancer Res., 59(5), pp. 1003-1007 (Mar. 1, 1999).
Rho et al., "Discovery of sialyl Lewis A and Lewis X modified protein cancer biomarkers using high density antibody array",. J Proteomics; 96:291-9 (2014).
Rho et al., "High-throughput screening for native autoantigen-autoantibody complexes using antibody microarrays", J Proteome Res. May 3, 2013;12(5):2311-20 (2013).
Ricardo et al., "Detection of glyco-mucin profiles improves specificity of MUC16 and MUC1 biomarkers in ovarian serous tumours", Mol Oncol. 9(2), 503-12 (2015).
Ricci et al., "ALDH enzymatic activity and CD133 positivity and response to chemotherapy in ovarian cancer patients", Am J Cancer Res, 3, pp. 221-229 (2013).
Richardson et al., "Intrabody-mediated knockout of the high-affinity IL-2 receptor in primary human T cells using a bicistronic lentivirus vector," Gene Ther., 5, pp. 635-644 (1998).
Riechmann et al., "Reshaping human antibodies for therapy", Nature, 332(6162), pp. 323-327 (Mar. 24, 1988).
Riethmuller, "Symmetry breaking: bispecific antibodies, the beginnings, and 50 years on," G., Cancer Immunity. 12, pp. 12-18 (2012).
Roguska et al., "Humanization of murine monoclonal antibodies through variable domain resurfacing", Proc Natl Acad Sci USA, 91(3), pp. 969-973 (Feb. 1, 1994).
Rozema et al., "Dynamic PolyConjugates for targeted in vivo delivery of siRNA to hepatocytes", Proc Natl Acad Sci USA, 104, pp. 12982-12887 (2007).
Sing et al., "ROCR: visualizing classifier performance in R", Bioinformatics, 21(20), pp. 3940-3941 (2005).
Rudikoff et al., "Single amino acid substitution altering antigen-binding specificity," Proc. Natl. Acad. Sci. USA, 79, pp. 1979-1983 (1982).
Sabbatini, P., "Consolidation therapy in ovarian cancer: a clinical update", Int J Gynecol Cancer, 19 Suppl 2, pp. S35-S39 (2009).
Saber et al., "An FDA oncology analysis of antibody-drug conjugates", Regul. Toxicol. Pharmacol. 71, pp. 444-452 (2015).
Saldova et al., "Glycosylation changes on serum glycoproteins in ovarian cancer may contribute to disease pathogenesis". Dis Markers 25, pp. 219-232 (2008).
Sato et al., "Carbohydrates, Lipids, and Other Natural Products: Identification of Oligo-N-Glycolylneuraminic Acid Residues in Mammal-derived Glycoprotiens by a Newly Developed Immunochemical Reagent and Biochemical Methods", J Biol Chem., 273, pp. 2575-2582 (1998).
Sato et al., "Frequent occurrence of pre-existing alpha 2->8-linked disialic and oligosialic acids with chain lengths up to7 Sia residues in mammalian brain glycoproteins. Prevalence revealed by highly sensitive chemical methods and anti-di-, oligo-, and poly-Sia antibodies specific for defined chain lengths". J Bioi Chem, vol. 276, pp. 15422-15431 (2000).
Singer et al., "Targeting BACE1 with siRNAs ameliorates Alzheimer disease neuropathology in a transgenic model", Nature Neuroscience, 8(10), pp. 1343-1349 (2005).
Schaefer et al., "Immunoglobulin domain crossover as a generic approach for the production of bispecific IgG antibodies," PNAS., 108(27); pp. 11187-11192 (2011).
Schauer et al., "Low incidence ofN-glycolylneuraminic acid in birds and reptiles and its absence in the platypus", Carbohydrate Research, 344(12), pp. 1494-1500 (2009).
Schauer, et al., "Chemistry, metabolism, and biological functions of sialic acids," R. Adv. Carbohydr. Chem. Biochem., vol. 40, pp. 131-234 (1982).
Schlom et al., "Tumor targeting with monoclonal antibody B72.3", Int. J. Rad. Appl. Instrum. B., 16, pp. 137-142 (1989).
Schlom et al., "Tumor targeting with monoclonal antibody B72.3: experimental and clinical results", Cancer Treat. Res., 51, pp. 313-335 (1990).
Schofield et al., "Application of phage display to high throughput antibody generation and characterization," Genome Biol. 8, R254, 18 pages (2007).
Schroder et al., "Screening and Prostate-Cancer Mortality in a Randomized European Study", New England Journal of Medicine, 360(13), pp. 1320-1328 (2009).
Sjoberg et al., "Natural Ligands of the B Cell Adhesion Molecule CD22j3 can be Masked by 9-0-Acetylalion of Sialic Acids", The Journal of Cell Biology; 126(2), pp. 549-562 (Jul. 1994).
Schultz et al., Regulation of the metastatic cell phenotype by sialylated glycans. Cancer metastasis reviews, 31:501-518(2012).
Schwarz et al., "A new kind of carbohydrate array, its use for profiling antiglycan antibodies, and the discovery of a novel human cellulose-binding antibody", Glycobiology, Oxford Univ. Press, US, vol. 13, No. 11 pp. 749-754 (Nov. 1, 2003).
Schwarzkopf et al., "Sialylation Is Essential for Early Development in Mice", Proc Natl Acad Sci USA, 99(8), pp. 5267-5270 (2002).
Second Examiner's Report dated Mar. 8, 2019 in corresponding Canadian Patent Application No. 2,967,595 (4 pages).
Sedlacek et al., "Neuraminidase and tumor immunotherapy", Klin Wochenschr., 55(5), pp. 199-214. (Mar. 1, 1977).
Sen et al., "Immunization of aged mice with a pneumococcal conjugate vaccine combined with an unmethylated CpG-containing oligodeoxynucleotide restores defective immunoglobulin G antipolysaccharide responses and specific CD4+-T-cell priming to young adult levels," Infection Immunity, 74(3), pp. 2177-2186 (2006).
Sewell et al., "The ST6GalNAc-I Sialyltransferase Localizes throughout the Golgi and Is Responsible for the Synthesis of the Tumor-associated Sialyl-Tn 0-Glycan in Human Breast Cancer", Journal of Biological Chemistry, 281 (6), pp. 3586-3594 (2006).
Shaw et al., "CMP-N-acetylneuraminic acid hydroxylase from mouse liver and pig submandibular glands", European Journal of Biochemistry, 219(3), pp. 1001-1011 (1994).
Shaw et al., "The biosynthesis of N-glycoloylneuraminic acid occurs by hydroxylation of the CMP-glycoside of N-acetylneuraminic acid," Biological Chemistry Hoppe-Seyler, 369(6), pp. 477-486 (1988).
Sherwood et al., "Controlled antibody delivery systems", Nature Biotechnology, 10, pp. 1446-1449 (1992).
Shi et al., "Sialic acid 9-O-acetylation on murine erythroleukemia cells affects complement activation, binding to I-type lectins, and tissue homing," J of Biol Chem., 271(49), pp. 31526-31532 (1996).
Shu et al., "Secretion of a single-gene-encoded immunoglobulin from myeloma cells", Proc Natl Acad Sci USA., 90 (17), pp. 7995-7999 (Sep. 1, 1993).
Siegel et al., Cancer statistics, 2013. CA: a cancer journal for clinicians 63, pp. 11-30 (2013).

(56) References Cited

OTHER PUBLICATIONS

Siegwart et al., "Combinatorial synthesis of chemically diverse core-shell nanoparticles for intracellular delivery", Proc Nall Acad Sci USA 108, pp. 12996-13001 (2011).
Skerra et al., "Assembly of a functional immunoglobulin Fv fragment in *Escherichia coli*", Science., 240(4855), pp. 1038-1041 (May 20, 1988).
Slovin et al., "Carbohydrate vaccines as immunotherapy for cancer", Immunology & Cell Biology, 83(4), pp. 418-428 (2005).
Song et al., "A Sialylated Glycan Microarray Reveals Novel Interactions of Modified Sialic Acids with Proteins and Viruses", Journal of Biological Chemistry, vol. 286, No. 36 pp. 31610-31622 (Jul. 12, 2011).
Sonnenburg et al., "Characterization of the Acid Stability of Glycosidically Linked Neuraminic Acid", The Journal of Biological Chemistry, 277(20), pp. 17502-17510 (May 17, 2002).
Soussi, T., "p53 Antibodies in the Sera of Patients with Various Types of Cancer: A Review", Cancer Research, 60 (7), pp. 1777-1788 (2000).
Srivastava et al., "Biomarkers in Cancer Screening: A Public Health Perspective", The Journal of Nutrition, 132(8), pp. 2471S-2475S (2002).
Stacker et al., "A new breast carcinoma antigen defined by a monoclonal antibody", Journal of the National Cancer Institute, 75(5), pp. 801-811 (1985).
Stancoviski et al., Proceeding of the National Academy of Science USA, 88, pp. 8691-8695 (1991).
Stanley and Ioffe, "Glycosyltransferase Mutants: Key to New Insights in Glycobiology." Faseb J, 9(14):1436-1444 (1995).
Steentoft, C. et al., Mining the O-glycoproteome using zinc-finger nuclease-glycoengineered SimpleCell lines. Nat Methods. Oct. 9, 2011;8(11):977-82.
Steinberger et al., "Generation and characterization of a recombinant human CCR5-specific antibody. A phage display approach for rabbit antibody humanization," Proc. Natl. Acad. Sci. USA 97:805-810 (2000).
Strohl, W.R., "Therapeutic Antibody Engineering", Woodhead Publishing, Philadelphia PA, Ch. 3, pp. 47-54 (2012).
Studnicka et al., "Human-engineered monoclonal antibodies retain full specific binding activity by preserving non-CDR complementarity-modulating residues", Protein Eng., 7(6), pp. 805-814 (Jun. 1994).
Takahashi et al., "Immunoglobulin G3 Monoclonal Antibody Directed to Tn Antigen(Tumor-associated alpha-N-ACETYLGALACTASAMINYL Epilope) That Does Not Crosss-React with Blood Group A Antigen", Cancer Res., 48, pp. 4361-4367 (1988).
Takematsu et al., "Reaction Mechanism Underlying CMP- N -Acetylneuraminic Acid Hydroxylation in Mouse Liver Formation of a Ternary Complex of Cytochrome b5, CMP-N-Acetylneuraminic Acid, and a Hydroxylation Enzyme", J. Biochem. (Tokyo), 115(3), pp. 381-386 (1994).
Takeshita et al., "CMC-544 (inotuzumab ozogamicin), an anti-CD22 immuno-conjugate of calicheamicin, alters the levels of target molecules of malignant B-cells," Leukemia, 23(7), pp. 1329-1336 (Jul. 2009).
Tamura J. et al. "RNAi-mediated gene silencing of ST6GalNAc I suppresses the metastatic potential in gastric cancer cells", Gastric Cancer, 19(1), pp. 85-97 (Dec. 23, 2014).
Tan et al., "Serum autoantibodies as biomarkers for early cancer detection", FEBS Journal, 276(23), pp. 6880-6904 (2009).
Tangvoranuntakul et al., "Human uptake and incorporation of an immunogenic nonhuman dietary sialic acid", Proceedings of the National Academy of Sciences, 100(21), pp. 12045-12050 (2003).
Taylor et al., "Novel mechanism for the generation of human xeno-autoantibodies against the nonhuman sialic acid N-glycolylneuraminic acid", The Journal of Experimental Medicine, 207(8), pp. 1637-1646 (2010).
Thapa et al., The Importance of CD44 as a Stem Cell Biomarker and Therapeutic Target in Cancer. Stem Cells Int., 2087204, 15 pages (2016).

Thompson et al., "Operating characteristics of prostate-specific antigen in men with an initial psa level of 3.0 ng/ml or lower", JAMA: The Journal of the American Medical Association, 294(1), pp. 66-70 (2005).
Tiller et al., "A fully synthetic human Fab antibody library based on fixed VH/VL framework pairings with favorable biophysical properties", mAbs, 5(3), pp. 445-470 (2013).
Tiscornia et al., "Production and purification of lentiviral vectors", Nature Protocols, 1 (1), pp. 241-245 (2006).
Toda et al., "Down-modulation of B cell signal transduction by ligation of mucins to CD22", Biochem Biophys Res Commun., 372(1), pp. 45-50 (2008).
Townsend et al., "High-frequency modification of plant genes using engineered zinc-finger nucleases", Nature.; 459 (7245), pp. 442-445 (May 21, 2009).
Traving et al., "Structure, Function and Metabolism of Sialic Acids." Cell Mol Life Sci, 54(12), pp. 1330-1349 (1998).
Tso et al., "Formation and transport of chylomicrons by enterocytes to the lymphatics," American Journal of Physiology, 250(6 Pt 1), G715-726 (1896).
Tutt, A. et al., Trispecific F(ab')3 derivatives that use cooperative signaling via the TCR/CD3 complex and CD2 to activate and redirect resting cytotoxic T cells. J Immunol. Jul. 1, 1991;147(1):60-69.
Tzanakakis, et al., "Determination and Distribution of N-Acetyl- and N-Glycolylneuraminic Acids in Culture Media and Cell-Associated Glycoconjugates from Human Malignant Mesothelioma and Adenocarcinoma Cells." Biomed Chromatogr, 20(5):434-439 (2006).
Uygur-Bayramicli, et al, "Type 2 diabetes mellitus and CA 19-9 levels", World Journal of Gastroenterology, 13 (40), pp. 5357-5359 (2007).
Vacchelli et al., Trial watch: Tumor-targeting monoclonal antibodies for oncological indications. Oncoimmunology 4, e985940 16 pages (2015).
Vajdos et al., "Comprehensive functional maps of the antigen-binding site of an anti-ErbB2 antibody obtained with shotgun scanning mutagenesis," J Mol. Biol., 320(2), pp. 415-428 (Jul. 5, 2002).
Vamecq et al., Studies on the metabolism of glycolyl-CoA, Biochem. Cell Biol., vol. 68, pp. 846-851 (1990).
Vamecq et al., "Subcellular distribution of glycolyltransferases in rodent liver and their significance in special reference to the synthesis of N-glycolyneuraminic acid", J Biochem, vol. 111, pp. 579-583 (1992).
Van Leeuwen, et al., "Prostate cancer mortality in screen and clinically detected prostate cancer: Estimating the screening benefit", European Journal of Cancer, 46(2),pp. 377-383 (2010).
Van Vliet et al., " I he C-Type Lectin Macrophage Galactose-Type Lectin Impedes Migration of Immature APCs", The Journal of Immunology, 181(5), pp. 3148-3155 (2008).
Van Vliet, SJ, "Novel insights into MGL-glycan interactions in the immune system", Thesis performed at the department of Molecular Cell Biology and Immunology of the VU University Medical Center, p. 1-232 (2007).
Varki et al., "Biomedical differences between human and nonhuman hominids: potential roles for uniquely human aspects of sialic acid biology", Annu Rev Pathol., 6, pp. 365-393 (2011).
Varki et al., "Glycosylation Changes in Cancer", Essentials of Glycobiology, Ch. 44, pp. 617-632 (2009).
Varki et al., "The release and purification of sialic acids from glycoconjugates: methods to minimize the loss and migration of O-acetyl groups", Anal. Biochem., vol. 137, pp. 236-247 (1984).
Varki et al., in Essentials of Glycobiology (Varki, A., et al., Eds.), Ch. 14, pp. 199-218, Cold Spring Harbor Laboratory Press, Cold Spring Harbor, NY (2009).
Varki, "Sialic Acids in Human Health and Disease," Trends Mol Med, 14(8), pp. 351-360 (2008).
Varki, A., "Glycan-based interactions involving vertebrate sialic-acid-recognizing proteins", Nature, 446, pp. 1023-1029 (2007).
Varki, A., "Loss of N-Glycolylneuraminic Acid in Humans: Mechanisms, Consequences, and Implications for Hominid Evolution", Yearbook of Physical Anthropology, 44, pp. 54-69 (2001).

(56) References Cited

OTHER PUBLICATIONS

Varki, A., "Multiple changes in sialic acid biology during human evolution", Glycoconjugate Journal, 26(3), pp. 231-245 (2009).
Varki, A., "N-glycolylneuraminic acid deficiency in humans", Biochimie, 83(7), pp. 615-622 (2001).
Varki, A., "Sialic acids such as ligands in recognition phenomena", The FASEB Journal, vol. 111, pp. 248-255 (Mar. 1997).
Varki, A., "Uniquely human evolution of sialic acid genetics and biology", Proceedings of the National Academy of Sciences, 107(Supplement 2), pp. 8939-8946 (2010).
Vazquez et al., "Generation of a murine monoclonal antibody specific for N-glycolylneuraminic acid-containing gangliosides that also recognizes sulfated glycolipids", HYBRIDOMA, vol. 14, pp. 551-556 (1995).
Di et al., "Multiple drug resistance due to resistance to stem cells and stem cell treatment progress in cancer (Review)", Exp Ther Med, 9, pp. 289-293 (2015).
Diaz et al., "Immune responses in breast cancer patients immunized with an anti-idiotype antibody mimicking NeuGc-containing gangliosides", Clinical Immunology 107(2), pp. 80-89 (2003).
Diaz et al., "Sensitive and Specific Detection of the Non-Human Sialic Acid N-Glycolylneuraminic Acid in Human Tissues and Biotherapeutic Products", Public Library of Science ONE, 4(1), pp. E4241-1-E4241-10 (2009).
Doyon et al., "Heritable targeted gene disruption in zebrafish using designed zinc-finger nucleases" Nat Biotechnol., 26(6), pp. 702-708 (Jun. 2008).
Drake et al., "Sweetening the Pot: Adding Glycosylation to the Biomarker Discovery Equation", Clinical Chemistry, 56 (2), pp. 223-236 (2010).
Du et al., "Metabolic glycoengineering: Sialic acid and beyond", Glycobiology, 19(12), pp. 1382-1401 (2009).
Dube, et al., "Glycans in cancer and inflammation—potential for therapeutics and diagnostics", Nature Reviews Drug Discovery, 4(6), pp. 477-488 (2005).
Eckhardt et al., "The Complete cDNA Sequence and Structural Polymorphism of the Polypeptide Chain of Porcine Submaxillary Mucin", Journal of Biological Chemistry, 272(52), pp. 33204-33210 (1997).
Edwards et al., "The remarkable flexibility of the human antibody repertoire; isolation of over one thousand different antibodies to a single protein, BLyS," JMB. 334, pp. 103-118 (2003).
El-Andaloussi et al., "Cell-penetrating peptides: mechanisms and applications", Curr. Pharm. Des. 11(28), pp. 3597-3611 (2003).
Engelmann et al., "MCF7 side population cells with characteristics of cancer stem/progenitor cells express the tumor antigen MUC1," Cancer research, 68, pp. 2419-2426 (2008).
Eppstein et al., "Biological activity of liposome-encapsulated murine interferon gamma is mediated by a cell membrane receptor", Proc Nall Acad Sci USA, 82(11), pp. 3688-3692 (Jun. 1985).
European Search Report in related EP Application No. EP 13 18 4707, dated Jun. 2, 2014 (13 pages).
Extended European Search Report dated May 17, 2017, received in EP Application No. 14852277.4 (12 pages).
Extended European Search Report in related EP Application No. EP 11 73 3477, dated Jun. 25, 2013 (12 pages).
Extended European Search Report dated Aug. 16, 2018 in corresponding European Patent No. 15859152.9 (22 pages).
Extended European Search Report dated Jul. 11, 2018 in correspondence European Patent No. 15848503.7 (14 pages).
Extended European Search Report dated Jul. 17, 2019 in corresponding European Patent Application No. 16865044.8 (10 pages).
Fawcett, T., "ROC Graphs: Notes and Practical Considerations for Data Mining Researchers", Intelligent Enterprise Technologies Laboratory, (HP Laboratories Palo Alto), pp. 1-27 (2004).
Federici et al., "Selection of carbohydrate antigens in human epithelial ovarian cancers as targets for immunotherapy: serous and mucinous tumors exhibit distinctive patterns of expression", Int J Cancer, 81(2), pp. 193-198 (1999).

Ferreira et al., "Overexpression of tumour-associated carbohydrate antigen sialyl-Tn in advanced bladder tumours," Molecular oncology, 7, pp. 719-731 (2013).
Ferris et al., "Tumor Antigen-Targeted, Monoclonal Antibody-Based Immunotherapy: Clinical Response, Cellular Immunity, and Immunoescape", Journal of Clinical Oncology, 28(28), pp. 4390-4399 (2010).
Finn, O.J., "Cancer Immunology", New England Journal of Medicine, 358(25), pp. 2704-2715 (2008).
Finney et al., "Activation of resting human primary T cells with chimeric receptors: costimulation from CD28, inducible costimulator, CD134, and CD137 in series with signals from the TCR zeta chain," J. Immunology, 172, pp. 104-113 (2004).
First Examiner's Report dated Feb. 19, 2018 in Canadian Patent Application No. 2,967,595 (3 pages).
Foster et al., "Ovarian cancer stem cells: working towards the root of stemness," Cancer letters, 338, pp. 147-157 (2013).
Fujii, Y. et al., "Specificities of human heterophilic Hanganutziu and Deicher (H-D) antibodies and avian antisera against H-D antigen-active glycosphingolipids", Mol Immunol., vol. 19, pp. 87-94 (1982).
Furukawa et al., "Analysis of the expression of N-glycolylneuraminic acid-containing gangliosides in cells and tissues using two human monoclonal antibodies", J Biol Chem., vol. 263, pp. 18507-18512 (1988).
Fuster et al., "The sweet and sour of cancer: glycans as novel therapeutic targets", Nat Rev Cancer., 5(7), pp. 526-542 (Jul. 2005).
Gao et al., "High-throughput screening using patient-derived tumor xenografls to predict clinical trial drug esponse", Nat Med. vol 21, No. 11, pp. 1318-1328 (2015).
Geurts et al., "Knockout rats via embryo microinjection of zinc-finger nucleases", Science, 325(5939), p. 433 (Jul. 24, 2009).
Ghaderi et al., "Implications of the presence of N-glycolylneuraminic acid in recombinant therapeutic glycoproteins", Nature Biotechnology, 28(8), pp. 863-867 (2010).
Gill et al., "Initiation of GalNAc-type O-glycosylation in the endoplasmic reticulum promotes cancer cell invasiveness", Proceedings of the National Academy of Sciences of the United States of America, 110, pp. E3152-E3161 (2013).
Gillies et al., "High-level expression of chimeric antibodies using adapted cDNA variable region cassettes", J Immunol Methods., 125(1-2), pp. 191-202 (Dec. 20, 1989).
Giusti et al., "Somatic diversification of S107 from an antiphosphocholine to an anti-DNA autoantibody is due to a single base change in its heavy chain variable region," Proc. Natl. Acad. Sci. USA, 84(9), pp. 2926-2930 (May 1987).
Glavey, SV., "The cancer glycome: carbohydrates as mediators of metastasis", Blood Rev., 29(4), pp. 269-279 (2015).
Goodman, M., "The genomic record of Humankind's evolutionary roots", Am. J. Hum. Genet., vol. 64, pp. 31-39 (1999).
Graille et al., "Crystal structure of a *Staphylococcus aureus* protein A domain complexed with the Fab fragment of a human IgM antibody: Structural basis for recognition of B-cell receptors and superantigen activity", PNAS, 97(10), pp. 5399-5404 (2000).
Greene et al., "Prostate Specific Antigen Best Practice Statement: 2009 Update", The Journal of Urology, 182(5), pp. 2232-2241 (2009).
Gupta et al., "Cancer stem cells: mirage or reality?," Nature medicine, 15, pp. 1010-1012 (2009).
Gupta et al., "Role of CA125 in predicting ovarian cancer survival—a review of the epidemiological literature", Journal of Ovarian Research, 2(1), p. 13 (2009).
Gussow et al., "Humanization of monoclonal antibodies," Methods in Enzymology, 203, pp. 99-121 (1991).
Hakomori, S., "Tumor-associated carbohydrate antigens defining tumor malignancy: basis for development of anti-cancer vaccines", Adv Exp Med Biol 491, pp. 369-402 (2001).
Hamilton et al., "Characterization of a human ovarian carcinoma cell line (NIH:OVCAR-3) with androgen and estrogen receptors," Cancer Res., 43, pp. 5379-5389 (1983).
Hara et al. "Highly sensitive determination of N-acetyl- and N-glycolylneuraminic acids in human serum and urine and rat

(56) References Cited

OTHER PUBLICATIONS serum by reversed-phase liquid chromatography with fluorescence detection", Journal of Chromatography, A 377, pp. 111-119 (1986).
Hassanzadeh et al., "The regulated expression of an intrabody produces a mutant phenotype in *Drosophila*," FEBS Lett., 437, pp. 81-86 (1998).
Hauselmann, I., "Altered Tumor-Cell Glycosylation Promotes Metastasis", Front. Oncol., 4, p. 28 (2014).
Hawkins, D. M., "The Problem of Overfitting", Journal of Chemical Information and Computer Sciences, 44(1), pp. 1-12 (2003).
Hayakawa et al., "Alu-mediated inactivation of the human CMP-N-acetylneuraminic acid hydroxylase gene", Proceedings of the National Academy of Sciences, 98(20), pp. 11399-11404 (2001).
Hedlund et al., "Evidence for a human-specific mechanism for diet and antibody-mediated inflammation in carcinoma progression", Proceedings of the National Academy of Sciences, 105(48), pp. 18936-18941 (2008).
Cazet et al., "Tumour-associated carbohydrate antigens in breast cancer," Breast cancer research: BCR, 12, p. 204 (2010).
Ceccaldi et al., "A unique subset of epithelial ovarian cancers with platinum sensitivity and PARP inhibitor resistance", Cancer Res; 75, pp. 628-634 (2015).
Chang et al., "Loop-sequence features and stability determinants in antibody variable domains by high-throughput experiments," Structure. 22(1), pp. 9-21 (Jan. 7, 2014).
Chao et al., "Isolating and engineering human antibodies using yeast surface display", Nat Protoc., 1(2), pp. 755-768 (2006).
Cheever et al., "The prioritization of cancer antigens: a national cancer institute pilot project for the acceleration of translational research", Clin Cancer Res., 15(17), pp. 5323-5337 (Sep. 1, 2009).
Chen et al., "Advances in the biology and chemistry of sialic acids", ACS Chem Biol., 5(2), pp. 163-176 (Feb. 19, 2010).
Chen et al., "Combined intra- and extracellular immunization against human immunodeficiency virus type 1 infection with a human anti-gp120 antibody," Proc. Natl. Acad. Sci USA, 91, pp. 5932-5936 (1994).
Chen et al., "Microarray Glycoprofiling of CA125 improves differential diagnosis of ovarian cancer," Journal of proteome research, 12, pp. 1408-1418 (2013).
Chenu et al., "Reduction of Cmp-N-Acetylneuraminic Acid Hydroxylase Activity in Engineered Chinese Hamster Ovary Cells Using an Antisense RNA Strategy", Biochim Biophys Acta, 1622(2), pp. 133-144 (2003).
Chien et al., "Significant structural and functional change of an antigen-binding site by a distant amino acid substitution: proposal of a structural mechanism, "Proc. Natl. Acad Sci. USA , 86(14), pp. 5532-5536 (Jul. 1989).
Choi et al., Platinum and PARP Inhibitor Resistance Due to Overexpression of MicroRNA-622 in BRCA1-Mutant Ovarian Cancer Cell Rep; 14, pp. 429-439 (2016).
Cholleti et al., "Automated Motif Discovery from Glycan Array Data", OMICS a Journal of Integrative Biology, 16 (10) pp. 497-512 (2012).
Chothia et al., "Canonical structures for the hypervariable regions of immunoglobulins," JJ Mol Biol.;196(4):901-17 (Aug. 20, 1987).
Chothia et al., "Conformations of immunoglobulin hypervariable regions," Nature 342(6252), pp. 877-883 (1989).
Chothia et al., "Structural repertoire of the human VH segments", J Mol Biol., 227(3), pp. 799-817 (Oct. 5, 1992).
Chou et al., "Inactivation of Cmp-N-Acetylneuraminic Acid Hydroxylase Occurred Prior to Brain Expansion During Human Evolution", Proc Nall Acad Sci USA, 99(18), pp. 11736-11741 (2002).
Chou et al., "A Mutation in Human Cmp-Sialic Acid Hydroxylase Occurred after the Homo-Pan Divergence", Proceedings of the National Academy of Sciences, 95(20), pp. 11751-11756 (1998).
Christiansen et al., "Cell surface protein glycosylation in cancer", Proteomics 14, pp. 525-546 (2014).
Chu et al., "GpG Oligodeoxynucleotides Act as Adjuvants for Pneumococcal Polysaccharide-Protein Conjugate Vaccines and Enhance Antipolysaccharide Immunoglobulin G2a (IgG2a) and IgG3 Antibodies", Infection Immunity, 68 (3), pp. 1450-1456 (2000).
Chung et al., "Cetuximab-induced anaphylaxis and IgE specific for galactose-alpha-1,3-galactose", N Engl J Med., 358(11); 1109-1117 (Mar. 13, 2008).
Cohen et al., "Characterization of a new intrabody directed against the N-terminal region of human p53", Oncogene 17, pp. 2445-2456 (1998).
Cohen et al., "In 2014, can we do better than CA125 in the early detection of ovarian cancer?", World J. Biol. Chem. 5, pp. 286-300 (2014).
Colby et al., "Potent inhibition of huntingtin aggregation and cytotoxicity by a disulfide bond-free single-domain intracellular antibody", Proc Natl Acad. Sci U.S.A., 101, pp. 17616-17621 (2004).
Colcher et al., "A spectrum of monoclonal antibodies reactive with human mammary tumor cells", Proc. Natl. Acad Sci USA, 78(5), pp. 3199-3203 (1981).
Coleman R.L., "Ovarian cancer in 2015: Insights into strategies for optimizing ovarian cancer care", Nat Rev Clin Oncol. 13(2), pp. 71-72 (2016).
Collins et al., "Conversion of cellular sialic acid Expression from N-acetyl- to N-glycolylneuraminic acid using a synthetic precursor, N-glycolylmannosamine pentaacetate: inhibition of myelin-associated glycoprotein binding to neural cells", Glycobiology, 10(1), pp. 11-20 (2000).
Conze et al., "MUC2 mucin is a major carrier of the cancer-associated sialyl-Tn antigen in intestinal metaplasia and gastric carcinomas", Glycobiology, 20(2), pp. 199-206 (2010).
Cooke et al., "Evolution of platinum resistance in high-grade serous ovarian cancer", Lancet Oncol, 12, pp. 1169-1174 (2011).
Cronican et al., "Potent delivery of functional proteins into Mammalian cells in vitro and in vivo using a supercharged protein", ACS Chem. Biol. 5, pp. 747-752 (2010).
Curley et al., "CD133 expression defines a tumor initiating cell population in primary human ovarian cancer", Stem Cells, 27, pp. 2875-2883 (2009).
Curley et al., "Evidence for cancer stem cells contributing to the pathogenesis of ovarian cancer", Front Biosci (Landmark Ed), 16, pp. 368-392 (2011).
Curry et al., "The use of a novel MUC1 antibody to identify cancer stem cells and circulating MUC1 in mice and patients with pancreatic cancer", J Surg Oneal, 107, pp. 713-722 (2013).
Dai et al., "Targeted Disruption of the Alpha1,3-Galactosyltransferase Gene in Cloned Pigs", Nat Biotechnol, 20(3), pp. 251-255 (2002).
Daugherty et al., "Formulation and delivery issues for monoclonal antibody therapeutics", Adv Drug Deliv Rev., 58 (5-6), pp. 686-706 (Aug. 7, 2006).
Davidson et al., "Expression of carbohydrate antigens in advanced-stage ovarian carcinomas and their metastases—A clinicopathologic study", Gynecol Oncol, 77, pp. 35-43 (2000).
Davis et al., "Evidence of RNAi in humans from systemically administered siRNA via targeted nanoparticles", Nature, 464, pp. 1067-1070 (2010).
Davis, "The first targeted delivery of siRNA in humans via a self-assembling, cyclodextrin polymer-based nanoparticle: from concept to clinic", Mol Pharm., 6, pp. 659-668 (2009).
De Goeij et al., New developments for antibody-drug conjugate-based therapeutic approaches. Curr Opin Immunol, 40, pp. 14-23 (2016).
De Leon et al. "Differential influence of the tumour-specific non-human sialic acid containing GM3 ganglioside on CD4+CD25- effector and naturally occurring CD4+CD25+ regulatory T cells function", International Immunology, 20(4), pp. 591-600 (2008).
De Pascalis et al.,"Grafting of "abbreviated" complementarity-determining regions containing specificity-determining residues essential for ligand contact to engineer a less immunogenic humanized monoclonal antibody," J. Immunol., 169(6), pp. 3076-3084 (2002).
De Visser et al. "De novo carcinogenesis promoted by chronic inflammation is B lymphocyte dependent", Cancer Cell, 7(5), pp. 411-423 (2005).
Dearnley et al., "Consolidation therapy in ovarian cancer: where do we stand?", Curr Opin Obstet Gynecol, 18, pp. 3-7 (2006).

(56) References Cited

OTHER PUBLICATIONS

Der Maur et al., "Direct in vivo screening of intrabody libraries constructed on a highly stable single-chain framework," J. Biol. Chem., 277, pp. 45075-45085 (2002).
Deshayes et al., "Cell-penetrating peptides: tools for intracellular delivery of therapeutics", Cell. Mol. Life Sci., 62 (16), pp. 1839-1849 (2005).
Desmetz et al., "Humoral response to cancer as a tool for biomarker discovery", Journal of Proteomics, 72(6), pp. 982-988 (2009).
Desmetz et al., "Identifying autoantibody signatures in cancer: a promising challenge", Expert Review of Proteomics, 6(4), pp. 377-386 (2009).
Devine et al., "The Breast Tumor-associated Epitope Defined by Monoclonal Antibody 3EL2 Is an 0-linked Mucin Carbohydrate Containing N-Glycolylneuraminic Acid", Cancer Research, 51(21), pp. 5826-5836 (1991).
Dharmawardhane et al., "Regulation of macropinocytosis by p21-activated kinase-1", Mol Biol Cell., 11(10), pp. 3341-3352 (Oct. 2000).
Eavarone et al., "Humanized anti-Sialyl-Tn antibodies for the treatment of ovarian carcinoma," PLoS ONE 13(7): e0201314, 18 pages, (2018).
Reichert et al., "Development trends for monoclonal antibody cancer therapeutics," Nature Reviews, vol. 6, pp. 349-356, (May 2007).
Agarwal et al., "Site-Specific Antibody-Drug Conjugates: The Nexus of Biorthogonal Chemistry, Protein Engineering, and Drug Development," Bioconjugate Chem., 2015, 26, 176-192 (17 pages).
Al-Alem et al., "Abstract LB-229: Utilizing a novel highly specific sialyl-Tn ELISA as a diagnostic for ovarian cancer," Cancer Research, vol. 79, Issue 13 supplement, Jul. 2019 (2 pages).
Amon et al., "A combined computational experimental approach to define the structural origin of antibody recognition of sialyl-Tn, a tumor associatedcarbohydrate antigen," Scientific Reports, 8:107086, Feb. 2018 (12 pages).
Brinkman-Van der Linden et al., "CD33/Siglec-3 Binding Specificity, Expression Pattern, and Consequences of Gene Deletion in Mice," Molecular and Cellular Biology, vol. 23, No. 12, Jun. 2003, p. 4199-4206 (8 pages).
Dorywalska et al., "Effect of Attachment Site on Stability of Cleavable Antibody Drug Conjugates," Bioconjugate Chem., 2015, 26, 650-659 (10 pages).
Dransfield et al., "Abstract B28: Targeting the tumor-associated carbohydrate antigen STn with humanized anti-Sialyl-Tn monoclonal antibody-drug conjugates inhibits ovarian cancer tumor growth in vitro and in vivo," Clinical Cancer Research, vol. 24, Issue 15 supplement, Aug. 2018 (2 pages).
Dransfield, et al. Abstract B114: Humanized anti-Sialyl-Tn monoclonal antibody-drug conjugates inhibit tumor growth in vitro and invivo. Molecular Cancer Therapeutics, Jan. 1, 2018, vol. 17, Issue 1 Supplement (2 pages).
Eavarone et al. "Abstract 5625: Myeloid derived suppressor cells (MDSCs) express Sialyl Tn (STn) and are a therapeutic target for anti-STn antibody drug conjugates," Cancer Research, vol. 78, Issue 13 supplement, Jul. 2018 (2 pages).
Eavarone et al., "Abstract 3640: Novel humanized anti-Sialyl-Tn, anti-CD3 bispecific antibodies demonstrate tumor anti T-cell specificity for immuneactivation at the tumor site," Cancer Research, vol. 77, Issue 13 supplement, Jul. 2017 (2 pages).
Jimeno et al., "Poster 478 Pharmacological disruption of the Astrocytic Elevated Gene-1 (AEG1) in anticancer intervention: PB0412_3 (PB03) as a first-in-class AEG1 interacting agent," Poster Session—Molecular Targeted Agents II, European Journal of Cancer, 50(6):156, Nov. 21, 2014 (1 page).
Kim et al., Abstract: "Session III: Translational Research/Basic Science—I Tetrathiomolybdate mediates the degradation of hypoxia-inducible,factor-1α," Abstracts, Gynecologic Oncology 139 (2015) (1 page).
Kristo et al., Abstract e24279: "Tumor associated carbohydrate antigens in prostatic adenocarcinoma (PAC): Correlation of sialyl-Tn with malignant phenotype," Journal of Clinical Oncology, 36, No. 15 supplemental, Jun. 1, 2018 (2 pages).
McCombs et al., "Antibody Drug Conjugates: Design and Selection of Linker, Payload and Conjugation Chemistry," The AAPS Journal, vol. 17, No. 2, Mar. 2015 (13 pages).
Padler-Karavani et al., "Abstract 67: Expression and antigenicity of tumor-associated Neu5Gc-containing O-glycans in human carcinomas," Conference Abstracts, Joint Meeting of the Society for Glycobiology & American Society for Matrix Biology, Glycobiology, vol. 22, Issue 11, p. 1542 (Nov. 1, 2012).
Padler-Karavani et al., "Expression of the tumor-associated antigen Neu5Gc-Sialyl-Tn in human carcinomas," J Immunol May 1, 2012, 188 (1 Supplement) 74.6 (2 pages).
Partial Extended Search Report issued in European Patent Application No. 18760528.2, dated Mar. 16, 2021 (21 pages).
Patel et al., "OB-BP1/Siglec-6, A Leptin- and Sialic Acid-Binding Protein of the Immunoglobulin Superfamily," The Journal of Biological Chemistry, vol. 274, No. 32, Issue 6, pp. 22729-22738, Apr. 9, 1999 (10 pages).
Prendergast et al., "Novel anti-Sialyl-Tn monoclonal antibodies and antibody-drug conjugates demonstrate tumor specificity and anti-tumor activity," MABS, vol. 9, No. 4, pp. 615-627 (2017).
Prendergast et al., Abstract 183: "Novel anti-Sialyl-Tn monoclonal antibodies and antibody drug conjugates (ADCs) target a cancer stem cell population and demonstrate in vitro and in vivo anti-tumor efficacy," Program and Abstracts for 2016 Annual Meeting of the Society for Glycobiology, Glycobiology, vol. 26, Issue 12, p. 1499, Dec. 1, 2016 (1 page).
Rueda et al., "Abstract MIP-071: Targeting a Chemoresistant Ovariancancer Cell Population via the Carbohydrate Antigensialyl Tn," Clinical Cancer Research, vol. 23, Issue 11, Jun. 2017 (2 pages).
Starbuck et al., "Treatment of ovarian cancer by targeting the tumor stem cell associated carbohydrate antigen, Sialyl-Thomsen-nouveau," Oncotarget, 2018, vol. 9, (No. 33), pp. 23289-23305 (17 pages).
Lofling et al., "A dietary non-human sialic acid may facilitate hemolytic-uremic syndrome", Kidney International, 76 (2), pp. 140-144 (2009).
Lonberg et al., "Human antibodies from transgenic mice", Int Rev Immunol., 13(1), pp. 65-93 (1995).
Long et al., "CD133+ ovarian cancer stem-like cells promote non-stem cancer cell metastasis via CCL5 induced epithelial-mesenchymal transition", Oncotarget, 6, pp. 5846-5859 (2015).
Loureiro et al., "Challenges in Antibody Development against Tn and Sialyl-Tn Antigens", Biomolecules 5, pp. 1783-1809 (2015).
Lowe and Marth, "A Genetic Approach to Mammalian Glycan Function," Annu Rev Biochem, 72:643-691 (2003).
Ludwig et al., "Biomarkers in Cancer Staging, Prognosis and Treatment Selection", Nature Reviews Cancer, 5(11), pp. 845-856 (2005).
MacCallum et al., "Antibody-antigen interactions: contact analysis and binding site topography," J. Mol. Biol., 262(5), pp 732-745 (Oct. 11, 1996).
Maccioni et al., "Organization of the synthesis of glycolipid oligosaccharides in the Golgi complex", FEBS Lett., 585 (11), pp. 1691-1698 (Jun. 6, 2011).
Mack et al., "A small bispecific antibody construct expressed as a functional single-chain molecule with high tumor cell cytotoxicity," Proc. Natl. Acad. Sci., 92, pp. 7021-7025 (1995).
Malphettes et al., "Highly efficient deletion of FUT8 in CHO cell lines using zinc-finger nucleases yields cells that produce completely nonfucosylated antibodies", Biotechnol Bioeng, 106(5), pp. 774-783 (Aug. 1, 2010).
Malykh et al.,"N-Glycolylneuraminic acid in human tumours", Biochimie, 83(7), pp. 623-634 (2001).
Manimala et al., "Carbohydrate Array Analysis of Anti-Tn Antibodies and Lectins Reveals Unexpected Specificities Implications for Diagnostic and Vaccine Development", ChemBioChem, 6, pp. 2229-2241 (2005).

(56) References Cited

OTHER PUBLICATIONS

Marasco et al., "Design, intracellular expression, and activity of a human anti-human immunodeficiency virus type 1 gp120 single-chain antibody", Proc Natl Acad. Sci USA, 90, pp. 7889-7893 (1993).
Marasco, "Intrabodies: turning the humoral immune system outside in for intracellular immunization", Gene Ther., 4, pp. 11-15 (1997).
Marasco, "Intracellular antibodies (intrabodies) as research reagents and therapeutic molecules for gene therapy", Immunotech, 1, pp. 1-19 (1995).
Marcial, V.A., "Carcinoma of the cervix. Present status and future", Cancer, 39(Supplement S2), pp. 945-958 (1977).
Mariuzza et al., "The structural basis of antigen-antibody recognition," Annu. Rev. Biophys. Biophys. Chem., 16, pp. 139-159 (1987).
Markman, M., "Rationale for maintenance or consolidation therapy in ovarian cancer", Clin Adv Hematol Oncol, 1, pp. 176-178 (2003).
Marquina et al., "Gangliosides Expressed in Human Breast Cancer", Cancer Research, 56, pp. 5165-5171 (Nov. 15, 1996).
Martin et al., "Abstract#4182", Blood, (Nov. 16, 2004) vol. 104, No. 11, Part2, pp. 132B. Meeting Info.: 46th Annual Meeting of the American-Society-of-Hematology_ San Diego, CA, USA. Dec. 4-7, 2004 (2 pages).
Martin et al., "Genetically Altered Mice with Different Sialyltransferase Deficiencies Show Tissuespecific Alterations in Sialylation and Sialic Acid 9-0-Acetylation", Journal of Biological Chemistry, 277(36), pp. 32930-32938 (2002).
Martin et al., "Irreversible coupling of immunoglobulin fragments to preformed vesicles. An improved method for liposome targeting", J Biol Chem. 257(1), pp. 286-288 (Jan. 10, 1982).
Marvin et al., "Recombinant approaches to IgG-like bispecific antibodies," Acta Pharmacologica Sinica. 26(6), pp. 549-658 (2005).
Massignani et al., "Cellular delivery of antibodies: effective targeted subcellular imaging and new therapeutic tool", Nature Proceedings, 17 pages (May 2010).
Matsuda et al., "The Complete Nucleotide Sequence of the Human Immunoglobulin Heavy Chain Variable Region Locus", The Journal of Experimental Medicine, 188(11), pp. 2151-2162 (1998).
McCafferty et al., "Phage antibodies: filamentous phage displaying antibody variable domains.," Nature. 348, pp. 552-554 (1990).
McCann et al., "Inhibition of Hedgehog signaling antagonizes serous ovarian cancer growth in a primary xenograft model," PloS one, 6, e28077, 9 pages (2011).
McDevitt et al., "An alpha-particle emitting antibody ([213Bi]J591) for radioimmunotherapy of prostate cancer," Cancer Res., 60, pp. 6095-6100 (Nov. 1, 2000).
McNaughton et al., "Mammalian cell penetration, siRNA transfection, and DNA transfection by supercharged proteins", Proc Natl Acad Sci. USA, 106, pp. 6111-6116 (2009).
Mechref et al., "Quantitative Serum Glycomics of Esophageal Adenocarcinoma and Other Esophageal Disease Onsets", Journal of Proteome Research, 8(6), pp. 2656-2666 (2009).
Medema et al., "Cancer stem cells: the challenges ahead," Nature cell biology, 15, pp. 338-344 (2013).
Meetze, et al., "The discovery and development of potent and specific anti-SialylTn antibodies for the treatment of solid tumors (479)", European Journal of Cancer, vol. 50, No. suppl 6, p. 156 (Nov. 1, 2014).
Meng et al., "Targeted gene inactivation in zebrafish using engineered zinc-finger nucleases", Nat Biotechnol., 26(6), pp. 697-701 (2008).

Merrick et al., "Characterization of the Hanganulziu-Deicher (serum-sickness) antigen as gangliosides containing n-glycolylneuraminic acid", Int. Arch Allergy Appl Immunol., vol. 57, pp. 477-480 (1978).
Meunier et al., "Effect of ovarian cancer ascites on cell migration and gene expression in an epithelial ovarian cancer in vitro model," Transl Oncol., 3(4), pp. 230-238 (2010).
Mhashilkar et al., "Inhibition of HIV-1 Tat-mediated LTR transactivation and HIV-1 infection by anti-Tat single chain intrabodies," EMBO J., 14, pp. 1542-1551 (1995).
Mhashilkar et al., "Intrabody-mediated phenotypic knockout of major histocompatibility complex class I expression in human and monkey cell lines and in primary human keratinocytes," Gene Ther., 9, pp. 307-319 (2002).
Miersch et al., "Synthetic antibodies: Concepts, potential and practical considerations", Methods, 57(4), pp. 486-498 (2012).
Miles et al., "Phase III multicenter clinical trial of the sialyl-TN (STn)-keyhole limpet hemocyanin (KLH) vaccine for metastatic breast cancer," The oncologist, 16, pp. 1092-1100 (2011).
Morito et al., "Studies on Hanganutziu-Deicher antigens-antibodies. I Hanganutziu-Deicher antibodies of IgG class in liver diseases", International Archives of Allergy and Applied Immunology, 81(3), pp. 204-208 (1986).
Morrison, S.L., "Transfectomas provide novel chimeric antibodies",Science, 229(4719), pp. 1202-1207 (Sep. 20, 1985).
Mortezai et al., "Tumor-associated Neu5Ac-Tn and Neu5Gc-Tn antigens bind to C-type lectin CLEC10A (CD301, MGL)," Glycobiology, 23(7), pp. 844-852 (2013).
Motoo et al., "Serum sialyl-Tn antigen levels in patients with digestive cancers", Oncology, 48(4), pp. 321-326 (1991).
Muchmore et al., "A Structural Difference Between the Cell Surfaces of Humans and the Great Apes", American Journal of Physical Anthropology, 107, pp. 187-198 (1998).
Muchmore et al., "Biosynthesis of N-glycolyneuraminic acid. The primary site of hydroxylation of N-acetylneuraminic acid is the cytosolic sugar nucleotide pool", J Biol Chem, vol. 264, pp. 20216-20223 (1989).
Mukherjee et al.,"Co-expression of 9-O-acetylated sialoglycoproteins and their binding proteins on lymphoblasts of childhood acute lymphoblastic leukemia: an anti-apoptotic role," Biol Chem, 390, pp. 325-335 (2009).
Mukherjee et al.,"O-acetylation of GD3 prevents its apoptotic effect and promotes survival of lymphoblasts in childhood acute lymphoblastic leukaemia," 2008. J Cell Biochem. 105, pp. 724-734 (2008).
Muraro et al., "Generation and characterization of B72.3 second generation monoclonal antibodies reactive with the tumor-associated glycoprotein 72 antigen," Cancer Res. 48, pp. 4588-4596 (1988).
Naito et al., "Germinal center marker GL7 probes activation-dependent repression of n-glycoylneuraminic acid, a sialic acid species involved in the negative modulation of B-cell activation", Mal. Cell. Biol., 27(8), pp. 3008-3022 (2007).
Naor et al., "Involvement of CD44, a molecule with a thousand faces, in cancer dissemination," Seminars in cancer biology, 18, pp. 260-267 (2008).
Andreu et al., "FcRgamma activation regulates inflammation-associated squamous carcinogenesis," Cancer Cell vol. 17, 2010, pp. 121-134.
Sinha et al., "Proinflammatory S100 Proteins Regulate the Accumulation of Myeloid-Derived Suppressor Cells," J Immunol. Oct. 1, 2008; 181(7): 4666-4675 (24 pages).

* cited by examiner

STn Binding Specificity (Group 1)

Detected epitope (largest ellipse)

STn Binding Specificity (Group 2)

Detected epitope (largest ellipse)

STn Binding Specificity (Group 3)

Detected epitope (largest ellipse)

STn Binding Specificity (Group 4)

Detected epitope (largest ellipse)

SEQUENCE LISTING

```
<160> NUMBER OF SEQ ID NOS: 108

<210> SEQ ID NO 1
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
```

```
<223> OTHER INFORMATION: Any amino acid
<220> FEATURE:
<221> NAME/KEY: MISC_FEATURE
<222> LOCATION: (9)..(9)
<223> OTHER INFORMATION: May or may not be present
<220> FEATURE:
<221> NAME/KEY: MOD_RES
<222> LOCATION: (111)..(111)
<223> OTHER INFORMATION: Any amino acid
<220> FEATURE:
<221> NAME/KEY: MISC_FEATURE
<222> LOCATION: (111)..(111)
<223> OTHER INFORMATION: May or may not be present

<400> SEQUENCE: 1

Gln Val Gln Leu Gln Gln Ser Asp Xaa Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Phe Ser Pro Gly Asn Asp Ile Lys Tyr Asn Glu Lys Phe
    50                  55                  60

Arg Gly Lys Ala Thr Leu Thr Ala Asp Lys Ser Ser Ser Thr Ala Tyr
65                  70                  75                  80

Met Gln Leu Asn Ser Leu Ser Ser Asp Asp Ser Ala Val Tyr Phe Cys
                85                  90                  95

Lys Arg Ser Leu Ser Thr Pro Tyr Trp Gly Gln Gly Thr Leu Xaa Thr
            100                 105                 110

Val Ser Ala
        115

<210> SEQ ID NO 2
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Arg
            20                  25                  30

Gly Asn His Lys Asn Tyr Leu Thr Trp Tyr Arg Gln Lys Pro Gly Leu
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ala Leu Thr
65                  70                  75                  80

Ile Ser Ser Val Gln Ala Glu Asp Leu Ala Val Tyr Tyr Cys Gln Asn
                85                  90                  95

Asp Tyr Thr Tyr Pro Tyr Thr Phe Gly Gly Gly Thr Lys Leu Glu Ile
            100                 105                 110

Lys Arg

<210> SEQ ID NO 3
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 3

Gly Tyr Thr Phe Thr Asp His Ala Ile His Trp Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Ser Pro Gly Asn Asp Asp Ile Lys Tyr
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Arg Ser Leu Ser Thr Pro Tyr
1               5

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ser Leu Leu Asn Arg Gly Asn His Lys Asn Tyr
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Ala Ser Thr Arg Glu Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Asn Asp Tyr Thr Tyr Pro Tyr Thr
1               5
```

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Tyr Thr Phe Thr Asp His Ala Ile His
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Phe Ser Pro Gly Asn Asp Asp Ile Lys Tyr Asn Glu Lys Phe Arg
1               5                   10                  15

Gly

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Leu Ser Thr Pro Tyr
1               5

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Ser Ser Gln Ser Leu Leu Asn Arg Gly Asn His Lys Asn Tyr Leu
1               5                   10                  15

Thr

<210> SEQ ID NO 13
<211> LENGTH: 330
<212> TYPE: PRT
<213> ORGANISM: Homo sapiens

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 107
<212> TYPE: PRT
<213> ORGANISM: Homo sapiens

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
```

-continued

<210> SEQ ID NO 15
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 16
<211> LENGTH: 450

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Gly Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 17
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 18
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
            115

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Tyr Thr Phe Thr Arg Tyr Thr Met His
1               5                   10

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 21

Tyr Ile Asn Pro Ser Arg Gly Tyr Thr Asn Tyr Asn Gln Lys Phe Lys
1               5                   10                  15
Asp

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Tyr Asp Asp His Tyr Cys Leu Asp Tyr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Ala Ser Ser Ser Val Ser Tyr Met Asn
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Thr Ser Lys Leu Ala Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Gln Trp Ser Ser Asn Pro Phe Thr
1               5

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Gly Gly Ser Gly Gly Gly Ser Gly Gly Gly Gly Ser
1               5                   10                  15
```

<210> SEQ ID NO 27
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Ser Thr Gly Gly Gly Gly Ser Gly Gly Gly Gly Ser Gly Gly Gly
1               5                   10                  15

Gly Ser Gly Gly Gly Gly Ser
            20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly Ser Gly Gly Gly Gly Ser Gly Gly Gly Gly Ser Gly
1               5                   10                  15

Gly Gly Gly Ser
            20

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Ser Thr Gly Gly Gly Gly Ser Gly Gly Gly Gly Ser Gly Gly Gly
1               5                   10                  15

Gly Ser

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Thr Gly Gly Gly Gly Ser Gly Gly Gly Gly Ser Gly Gly Gly Gly
1               5                   10                  15

Ser Asp Ile

<210> SEQ ID NO 31
<211> LENGTH: 296
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
caggttcagc tggtgcagtc tggagctgag gtgaagaagc ctggggcctc agtgaaggtc      60
tcctgcaagg cttctggtta cacctttacc agctatggta tcagctgggt gcgacaggcc     120

```
cctggacaag ggcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagaga        296
```

<210> SEQ ID NO 32
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
caggtgcagc tgttggagtc tgggggaggc ttggtcaagc ctggagggtc cctgagactc    60
tcctgtgcag cctctggatt caccttcagt gactactaca tgagctggat ccgccaggct    120
ccagggaagg gctggagtg gtttcatac attagtagta gtagtagtta cacaaactac     180
gcagactctg tgaagggccg attcaccatc tccagagaca acgccaagaa ctcactgtat    240
ctgcaaatga acagcctgag agccgaggac acggccgtgt attactgtgc gaga          294
```

<210> SEQ ID NO 33
<211> LENGTH: 286
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
gacatccaga tgacccagtc tccatcctcc ctgtctgcat ctgtaggaga cagagtcacc    60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctc                   286
```

<210> SEQ ID NO 34
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
gacatcgtga tgacccagtc tccagactcc ctggctgtgt ctctgggcga gagggccacc    60
atcaactgca agtccagcca gagtgtttta tacagctcca acaataagaa ctacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
cctcc                                                               305
```

<210> SEQ ID NO 35
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 36
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 37
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Ser Tyr Ser Thr Pro
                    85                  90                  95

<210> SEQ ID NO 38
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Cys
                100

<210> SEQ ID NO 39
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 40
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Val Gln Leu Leu Glu Ser Gly Gly Gly Leu Val Lys Pro Gly Gly
1               5                   10                  15

Ser Leu Arg Leu Ser Cys Ala Ala Ser
            20                  25

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 42
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Val Arg Gln Ala Pro Gly Gln Gly Leu Glu Trp Met Gly
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Trp Ile Arg Gln Ala Pro Gly Lys Gly Leu Glu Trp Val Ser
1               5                   10

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Trp Tyr Gln Gln Lys Pro Gly Lys Ala Pro Lys Leu Leu Ile Tyr
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Trp Tyr Gln Gln Lys Pro Gly Gln Pro Pro Lys Leu Leu Ile Tyr
1               5                   10                  15

<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 51

Trp Gly Gln Gly Thr Leu Val Thr Val Ser Ser
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Phe Gly Gln Gly Thr Lys Val Glu Ile Lys
1               5                   10

<210> SEQ ID NO 53
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Arg
            20                  25                  30

Gly Asn His Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Tyr Thr Phe Gly Gln Gly Thr Lys Val Glu Ile
            100                 105                 110

Lys

<210> SEQ ID NO 54
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Arg
            20                  25                  30

Gly Asn His Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Val Tyr Tyr Cys Gln Asn
                85                  90                  95

Asp Tyr Thr Tyr Pro Tyr Thr Phe Gly Gln Gly Thr Lys Val Glu Ile
            100                 105                 110

Lys

<210> SEQ ID NO 55
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Val Met Thr Gln Ser Pro Asp Ser Leu Ser Val Ser Asp Gly
1               5                   10                  15

Glu Arg Ala Thr Ile Asn Cys Lys Ser Ser Gln Ser Leu Leu Asn Arg
            20                  25                  30

Gly Asn His Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Glu Gly Val Tyr Tyr Cys Gln Asn
                85                  90                  95

Asp Tyr Thr Tyr Pro Tyr Thr Phe Gly Gly Gly Thr Lys Val Glu Ile
            100                 105                 110

Gln

<210> SEQ ID NO 56
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Val Met Thr Gln Ser Pro Asp Ser Leu Ser Val Ser Asp Gly
1               5                   10                  15

Glu Arg Ala Thr Ile Asn Cys Lys Ser Ser Gln Ser Leu Leu Asn Arg
            20                  25                  30

Gly Asn His Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Glu Gly Val Tyr Tyr Cys Gln Asn
                85                  90                  95

Asp Tyr Thr Tyr Pro Tyr Thr Phe Gly Cys Gly Thr Lys Val Glu Ile
            100                 105                 110

Gln

<210> SEQ ID NO 57
```

<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly Tyr Phe Ser Pro Gly Asn Asp Asp Ile Lys Tyr Asn Glu Lys Phe
    50                  55                  60

Arg Gly Arg Val Thr Met Thr Thr Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Leu Ser Thr Pro Tyr Trp Gly Gln Gly Thr Leu Val Thr
            100                 105                 110

Val Ser Ser
        115

<210> SEQ ID NO 58
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly Tyr Phe Ser Pro Gly Asn Asp Asp Ile Lys Tyr Asn Glu Lys Phe
    50                  55                  60

Arg Gly Arg Val Thr Met Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
            100                 105                 110

Val Ser Ser
        115

<210> SEQ ID NO 59
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Arg Gln Ala Pro Gly Gln Gly Leu Glu Trp Ile
            35                  40                  45

Gly Tyr Phe Ser Pro Gly Asn Asp Asp Ile Lys Tyr Asn Glu Lys Phe
        50                  55                  60

Arg Gly Arg Val Thr Leu Thr Ala Asp Lys Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
                100                 105                 110

Val Ser Ser
        115

<210> SEQ ID NO 60
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Gly Leu Glu Trp Met
            35                  40                  45

Gly Tyr Phe Ser Pro Gly Asn Asp Asp Ile Lys Tyr Asn Glu Lys Phe
        50                  55                  60

Arg Gly Arg Val Thr Met Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
                100                 105                 110

Val Ser Ser
        115

<210> SEQ ID NO 61
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Arg Gln Ala Pro Gly Gln Gly Leu Glu Trp Ile
            35                  40                  45

Gly Tyr Phe Ser Pro Gly Asn Asp Asp Ile Lys Tyr Asn Glu Lys Phe
    50                  55                  60

Arg Gly Arg Val Thr Leu Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
                100                 105                 110

Val Ser Ser
       115

<210> SEQ ID NO 62
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Gln Ser Gly Ala Glu Asp Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Gly Leu Glu Trp Met
            35                  40                  45

Gly Tyr Phe Ser Pro Gly Asn Asp Asp Ile Lys Tyr Asn Glu Lys Phe
    50                  55                  60

Arg Gly Arg Ala Thr Leu Thr Ala Asp Lys Ser Ser Ser Thr Ala Tyr
65                  70                  75                  80

Met Glu Leu Asn Ser Leu Arg Ser Asp Asp Thr Ala Val Tyr Phe Cys
                85                  90                  95

Lys Arg Ser Leu Ser Thr Pro Tyr Trp Gly Gln Gly Thr Ser Val Thr
                100                 105                 110

Val Ser Ser
       115

<210> SEQ ID NO 63
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Val Gln Ser Gly Ala Glu Asp Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Cys Leu Glu Trp Met
            35                  40                  45

Gly Tyr Phe Ser Pro Gly Asn Asp Asp Ile Lys Tyr Asn Glu Lys Phe
    50                  55                  60

Arg Gly Arg Ala Thr Leu Thr Ala Asp Lys Ser Ser Ser Thr Ala Tyr
65                  70                  75                  80

Met Glu Leu Asn Ser Leu Arg Ser Asp Asp Thr Ala Val Tyr Phe Cys
                85                  90                  95

-continued

Lys Arg Ser Leu Ser Thr Pro Tyr Trp Gly Gln Gly Thr Ser Val Thr
                100                 105                 110

Val Ser Ser
        115

<210> SEQ ID NO 64
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Glu Gln Ser Gly Gly Gly Leu Val Lys Pro Gly Gly
1               5                   10                  15

Ser Leu Arg Leu Ser Cys Ala Ala Ser Gly Tyr Thr Phe Thr Arg Tyr
                20                  25                  30

Thr Met His Trp Ile Arg Gln Ala Pro Gly Lys Gly Leu Glu Trp Val
            35                  40                  45

Ser Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Leu Val Thr Val Ser Ser
        115

<210> SEQ ID NO 65
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Glu Gln Ser Gly Gly Gly Asp Val Lys Pro Gly Gly
1               5                   10                  15

Ser Leu Arg Leu Ser Cys Lys Ala Ser Gly Tyr Thr Phe Thr Arg Tyr
                20                  25                  30

Thr Met His Trp Val Lys Gln Ala Pro Gly Lys Cys Leu Glu Trp Val
            35                  40                  45

Gly Tyr Ile Asn Pro Ser Arg Gly Tyr Thr Asn Tyr Asn Gln Lys Phe
    50                  55                  60

Lys Asp Arg Ala Thr Ile Ser Arg Asp Lys Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Ser Leu Asp Tyr Trp Gly Gln Gly
                100                 105                 110

Thr Thr Val Thr Val Ser Ser
        115

<210> SEQ ID NO 66
<211> LENGTH: 119

-continued

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Glu Gln Ser Gly Gly Gly Asp Val Lys Pro Asp Gly
1               5                   10                  15

Ser Leu Arg Leu Ser Cys Lys Ala Ser Gly Tyr Thr Phe Thr Arg Tyr
            20                  25                  30

Thr Met His Trp Val Lys Gln Ala Pro Gly Lys Gly Leu Glu Trp Val
        35                  40                  45

Gly Tyr Ile Asn Pro Ser Arg Gly Tyr Thr Asn Tyr Asn Gln Lys Phe
    50                  55                  60

Lys Asp Arg Ala Thr Ile Ser Arg Asp Lys Ala Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser
        115

<210> SEQ ID NO 67
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Glu Gln Ser Gly Gly Gly Leu Val Lys Pro Gly Gly
1               5                   10                  15

Ser Leu Arg Leu Ser Cys Lys Ala Ser Gly Tyr Thr Phe Thr Arg Tyr
            20                  25                  30

Thr Met His Trp Val Lys Gln Ala Pro Gly Lys Gly Leu Glu Trp Val
        35                  40                  45

Gly Tyr Ile Asn Pro Ser Arg Gly Tyr Thr Asn Tyr Asn Gln Lys Phe
    50                  55                  60

Lys Asp Arg Ala Thr Ile Ser Arg Asp Lys Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Leu Val Thr Val Ser Ser
        115

<210> SEQ ID NO 68
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Gln Leu Glu Gln Ser Gly Gly Gly Asp Val Lys Pro Asp Gly

```
                1               5                   10                  15
Ser Leu Arg Leu Ser Cys Lys Ala Ser Gly Tyr Thr Phe Thr Arg Tyr
                    20                  25                  30

Thr Met His Trp Val Lys Gln Ala Pro Gly Lys Gly Leu Glu Trp Val
            35                  40                  45

Gly Tyr Ile Asn Pro Ser Arg Gly Tyr Thr Asn Tyr Asn Gln Lys Phe
        50                  55                  60

Lys Asp Arg Ala Thr Ile Ser Arg Asp Lys Ala Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Tyr Tyr Asp Asp His Tyr Cys Leu Asp Tyr Trp Gly Gln Gly
                    100                 105                 110

Thr Thr Val Thr Val Ser Ser
            115
```

<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Lys Pro Gly Lys Ala Pro Lys Leu Leu Ile Tyr
                35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Phe Thr
                85                  90                  95

Phe Gly Gln Gly Thr Lys Val Glu Ile Lys Arg
                100                 105
```

<210> SEQ ID NO 70
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Lys Pro Gly Lys Ala Pro Lys Arg Trp Ile Tyr
                35                  40                  45

Asp Thr Ser Lys Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
```

-continued

```
                65                  70                  75                  80
Asp Glu Ala Thr Tyr Tyr Cys Gln Gln Trp Ser Ser Asn Pro Phe Thr
                    85                  90                  95

Phe Gly Cys Gly Thr Lys Val Glu Val Gln Gly
            100                 105

<210> SEQ ID NO 71
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Ile Gln Leu Thr Gln Ser Pro Ser Ser Leu Glu Ala Ser Val Gly
1               5                   10                  15

Asp Arg Val Thr Ile Thr Cys Ser Ala Ser Ser Ser Val Ser Tyr Met
                20                  25                  30

Asn Trp Tyr Gln Gln Lys Pro Gly Lys Ala Pro Lys Arg Trp Ile Tyr
            35                  40                  45

Asp Thr Ser Lys Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Glu Gly Thr Tyr Tyr Cys Gln Gln Trp Ser Ser Asn Pro Phe Thr
                85                  90                  95

Phe Gly Gly Gly Thr Lys Val Glu Val Gln Gly
            100                 105

<210> SEQ ID NO 72
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

Asn Trp Tyr Gln Gln Lys Pro Gly Lys Ala Pro Lys Arg Trp Ile Tyr
            35                  40                  45

Asp Thr Ser Lys Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Phe Thr
                85                  90                  95

Phe Gly Gln Gly Thr Lys Val Glu Val Lys Arg
            100                 105

<210> SEQ ID NO 73
<211> LENGTH: 249
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 73

Gln Val Gln Leu Glu Gln Ser Gly Gly Gly Leu Val Lys Pro Gly
1               5                   10                  15

Ser Leu Arg Leu Ser Cys Ala Ala Ser Gly Tyr Thr Phe Thr Arg Tyr
            20                  25                  30

Thr Met His Trp Ile Arg Gln Ala Pro Gly Lys Gly Leu Glu Trp Val
        35                  40                  45

Ser Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser Ala Ser Thr Gly Gly Gly Gly Ser Gly
        115                 120                 125

Gly Gly Gly Ser Gly Gly Gly Ser Gly Gly Gly Gly Ser Asp Ile
    130                 135                 140

Gln Met Thr Gln Ser Pro Ser Ser Leu Ser Ala Ser Val Gly Asp Arg
145                 150                 155                 160

Val Thr Ile Thr Cys Ser Ala Ser Ser Val Ser Tyr Met Asn Trp
            165                 170                 175

Tyr Gln Gln Lys Pro Gly Lys Ala Pro Lys Leu Leu Ile Tyr Asp Thr
            180                 185                 190

Ser Lys Leu Ala Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Trp Ser Ser Asn Pro Phe Thr Phe Gly
225                 230                 235                 240

Gln Gly Thr Lys Val Glu Ile Lys Arg
                245

<210> SEQ ID NO 74
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Gln Leu Glu Gln Ser Gly Gly Gly Leu Val Lys Pro Gly Gly
1               5                   10                  15

Ser Leu Arg Leu Ser Cys Lys Ala Ser Gly Tyr Thr Phe Thr Arg Tyr
            20                  25                  30

Thr Met His Trp Val Lys Gln Ala Pro Gly Lys Gly Leu Glu Trp Val
        35                  40                  45

Gly Tyr Ile Asn Pro Ser Arg Gly Tyr Thr Asn Tyr Asn Gln Lys Phe
    50                  55                  60

Lys Asp Arg Ala Thr Ile Ser Arg Asp Lys Ala Lys Asn Ser Leu Tyr
65                  70                  75                  80

Leu Gln Met Asn Ser Leu Arg Ala Glu Asp Thr Ala Val Tyr Tyr Cys

Ala Arg Tyr Tyr Asp Asp His Tyr Ser Leu Asp Tyr Trp Gly Gln Gly
            100                 105                 110

Thr Leu Val Thr Val Ser Ser Ala Ser Thr Gly Gly Gly Gly Ser Gly
            115                 120                 125

Gly Gly Gly Ser Gly Gly Gly Ser Gly Gly Gly Ser Gln Ile
130                 135                 140

Gln Leu Thr Gln Ser Pro Ser Ser Leu Ser Ala Ser Val Gly Asp Arg
145                 150                 155                 160

Val Thr Ile Thr Cys Ser Ala Ser Ser Val Ser Tyr Met Asn Trp
            165                 170                 175

Tyr Gln Gln Lys Pro Gly Lys Ala Pro Lys Arg Trp Ile Tyr Asp Thr
            180                 185                 190

Ser Lys Leu Ala Ser Gly Val Pro Ser Arg Phe Ser Gly Ser Gly Ser
            195                 200                 205

Gly Thr Asp Tyr Thr Leu Thr Ile Ser Ser Leu Gln Pro Glu Asp Phe
    210                 215                 220

Ala Thr Tyr Tyr Cys Gln Gln Trp Ser Ser Asn Pro Phe Thr Phe Gly
225                 230                 235                 240

Gln Gly Thr Lys Val Glu Val Lys Arg
            245

<210> SEQ ID NO 75
<211> LENGTH: 249
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 75

Gln Val Gln Leu Glu Gln Ser Gly Gly Gly Asp Val Lys Pro Asp Gly
1               5                   10                  15

Ser Leu Arg Leu Ser Cys Lys Ala Ser Gly Tyr Thr Phe Thr Arg Tyr
            20                  25                  30

Thr Met His Trp Val Lys Gln Ala Pro Gly Lys Gly Leu Glu Trp Val
        35                  40                  45

Gly Tyr Ile Asn Pro Ser Arg Gly Tyr Thr Asn Tyr Asn Gln Lys Phe
    50                  55                  60

Lys Asp Arg Ala Thr Ile Ser Arg Asp Lys Ala Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Ala Ser Thr Gly Gly Gly Gly Ser Gly
            115                 120                 125

Gly Gly Gly Ser Gly Gly Gly Ser Gly Gly Gly Ser Gln Ile
130                 135                 140

Gln Leu Thr Gln Ser Pro Ser Ser Leu Glu Ala Ser Val Gly Asp Arg
145                 150                 155                 160

Val Thr Ile Thr Cys Ser Ala Ser Ser Val Ser Tyr Met Asn Trp
            165                 170                 175

Tyr Gln Gln Lys Pro Gly Lys Ala Pro Lys Arg Trp Ile Tyr Asp Thr
            180                 185                 190

```
Ser Lys Leu Ala Ser Gly Val Pro Ser Arg Phe Ser Gly Ser Gly Ser
            195                 200                 205

Gly Thr Asp Tyr Thr Leu Thr Ile Ser Ser Leu Gln Pro Glu Asp Glu
        210                 215                 220

Gly Thr Tyr Tyr Cys Gln Gln Trp Ser Ser Asn Pro Phe Thr Phe Gly
225                 230                 235                 240

Gly Gly Thr Lys Val Glu Val Gln Gly
                245

<210> SEQ ID NO 76
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Val Gln Leu Glu Gln Ser Gly Gly Asp Val Lys Pro Asp Gly
1               5                   10                  15

Ser Leu Arg Leu Ser Cys Lys Ala Ser Gly Tyr Thr Phe Thr Arg Tyr
            20                  25                  30

Thr Met His Trp Val Lys Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Ala Thr Ile Ser Arg Asp Lys Ala Lys Asn Thr Ala Tyr
65                  70                  75                  80

Leu Gln Met Asn Ser Leu Arg Gly Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Ala Ser Thr Gly Gly Gly Gly Ser Gly
        115                 120                 125

Gly Gly Gly Ser Gly Gly Gly Ser Gln Ile Gln Leu Thr Gln Ser
    130                 135                 140

Pro Ser Ser Leu Glu Ala Ser Val Gly Asp Arg Val Thr Ile Thr Cys
145                 150                 155                 160

Ser Ala Ser Ser Ser Val Ser Tyr Met Asn Trp Tyr Gln Gln Lys Pro
                165                 170                 175

Gly Lys Ala Pro Lys Arg Trp Ile Tyr Asp Thr Ser Lys Leu Ala Ser
            180                 185                 190

Gly Val Pro Ser Arg Phe Ser Gly Ser Gly Ser Gly Thr Asp Tyr Thr
        195                 200                 205

Leu Thr Ile Ser Ser Leu Gln Pro Glu Asp Glu Gly Thr Tyr Tyr Cys
    210                 215                 220

Gln Gln Trp Ser Ser Asn Pro Phe Thr Phe Gly Gly Gly Thr Lys Val
225                 230                 235                 240

Glu Val Gln Gly

<210> SEQ ID NO 77
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 77

Gln Ile Gln Leu Thr Gln Ser Pro Ser Leu Glu Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Glu Gly Thr Tyr Tyr Cys Gln Gln Trp Ser Ser Asn Pro Phe Thr
                85                  90                  95

Phe Gly Gly Gly Thr Lys Val Glu Val Gln Gly Gly Gly Gly Ser
            100                 105                 110

Gly Gly Gly Gly Ser Gly Gly Gly Ser Gly Gly Gly Ser Gln
            115                 120                 125

Val Gln Leu Glu Gln Ser Gly Gly Asp Val Lys Pro Asp Gly Ser
    130                 135                 140

Leu Arg Leu Ser Cys Lys Ala Ser Gly Tyr Thr Phe Thr Arg Tyr Thr
145                 150                 155                 160

Met His Trp Val Lys Gln Ala Pro Gly Lys Gly Leu Glu Trp Val Gly
                165                 170                 175

Tyr Ile Asn Pro Ser Arg Gly Tyr Thr Asn Tyr Asn Gln Lys Phe Lys
            180                 185                 190

Asp Arg Ala Thr Ile Ser Arg Asp Lys Ala Lys Asn Thr Leu Tyr Leu
        195                 200                 205

Gln Met Asn Ser Leu Arg Gly Glu Asp Thr Ala Val Tyr Tyr Cys Ala
    210                 215                 220

Arg Tyr Tyr Asp Asp His Tyr Ser Leu Asp Tyr Trp Gly Gln Gly Thr
225                 230                 235                 240

Thr Val Thr Val Ser Ser Ala Ser Thr
                245

<210> SEQ ID NO 78
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

Gln Val Gln Leu Glu Gln Ser Gly Gly Asp Val Lys Pro Gly Gly
1               5                   10                  15

Ser Leu Arg Leu Ser Cys Lys Ala Ser Gly Tyr Thr Phe Thr Arg Tyr
            20                  25                  30

Thr Met His Trp Val Lys Gln Ala Pro Gly Lys Cys Leu Glu Trp Val
        35                  40                  45

Gly Tyr Ile Asn Pro Ser Arg Gly Tyr Thr Asn Tyr Asn Gln Lys Phe
    50                  55                  60

Lys Asp Arg Ala Thr Ile Ser Arg Asp Lys Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Ala Ser Thr Gly Gly Gly Ser Gly
        115                 120                 125

Gly Gly Gly Ser Gly Gly Gly Ser Gly Gly Gly Ser Gln Ile
        130                 135                 140

Gln Leu Thr Gln Ser Pro Ser Ser Leu Ser Ala Ser Val Gly Asp Arg
145                 150                 155                 160

Val Thr Ile Thr Cys Ser Ala Ser Ser Val Ser Tyr Met Asn Trp
                165                 170                 175

Tyr Gln Gln Lys Pro Gly Lys Ala Pro Lys Arg Trp Ile Tyr Asp Thr
                180                 185                 190

Ser Lys Leu Ala Ser Gly Val Pro Ser Arg Phe Ser Gly Ser
        195                 200                 205

Gly Thr Asp Tyr Thr Leu Thr Ile Ser Ser Leu Gln Pro Glu Asp Glu
        210                 215                 220

Ala Thr Tyr Tyr Cys Gln Gln Trp Ser Ser Asn Pro Phe Thr Phe Gly
225                 230                 235                 240

Cys Gly Thr Lys Val Glu Val Gln Gly
                245

<210> SEQ ID NO 79
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
                20                  25                  30

Asn Trp Tyr Gln Gln Lys Pro Gly Lys Ala Pro Lys Arg Trp Ile Tyr
                35                  40                  45

Asp Thr Ser Lys Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Glu Ala Thr Tyr Tyr Cys Gln Gln Trp Ser Ser Asn Pro Phe Thr
                85                  90                  95

Phe Gly Cys Gly Thr Lys Val Glu Val Gln Gly Gly Gly Gly Ser
                100                 105                 110

Gly Gly Gly Gly Ser Gly Gly Gly Ser Gly Gly Gly Gly Ser Gln
        115                 120                 125

Val Gln Leu Glu Gln Ser Gly Gly Asp Val Lys Pro Gly Gly Ser
        130                 135                 140

Leu Arg Leu Ser Cys Lys Ala Ser Gly Tyr Thr Phe Thr Arg Tyr Thr
145                 150                 155                 160

Met His Trp Val Lys Gln Ala Pro Gly Lys Cys Leu Glu Trp Val Gly
                165                 170                 175

Tyr Ile Asn Pro Ser Arg Gly Tyr Thr Asn Tyr Asn Gln Lys Phe Lys
                180                 185                 190

Asp Arg Ala Thr Ile Ser Arg Asp Lys Ala Lys Asn Thr Leu Tyr Leu
                195                 200                 205

-continued

Gln Met Asn Ser Leu Arg Ala Glu Asp Thr Ala Val Tyr Tyr Cys Ala
    210                 215                 220

Arg Tyr Tyr Asp Asp His Tyr Ser Leu Asp Tyr Trp Gly Gln Gly Thr
225                 230                 235                 240

Thr Val Thr Val Ser Ser Ala Ser Thr
            245

<210> SEQ ID NO 80
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Glu Gln Ser Gly Gly Gly Asp Val Lys Pro Asp Gly
1               5                   10                  15

Ser Leu Arg Leu Ser Cys Lys Ala Ser Gly Tyr Thr Phe Thr Arg Tyr
            20                  25                  30

Thr Met His Trp Val Lys Gln Ala Pro Gly Lys Gly Leu Glu Trp Val
        35                  40                  45

Gly Tyr Ile Asn Pro Ser Arg Gly Tyr Thr Asn Tyr Asn Gln Lys Phe
    50                  55                  60

Lys Asp Arg Ala Thr Ile Ser Arg Asp Lys Ala Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Ala Ser Thr Gly Gly Gly Gly Ser Gly
        115                 120                 125

Gly Gly Gly Ser Gly Gly Gly Ser Gly Gly Gly Ser Gln Ile
    130                 135                 140

Gln Leu Thr Gln Ser Pro Ser Ser Leu Glu Ala Ser Val Gly Asp Arg
145                 150                 155                 160

Val Thr Ile Thr Cys Ser Ala Ser Ser Val Ser Tyr Met Asn Trp
                165                 170                 175

Tyr Gln Gln Lys Pro Gly Lys Ala Pro Lys Arg Trp Ile Tyr Asp Thr
            180                 185                 190

Ser Lys Leu Ala Ser Gly Val Pro Ser Arg Phe Ser Gly Ser Gly Ser
        195                 200                 205

Gly Thr Asp Tyr Thr Leu Thr Ile Ser Ser Leu Gln Pro Glu Asp Glu
    210                 215                 220

Gly Thr Tyr Tyr Cys Gln Gln Trp Ser Ser Asn Pro Phe Thr Phe Gly
225                 230                 235                 240

Gly Gly Thr Lys Val Glu Val Gln Gly
                245

<210> SEQ ID NO 81
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Ser Thr Gly Gly Gly Gly Ser Gly
        115                 120                 125

Gly Gly Gly Ser Gly Gly Gly Gly Ser Gly Gly Gly Gly Ser Asp Ile
    130                 135                 140

Gln Leu Thr Gln Ser Pro Ala Ile Met Ser Ala Ser Pro Gly Glu Lys
145                 150                 155                 160

Val Thr Met Thr Cys Arg Ala Ser Ser Val Ser Tyr Met Asn Trp
                165                 170                 175

Tyr Gln Gln Lys Ser Gly Thr Ser Pro Lys Arg Trp Ile Tyr Asp Thr
            180                 185                 190

Ser Lys Val Ala Ser Gly Val Pro Tyr Arg Phe Ser Gly Ser Gly Ser
        195                 200                 205

Gly Thr Ser Tyr Ser Leu Thr Ile Ser Ser Met Glu Ala Glu Asp Ala
    210                 215                 220

Ala Thr Tyr Tyr Cys Gln Gln Trp Ser Ser Asn Pro Leu Thr Phe Gly
225                 230                 235                 240

Ala Gly Thr Lys Leu Glu Leu Gln Gly
            245

<210> SEQ ID NO 82
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
```

```
                      100                 105                 110
Thr Thr Leu Thr Val Ser Ser Ala Ser Thr Gly Gly Gly Ser Gly
            115                 120                 125
Gly Gly Gly Ser Gly Gly Gly Ser Gly Gly Gly Ser Gln Ile
            130                 135                 140
Val Leu Thr Gln Ser Pro Ala Ile Met Ser Ala Ser Pro Gly Glu Lys
145                 150                 155                 160
Val Thr Met Thr Cys Ser Ala Ser Ser Val Ser Tyr Met Asn Trp
                165                 170                 175
Tyr Gln Gln Lys Ser Gly Thr Ser Pro Lys Arg Trp Ile Tyr Asp Thr
                180                 185                 190
Ser Lys Leu Ala Ser Gly Val Pro Ala His Phe Arg Gly Ser Gly Ser
            195                 200                 205
Gly Thr Ser Tyr Ser Leu Thr Ile Ser Gly Met Glu Ala Glu Asp Ala
            210                 215                 220
Ala Thr Tyr Tyr Cys Gln Gln Trp Ser Ser Asn Pro Phe Thr Phe Gly
225                 230                 235                 240
Ser Gly Thr Lys Leu Glu Ile Asn Arg
                245

<210> SEQ ID NO 83
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Val Gln Leu Gln Gln Ser Gly Ala Glu Leu Ala Arg Pro Gly Ala
1               5                   10                  15
Ser Val Lys Met Ser Cys Lys Ala Ser Gly Tyr Thr Phe Thr Arg Tyr
                20                  25                  30
Thr Met His Trp Val Lys Gln Arg Pro Gly Gln Gly Leu Glu Trp Ile
            35                  40                  45
Gly Tyr Ile Asn Pro Ser Arg Gly Tyr Thr Asn Tyr Asn Gln Lys Phe
        50                  55                  60
Lys Asp Lys Ala Thr Leu Thr Thr Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Tyr Tyr Asp Asp His Tyr Cys Leu Asp Tyr Trp Gly Gln Gly
                100                 105                 110
Thr Thr Leu Thr Val Ser Ser Ala Ser Thr Gly Gly Gly Ser Gly
            115                 120                 125
Gly Gly Gly Ser Gly Gly Gly Ser Gln Ile Val Leu Thr Gln Ser
            130                 135                 140
Pro Ala Ile Met Ser Ala Ser Pro Gly Glu Lys Val Thr Met Thr Cys
145                 150                 155                 160
Ser Ala Ser Ser Val Ser Tyr Met Asn Trp Tyr Gln Gln Lys Ser
                165                 170                 175
Gly Thr Ser Pro Lys Arg Trp Ile Tyr Asp Thr Ser Lys Leu Ala Ser
            180                 185                 190
Gly Val Pro Ala His Phe Arg Gly Ser Gly Ser Gly Thr Ser Tyr Ser
            195                 200                 205
```

```
Leu Thr Ile Ser Gly Met Glu Ala Glu Asp Ala Ala Thr Tyr Tyr Cys
    210                 215                 220

Gln Gln Trp Ser Ser Asn Pro Phe Thr Phe Gly Ser Gly Thr Lys Leu
225                 230                 235                 240

Glu Ile Asn Arg

<210> SEQ ID NO 84
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ser Thr Gly Gly Gly Ser Gly Gly
        115                 120                 125

Gly Gly Ser Gly Gly Gly Ser Asp Ile Gln Ile Val Leu Thr Gln
    130                 135                 140

Ser Pro Ala Ile Met Ser Ala Ser Pro Gly Glu Lys Val Thr Met Thr
145                 150                 155                 160

Cys Ser Ala Ser Ser Ser Val Ser Tyr Met Asn Trp Tyr Gln Gln Lys
                165                 170                 175

Ser Gly Thr Ser Pro Lys Arg Trp Ile Tyr Asp Thr Ser Lys Leu Ala
            180                 185                 190

Ser Gly Val Pro Ala His Phe Arg Gly Ser Gly Ser Gly Thr Ser Tyr
        195                 200                 205

Ser Leu Thr Ile Ser Gly Met Glu Ala Glu Asp Ala Ala Thr Tyr Tyr
    210                 215                 220

Cys Gln Gln Trp Ser Ser Asn Pro Phe Thr Phe Gly Ser Gly Thr Lys
225                 230                 235                 240

Leu Glu Ile Asn Arg
                245

<210> SEQ ID NO 85
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Gln Ser Gly Ala Glu Asp Lys Lys Pro Gly Ala
```

```
                1               5                   10                  15
            Ser Val Lys Val Ser Cys Lys Ala Ser Gly Tyr Thr Phe Thr Asp His
                           20                  25                  30

Ala Ile His Trp Val Arg Gln Ala Pro Gly Gln Gly Leu Glu Trp Met
                           35                  40                  45

Gly Tyr Phe Ser Pro Gly Asn Asp Asp Ile Lys Tyr Asn Glu Lys Phe
                           50                  55                  60

Arg Gly Arg Ala Thr Leu Thr Ala Asp Lys Ser Ser Ser Thr Ala Tyr
             65                70                  75                  80

Met Glu Leu Asn Ser Leu Arg Ser Asp Asp Thr Ala Val Tyr Phe Cys
                           85                  90                  95

Lys Arg Ser Leu Ser Thr Pro Tyr Trp Gly Gln Gly Thr Ser Val Thr
                           100                 105                 110

Val Ser Ser Ala Ser Thr Gly Gly Gly Gly Ser Gly Gly Gly Gly Ser
                           115                 120                 125

Gly Gly Gly Gly Ser Gly Gly Gly Gly Ser Asp Ile Val Met Thr Gln
                           130                 135                 140

Ser Pro Asp Ser Leu Ser Val Ser Asp Gly Glu Arg Ala Thr Ile Asn
            145                150                 155                 160

Cys Lys Ser Ser Gln Ser Leu Leu Asn Arg Gly Asn His Lys Asn Tyr
                           165                 170                 175

Leu Thr Trp Tyr Gln Gln Lys Pro Gly Gln Pro Pro Lys Leu Leu Ile
                           180                 185                 190

Tyr Trp Ala Ser Thr Arg Glu Ser Gly Val Pro Asp Arg Phe Ser Gly
                           195                 200                 205

Ser Gly Ser Gly Thr Asp Phe Thr Leu Thr Ile Ser Ser Leu Gln Ala
                           210                 215                 220

Glu Asp Glu Gly Val Tyr Tyr Cys Gln Asn Asp Tyr Thr Tyr Pro Tyr
            225                230                 235                 240

Thr Phe Gly Gly Gly Thr Lys Val Glu Ile Gln
                           245                 250

<210> SEQ ID NO 86
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Val Gln Leu Val Gln Ser Gly Ala Glu Asp Lys Lys Pro Gly Ala
             1               5                   10                  15

Ser Val Lys Val Ser Cys Lys Ala Ser Gly Tyr Thr Phe Thr Asp His
                           20                  25                  30

Ala Ile His Trp Val Arg Gln Ala Pro Gly Gln Cys Leu Glu Trp Met
                           35                  40                  45

Gly Tyr Phe Ser Pro Gly Asn Asp Asp Ile Lys Tyr Asn Glu Lys Phe
                           50                  55                  60

Arg Gly Arg Ala Thr Leu Thr Ala Asp Lys Ser Ser Ser Thr Ala Tyr
             65                70                  75                  80

Met Glu Leu Asn Ser Leu Arg Ser Asp Asp Thr Ala Val Tyr Phe Cys
                           85                  90                  95

Lys Arg Ser Leu Ser Thr Pro Tyr Trp Gly Gln Gly Thr Ser Val Thr
                           100                 105                 110
```

```
Val Ser Ser Ala Ser Thr Gly Gly Gly Ser Gly Gly Gly Ser
            115                 120                 125

Gly Gly Gly Gly Ser Gly Gly Gly Ser Asp Ile Val Met Thr Gln
        130                 135                 140

Ser Pro Asp Ser Leu Ser Val Ser Asp Gly Glu Arg Ala Thr Ile Asn
145                 150                 155                 160

Cys Lys Ser Ser Gln Ser Leu Leu Asn Arg Gly Asn His Lys Asn Tyr
                165                 170                 175

Leu Thr Trp Tyr Gln Gln Lys Pro Gly Gln Pro Pro Lys Leu Leu Ile
            180                 185                 190

Tyr Trp Ala Ser Thr Arg Glu Ser Gly Val Pro Asp Arg Phe Ser Gly
            195                 200                 205

Ser Gly Ser Gly Thr Asp Phe Thr Leu Thr Ile Ser Ser Leu Gln Ala
        210                 215                 220

Glu Asp Glu Gly Val Tyr Tyr Cys Gln Asn Asp Tyr Thr Tyr Pro Tyr
225                 230                 235                 240

Thr Phe Gly Cys Gly Thr Lys Val Glu Ile Gln
            245                 250

<210> SEQ ID NO 87
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Ile Val Met Thr Gln Ser Pro Asp Ser Leu Ser Val Ser Asp Gly
1               5                   10                  15

Glu Arg Ala Thr Ile Asn Cys Lys Ser Ser Gln Ser Leu Leu Asn Arg
            20                  25                  30

Gly Asn His Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Glu Gly Val Tyr Tyr Cys Gln Asn
                85                  90                  95

Asp Tyr Thr Tyr Pro Tyr Thr Phe Gly Gly Gly Thr Lys Val Glu Ile
            100                 105                 110

Lys Arg Thr Gly Gly Gly Gly Ser Gly Gly Gly Gly Ser Gly Gly Gly
        115                 120                 125

Gly Ser Glu Val Gln Leu Val Gln Ser Gly Ala Glu Asp Lys Lys Pro
    130                 135                 140

Gly Ala Ser Val Lys Val Ser Cys Lys Ala Ser Gly Tyr Thr Phe Thr
145                 150                 155                 160

Asp His Ala Ile His Trp Val Arg Gln Ala Pro Gly Gln Gly Leu Glu
                165                 170                 175

Trp Met Gly Tyr Phe Ser Pro Gly Asn Asp Asp Ile Lys Tyr Asn Glu
            180                 185                 190

Lys Phe Arg Gly Arg Ala Thr Leu Thr Ala Asp Lys Ser Ser Ser Thr
        195                 200                 205

Ala Tyr Met Glu Leu Asn Ser Leu Arg Ser Asp Asp Thr Ala Val Tyr
    210                 215                 220
```

```
Phe Cys Lys Arg Ser Leu Ser Thr Pro Tyr Trp Gly Gln Gly Thr Ser
225                 230                 235                 240

Val Thr Val Ser Ser
                245

<210> SEQ ID NO 88
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Gly Leu Glu Trp Met
            35                  40                  45

Gly Tyr Phe Ser Pro Gly Asn Asp Asp Ile Lys Tyr Asn Glu Lys Phe
    50                  55                  60

Arg Gly Arg Val Thr Met Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
    195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
    275                 280                 285

Pro Arg Glu Glu Gln Tyr Gln Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
```

```
                325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
            355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Gly Gly Gly Gly
            435                 440                 445
Ser Gly Gly Gly Gly Ser Gly Gly Gly Gly Ser Gln Val Gln Leu Glu
            450                 455                 460
Gln Ser Gly Gly Gly Leu Val Lys Pro Gly Gly Ser Leu Arg Leu Ser
465                 470                 475                 480
Cys Ala Ala Ser Gly Tyr Thr Phe Thr Arg Tyr Thr Met His Trp Ile
                485                 490                 495
Arg Gln Ala Pro Gly Lys Gly Leu Glu Trp Val Ser Tyr Ile Asn Pro
            500                 505                 510
Ser Arg Gly Tyr Thr Asn Tyr Asn Gln Lys Phe Lys Asp Arg Phe Thr
            515                 520                 525
Ile Ser Arg Asp Asn Ala Lys Asn Ser Leu Tyr Leu Gln Met Asn Ser
            530                 535                 540
Leu Arg Ala Glu Asp Thr Ala Val Tyr Tyr Cys Ala Arg Tyr Tyr Asp
545                 550                 555                 560
Asp His Tyr Cys Leu Asp Tyr Trp Gly Gln Gly Thr Leu Val Thr Val
                565                 570                 575
Ser Ser Ala Ser Thr Gly Gly Gly Gly Ser Gly Gly Gly Gly Ser Gly
            580                 585                 590
Gly Gly Gly Ser Gly Gly Gly Ser Asp Ile Gln Met Thr Gln Ser
            595                 600                 605
Pro Ser Ser Leu Ser Ala Ser Val Gly Asp Arg Val Thr Ile Thr Cys
            610                 615                 620
Ser Ala Ser Ser Ser Val Ser Tyr Met Asn Trp Tyr Gln Gln Lys Pro
625                 630                 635                 640
Gly Lys Ala Pro Lys Leu Leu Ile Tyr Asp Thr Ser Lys Leu Ala Ser
                645                 650                 655
Gly Val Pro Ser Arg Phe Ser Gly Ser Gly Ser Gly Thr Asp Phe Thr
            660                 665                 670
Leu Thr Ile Ser Ser Leu Gln Pro Glu Asp Phe Ala Thr Tyr Tyr Cys
            675                 680                 685
Gln Gln Trp Ser Ser Asn Pro Phe Thr Phe Gly Gln Gly Thr Lys Val
            690                 695                 700
Glu Ile Lys Arg
705

<210> SEQ ID NO 89
<211> LENGTH: 220
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 89

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Arg
            20                  25                  30

Gly Asn His Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 90
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly Tyr Phe Ser Pro Gly Asn Asp Asp Ile Lys Tyr Asn Glu Lys Phe
    50                  55                  60

Arg Gly Arg Val Thr Met Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
            100                 105                 110

```
Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Gln Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Gly Gly Gly Gly Ser Gly Gly Gly Gly Ser Gln Val Gln Leu Glu
    450                 455                 460

Gln Ser Gly Gly Gly Leu Val Lys Pro Gly Gly Ser Leu Arg Leu Ser
465                 470                 475                 480

Cys Lys Ala Ser Gly Tyr Thr Phe Thr Arg Tyr Thr Met His Trp Val
                485                 490                 495

Lys Gln Ala Pro Gly Lys Gly Leu Glu Trp Val Gly Tyr Ile Asn Pro
            500                 505                 510

Ser Arg Gly Tyr Thr Asn Tyr Asn Gln Lys Phe Lys Asp Arg Ala Thr
        515                 520                 525
```

```
Ile Ser Arg Asp Lys Ala Lys Asn Ser Leu Tyr Leu Gln Met Asn Ser
    530                 535                 540

Leu Arg Ala Glu Asp Thr Ala Val Tyr Tyr Cys Ala Arg Tyr Tyr Asp
545                 550                 555                 560

Asp His Tyr Ser Leu Asp Tyr Trp Gly Gln Gly Thr Leu Val Thr Val
                565                 570                 575

Ser Ser Ala Ser Thr Gly Gly Gly Ser Gly Gly Gly Gly Ser Gly
            580                 585                 590

Gly Gly Gly Ser Gly Gly Gly Ser Gln Ile Gln Leu Thr Gln Ser
            595                 600                 605

Pro Ser Ser Leu Ser Ala Ser Val Gly Asp Arg Val Thr Ile Thr Cys
610                 615                 620

Ser Ala Ser Ser Val Ser Tyr Met Asn Trp Tyr Gln Gln Lys Pro
625                 630                 635                 640

Gly Lys Ala Pro Lys Arg Trp Ile Tyr Asp Thr Ser Lys Leu Ala Ser
                645                 650                 655

Gly Val Pro Ser Arg Phe Ser Gly Ser Gly Ser Gly Thr Asp Tyr Thr
                660                 665                 670

Leu Thr Ile Ser Ser Leu Gln Pro Glu Asp Phe Ala Thr Tyr Tyr Cys
                675                 680                 685

Gln Gln Trp Ser Ser Asn Pro Phe Thr Phe Gly Gln Gly Thr Lys Val
                690                 695                 700

Glu Val Lys Arg
705

<210> SEQ ID NO 91
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Gly Leu Glu Trp Met
            35                  40                  45

Gly Tyr Phe Ser Pro Gly Asn Asp Asp Ile Lys Tyr Asn Glu Lys Phe
        50                  55                  60

Arg Gly Arg Val Thr Met Thr Ala Asp Lys Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

```
Leu Tyr Ser Leu Ser Ser Val Thr Val Pro Ser Ser Leu Gly
            180                 185             190

Thr Gln Thr Tyr Ile Cys Asn Val Asn His Lys Pro Ser Asn Thr Lys
            195                 200             205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225             230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Gln Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
            435                 440                 445

Ser Gly Gly Gly Gly Ser Gly Gly Gly Gly Ser Gln Val Gln Leu Glu
450                 455                 460

Gln Ser Gly Gly Gly Asp Val Lys Pro Asp Gly Ser Leu Arg Leu Ser
465                 470                 475                 480

Cys Lys Ala Ser Gly Tyr Thr Phe Thr Arg Tyr Thr Met His Trp Val
                485                 490                 495

Lys Gln Ala Pro Gly Lys Gly Leu Glu Trp Val Gly Tyr Ile Asn Pro
            500                 505                 510

Ser Arg Gly Tyr Thr Asn Tyr Asn Gln Lys Phe Lys Asp Arg Ala Thr
            515                 520                 525

Ile Ser Arg Asp Lys Ala Lys Asn Thr Leu Tyr Leu Gln Met Asn Ser
            530                 535                 540

Leu Arg Gly Glu Asp Thr Ala Val Tyr Tyr Cys Ala Arg Tyr Tyr Asp
545                 550                 555                 560

Asp His Tyr Ser Leu Asp Tyr Trp Gly Gln Gly Thr Val Thr Val
                565                 570                 575

Ser Ser Ala Ser Thr Gly Gly Gly Gly Ser Gly Gly Gly Gly Ser Gly
            580                 585                 590
```

```
Gly Gly Gly Ser Gly Gly Gly Ser Gln Ile Gln Leu Thr Gln Ser
            595                 600                 605

Pro Ser Ser Leu Glu Ala Ser Val Gly Asp Arg Val Thr Ile Thr Cys
    610                 615                 620

Ser Ala Ser Ser Val Ser Tyr Met Asn Trp Tyr Gln Gln Lys Pro
625                 630                 635                 640

Gly Lys Ala Pro Lys Arg Trp Ile Tyr Asp Thr Ser Lys Leu Ala Ser
                645                 650                 655

Gly Val Pro Ser Arg Phe Ser Gly Ser Gly Ser Gly Thr Asp Tyr Thr
            660                 665                 670

Leu Thr Ile Ser Ser Leu Gln Pro Glu Asp Glu Gly Tyr Tyr Cys
            675                 680                 685

Gln Gln Trp Ser Ser Asn Pro Phe Thr Phe Gly Gly Gly Thr Lys Val
    690                 695                 700

Glu Val Gln Gly
705
```

<210> SEQ ID NO 92
<211> LENGTH: 708
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Gly Leu Glu Trp Met
            35                  40                  45

Gly Tyr Phe Ser Pro Gly Asn Asp Asp Ile Lys Tyr Asn Glu Lys Phe
    50                  55                  60

Arg Gly Arg Val Thr Met Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240
```

Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Gln Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Gly Gly Gly
            435                 440                 445

Ser Gly Gly Gly Gly Ser Gly Gly Gly Gly Ser Gln Ile Gln Leu Thr
450                 455                 460

Gln Ser Pro Ser Ser Leu Glu Ala Ser Val Gly Asp Arg Val Thr Ile
465                 470                 475                 480

Thr Cys Ser Ala Ser Ser Ser Val Ser Tyr Met Asn Trp Tyr Gln Gln
            485                 490                 495

Lys Pro Gly Lys Ala Pro Lys Arg Trp Ile Tyr Asp Thr Ser Lys Leu
            500                 505                 510

Ala Ser Gly Val Pro Ser Arg Phe Ser Gly Ser Gly Ser Gly Thr Asp
            515                 520                 525

Tyr Thr Leu Thr Ile Ser Ser Leu Gln Pro Glu Asp Glu Gly Thr Tyr
            530                 535                 540

Tyr Cys Gln Gln Trp Ser Ser Asn Pro Phe Thr Phe Gly Gly Gly Thr
545                 550                 555                 560

Lys Val Glu Val Gln Gly Gly Gly Gly Ser Gly Gly Gly Gly Ser
                565                 570                 575

Gly Gly Gly Gly Ser Gly Gly Gly Ser Gln Val Gln Leu Glu Gln
            580                 585                 590

Ser Gly Gly Gly Asp Val Lys Pro Asp Gly Ser Leu Arg Leu Ser Cys
            595                 600                 605

Lys Ala Ser Gly Tyr Thr Phe Thr Arg Tyr Thr Met His Trp Val Lys
610                 615                 620

Gln Ala Pro Gly Lys Gly Leu Glu Trp Val Gly Tyr Ile Asn Pro Ser
625                 630                 635                 640

Arg Gly Tyr Thr Asn Tyr Asn Gln Lys Phe Lys Asp Arg Ala Thr Ile
            645                 650                 655

```
Ser Arg Asp Lys Ala Lys Asn Thr Leu Tyr Leu Gln Met Asn Ser Leu
            660                 665                 670

Arg Gly Glu Asp Thr Ala Val Tyr Tyr Cys Ala Arg Tyr Tyr Asp Asp
            675                 680                 685

His Tyr Ser Leu Asp Tyr Trp Gly Gln Gly Thr Thr Val Thr Val Ser
        690                 695                 700

Ser Ala Ser Thr
705
```

<210> SEQ ID NO 93
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly Tyr Phe Ser Pro Gly Asn Asp Asp Ile Lys Tyr Asn Glu Lys Phe
    50                  55                  60

Arg Gly Arg Val Thr Met Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Gln Ser Thr Tyr Arg Val Val Ser Val Leu
    290                 295                 300
```

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Gly Gly Gly Gly Ser Gly Gly Gly Gly Ser Gln Val Gln Leu Glu
450                 455                 460

Gln Ser Gly Gly Gly Asp Val Lys Pro Gly Gly Ser Leu Arg Leu Ser
465                 470                 475                 480

Cys Lys Ala Ser Gly Tyr Thr Phe Thr Arg Tyr Thr Met His Trp Val
                485                 490                 495

Lys Gln Ala Pro Gly Lys Cys Leu Glu Trp Val Gly Tyr Ile Asn Pro
            500                 505                 510

Ser Arg Gly Tyr Thr Asn Tyr Asn Gln Lys Phe Lys Asp Arg Ala Thr
            515                 520                 525

Ile Ser Arg Asp Lys Ala Lys Asn Thr Leu Tyr Leu Gln Met Asn Ser
        530                 535                 540

Leu Arg Ala Glu Asp Thr Ala Val Tyr Tyr Cys Ala Arg Tyr Tyr Asp
545                 550                 555                 560

Asp His Tyr Ser Leu Asp Tyr Trp Gly Gln Gly Thr Thr Val Thr Val
                565                 570                 575

Ser Ser Ala Ser Thr Gly Gly Gly Gly Ser Gly Gly Gly Gly Ser Gly
            580                 585                 590

Gly Gly Ser Gly Gly Gly Gly Ser Gln Ile Gln Leu Thr Gln Ser
        595                 600                 605

Pro Ser Ser Leu Ser Ala Ser Val Gly Asp Arg Val Thr Ile Thr Cys
        610                 615                 620

Ser Ala Ser Ser Val Ser Tyr Met Asn Trp Tyr Gln Gln Lys Pro
625                 630                 635                 640

Gly Lys Ala Pro Lys Arg Trp Ile Tyr Asp Thr Ser Lys Leu Ala Ser
            645                 650                 655

Gly Val Pro Ser Arg Phe Ser Gly Ser Gly Ser Gly Thr Asp Tyr Thr
                660                 665                 670

Leu Thr Ile Ser Ser Leu Gln Pro Glu Asp Glu Ala Thr Tyr Tyr Cys
        675                 680                 685

Gln Gln Trp Ser Ser Asn Pro Phe Thr Phe Gly Cys Gly Thr Lys Val
        690                 695                 700

Glu Val Gln Gly
705

<210> SEQ ID NO 94
<211> LENGTH: 708
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly Tyr Phe Ser Pro Gly Asn Asp Asp Ile Lys Tyr Asn Glu Lys Phe
    50                  55                  60

Arg Gly Arg Val Thr Met Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Gln Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

```
Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Gly Gly Gly Ser Gly Gly Gly Ser Gln Ile Gln Leu Thr
450                 455                 460

Gln Ser Pro Ser Ser Leu Ser Ala Ser Val Gly Asp Arg Val Thr Ile
465                 470                 475                 480

Thr Cys Ser Ala Ser Ser Ser Val Ser Tyr Met Asn Trp Tyr Gln Gln
                485                 490                 495

Lys Pro Gly Lys Ala Pro Lys Arg Trp Ile Tyr Asp Thr Ser Lys Leu
            500                 505                 510

Ala Ser Gly Val Pro Ser Arg Phe Ser Gly Ser Gly Ser Gly Thr Asp
        515                 520                 525

Tyr Thr Leu Thr Ile Ser Ser Leu Gln Pro Glu Asp Glu Ala Thr Tyr
530                 535                 540

Tyr Cys Gln Gln Trp Ser Ser Asn Pro Phe Thr Phe Gly Cys Gly Thr
545                 550                 555                 560

Lys Val Glu Val Gln Gly Gly Gly Gly Ser Gly Gly Gly Gly Ser
                565                 570                 575

Gly Gly Gly Gly Ser Gly Gly Gly Gly Ser Gln Val Gln Leu Glu Gln
            580                 585                 590

Ser Gly Gly Gly Asp Val Lys Pro Gly Gly Ser Leu Arg Leu Ser Cys
        595                 600                 605

Lys Ala Ser Gly Tyr Thr Phe Thr Arg Tyr Thr Met His Trp Val Lys
610                 615                 620

Gln Ala Pro Gly Lys Cys Leu Glu Trp Val Gly Tyr Ile Asn Pro Ser
625                 630                 635                 640

Arg Gly Tyr Thr Asn Tyr Asn Gln Lys Phe Lys Asp Arg Ala Thr Ile
                645                 650                 655

Ser Arg Asp Lys Ala Lys Asn Thr Leu Tyr Leu Gln Met Asn Ser Leu
            660                 665                 670

Arg Ala Glu Asp Thr Ala Val Tyr Tyr Cys Ala Arg Tyr Tyr Asp Asp
        675                 680                 685

His Tyr Ser Leu Asp Tyr Trp Gly Gln Gly Thr Thr Val Thr Val Ser
690                 695                 700

Ser Ala Ser Thr
705

<210> SEQ ID NO 95
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Gln Ser Gly Ala Glu Val Lys Lys Pro Gly Ala
```

-continued

```
1               5                   10                  15
Ser Val Lys Val Ser Cys Lys Ala Ser Gly Tyr Thr Phe Thr Asp His
            20                  25                  30
Ala Ile His Trp Val Arg Gln Ala Pro Gly Gln Gly Leu Glu Trp Met
            35                  40                  45
Gly Tyr Phe Ser Pro Gly Asn Asp Ile Lys Tyr Asn Glu Lys Phe
        50                  55                  60
Arg Gly Arg Val Thr Met Thr Ala Asp Lys Ser Ser Thr Ala Tyr
65                  70                  75                  80
Met Glu Leu Arg Ser Leu Arg Ser Asp Asp Thr Ala Val Tyr Phe Cys
            85                  90                  95
Lys Arg Ser Leu Ser Thr Pro Tyr Trp Gly Gln Gly Thr Leu Val Thr
            100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
            130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
            195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
            275                 280                 285
Pro Arg Glu Glu Gln Tyr Gln Ser Thr Tyr Arg Val Val Ser Val Leu
            290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
            355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
```

```
His Tyr Thr Gln Lys Ser Leu Ser Leu Ser Pro Gly Gly Gly Gly
        435                 440                 445
Ser Gly Gly Gly Ser Gly Gly Gly Ser Gln Val Gln Leu Glu
    450                 455                 460
Gln Ser Gly Gly Gly Asp Val Lys Pro Asp Gly Ser Leu Arg Leu Ser
465                 470                 475                 480
Cys Lys Ala Ser Gly Tyr Thr Phe Thr Arg Tyr Thr Met His Trp Val
                485                 490                 495
Lys Gln Ala Pro Gly Lys Gly Leu Glu Trp Val Gly Tyr Ile Asn Pro
                500                 505                 510
Ser Arg Gly Tyr Thr Asn Tyr Asn Gln Lys Phe Lys Asp Arg Ala Thr
            515                 520                 525
Ile Ser Arg Asp Lys Ala Lys Asn Thr Leu Tyr Leu Gln Met Asn Ser
        530                 535                 540
Leu Arg Gly Glu Asp Thr Ala Val Tyr Tyr Cys Ala Arg Tyr Tyr Asp
545                 550                 555                 560
Asp His Tyr Cys Leu Asp Tyr Trp Gly Gln Gly Thr Thr Val Thr Val
                565                 570                 575
Ser Ser Ala Ser Thr Gly Gly Gly Ser Gly Gly Gly Ser Gly
            580                 585                 590
Gly Gly Gly Ser Gly Gly Gly Gly Ser Gln Ile Gln Leu Thr Gln Ser
                595                 600                 605
Pro Ser Ser Leu Glu Ala Ser Val Gly Asp Arg Val Thr Ile Thr Cys
            610                 615                 620
Ser Ala Ser Ser Ser Val Ser Tyr Met Asn Trp Tyr Gln Gln Lys Pro
625                 630                 635                 640
Gly Lys Ala Pro Lys Arg Trp Ile Tyr Asp Thr Ser Lys Leu Ala Ser
                645                 650                 655
Gly Val Pro Ser Arg Phe Ser Gly Ser Gly Ser Gly Thr Asp Tyr Thr
                660                 665                 670
Leu Thr Ile Ser Ser Leu Gln Pro Glu Asp Glu Gly Thr Tyr Tyr Cys
            675                 680                 685
Gln Gln Trp Ser Ser Asn Pro Phe Thr Phe Gly Gly Gly Thr Lys Val
        690                 695                 700
Glu Val Gln Gly
705

<210> SEQ ID NO 96
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp His
            20                  25                  30
Ala Ile His Trp Val Arg Gln Ala Pro Gly Gln Gly Leu Glu Trp Met
        35                  40                  45
Gly Tyr Phe Ser Pro Gly Asn Asp Asp Ile Lys Tyr Asn Glu Lys Phe
    50                  55                  60
Arg Gly Arg Val Thr Met Thr Ala Asp Lys Ser Ser Ser Thr Ala Tyr
```

```
                65                  70                  75                  80
Met Glu Leu Arg Ser Leu Arg Ser Asp Asp Thr Ala Val Tyr Phe Cys
                    85                  90                  95
Lys Arg Ser Leu Ser Thr Pro Tyr Trp Gly Gln Gly Thr Leu Val Thr
                100                 105                 110
Val Ser Ser Ala Ser Thr Lys Gly Pro Ser Val Phe Pro Leu Ala Pro
                115                 120                 125
Ser Ser Lys Ser Thr Ser Gly Gly Thr Ala Ala Leu Gly Cys Leu Val
                130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                    165                 170                 175
Leu Tyr Ser Leu Ser Ser Val Val Thr Val Pro Ser Ser Ser Leu Gly
                180                 185                 190
Thr Gln Thr Tyr Ile Cys Asn Val Asn His Lys Pro Ser Asn Thr Lys
                    195                 200                 205
Val Asp Lys Lys Val Glu Pro Lys Ser Cys Asp Lys Thr His Thr Cys
                210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                    245                 250                 255
Val Thr Cys Val Val Val Asp Val Ser His Glu Asp Pro Glu Val Lys
                260                 265                 270
Phe Asn Trp Tyr Val Asp Gly Val Glu Val His Asn Ala Lys Thr Lys
                    275                 280                 285
Pro Arg Glu Glu Gln Tyr Gln Ser Thr Tyr Arg Val Val Ser Val Leu
                290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                    325                 330                 335
Ala Lys Gly Gln Pro Arg Glu Pro Gln Val Tyr Thr Leu Pro Pro Ser
                340                 345                 350
Arg Glu Glu Met Thr Lys Asn Gln Val Ser Leu Thr Cys Leu Val Lys
                    355                 360                 365
Gly Phe Tyr Pro Ser Asp Ile Ala Val Glu Trp Glu Ser Asn Gly Gln
                370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                    405                 410                 415
Gln Gly Asn Val Phe Ser Cys Ser Val Met His Glu Ala Leu His Asn
                420                 425                 430
His Tyr Thr Gln Lys Ser Leu Ser Leu Ser Pro Gly Gly Gly Gly Gly
                    435                 440                 445
Ser Gly Gly Gly Gly Ser Gly Gly Gly Gly Ser Asp Ile Lys Leu Gln
                450                 455                 460
Gln Ser Gly Ala Glu Leu Ala Arg Pro Gly Ala Ser Val Lys Met Ser
465                 470                 475                 480
Cys Lys Thr Ser Gly Tyr Thr Phe Thr Arg Tyr Thr Met His Trp Val
                    485                 490                 495
```

```
Lys Gln Arg Pro Gly Gln Gly Leu Glu Trp Ile Gly Tyr Ile Asn Pro
                500                 505                 510

Ser Arg Gly Tyr Thr Asn Tyr Asn Gln Lys Phe Lys Asp Lys Ala Thr
            515                 520                 525

Leu Thr Thr Asp Lys Ser Ser Ser Thr Ala Tyr Met Gln Leu Ser Ser
530                 535                 540

Leu Thr Ser Glu Asp Ser Ala Val Tyr Tyr Cys Ala Arg Tyr Tyr Asp
545                 550                 555                 560

Asp His Tyr Cys Leu Asp Tyr Trp Gly Gln Gly Thr Thr Leu Thr Val
                565                 570                 575

Ser Ser Ala Ser Thr Gly Gly Gly Ser Gly Gly Gly Ser Gly
            580                 585                 590

Gly Gly Gly Ser Gly Gly Gly Ser Asp Ile Gln Leu Thr Gln Ser
                595                 600                 605

Pro Ala Ile Met Ser Ala Ser Pro Gly Glu Lys Val Thr Met Thr Cys
            610                 615                 620

Arg Ala Ser Ser Ser Val Ser Tyr Met Asn Trp Tyr Gln Gln Lys Ser
625                 630                 635                 640

Gly Thr Ser Pro Lys Arg Trp Ile Tyr Asp Thr Ser Lys Val Ala Ser
                645                 650                 655

Gly Val Pro Tyr Arg Phe Ser Gly Ser Gly Ser Gly Thr Ser Tyr Ser
                660                 665                 670

Leu Thr Ile Ser Ser Met Glu Ala Glu Asp Ala Ala Thr Tyr Tyr Cys
                675                 680                 685

Gln Gln Trp Ser Ser Asn Pro Leu Thr Phe Gly Ala Gly Thr Lys Leu
                690                 695                 700

Glu Leu Gln Gly
705

<210> SEQ ID NO 97
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Gly Leu Glu Trp Met
            35                  40                  45

Gly Tyr Phe Ser Pro Gly Asn Asp Asp Ile Lys Tyr Asn Glu Lys Phe
    50                  55                  60

Arg Gly Arg Val Thr Met Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
```

```
            130                 135                 140
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
            210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Gln Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Gly Gly Gly Gly
            435                 440                 445

Ser Gly Gly Gly Gly Ser Gly Gly Gly Gly Ser Gln Val Gln Leu Gln
450                 455                 460

Gln Ser Gly Ala Glu Leu Ala Arg Pro Gly Ala Ser Val Lys Met Ser
465                 470                 475                 480

Cys Lys Ala Ser Gly Tyr Thr Phe Thr Arg Tyr Thr Met His Trp Val
                485                 490                 495

Lys Gln Arg Pro Gly Gln Gly Leu Glu Trp Ile Gly Tyr Ile Asn Pro
                500                 505                 510

Ser Arg Gly Tyr Thr Asn Tyr Asn Gln Lys Phe Lys Asp Lys Ala Thr
            515                 520                 525

Leu Thr Thr Asp Lys Ser Ser Ser Thr Ala Tyr Met Gln Leu Ser Ser
            530                 535                 540

Leu Thr Ser Glu Asp Ser Ala Val Tyr Tyr Cys Ala Arg Tyr Tyr Asp
545                 550                 555                 560
```

Asp His Tyr Cys Leu Asp Tyr Trp Gly Gln Gly Thr Leu Thr Val
            565                 570                 575

Ser Ser Ala Ser Thr Gly Gly Gly Ser Gly Gly Gly Ser Gly
        580                 585                 590

Gly Gly Gly Ser Gly Gly Gly Ser Gln Ile Val Leu Thr Gln Ser
            595                 600                 605

Pro Ala Ile Met Ser Ala Ser Pro Gly Glu Lys Val Thr Met Thr Cys
        610                 615                 620

Ser Ala Ser Ser Ser Val Ser Tyr Met Asn Trp Tyr Gln Gln Lys Ser
625                 630                 635                 640

Gly Thr Ser Pro Lys Arg Trp Ile Tyr Asp Thr Ser Lys Leu Ala Ser
            645                 650                 655

Gly Val Pro Ala His Phe Arg Gly Ser Gly Ser Gly Thr Ser Tyr Ser
            660                 665                 670

Leu Thr Ile Ser Gly Met Glu Ala Glu Asp Ala Ala Thr Tyr Tyr Cys
            675                 680                 685

Gln Gln Trp Ser Ser Asn Pro Phe Thr Phe Gly Ser Gly Thr Lys Leu
        690                 695                 700

Glu Ile Asn Arg
705

<210> SEQ ID NO 98
<211> LENGTH: 703
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly Tyr Phe Ser Pro Gly Asn Asp Asp Ile Lys Tyr Asn Glu Lys Phe
    50                  55                  60

Arg Gly Arg Val Thr Met Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
            85                  90                  95

Lys Arg Ser Leu Ser Thr Pro Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys

```
                195                 200                 205
Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
        245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Gln Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Gly Gly Gly Gly Ser Gly Gly Gly Gly Ser Gln Val Gln Leu Gln
450                 455                 460

Gln Ser Gly Ala Glu Leu Ala Arg Pro Gly Ala Ser Val Lys Met Ser
465                 470                 475                 480

Cys Lys Ala Ser Gly Tyr Thr Phe Thr Arg Tyr Thr Met His Trp Val
                485                 490                 495

Lys Gln Arg Pro Gly Gln Gly Leu Glu Trp Ile Gly Tyr Ile Asn Pro
            500                 505                 510

Ser Arg Gly Tyr Thr Asn Tyr Asn Gln Lys Phe Lys Asp Lys Ala Thr
        515                 520                 525

Leu Thr Thr Asp Lys Ser Ser Ser Thr Ala Tyr Met Gln Leu Ser Ser
        530                 535                 540

Leu Thr Ser Glu Asp Ser Ala Val Tyr Tyr Cys Ala Arg Tyr Tyr Asp
545                 550                 555                 560

Asp His Tyr Cys Leu Asp Tyr Trp Gly Gln Gly Thr Thr Leu Thr Val
                565                 570                 575

Ser Ser Ala Ser Thr Gly Gly Gly Gly Ser Gly Gly Gly Gly Ser Gly
            580                 585                 590

Gly Gly Gly Ser Gln Ile Val Leu Thr Gln Ser Pro Ala Ile Met Ser
        595                 600                 605

Ala Ser Pro Gly Glu Lys Val Thr Met Thr Cys Ser Ala Ser Ser Ser
610                 615                 620
```

-continued

```
Val Ser Tyr Met Asn Trp Tyr Gln Gln Lys Ser Gly Thr Ser Pro Lys
625                 630                 635                 640

Arg Trp Ile Tyr Asp Thr Ser Lys Leu Ala Ser Gly Val Pro Ala His
            645                 650                 655

Phe Arg Gly Ser Gly Ser Gly Thr Ser Tyr Ser Leu Thr Ile Ser Gly
        660                 665                 670

Met Glu Ala Glu Asp Ala Ala Thr Tyr Tyr Cys Gln Gln Trp Ser Ser
    675                 680                 685

Asn Pro Phe Thr Phe Gly Ser Gly Thr Lys Leu Glu Ile Asn Arg
690                 695                 700

<210> SEQ ID NO 99
<211> LENGTH: 703
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly Tyr Phe Ser Pro Gly Asn Asp Ile Lys Tyr Asn Glu Lys Phe
    50                  55                  60

Arg Gly Arg Val Thr Met Thr Ala Asp Lys Ser Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
```

-continued

```
            275                 280                 285
Pro Arg Glu Glu Gln Tyr Gln Ser Thr Tyr Arg Val Val Ser Val Leu
            290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
                340                 345                 350
Arg Glu Glu Met Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
                420                 425                 430
His Tyr Thr Gln Lys Ser Leu Ser Leu Ser Pro Gly Gly Gly Gly Gly
                435                 440                 445
Ser Gly Gly Gly Gly Ser Gly Gly Gly Gly Ser Gln Val Gln Leu Glu
            450                 455                 460
Gln Ser Gly Gly Gly Asp Val Lys Pro Asp Gly Ser Leu Arg Leu Ser
465                 470                 475                 480
Cys Lys Ala Ser Gly Tyr Thr Phe Thr Arg Tyr Thr Met His Trp Val
                485                 490                 495
Lys Gln Ala Pro Gly Lys Gly Leu Glu Trp Ile Gly Tyr Ile Asn Pro
                500                 505                 510
Ser Arg Gly Tyr Thr Asn Tyr Asn Gln Lys Phe Lys Asp Arg Ala Thr
            515                 520                 525
Ile Ser Arg Asp Lys Ala Lys Asn Thr Ala Tyr Leu Gln Met Asn Ser
            530                 535                 540
Leu Arg Gly Glu Asp Thr Ala Val Tyr Tyr Cys Ala Arg Tyr Tyr Asp
545                 550                 555                 560
Asp His Tyr Ser Leu Asp Tyr Trp Gly Gln Gly Thr Thr Val Thr Val
                565                 570                 575
Ser Ser Ala Ser Thr Gly Gly Gly Ser Gly Gly Gly Gly Ser Gly
                580                 585                 590
Gly Gly Ser Gln Ile Gln Leu Thr Gln Ser Pro Ser Ser Leu Glu
            595                 600                 605
Ala Ser Val Gly Asp Arg Val Thr Ile Thr Cys Ser Ala Ser Ser Ser
            610                 615                 620
Val Ser Tyr Met Asn Trp Tyr Gln Gln Lys Pro Gly Lys Ala Pro Lys
625                 630                 635                 640
Arg Trp Ile Tyr Asp Thr Ser Lys Leu Ala Ser Gly Val Pro Ser Arg
                645                 650                 655
Phe Ser Gly Ser Gly Ser Gly Thr Asp Tyr Thr Leu Thr Ile Ser Ser
                660                 665                 670
Leu Gln Pro Glu Asp Glu Gly Thr Tyr Tyr Cys Gln Gln Trp Ser Ser
            675                 680                 685
Asn Pro Phe Thr Phe Gly Gly Gly Thr Lys Val Glu Val Gln Gly
            690                 695                 700
```

-continued

```
<210> SEQ ID NO 100
<211> LENGTH: 704
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly Tyr Phe Ser Pro Gly Asn Asp Asp Ile Lys Tyr Asn Glu Lys Phe
    50                  55                  60

Arg Gly Arg Val Thr Met Thr Ala Asp Lys Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Gln Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
```

```
                355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Gly Gly Gly
            435                 440                 445
Ser Gly Gly Gly Gly Ser Gly Gly Gly Gly Ser Gln Val Gln Leu Gln
450                 455                 460
Gln Ser Gly Ala Glu Leu Ala Arg Pro Gly Ala Ser Val Lys Met Ser
465                 470                 475                 480
Cys Lys Ala Ser Gly Tyr Thr Phe Thr Arg Tyr Thr Met His Trp Val
                485                 490                 495
Lys Gln Arg Pro Gly Gln Gly Leu Glu Trp Ile Gly Tyr Ile Asn Pro
            500                 505                 510
Ser Arg Gly Tyr Thr Asn Tyr Asn Gln Lys Phe Lys Asp Lys Ala Thr
            515                 520                 525
Leu Thr Thr Asp Lys Ser Ser Ser Thr Ala Tyr Met Gln Leu Ser Ser
530                 535                 540
Leu Thr Ser Glu Asp Ser Ala Val Tyr Tyr Cys Ala Arg Tyr Tyr Asp
545                 550                 555                 560
Asp His Tyr Cys Leu Asp Tyr Trp Gly Gln Gly Thr Thr Leu Thr Val
                565                 570                 575
Ser Ser Ser Thr Gly Gly Gly Gly Ser Gly Gly Gly Ser Gly Gly
            580                 585                 590
Gly Gly Ser Asp Ile Gln Ile Val Leu Thr Gln Ser Pro Ala Ile Met
            595                 600                 605
Ser Ala Ser Pro Gly Glu Lys Val Thr Met Thr Cys Ser Ala Ser Ser
610                 615                 620
Ser Val Ser Tyr Met Asn Trp Tyr Gln Gln Lys Ser Gly Thr Ser Pro
625                 630                 635                 640
Lys Arg Trp Ile Tyr Asp Thr Ser Lys Leu Ala Ser Gly Val Pro Ala
                645                 650                 655
His Phe Arg Gly Ser Gly Ser Gly Thr Ser Tyr Ser Leu Thr Ile Ser
            660                 665                 670
Gly Met Glu Ala Glu Asp Ala Ala Thr Tyr Tyr Cys Gln Gln Trp Ser
            675                 680                 685
Ser Asn Pro Phe Thr Phe Gly Ser Gly Thr Lys Leu Glu Ile Asn Arg
690                 695                 700

<210> SEQ ID NO 101
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Gln Gln Ser Gly Ala Glu Leu Ala Arg Pro Gly Ala
1               5                   10                  15
```

```
Ser Val Lys Met Ser Cys Lys Ala Ser Gly Tyr Thr Phe Thr Arg Tyr
            20                  25                  30
Thr Met His Trp Val Lys Gln Arg Pro Gly Gln Gly Leu Glu Trp Ile
        35                  40                  45
Gly Tyr Ile Asn Pro Ser Arg Gly Tyr Thr Asn Tyr Asn Gln Lys Phe
    50                  55                  60
Lys Asp Lys Ala Thr Leu Thr Thr Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Tyr Tyr Asp Asp His Tyr Cys Leu Asp Tyr Trp Gly Gln Gly
            100                 105                 110
Thr Thr Leu Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Gln Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
```

```
                    435                 440                 445
    Gly Gly Gly Gly Ser Gly Gly Gly Ser Gly Gly Gly Ser Glu
        450                 455                 460

Val Gln Leu Val Gln Ser Gly Ala Glu Asp Lys Lys Pro Gly Ala Ser
    465                 470                 475                 480

Val Lys Val Ser Cys Lys Ala Ser Gly Tyr Thr Phe Thr Asp His Ala
                    485                 490                 495

Ile His Trp Val Arg Gln Ala Pro Gly Gln Gly Leu Glu Trp Met Gly
                500                 505                 510

Tyr Phe Ser Pro Gly Asn Asp Asp Ile Lys Tyr Asn Glu Lys Phe Arg
                515                 520                 525

Gly Arg Ala Thr Leu Thr Ala Asp Lys Ser Ser Thr Ala Tyr Met
    530                 535                 540

Glu Leu Asn Ser Leu Arg Ser Asp Asp Thr Ala Val Tyr Phe Cys Lys
    545                 550                 555                 560

Arg Ser Leu Ser Thr Pro Tyr Trp Gly Gln Gly Thr Ser Val Thr Val
                    565                 570                 575

Ser Ser Ala Ser Thr Gly Gly Gly Gly Ser Gly Gly Gly Gly Ser Gly
                580                 585                 590

Gly Gly Ser Gly Gly Gly Ser Asp Ile Val Met Thr Gln Ser
                595                 600                 605

Pro Asp Ser Leu Ser Val Ser Asp Gly Glu Arg Ala Thr Ile Asn Cys
                610                 615                 620

Lys Ser Ser Gln Ser Leu Leu Asn Arg Gly Asn His Lys Asn Tyr Leu
    625                 630                 635                 640

Thr Trp Tyr Gln Gln Lys Pro Gly Gln Pro Pro Lys Leu Leu Ile Tyr
                    645                 650                 655

Trp Ala Ser Thr Arg Glu Ser Gly Val Pro Asp Arg Phe Ser Gly Ser
                660                 665                 670

Gly Ser Gly Thr Asp Phe Thr Leu Thr Ile Ser Ser Leu Gln Ala Glu
                675                 680                 685

Asp Glu Gly Val Tyr Tyr Cys Gln Asn Asp Tyr Thr Tyr Pro Tyr Thr
    690                 695                 700

Phe Gly Gly Gly Thr Lys Val Glu Ile Gln
    705                 710

<210> SEQ ID NO 102
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Ile Val Leu Thr Gln Ser Pro Ala Ile Met Ser Ala Ser Pro Gly
    1               5                   10                  15

Glu Lys Val Thr Met Thr Cys Ser Ala Ser Ser Ser Val Ser Tyr Met
                    20                  25                  30

Asn Trp Tyr Gln Gln Lys Ser Gly Thr Ser Pro Lys Arg Trp Ile Tyr
                35                  40                  45

Asp Thr Ser Lys Leu Ala Ser Gly Val Pro Ala His Phe Arg Gly Ser
            50                  55                  60

Gly Ser Gly Thr Ser Tyr Ser Leu Thr Ile Ser Gly Met Glu Ala Glu
    65                  70                  75                  80
```

```
Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 103
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

-continued

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gln Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Gly Gly Ser Gly Gly Gly Ser Gly Gly Gly Gly Ser Glu
450                 455                 460

Val Gln Leu Val Gln Ser Gly Ala Glu Asp Lys Lys Pro Gly Ala Ser
465                 470                 475                 480

Val Lys Val Ser Cys Lys Ala Ser Gly Tyr Thr Phe Thr Asp His Ala
                485                 490                 495

Ile His Trp Val Arg Gln Ala Pro Gly Gln Cys Leu Glu Trp Met Gly
            500                 505                 510

Tyr Phe Ser Pro Gly Asn Asp Asp Ile Lys Tyr Asn Glu Lys Phe Arg
        515                 520                 525

Gly Arg Ala Thr Leu Thr Ala Asp Lys Ser Ser Ser Thr Ala Tyr Met
        530                 535                 540

Glu Leu Asn Ser Leu Arg Ser Asp Asp Thr Ala Val Tyr Phe Cys Lys
545                 550                 555                 560

Arg Ser Leu Ser Thr Pro Tyr Trp Gly Gln Gly Thr Ser Val Thr Val
                565                 570                 575

Ser Ser Ala Ser Thr Gly Gly Gly Ser Gly Gly Gly Gly Ser Gly
            580                 585                 590

Gly Gly Ser Gly Gly Gly Gly Ser Asp Ile Val Met Thr Gln Ser
        595                 600                 605

Pro Asp Ser Leu Ser Val Ser Asp Gly Glu Arg Ala Thr Ile Asn Cys
        610                 615                 620

Lys Ser Ser Gln Ser Leu Leu Asn Arg Gly Asn His Lys Asn Tyr Leu
625                 630                 635                 640
```

```
Thr Trp Tyr Gln Gln Lys Pro Gly Gln Pro Pro Lys Leu Leu Ile Tyr
                645                 650                 655

Trp Ala Ser Thr Arg Glu Ser Gly Val Pro Asp Arg Phe Ser Gly Ser
            660                 665                 670

Gly Ser Gly Thr Asp Phe Thr Leu Thr Ile Ser Ser Leu Gln Ala Glu
        675                 680                 685

Asp Glu Gly Val Tyr Tyr Cys Gln Asn Asp Tyr Thr Tyr Pro Tyr Thr
    690                 695                 700

Phe Gly Cys Gly Thr Lys Val Glu Ile Gln
705                 710

<210> SEQ ID NO 104
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Gly Gly Gly Gly Ser Gly Gly Gly Gly Ser Gly Gly Gly Gly Ser Asp
    450                 455                 460

Ile Val Met Thr Gln Ser Pro Asp Ser Leu Ser Val Ser Asp Gly Glu
465                 470                 475                 480

Arg Ala Thr Ile Asn Cys Lys Ser Ser Gln Ser Leu Leu Asn Arg Gly
                485                 490                 495

Asn His Lys Asn Tyr Leu Thr Trp Tyr Gln Gln Lys Pro Gly Gln Pro
            500                 505                 510

Pro Lys Leu Leu Ile Tyr Trp Ala Ser Thr Arg Glu Ser Gly Val Pro
    515                 520                 525

Asp Arg Phe Ser Gly Ser Gly Ser Gly Thr Asp Phe Thr Leu Thr Ile
    530                 535                 540

Ser Ser Leu Gln Ala Glu Asp Glu Gly Val Tyr Tyr Cys Gln Asn Asp
545                 550                 555                 560

Tyr Thr Tyr Pro Tyr Thr Phe Gly Gly Gly Thr Lys Val Glu Ile Lys
                565                 570                 575

Arg Thr Gly Gly Gly Gly Ser Gly Gly Gly Gly Ser Gly Gly Gly Gly
            580                 585                 590

Ser Glu Val Gln Leu Val Gln Ser Gly Ala Glu Asp Lys Lys Pro Gly
    595                 600                 605

Ala Ser Val Lys Val Ser Cys Lys Ala Ser Gly Tyr Thr Phe Thr Asp
610                 615                 620

His Ala Ile His Trp Val Arg Gln Ala Pro Gly Gln Gly Leu Glu Trp
625                 630                 635                 640

Met Gly Tyr Phe Ser Pro Gly Asn Asp Asp Ile Lys Tyr Asn Glu Lys
                645                 650                 655

Phe Arg Gly Arg Ala Thr Leu Thr Ala Asp Lys Ser Ser Ser Thr Ala
            660                 665                 670

Tyr Met Glu Leu Asn Ser Leu Arg Ser Asp Asp Thr Ala Val Tyr Phe
    675                 680                 685

Cys Lys Arg Ser Leu Ser Thr Pro Tyr Trp Gly Gln Gly Thr Ser Val
    690                 695                 700
```

```
Thr Val Ser Ser
705

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Cys Gln Phe Asp Leu Ser Thr Arg Arg Leu Lys Cys
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Cys Gln Tyr Asn Leu Ser Ser Arg Ala Leu Lys Cys
1               5                   10

<210> SEQ ID NO 107
<211> LENGTH: 10
<212> TYPE: PRT
<213> ORGANISM: Homo sapiens

<400> SEQUENCE: 107

Glu Gln Lys Leu Ile Ser Glu Glu Asp Leu
1               5                   10

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Tyr Lys Asp Asp Asp Asp Lys
1               5
```

GLYCAN-INTERACTING COMPOUNDS AND METHODS OF USE

CROSS REFERENCE TO RELATED APPLICATIONS

This application is a 35 U.S.C. § 371 U.S. National Stage Entry of International Application No. PCT/US2017/062155 filed Nov. 17, 2017, which claims the benefit of priority to U.S. Provisional Application No. 62/423,575 filed on Nov. 17, 2016 entitled Glycan-Interacting Compounds and Methods of Use, U.S. Provisional Application No. 62/443,935 filed on Jan. 9, 2017 entitled Glycan-Interacting Compounds and Methods of Use, and U.S. Provisional Application No. 62/480,077 filed on Mar. 31, 2017 entitled Glycan-Interacting Compounds and Methods of Use, the contents of each of which are herein incorporated by reference in their entirety.

SEQUENCE LISTING

The instant application contains a Sequence Listing which has been submitted electronically in ASCII format and is hereby incorporated by reference in its entirety. Said ASCII copy, created on May 17, 2019, is named 2033_1022US371_SL.txt and is 188,313 bytes in size.

BACKGROUND OF THE INVENTION

T cells are immune cells capable of cytotoxic destruction of target cells (Garrido, M. A. et al., 1990. Cancer Research, 50: 4227-32). These cells can be directed to specific target cells using bispecific antibodies that bind both T cells and target cell antigens. These antibodies can be further designed to activate T cell cytotoxicity by specifically binding the T cell receptor (TCR) complex, for example, by binding to CD3.

Cancer cells represent a possible target for T cell destruction using bispecific antibodies. Cellular antigens specific for cancer cells are required to limit T cell destruction to cancer cells only. Aberrant glycosylation accompanies some of the other mutations commonly observed in carcinomas. It has been estimated that about 80% of all carcinomas express the truncated glycans, the Tn Antigen and the sialylated form, Sialyl Tn (STn). With few exceptions, Tn and STn are not expressed in normal, healthy tissues. Furthermore, the non-human immunogenic sialic acid, N-glycolylneuraminic acid (Neu5Gc), seems to be differentially expressed on carcinomas such as breast cancer in the form of Neu5Gc-STn (GcSTn).

There remains a need in the art for therapeutic antibodies capable of recruiting T cells to cells associated with disease, such as cancer cells. Also needed are related compositions and methods of treatment. The present disclosure meets these needs by providing related compounds and methods.

SUMMARY OF THE INVENTION

In some embodiments, the present disclosure provides an antibody comprising: a heavy chain variable domain (VH) comprising an amino acid sequence with at least 90% sequence identity to an amino acid sequence selected from the group consisting of SEQ ID NOs: 66, 64, 65, 67, and 68; and a light chain variable domain (VL) comprising an amino acid sequence with at least 90% sequence identity to an amino acid sequence selected from the group consisting of SEQ ID NOs: 71, 69, 70, and 72. The VH and VL may be joined by a linker. The linker may include two or more glycine residues. The linker may be selected from the group consisting of SEQ ID NOs: 27, 26, and 28-31. The VH and VL may be part of a single-chain variable fragment (scFv). The scFv may include an amino acid sequence with at least 95% sequence identity to an amino acid sequence selected from the group consisting of SEQ ID NOs: 75, 73, 74, and 76-80. The antibody may include an antibody heavy chain and an antibody light chain. The scFv may be associated with the C-terminus of the antibody heavy chain. The antibody heavy chain may include a heavy chain constant domain (CH) with an amino acid sequence selected from the group consisting of SEQ ID NOs: 13 and 15. The antibody light chain may include a light chain constant domain (CL) with the amino acid sequence of SEQ ID NO: 14.

Antibodies disclosed herein may include a glycan-interacting region. The glycan-interacting region may associate with a tumor-associated carbohydrate antigen. The glycan-interacting region may associate with sialyl Tn (STn). The glycan-interacting region may include: (1) a VH having a complementarity determining region (CDR)-H1 with an amino acid sequence having at least 50% sequence identity to at least one of SEQ ID NOs: 9 and 3; a CDR-H2 with an amino acid sequence having at least 50% sequence identity to at least one of SEQ ID NOs: 10 and 4; and a CDR-H3 with an amino acid sequence having at least 50% sequence identity to at least one of SEQ ID NOs: 11 and 5; and (2) a VL having a CDR-L1 with an amino acid sequence having at least 50% sequence identity to at least one of SEQ ID NO: 12 and 6; a CDR-L2 with an amino acid sequence having at least 50% sequence identity to SEQ ID NO: 7; and a CDR-L3 with an amino acid sequence having at least 50% sequence identity to SEQ ID NO: 8. The glycan-interacting region may include a VH with an amino acid sequence with at least 90% sequence identity to an amino acid sequence selected from the group consisting of SEQ ID NOs: 60, 57-59, and 61-63; and a VL with an amino acid sequence with at least 90% sequence identity to an amino acid sequence selected from the group consisting of SEQ ID NOs: 53-56. The antibodies may include an antibody heavy chain comprising an amino acid sequence with at least 95% sequence identity to an amino acid sequence selected from the group consisting of SEQ ID NOs: 91, 88, 90, and 92-95; and an antibody light chain having an amino acid sequence with at least 95% sequence identity to SEQ ID NO: 89.

In some embodiments, the present disclosure provides an antibody having a glycan-interacting region, wherein the glycan-interacting region binds STn and a T cell-interacting region. The T cell-interacting region may bind CD3. The T cell-interacting region may include at least one CDR with an amino acid sequence having at least 50% sequence identity to an amino acid sequence selected from the group consisting of SEQ ID NOs 20-25. The T cell-interacting region may include: (1) a VH having a CDR-H1 with an amino acid sequence having at least 50% sequence identity to SEQ ID NO: 20; a CDR-H2 with an amino acid sequence having at least 50% sequence identity to SEQ ID NO: 21; and a CDR-H3 with an amino acid sequence having at least 50% sequence identity to SEQ ID NO: 22; and (2) a VL having a CDR-L1 with an amino acid sequence having at least 50% sequence identity to SEQ ID NO: 23; a CDR-L2 with an amino acid sequence having at least 50% sequence identity to SEQ ID NO: 24; and a CDR-L3 with an amino acid sequence having at least 50% sequence identity to SEQ ID NO: 25.

Antibodies of the present disclosure may include a T cell-interacting region with at least one human framework region, wherein the at least one human framework region includes an amino acid sequence with at least 50% sequence identity to an amino acid sequence selected from the group the consisting of SEQ ID NOs: 39-52. The T cell-interacting region may include a VH with an amino acid sequence with at least 90% sequence identity to an amino acid sequence selected from the group consisting of SEQ ID NOs: 64-68; and a VL with an amino acid sequence with at least 90% sequence identity to an amino acid sequence selected from the group consisting of SEQ ID NOs: 69-72.

Antibodies of the present disclosure may include a glycan-interacting region, wherein the glycan-interacting region associates with a cell, wherein the cell includes surface-associated STn. The cell may be a cancer cell. The cancer cell may be a tumor cell. The tumor cell may be selected from one or more of an ovarian tumor cell, a pancreatic tumor cell, a colon tumor cell, a prostate tumor cell, and a breast tumor cell.

Some antibodies of the present disclosure simultaneously bind a T cell and a cancer cell. The antibody may bind to the T cell and/or the cancer cell with a half maximal effective concentration of from about 0.01 nM to about 50 nM. The antibody may activate the T cell. The antibody may induce killing of the cancer cell by the T cell. The antibody may bind to STn associated with the cancer cell, wherein the antibody binds an epitope on STn that does not extend to any protein associated with the STn. Antibodies of the present disclosure may be human, humanized, and/or chimeric.

In some embodiments, the present disclosure provides a composition that includes any of the antibodies disclosed herein and at least one excipient.

Methods of the present disclosure may include methods of killing a cancer cell using any of the antibodies or compositions disclosed herein. The antibodies or compositions may be administered to a subject. The antibody may recruit at least one T cell to the cancer cell. The antibody or composition may be administered without harming non-cancer cells. The cancer cell may be resistant to at least one chemotherapeutic agent.

In some embodiments, the present disclosure provides a method of stimulating anti-tumor immune activity in a subject, the method comprising contacting the subject with an antibody or composition described herein. In other embodiments, the present disclosure provides a method of reducing or preventing metastasis of at least one cancer cell in a subject by contacting the subject with an antibody or composition described herein. In some aspects, the disclosure provides a medicament for carrying out any of the methods described herein.

In some embodiments, the disclosure provides a vector encoding any of the antibodies described herein. In some aspects, cells with such vectors are provided. Further provided are antibodies produced from such cells.

Antibodies of the present disclosure may be bispecific antibodies, wherein the antibodies bind a T cell and at least one other cell type. The at least one other cell type may be a cancer cell. The cancer cell may be a tumor cell. In some aspects, compositions with bispecific antibodies are provided. Methods of the disclosure may include using a bispecific antibody described herein or a bispecific antibody composition to kill a cell and/or treat a subject. Further provided are medicaments for carrying out such methods.

BRIEF DESCRIPTION OF THE FIGURES

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

DETAILED DESCRIPTION

Introduction

Figure 1A:
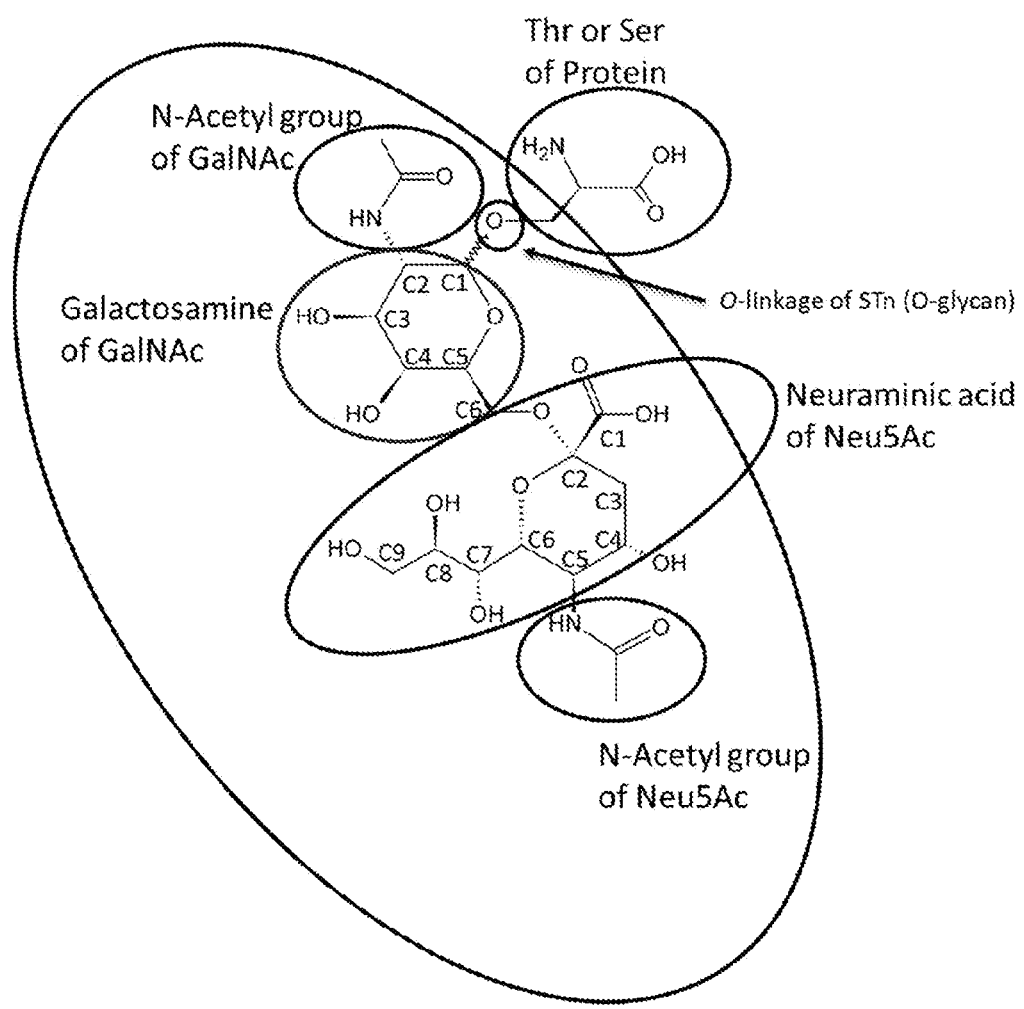
FIGS. 1A-1D are diagrams depicting α2,6-sialylated N-acetylgalactosamine (STn) and indicating putative epitopes involved in anti-STn antibody binding. The largest ellipse in each diagram indicates the specific region of STn targeted by each of 4 antibody groups. These groups include Group 1 antibodies (binding to the large elliptical region indicated in FIG. 1A), Group 2 antibodies (binding to the large elliptical region indicated in FIG. 1B), Group 3 antibodies (binding to the large elliptical region indicated in FIG. 1C) and Group 4 antibodies (binding to the large elliptical region indicated in FIG. 1D).

In some embodiments, the present disclosure provides antibodies that include T cell-interacting regions. These antibodies may be used to bind T cells and may activate T cells upon binding. T cell epitopes may include CD3. Some T cell-interacting antibodies include at least one additional binding region. The additional binding region may facilitate T cell-mediated destruction of a target cell. In some embodiments, the additional binding region is a "glycan-interacting region," which is a region capable of interacting with a carbohydrate group or "glycan." Glycan-interacting regions may bind to glycans present on the surface of target cells. These antibodies may be attractive candidates as biotherapeutics where the surface glycan is a cancer-related glycan antigen. Such antibodies may be engineered using antibody amino acid sequences and antibody fragments described herein.

In nature, α2,6-sialylated N-acetylgalactosamine (STn) is a cancer-related glycan antigen that may be sialylated with N-acetylneuraminic acid (Neu5Ac) or N-glycolyl-neuraminic acid (Neu5Gc). Glycan-interacting antibody regions may be directed to either STn form (pan-STn antibodies), STn that includes Neu5Ac specifically (Ac-STn), or STn that includes Neu5Gc specifically (GcSTn).

STn-CD3 bispecific antibodies may be used to reduce and/or eliminate cancer cells expressing STn. Where the cancer cells include tumor cells, the antibodies may be used to reduce tumor volume and/or eliminate tumors. In some embodiments, the present disclosure provides methods of treating cancer by providing STn-CD3 bispecific antibodies to subjects with cancer. The antibodies may be used alone or in combination with chemotherapeutic agents.

These and other embodiments of the present disclosure are further described herein.

Definitions

Adjacent: As used herein, the term "adjacent" refers to something that is adjoining, neighboring or next to a given entity. In some embodiments, "adjacent residues" are sugar residues within a glycan chain that are linked to one another. In some embodiments, "adjacent glycans" are glycan chains that are next to each other, either in direct contact or within close proximity and without another glycan in between the two.

Administered in combination: As used herein, the term "administered in combination" or "combined administration" means that a subject is simultaneously exposed to two or more agents administered at the same time or within an interval of time such that the subject is at some point in time simultaneously exposed to both and/or such that there may be an overlap in the effect of each agent on the patient. In some embodiments, at least one dose of one or more agents is administered within about 24 hours, 12 hours, 6 hours, 3 hours, 1 hour, 30 minutes, 15 minutes, 10 minutes, 5 minutes, or 1 minute of at least one dose of one or more other agents. In some embodiments, administration occurs in overlapping dosage regimens. As used herein, the term "dosage regimen" refers to a plurality of doses spaced apart in time. Such doses may occur at regular intervals or may include one or more hiatus in administration. In some embodiments, the administration of individual doses of one or more glycan-interacting antibodies, as described herein, are spaced sufficiently closely together such that a combinatorial (e.g., a synergistic) effect is achieved.

Amino acid: As used herein, the terms "amino acid" and "amino acids" refer to all naturally occurring L-alpha-amino acids as well as non-naturally occurring amino acids. Amino acids are identified by either the one-letter or three-letter designations as follows: aspartic acid (Asp:D), isoleucine (Ile:I), threonine (Thr:T), leucine (Leu:L), serine (Ser:S), tyrosine (Tyr:Y), glutamic acid (Glu:E), phenylalanine (Phe:F), proline (Pro:P), histidine (His:H), glycine (Gly:G), lysine (Lys:K), alanine (Ala:A), arginine (Arg:R), cysteine (Cys:C), tryptophan (Trp:W), valine (Val:V), glutamine (Gln:Q) methionine (Met:M), asparagine (Asn:N), where the amino acid is listed first followed parenthetically by the three and one letter codes, respectively.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Antigen-binding region: As used herein, the term "antigen-binding region" refers to the portion of an antibody, antibody fragment, or related molecule that directly interacts with a target molecule or epitope. Antigen-binding regions typically include a variable domain pair, as in the Fab region of an antibody or as linked together in a scFv.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may affect the same outcome or a different outcome. The structure that produces the function may be the same or different.

Biomolecule: As used herein, the term "biomolecule" is any natural molecule which is amino acid-based, nucleic acid-based, carbohydrate-based or lipid-based, and the like.

Bispecific antibody: As used herein, the term "bispecific antibody" refers to an antibody capable of binding two different antigens. Such antibodies typically include regions from at least two different antibodies. Bispecific antibodies may include any of those described in Riethmuller, G. 2012. Cancer Immunity. 12:12-18, Marvin, J. S. et al., 2005. Acta Pharmacologica Sinica. 26(6):649-58 and Schaefer, W. et al., 2011. PNAS. 108(27):11187-92, the contents of each of which are herein incorporated by reference in their entirety.

Branch: As used herein, the term "branch" refers to an entity, moiety or appendage that is linked or extends out from a main entity or source. In some embodiments, a "branch chain" or "branching chain" includes one or more residues (including, but not limited to sugar residues) that extend from a parent chain. As used herein, a "parent chain" is used to refer to a chain of residues (including, but not limited to sugar residues) from which a branching chain is linked. In the case of a glycan with multiple branches, the parent chain may also refer to the source chain from which all such branches are directly or indirectly attached. In the case of a polysaccharide having a chain of hexose residues, parent chain linkages typically occur between carbons 1 and 4 of adjacent residues while branching chains are attached to a parent chain through a linkage between carbon 1 of the branching residue and carbon 3 of the parent residue from which the branch extends. As used herein, the term "branching residue" refers to the residue attached to the parent chain in a branching chain.

Cancer stem cells: As used herein, cancer stem cells (CSCs) refer to a subset of tumor cells that have the ability to self-renew. CSCs may be able to regenerate diverse cell types. In some cases, these cells are difficult or impossible to remove through surgical or chemical treatment of a tumor.

Compound: As used herein, the term "compound," refers to a distinct chemical entity. In some embodiments, a particular compound may exist in one or more isomeric or isotopic forms (including, but not limited to stereoisomers, geometric isomers and isotopes). In some embodiments, a compound is provided or utilized in only a single such form.

In some embodiments, a compound is provided or utilized as a mixture of two or more such forms (including, but not limited to a racemic mixture of stereoisomers). Those of skill in the art appreciate that some compounds exist in different such forms, show different properties and/or activities (including, but not limited to biological activities). In such cases it is within the ordinary skill of those in the art to select or avoid particular forms of the compound for use in accordance with the present invention. For example, compounds that contain asymmetrically substituted carbon atoms can be isolated in optically active or racemic forms. Methods on how to prepare optically active forms from optically active starting materials are known in the art, such as by resolution of racemic mixtures or by stereoselective synthesis.

Cyclic or Cyclized: As used herein, the term "cyclic" refers to the presence of a continuous loop. Cyclic molecules need not be circular, only joined to form an unbroken chain of subunits.

Cytidine monophosphate-N-acetylneuraminic acid hydroxylase: As used herein, the term "cytidine monophosphate-N-acetylneuraminic acid hydroxylase" or "CMAH" refers to an enzyme, absent in humans, but present in most other mammals (including, but not limited to mice, pigs and chimpanzees) that catalyzes the formation of N-glycolyl-neuraminic acid from N-acetylneuraminic acid. The absence of the enzyme in humans is due to a frameshift mutation resulting in the premature termination of the CMAH transcript and the production of a non-functional protein.

Cytotoxic: As used herein, the term "cytotoxic" is used to refer to an agent that kills or causes injurious, toxic, or deadly effects on a cell (e.g., a mammalian cell (e.g., a human cell)), bacterium, virus, fungus, protozoan, parasite, prion, or a combination thereof.

Delivery: As used herein, "delivery" refers to the act or manner of transporting a compound, substance, entity, moiety, cargo or payload to an intended destination.

Delivery Agent: As used herein, "delivery agent" refers to any substance which facilitates, at least in part, the in vivo delivery of a compound, substance, entity, moiety, cargo or payload.

Detectable label: As used herein, "detectable label" refers to one or more markers, signals, or moieties which are attached, incorporated or associated with another entity, which markers, signals or moieties are readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the entity with which they are attached, incorporated or associated. For example, when attached, incorporated in or associated with a peptide or protein, they may be within the amino acids, the peptides, or proteins, or located at the N- or C-termini.

Display library: As used herein, the term "display library" refers to a tool used in scientific discovery to identify biomolecular interactions. Different variations of display libraries exist that include the utilization of bacteriophages, yeast and ribosomes. In each case, proteins within a given library (also referred to herein as "library members") are linked (physically or through association with a host) to the nucleic acid which encodes the protein. When a target molecule is incubated with the members of a display library, any library members that bind to the target may be isolated and the sequences encoding the bound protein may be determined through analysis of the linked nucleic acid. In some embodiments, display libraries are "phage display libraries" wherein the display library is made up of bacteriophage viral particles (also referred to herein as "phage particles") wherein nucleic acids have been incorporated into the phage genome resulting in the production of viral coat proteins that are fused to proteins encoded by the nucleic acids that have been introduced. Such fused proteins are "displayed" on the outer surface of the assembled phage particles where they may interact with a given target.

Distal: As used herein, the term "distal" means situated away from the center or away from a point or region of interest.

Engineered: As used herein, embodiments of the invention are "engineered" when they are designed to have a feature or property, whether structural or chemical, that varies from a starting point, wild type or native molecule. Thus, engineered agents or entities are those whose design and/or production include an act of the hand of man.

Epitope: As used herein, an "epitope" refers to a surface or region on a molecule that is capable of interacting with components of the immune system, including, but not limited to antibodies. In some embodiments, an epitope may include a target site. Epitopes may include a region on an antigen or between two or more antigens that is specifically recognized and bound by a corresponding antibody. Some epitopes may include one or more sugar residues along one or more glycan. Such epitopes may include 1, 2, 3, 4, 5, 6, 7, 8, 9 or at least 10 sugar residues. Epitopes may also include one or more regions of interaction between entities. In some embodiments, epitopes may include a junction between two sugar residues, between a branching chain and a parent chain or between a glycan and a protein.

Ether bond: As used herein, an "ether bond" refers to a chemical bond that includes an oxygen bonded between two carbon atoms. In some embodiments, ether bonds link sugar residues to other entities, including, but not limited to other sugar residues to form a glycan chain. Such bonds are also referred to as "glycosidic bonds" or "glycosidic linkages". In the context of at least one sugar residue, the terms "link" and/or "linkage" are also used herein when referring to a glycosidic linkage. In some embodiments, linkages may link glycans to other entities, including, but not limited to proteins, lipids, phospholipids and sphingolipids. In some embodiments, sugar residues may be linked to protein, typically forming a link between a sugar residue and an amino acid residue. Such amino acid residues include serine and threonine. In some embodiments, ether bonds link glycans to a glycan array through a carbohydrate linker that participates in bond formation. Glycosidic linkages may differ in their stereochemical properties. In some embodiments, alpha oriented glycosidic linkages (also referred to herein as "alpha linkages") result in an axial orientation between the bonded oxygen of the ether bond and the cyclohexane ring of the sugar reside. In some embodiments, beta oriented glycosidic linkages (also referred to herein as "beta linkages") result in an equatorial orientation between the bonded oxygen of the ether bond and the cyclohexane ring of the sugar residue.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; (4) folding of a polypeptide or protein; and (5) post-translational modification of a polypeptide or protein.

Feature: As used herein, a "feature" refers to a characteristic, a property, or a distinctive element.

Formulation: As used herein, a "formulation" refers to a material or mixture prepared according to a formula and which may include at least one antibody, compound, substance, entity, moiety, cargo or payload and a delivery agent, carrier or excipient.

Functional: As used herein, a "functional" biological molecule is a biological entity with a structure and in a form in which it exhibits a property and/or activity by which it is characterized. As used herein, a "functional group" or "chemical group" refers to a characteristic group of atoms or chemical bonds that are part of a larger molecule. In some embodiments, functional groups may be associated with different molecules, but may participate in similar chemical reactions regardless of the molecule of which they are a part. Common functional groups include, but are not limited to carboxyl groups (—COOH), acetyl groups (—COH), amino groups (—NH$_2$), methyl groups (—CH$_3$), sulfate groups (—SO$_3$H) and acyl groups. In some embodiments, the addition of one or more functional group to a molecule may be conveyed using terms that modify the name of the functional group with the ending "-ylated", e.g., acetylated, methylated and sulfated.

Glycan: As used herein, the terms "glycan", "oligosaccharide" and "polysaccharide" are used interchangeably and refer to polymers made up of sugar monomers, typically joined by glycosidic bonds also referred to herein as linkages. In some embodiments, the terms "glycan", "oligosaccharide" and "polysaccharide" may be used to refer to the carbohydrate portion of a glycoconjugate (e.g., glycoprotein, glycolipid or proteoglycan).

Glycan chain: As used herein, the term "glycan chain" refers to a sugar polymer that includes two or more sugars. In some embodiments, glycan chains are covalently linked to proteins through serine or threonine residues on the protein.

Glycan-rich composition: As used herein, the term "glycan-rich composition" refers to a mixture that includes a large percentage of glycans. In some embodiments, glycans within a glycan-rich composition may make up from about 1% to about 10%, from about 5% to about 15%, from about 20% to about 40%, from about 30% to about 50%, from about 60% to about 80%, from about 70% to about 90% or at least 100% of the total weight of the composition.

Glycosidic bond: As used herein, the term "glycosidic bond" refers to a covalent bond formed between a carbohydrate and another chemical group. In some embodiments, glycosidic bonds are formed between the reducing end of one sugar molecule and the non-reducing end of a second sugar molecule or polysaccharide chain. Such glycosidic bonds are also known as O-glycosidic bonds due to the oxygen (or ether bond) between the joined sugars. In some embodiments, a glycosidic bond between two sugars or between a sugar and a linker may also be referred to as a "linkage".

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" is synonymous with "separated", but carries with it the inference separation was carried out by the hand of man. In one embodiment, an isolated substance or entity is one that has been separated from at least some of the components with which it was previously associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Kit: As used herein, the term "kit" refers to a set that includes one or more components adapted for a cooperative purpose and instructions for use thereof.

Knockout: As used herein, the term "knockout" refers to an organism wherein an existing gene has been inactivated through a process that typically involves the hand of man. In a knockout organism, a gene that has been inactivated is said to have been "knocked out". In some embodiments, the knocked-out gene may be inactivated through the insertion of a nucleotide sequence into the gene or through replacement of the gene entirely.

Linker: As used herein, a "linker" refers to a moiety that connects two or more domains, moieties or entities. In one embodiment, a linker may include 10, 11, 12, 13, 14, 15 or more atoms. In a further embodiment, a linker may include a group of atoms, e.g., 10-1,000 atoms. Such atoms or groups thereof may include, but are not limited to, carbon, amino, alkylamino, oxygen, sulfur, sulfoxide, sulfonyl, carbonyl, and imine. In some embodiments, the linker may include an amino acid, peptide, polypeptide or protein. In some embodiments, a moiety bound by a linker may include, but is not limited to an atom, a chemical group, a nucleoside, a nucleotide, a nucleobase, a sugar, a nucleic acid, an amino acid, a peptide, a polypeptide, a protein, a protein complex, a payload (e.g., a therapeutic agent) or a marker (including, but not limited to a chemical, fluorescent, radioactive or bioluminescent marker). The linker can be used for any useful purpose, such as to form multimers or conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers, Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bonds include an amido bond which may be cleaved for example by the use of tris(2-carboxyethyl)phosphine (TCEP), or other reducing agents, and/or photolysis, as well as an ester bond which may be cleaved for example by acidic or basic hydrolysis. In some embodiments, a linker is a carbohydrate moiety used to link glycans to a substrate, such as in a glycan array. Such carbohydrate linkers include, but are not limited to —O(CH$_2$)$_2$CH$_2$HN$_2$ and —O(CH$_2$)$_3$NHCOCH$_2$(OCH$_2$CH$_2$)$_6$NH$_2$.

Medicament: As used herein, the term "medicament" refers to any substance or composition that is used for medical treatment.

mRNA: As used herein, the term "mRNA" refers to messenger RNA produced as a result of gene transcription and processing of the generated transcript. In some embodiments, mRNA that has left the nucleus of the cell may be extracted from a cell or set of cells and analyzed to determine which genes have undergone transcription at a given time or under a given set of circumstances.

Mucin: As used herein, the term "mucin" refers to a family of proteins that are heavily glycosylated. In some embodiments mucins are produced by the submaxillary glands and are found in saliva and mucous.

Negative selection: As used herein, the term "negative selection" refers to the selection of library members from a display library based on their ability to bind entities and/or components of a composition that do not include a target antigen. In some embodiments, negative selection is used prior to positive selection to remove elements that might bind non-specifically to the target.

Off-target: As used herein, "off target" refers to any unintended effect on any one or more target, gene, or cellular transcript.

Patient: As used herein, "patient" refers to a subject who may seek or be in need of treatment, requires treatment, is receiving treatment, will receive treatment, or a subject who is under care by a trained (e.g., licensed) professional for a particular disease or condition.

Peptide: As used herein, "peptide" is a protein or polypeptide which is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than active agents (e.g., as described herein) present in a pharmaceutical composition and having the properties of being substantially nontoxic and non-inflammatory in a patient. In some embodiments, a pharmaceutically acceptable excipient is a vehicle capable of suspending or dissolving the active agent. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, dispensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: Pharmaceutically acceptable salts of the compounds described herein are forms of the disclosed compounds wherein the acid or base moiety is in its salt form (e.g., as generated by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Pharmaceutically acceptable salts include the conventional non-toxic salts, for example, from non-toxic inorganic or organic acids. In some embodiments, a pharmaceutically acceptable salt is prepared from a parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety. Pharmaceutically acceptable solvate: The term "pharmaceutically acceptable solvate," as used herein, refers to a crystalline form of a compound wherein molecules of a suitable solvent are incorporated in the crystal lattice. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate." In some embodiments, the solvent incorporated into a solvate is of a type or at a level that is physiologically tolerable to an organism to which the solvate is administered (e.g., in a unit dosage form of a pharmaceutical composition).

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Positive selection: As used herein, the term "positive selection" refers to the selection of a given entity from a group of unique entities. Such entities and groups thereof may be, for example antibodies. In some cases, they may be antibody fragments or antibody fragments expressed in association with an agent capable of expressing such fragments (e.g. library members from a display library). Selection may be based on the ability of selected entities to bind to a desired target or epitope. In some embodiments, positive selection may be used with phage display libraries to identify phage particles expressing scFvs that bind to the desired target. In other embodiments, positive selection may refer to the selection of antibody candidates from among a pool of antibodies. In other cases, entities may be cells, cell lines or clones as in the selection of clones during hybridoma selection. In such cases, positive selection may refer to clonal selection based on one or more features of antibodies (e.g. specificity for one or more desired epitopes) produced by such clones. In some cases, desired epitopes in positive selection methods may include STn (e.g. AcSTn and/or GcSTn).

Conversely, "negative selection," as used herein, included the same principles and examples described for positive selection, but with the distinguishing characteristic that it is used for removal of undesired entities from a group of unique entities.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proximal: As used herein, the term "proximal" means situated nearer to the center or to a point or region of interest.

Region of interaction: As used herein, the term "region of interaction" refers to a region along any of two or more entities where such entities interact or overlap. In some embodiments, a region of interaction may include one or more sugar residues along a glycan chain that contacts a second glycan chain. In some embodiments, the glycan chains are branching chains from the same parent chain. In some embodiments, a region of interaction may occur between two glycan chains wherein one chain is a branching chain and the second chain is a parent chain. In the case of glycan chains, regions of interaction may include 1, 2, 3, 4, 5, 6, 7, 8, 9 or at least 10 sugar residues. In some embodiments, regions of interaction may also occur between glycans and proteins or between glycans and lipids.

Residue: As used herein, the term "residue" refers to a monomer associated with or capable of associating with a polymer. In some embodiments, residues include sugar molecules including, but not limited to glucose, galactose, N-acetylglucosamine, N-acetylgalactosamine, sialic acids. In some embodiments, residues include amino acids.

Sample: As used herein, the term "sample" refers to an aliquot or portion taken from a source and/or provided for analysis or processing. In some embodiments, a sample is from a biological source (also referred to herein as a "biological sample") such as a tissue, cell or component part (e.g. a body fluid, including but not limited to blood, plasma, serum, mucus, lymphatic fluid, synovial fluid, cerebrospinal fluid, saliva, amniotic fluid, amniotic cord blood, urine, vaginal fluid and semen). In some embodiments, a sample may be or include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In some embodiments, a sample includes a medium, such as a nutrient broth or gel, which may contain cellular components, such as proteins or nucleic acid molecule. In some embodiments, a "primary" sample is an aliquot of the source. In some embodiments, a primary sample is subjected to one or more processing (e.g., separation, purification, etc.) steps to prepare a sample for analysis or other use.

Sialyl: As used herein, the prefix "sialyl" as well as the term "sialylated" describe compounds including sialic acid.

Single unit dose: As used herein, a "single unit dose" is a dose of any therapeutic administered in one dose/at one time/single route/single point of contact, i.e., single administration event. In some embodiments, a single unit dose is provided as a discrete dosage form (e.g., a tablet, capsule, patch, loaded syringe, vial, etc.).

Split dose: As used herein, a "split dose" is the division of single unit dose or total daily dose into two or more doses.

Stable: As used herein "stable" refers to a compound or entity that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable. In some embodiments, stability is measured relative to an absolute value. In some embodiments, stability is measured relative to a reference compound or entity.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Submaxillary glands: As used herein, the term "submaxillary glands" or "submandibular glands" refers to mucous producing glands located beneath the mouth floor. These glands are capable of producing mucins and in some embodiments, may be extracted from mammals as a source of mucin.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Synthetic: The term "synthetic" means produced, prepared, and/or manufactured by the hand of man. Synthesis of polynucleotides or polypeptides or other molecules of the present invention may be chemical or enzymatic.

Target: As used herein, the term "target" refers to an object or entity to be affected by an action. In some embodiments, targets refer to antigens to be used for the development of antibodies that specifically bind the antigens.

Target screening: As used herein, the term "target screening" refers to the use of a target substance to identify binding partners for that substance.

Target site: As used herein, the term "target site" refers to a region on or within one or more glycans, glycoproteins, biomolecules and/or biostructures on or within a cell, the extracellular space, a tissue, an organ and/or an organism that is recognized by a binding agent or effector molecule (e.g., an antibody). In some embodiments, glycan target sites may reside exclusively on one sugar residue, may be formed by two or more residues, or may include both glycan and non-glycan components. In some embodiments, target sites are formed between two or more glycans or glycoproteins. In some embodiments, target sites are formed between branching chains of the same glycan or between one or more branching chains and a parent chain.

Target cell: As used herein, a "target cell" refers to cells of interest, including a cell intended to be affected by a given action or process. In some embodiments, a cell that interacts with an antibody is referred to as a "target" of that antibody. The target cell may be a cell that is disrupted or killed by an antibody carrying a cytotoxic conjugate. Target cells may be found in vitro, in vivo, in situ or in the tissue or organ of an organism. The organism may be an animal, mammal, or human (e.g., a human patient).

Terminal residue: As used herein, the term "terminal residue" refers to the last residue in a polymeric chain. In some embodiments, terminal residues are sugar residues located at the non-reducing end of a polysaccharide chain.

Therapeutic agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In some embodiments, a therapeutically effective amount is provided in a single dose. In some embodiments, a therapeutically effective amount is administered in a dosage regimen that includes a plurality of doses. Those skilled in the art will appreciate that in some embodiments, a unit dosage form may be considered to include a therapeutically effective amount of a particular agent or entity if it includes an amount that is effective when administered as part of such a dosage regimen.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Transgenic: As used herein, the term "transgenic" refers to an organism that includes one or more genes incorporated within the organism's genome that are not naturally found in that organism.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Tumor cell: As used herein, the term "tumor cell" refers to any cancer cell, whether derived from a tumor or capable of forming a tumor through cell division. Tumors are clusters of cancerous cells that include two or more cancer cells.

Variable region: As used herein, the term "variable region" or "variable domain" refers to specific antibody domains that differ extensively in sequence among antibodies and are used in the binding and specificity of each particular antibody for its particular antigen.

Whole IgG: As used herein, the term "whole IgG" refers to a complete IgG molecule. In some embodiments, whole IgG molecules include regions found naturally in two or more other organisms.

Wild type: As used herein, the term "wild type" refers to an organism that includes a natural genome (free from genes derived from other organisms).

I. Compositions of the Invention

In some embodiments, the present invention provides compounds as well as compositions that include at least one glycan-interacting antibody. Within a glycan, monosaccharide monomers may all be the same or they may differ. Common monomers include, but are not limited to trioses, tetroses, pentoses, glucose, fructose, galactose, xylose, arabinose, lyxose, allose, altrose, mannose, gulose, iodose, ribose, mannoheptulose, sedoheptulose and talose. Amino sugars may also be monomers within a glycan. Glycans including such sugars are herein referred to as aminoglycans. Amino sugars, as used herein, are sugar molecules that include an amine group in place of a hydroxyl group, or in some embodiments, a sugar derived from such a sugar. Examples of amino sugars include, but are not limited to glucosamine, galactosamine, N-acetylglucosamine, N-acetylgalactosamine, sialic acids (including, but not limited to, N-acetylneuraminic acid and N-glycolylneuraminic acid) and L-daunosamine.

As used herein the term "glycan-interacting antibody" refers to an antibody that can interact with a glycan moiety. Such antibodies may bind to a glycan moiety alone, to multiple glycan moieties, or to epitopes that include both glycan and non-glycan components. Non-glycan components may include, but are not limited to proteins, protein-associated moieties (such post-translational modifications), cells, and cell-associated molecules/structures. In some embodiments, glycan-interacting antibodies include bispecific antibodies, wherein such antibodies bind to two different glycans or to a glycan and a non-glycan epitope. Some glycan-interacting bispecific antibodies include glycan-CD3 bispecific antibodies. Such antibodies bind to at least one glycan as well as CD3. Glycan-CD3 bispecific antibodies may include STn-CD3 bispecific antibodies that bind to both STn and CD3.

Glycan-interacting antibodies may function to bind to, alter, activate, inhibit, stabilize, degrade and/or modulate a glycan or a glycan-associated molecule or entity. In so doing, glycan-interacting antibodies may function as a therapeutic, whether palliative, prophylactic or as an ongoing treatment composition. In some embodiments, glycan-interacting antibodies may include conjugates or combinations with other molecules. In some embodiments, glycan-interacting antibodies are directed toward glycans having one or more amino sugar. In a further embodiment, one or more amino sugars is a sialic acid. In a further embodiment, one or more sialic acids is N-acetylneuraminic acid and/or N-glycolylneuraminic acid.

Antibodies

Glycan-interacting antibodies may include entire antibodies or fragments thereof. As used herein, the term "antibody" is used in the broadest sense and embraces various formats including, but not limited to monoclonal antibodies, polyclonal antibodies, multispecific antibodies (e.g., bispecific antibodies formed from at least two intact antibodies), antibody conjugates (including, but not limited to antibody-drug conjugates), antibody variants [including, but not limited to antibody mimetics, chimeric antibodies (e.g. antibodies with amino acid sequences derived from more than one species), and synthetic variants], and antibody fragments, so long as they exhibit a desired biological activity (e.g., binding, activating, inhibiting, stabilizing, degrading, and/or modulating one or more targets). Antibodies are primarily amino-acid based molecules but may include one or more post-translational or synthetic modifications. Post-translational modifications may include glycosylation.

As used herein, the term "antibody fragment" refers to a portion of an intact antibody or fusion-protein thereof, in some cases including at least one antigen binding region. Examples of antibody fragments include Fab, Fab', F(ab')$_2$, FAT fragments, single-chain variable fragments (scFvs); diabodies; tri(a)bodies; linear antibodies; single-chain antibody molecules; and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an F(ab')$_2$ fragment that has two antigen-binding sites and is still capable of cross-linking antigen. Glycan-interacting antibodies may include one or more of these fragments and may, for example, be generated through enzymatic digestion of whole antibodies or through recombinant expression.

"Native antibodies" are usually heterotetrameric glycoproteins of about 150,000 Daltons, composed of two identical light (L) chains and two identical heavy (H) chains. Genes encoding antibody heavy and light chains are known and segments making up each have been well characterized and described (Matsuda, F. et al., 1998. The Journal of Experimental Medicine. 188(11); 2151-62 and Li, A. et al., 2004. Blood. 103(12: 4602-9, the content of each of which are herein incorporated by reference in their entirety). Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain.

As used herein, the term "variable domain" refers to specific antibody domains found on both the antibody heavy and light chains that differ extensively in sequence among antibodies and are used in the binding and specificity of each particular antibody for its particular antigen. Variable domains include hypervariable regions. As used herein, the term "hypervariable region" refers to a region within a variable domain that includes amino acid residues responsible for antigen binding. The amino acids present within the hypervariable regions determine the structure of the complementarity determining regions (CDRs) that become part of the antigen-binding site of the antibody. As used herein, the term "CDR" refers to a region of an antibody that includes a structure that is complimentary to its target antigen or epitope. Other portions of the variable domain, not interacting with the antigen, are referred to as framework (FW) regions. The antigen-binding site (also known as the antigen combining site or paratope) includes the amino acid residues necessary to interact with a particular antigen. The exact residues making up the antigen-binding site are typically elucidated by co-crystallography with bound antigen, however computational assessments can also be used based on comparisons with other antibodies (Strohl, W. R. Therapeutic Antibody Engineering. Woodhead Publishing, Philadelphia Pa. 2012. Ch. 3, p 47-54, the contents of which are herein incorporated by reference in their entirety). Determining residues making up CDRs may include the use of numbering schemes including, but not limited to, those taught by Kabat [Wu, T. T. et al., 1970, JEM, 132(2):211-50 and Johnson, G. et al., 2000, Nucleic Acids Res. 28(1): 214-8, the contents of each of which are herein incorporated by reference in their entirety], Chothia [Chothia and Lesk, J. Mol. Biol. 196, 901 (1987), Chothia et al., Nature 342, 877 (1989) and Al-Lazikani, B. et al., 1997, J. Mol. Biol. 273(4):927-48, the contents of each of which are herein incorporated by reference in their entirety], Lefranc (Lefranc, M. P. et al., 2005, Immunome Res. 1:3) and Honegger (Honegger, A. and Pluckthun, A. 2001. J. Mol. Biol. 309(3):657-70, the contents of which are herein incorporated by reference in their entirety).

VH and VL domains have three CDRs each. VL CDRs are referred to herein as CDR-L1, CDR-L2 and CDR-L3, in order of occurrence when moving from N- to C-terminus along the variable domain polypeptide. VH CDRs are referred to herein as CDR-H1, CDR-H2 and CDR-H3, in order of occurrence when moving from N- to C-terminus along the variable domain polypeptide. Each of CDRs have favored canonical structures with the exception of the CDR-H3, which includes amino acid sequences that may be highly variable in sequence and length between antibodies resulting in a variety of three-dimensional structures in antigen-binding domains (Nikoloudis, D. et al., 2014. PeerJ. 2:e456). In some cases, CDR-H3s may be analyzed among a panel of related antibodies to assess antibody diversity. Various methods of determining CDR sequences are known in the art and may be applied to known antibody sequences (Strohl, W. R. Therapeutic Antibody Engineering. Woodhead Publishing, Philadelphia Pa. 2012. Ch. 3, p 47-54, the contents of which are herein incorporated by reference in their entirety).

As used herein, the term "Fv" refers to an antibody fragment that includes the minimum fragment on an antibody needed to form a complete antigen-binding site. These regions consist of a dimer of one heavy chain and one light chain variable domain in tight, non-covalent association. Fv fragments can be generated by proteolytic cleavage, but are largely unstable. Recombinant methods are known in the art for generating stable Fv fragments, typically through insertion of a flexible linker between the light chain variable domain and the heavy chain variable domain [to form a single chain Fv (scFv)] or through the introduction of a disulfide bridge between heavy and light chain variable domains (Strohl, W. R. Therapeutic Antibody Engineering. Woodhead Publishing, Philadelphia Pa. 2012. Ch. 3, p 46-47, the contents of which are herein incorporated by reference in their entirety).

Antibody "light chains" from any vertebrate species can be assigned to one of two clearly distinct types, called kappa and lambda based on amino acid sequences of their constant domains. Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2a, IgG2b, IgG2c, IgG3, IgG4, IgA, and IgA2.

As used herein, the term "single chain Fv" or "scFv" refers to a fusion protein of VH and VL antibody domains, wherein these domains are linked together into a single polypeptide chain by a flexible peptide linker. In some embodiments, the Fv polypeptide linker enables the scFv to form the desired structure for antigen binding. In some embodiments, scFvs are utilized in conjunction with phage display, yeast display or other display methods where they may be expressed in association with a surface member (e.g. phage coat protein) and used in the identification of high affinity peptides for a given antigen.

The term "diabodies" refers to small antibody fragments with two antigen-binding sites, which fragments include a heavy chain variable domain $V_H$ connected to a light chain variable domain $V_L$ in the same polypeptide chain By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993), the contents of each of which are incorporated herein by reference in their entirety.

The term "intrabody" refers to a form of antibody that is not secreted from a cell in which it is produced, but instead target one or more intracellular protein. Intrabodies may be used to affect a multitude of cellular processes including, but not limited to intracellular trafficking, transcription, translation, metabolic processes, proliferative signaling and cell division. In some embodiments, methods of the present invention may include intrabody-based therapies. In some such embodiments, variable domain sequences and/or CDR sequences disclosed herein may be incorporated into one or more construct for intrabody-based therapy. In some cases, intrabodies of the invention may target one or more glycated intracellular protein or may modulate the interaction between one or more glycated intracellular protein and an alternative protein.

The term "chimeric antigen receptor" or "CAR" as used herein, refers to artificial receptors that are engineered to be expressed on the surface of immune effector cells resulting in specific targeting of such immune effector cells to cells expressing entities that bind with high affinity to the artificial receptors. CARs may be designed to include one or more segments of an antibody, antibody variable domain and/or antibody CDR, such that when such CARs are expressed on immune effector cells, the immune effector cells bind and clear any cells that are recognized by the antibody portions of the CARs. In some cases, CARs are designed to specifically bind cancer cells, leading to immune-regulated clearance of the cancer cells.

The term "monoclonal antibody" as used herein refers to an antibody obtained from a population of substantially homogeneous cells (or clones), i.e., the individual antibodies making up the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen The modifier "monoclonal" indicates the character of the antibody as being obtained from a substantially homogeneous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

"Humanized" forms of non-human (e.g., murine) antibodies are chimeric antibodies that contain minimal sequences derived from non-human immunoglobulins. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and capacity. Humanized antibodies may include one or more back-mutation that include the reversion of one or more amino acids back to amino acids found in a donor antibody. Conversely, residues from donor antibodies included in humanized antibodies may be mutated to match residues present in human recipient antibodies.

In some embodiments, glycan-interacting antibodies of the present invention may be antibody mimetics. The term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (U.S. Pat. Nos. 6,673,901; 6,348,584). In some embodiments, antibody mimetics may be those known in the art including, but are not limited to affibody molecules, affilins, affitins, anticalins, avimers, DARPins, Fynomers and Kunitz and domain peptides. In other embodiments, antibody mimetics may include one or more non-peptide region.

As used herein, the term "antibody variant" refers to a biomolecule resembling an antibody in structure, sequence and/or function, but including some differences in their amino acid sequence, composition or structure as compared to another antibody or a native antibody.

Antibody Development

Antibodies of the present disclosure are developed to bind antigens such as those described herein. As used herein, an "antigen" is an entity which induces or evokes an immune response in an organism. An immune response is characterized by the reaction of the cells, tissues and/or organs of an organism to the presence of a foreign entity. Such an immune response typically leads to the production by the organism of one or more antibodies against the foreign entity, e.g., antigen or a portion of the antigen. In some cases, methods of immunization may be altered based on one or more desired immunization outcomes. As used here, the term "immunization outcome" refers to one or more desired effects of immunization. Examples include high antibody titers and/or increased antibody specificity for a target of interest.

Antigens of the invention may include glycans, glycoconjugates (including, but not limited to glycoproteins and glycolipids), peptides, polypeptides, fusion proteins, or any of the foregoing and may be conjugated or complexed to one or more separate adjuvants or heterologous proteins. In some embodiments, antigens used according to methods of the present invention may include sialylated glycans, such as STn. Antigens having STn may include mucins. Mucins are a family of proteins that are heavily glycosylated. They are a component of many tumors originating from epithelial cells (Ishida, A. et al., 2008. Proteomics. 8: 3342-9, the contents of which are herein incorporated by reference in their entirety). They are highly expressed by submaxillary glands and can be found at high levels in saliva and mucous. Animal-derived submaxillary mucins may be used as antigens to generate anti-STn antibodies in immunogenic hosts. Submaxillary mucin from different species differ in their STn content with regard to AcSTn versus GcSTn forms. Porcine submaxillary mucin (PSM) is particularly rich in GcSTn, which makes up about 90% of total STn. STn from bovine submaxillary mucin (BSM) includes roughly equal percentages of GcSTn and AcSTn. Ovine submaxillary mucin (OSM) is particularly rich in AcSTn, which makes up about 90% of total STn. In some cases, solutions prepared for immunization may be modified to include one or more of PSM, BSM and OSM depending on the desired target of antibodies resulting from such immunization. PSM may be used in immunizations to generate antibodies in immunogenic hosts that are more likely to be specific for GcSTn. PSM is rich in Neu5Gc-containing mucin-type, glycoproteins that are decorated with GcSTn. Among the currently known sources of high Neu5Gc content is red meat; especially submaxillary glands were previously described as a rich source of Neu5Gc due to the high expression of the CMAH enzyme, which catalyzes the reaction to produce the Neu5Gc precursor, CMP-Neu5Ac. In some cases, PSM may be used to prevent a pan-anti-Neu5Gc response and induce a more specific immune response against GcSTn. OSM may be used in immunizations to generate antibodies in immunogenic hosts that are more likely to be specific for AcSTn.

In one embodiment, the present invention provides a glycan-interacting antibody that is GcSTn-specific. The antibody has little cross-reactivity to Neu5Ac-STn or Tn. The antibody can bind GcSTn but has reduced affinity for AcSTn.

In some embodiments, antigens may be subjected to enzymatic digestion prior to immunization to modulate the resulting immune response in immunogenic hosts. In one example, submaxillary mucins may be treated with trypsin or proteinase K enzymes prior to immunization. The activity of such enzymes may help to cleave off and thereby reduce the percentage and variability of non-STn epitopes. Glycan moieties may shield regions of the peptide where they are attached from enzymatic proteolysis and thereby remain intact.

Antibody titers resulting from immunizations may have different antibody levels depending on the type and amount of antigen used in such immunizations. In some cases, certain antigens may be selected for use in immunizations based on the expected titer.

As used herein, an "adjuvant" is a pharmacological or immunological agent that modifies the effect of other agents. Adjuvants according to the present invention include, but are not limited chemical compositions, biomolecules, therapeutics, and/or therapeutic regimens. Adjuvants may include Freund's adjuvant (complete and/or incomplete), immunostimulatory oligonucleotides [e.g. CpG oligodeoxynucleotides (ODNs)], mineral-containing compositions, bacterial ADP-ribosylating toxins, bioadhesives, mucoadhesives, microparticles, lipids, liposomes, muramyl peptides, N-oxidized polyethylene-piperazine derivatives, saponins and/or immune stimulating complexes (ISCOs). In some embodiments, adjuvants may include oil-in-water emulsions (e.g. sub-micron oil-in-water emulsions). Adjuvants according to the present invention may also include any of those disclosed in US Patent Publication No. US20120027813 and/or U.S. Pat. No. 8,506,966, the contents of each of which are herein incorporated by reference in their entirety.

Antibodies of the present invention may be polyclonal or monoclonal or recombinant, produced by methods known in the art or as described in this application. In some embodiments, the antibodies of the present invention may be labeled for purposes of detection with a detectable label known by one of skill in the art. The label can be a radioisotope, fluorescent compound, chemiluminescent compound, enzyme, or enzyme co-factor, or any other labels known in the art. In some aspects, the antibody that binds to a desired antigen is not labeled, but may be detected by binding of a labeled secondary antibody that specifically binds to the primary antibody.

Antibodies of the present invention (e.g., glycan-interacting antibodies) include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly made antibodies (i.e., intrabodies), and epitope-binding fragments of any of the above. Antibodies of the present invention (e.g., glycan-interacting antibodies) can be from any animal origin including birds and mammals. Preferably, such antibodies are of human, murine (e.g., mouse and rat), donkey, sheep, rabbit, goat, guinea pig, camel, horse, or chicken origin. The antibodies of the present invention can be monospecific or multispecific (e.g., bispecific, trispecific, or of greater multispecificity). Multispecific antibodies can be specific for different epitopes of a target antigen of the present invention, or can be specific for both a target antigen of the present invention, and a heterologous epitope, such as a heterologous glycan, peptide or solid support material. (See, e.g., WO 93/17715; WO 92/08802; WO 91/00360; WO 92/05793; Tutt, A. et al., *Trispecific F(ab') 3 derivatives that use cooperative signaling via the TCR/CD3 complex and CD2 to activate and redirect resting cytotoxic T cells*. J Immunol. 1991 Jul. 1; 147(1):60-9; U.S. Pat. Nos. 4,474,893; 4,714,681; 4,925,648; 5,573,920; 5,601,819; and Kostelny, S. A. et al., Formation of a bispecific antibody by the use of leucine zippers. J Immunol. 1992 Mar. 1; 148(5): 1547-53).

Glycan-interacting antibodies of the present disclosure may be prepared using well-established methods known in the art for developing monoclonal antibodies. In one embodiment, the monoclonal antibodies are prepared using hybridoma technology (Kohler, G. et al., *Continuous cultures of fused cells secreting antibody of predefined specificity*. Nature. 1975 Aug. 7; 256(5517):495-7). For hybridoma formations, first, a mouse, hamster, or other appropriate host animal, is typically immunized with an immunizing agent (e.g., a target antigen of the invention) to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell (Goding, J. W., *Monoclonal Antibodies: Principles and Practice*. Academic Press. 1986; 59-1031). Immortalized cell lines are usually transformed mammalian cells, particularly myeloma cells of rodent, rabbit, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, D. et al., *A human hybrid myeloma for production of human monoclonal antibodies*. J Immunol. 1984 December; 133(6):3001-5; Brodeur, B. et al., Monoclonal Antibody Production Techniques and Applications. Marcel Dekker, Inc., New York. 1987; 33:51-63).

In some embodiments, myeloma cells may be subjected to genetic manipulation. Such manipulation may be carried out using zinc-finger nuclease (ZFN) mutagenesis as described herein. Alternatively, transfection methods known in the art may be used. NS0 myeloma cells or other mouse myeloma cell lines may be used. For example, Sp2/0-Ag14 can be an alternative cell line for hybridoma development.

Transcription Activator-Like Effector Nucleases (TALENs)-induced gene editing provides an alternative gene knock out method. TALENs are artificial restriction enzymes generated by fusing the TAL effector DNA binding domain to a DNA cleavage domain. Similar to ZFNs, TALENs induce double-strand breaks at desired loci that can be repaired by error-prone NHEJ to yield insertions/deletions at the break sites (Wood, A. J. et al., Targeted genome editing across species using ZFNs and TALENs. Science. 2011 Jul. 15; 333(6040):307). Cellectis Bioresearch (Cambridge, Mass.) provides the service of TALEN design and plasmid construction. The culture medium in which the hybridoma cells are cultured can then be assayed for the presence of monoclonal antibodies. Preferably, the binding specificity (i.e., specific immunoreactivity) of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known by those skilled in the art. The binding specificity of the monoclonal antibody can, for example, be determined by Scatchard analysis (Munson, P. J. et al., *Ligand: a versatile computerized approach for characterization of ligand-binding systems*. Anal Biochem. 1980 Sep. 1; 107(1):220-39). In some cases, antibody specificity for regions of a given antigen may be characterized by chemically modifying the antigens prior to assaying for antibody binding. In one example, periodate treatment may be used to destroy the C6 side chain of sialic acids. Assays may be conducted with and without periodate treatment to reveal whether or not binding in untreated samples is sialic acid-specific. In some cases, antigens having 9-O-acetylated sialic acid may be subjected to mild base treatment (e.g. with 0.1 M NaOH) to destroy 9-O-acetyl groups. Assays may be conducted with and without mild base treatment to reveal whether or not binding in untreated samples depends on 9-O-acetylation of sialic acid.

After the desired hybridoma cells are identified, the clones may be subcloned by limiting dilution procedures and grown by standard methods. Suitable culture media for this purpose include, for example, Dulbecco's Modified Eagle's Medium or RPMI-1640 medium. Alternatively, the hybridoma cells may be grown in vivo as ascites in a mammal.

Alternative methods to clone hybridomas may include those provided by kits from STEMCELL™ Technologies (Vancouver, BC, Canada), e.g. CLONACELL™-HY kit, containing methylcellulose-based semi-solid medium and other media and reagents, to support the selection and growth of hybridoma clones. However, the media in this kit contain FCS, which provides an exogenous source for Neu5Gc incorporation. Though the machinery for endogenous Neu5Gc synthesis is destroyed in $Cmah^{-/-}$ hybridoma, Neu5Gc incorporated from the culture media may also pose a problem in some cases (Bardor, M. et al., Mechanism of uptake and incorporation of the non-human sialic acid N-glycolylneuraminic acid into human cells. J Biol Chem. 2005. 280: 4228-4237). In such instances, the culture media may be supplemented with Neu5Ac to eliminate Neu5Gc incorporation by metabolic competition (Ghaderi, D. et al., Implications of the presence of N-glycolylneuraminic acid in recombinant therapeutic glycoproteins. Nat Biotechnol. 2010. 28: 863-867).

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In another embodiment, the monoclonal antibodies of the present invention can also be made by recombinant DNA methods, such as those described in U.S. Pat. No. 4,816,567, which is hereby incorporated by reference in its entirety. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of DNA. Once isolated, the DNA can be placed into expression vectors, which are then transfected into host cells. Host cells may include, but are not limited to HEK293 cells, HEK293T cells, simian COS cells, Chinese hamster ovary (CHO) cells, and myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

In some embodiments, antibodies of the present invention (e.g., glycan-interacting antibodies) may be produced by various procedures known by those skilled in the art. For the production of polyclonal antibodies in vivo, host animals, such as rabbits, rats, mice, cows, horses, donkeys, chickens, monkeys, sheep or goats, are immunized with either free or carrier-coupled antigens, for example, by intraperitoneal and/or intradermal injection. In some embodiments, injection material may be an emulsion containing about 100 µg of antigen or carrier protein. In some embodiments, injection materials may include a glycan-rich composition such as non-human mammalian submaxillary mucin in solution. Various adjuvants can also be used to increase the immunological response, depending on the host species. Adjuvants include, but are not limited to, Freund's (complete and incomplete), mineral gels such as aluminum hydroxide, surface active substances such as lysolecithin, pluronic polyols, polyanions, peptides, oil emulsions, TITERMAX® (CytRx Corp, Los Angeles, Calif.), keyhole limpet hemocyanins, dinitrophenol, and potentially useful human adjuvants such as BCG (bacille Calmette-Guerin) and *Corynebacterium parvum*. Such adjuvants are also well known in the art. Several booster injections may be needed, for instance, at intervals of about two weeks, to provide a useful titer of antibody which can be detected, for example, by ELISA assay using glycans and/or free peptide adsorbed to a solid surface. The titer of antibodies in serum from an immunized animal can be increased by selection of antibodies, e.g., by adsorption of antigens onto a solid support and elution of the selected antibodies according to methods well known in the art.

Glycan-interacting antibodies, variants and fragments thereof may be selected and produced using high throughput methods of discovery. In one embodiment, glycan-interacting antibodies that include synthetic antibodies, variants and fragments thereof are produced through the use of display libraries. The term "display" as used herein, refers to the expression or "display" of proteins or peptides on the surface of a given host. The term "library" as used herein, refers to a collection of unique cDNA sequences and/or the proteins that are encoded by them. A library may contain from as little as two unique cDNAs to hundreds of billions of unique cDNAs. In some embodiments, glycan-interacting antibodies that are synthetic antibodies are produced using antibody display libraries or antibody fragment display libraries. The term "antibody fragment display library" as used herein, refers to a display library wherein each member encodes an antibody fragment containing at least one variable region of an antibody. Such antibody fragments are preferably Fab fragments, but other antibody fragments such as single-chain variable fragments (scFvs) are contemplated as well. In a Fab antibody fragment library, each Fab encoded may be identical except for the amino acid sequence contained within the variable loops of the complementarity determining regions (CDRs) of the Fab fragment. In an alternative or additional embodiment, amino acid sequences within the individual $V_H$ and/or $V_L$ regions may differ as well.

Display libraries may be expressed in a number of possible hosts including, but not limited to yeast, bacteriophage, bacteria and retroviruses. Additional display technologies that may be used include ribosome-display, microbead-display and protein-DNA linkage techniques. In a preferred embodiment, Fab display libraries are expressed in yeast or in bacteriophages (also referred to herein as "phages" or "phage particles". When expressed, the Fabs decorate the surface of the phage or yeast where they can interact with a given antigen. An antigen that includes a glycan or other antigen from a desired target may be used to select phage particles or yeast cells expressing antibody fragments with the highest affinity for that antigen. The DNA sequence encoding the CDR of the bound antibody fragment can then be determined through sequencing using the bound particle or cell. In one embodiment, positive selection is used in the development of antibodies. In some embodiments, negative selection is utilized in the development of antibodies. In some embodiments, both positive and negative selection methods are utilized during multiple rounds of selection in the development of antibodies using display libraries.

In yeast display, cDNA encoding different antibody fragments are introduced into yeast cells where they are expressed and the antibody fragments are "displayed" on the cell surface as described by Chao et al. (Chao, G. et al., *Isolating and engineering human antibodies using yeast surface display*. Nat Protoc. 2006; 1(2):755-68). In yeast surface display, expressed antibody fragments may contain an additional domain that includes the yeast agglutinin protein, Aga2p. This domain allows the antibody fragment fusion protein to attach to the outer surface of the yeast cell through the formation of disulfide bonds with surface-expressed Aga1p. The result is a yeast cell, coated in a particular antibody fragment. Display libraries of cDNA encoding these antibody fragments are utilized initially in which the antibody fragments each have a unique sequence. These fusion proteins are expressed on the cell surface of millions of yeast cells where they can interact with a desired antigenic target antigen, incubated with the cells. Target antigens may be covalently or otherwise modified with a chemical or magnetic group to allow for efficient cell sorting after successful binding with a suitable antibody fragment takes place. Recovery may be by way of magnetic-activated cell sorting (MACS), fluorescence-activated cell sorting (FACS) or other cell sorting methods known in the art. Once a subpopulation of yeast cells is selected, the corresponding plasmids may be analyzed to determine the CDR sequence.

Bacteriophage display technology typically utilizes filamentous phage including, but not limited to fd, F1 and M13 virions. Such strains are non-lytic, allowing for continued propagation of the host and increased viral titers. Examples of phage display methods that can be used to make the antibodies of the present invention include those disclosed in Miersch et al. (Miersch, S. et al., *Synthetic antibodies: Concepts, potential and practical considerations*. Methods. 2012 August; 57(4):486-98), Bradbury et al. (Bradbury, A. R. et al., *Beyond natural antibodies: the power of in vitro display technologies*. Nat Biotechnol. 2011 March; 29(3): 245-54), Brinkman et al. (Brinkmann, U. et al., *Phage display of disulfide-stabilized Fv fragments*. J Immunol Methods. 1995 May 11; 182(1):41-50); Ames et al. (Ames, R. S. et al., *Conversion of murine Fabs isolated from a combinatorial phage display library to full length immunoglobulins*. J Immunol Methods. 1995 Aug. 18; 184(2):177-86); Kettleborough et al. (Kettleborough, C. A. et al., *Isolation of tumor cell-specific single-chain Fv from immunized mice using phage-antibody libraries and the re-construction of whole antibodies from these antibody fragments*. Eur J Immunol. 1994 April; 24(4):952-8); Persic et al. (Persic, L. et al., *An integrated vector system for the eukaryotic expression of antibodies or their fragments after selection from phage display libraries*. Gene. 1997 Mar. 10; 187(1):9-18); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5, 969,108, each of which is incorporated herein by reference in its entirety. Antibody fragment expression on bacteriophages may be carried out by inserting the cDNA encoding the fragment into the gene expressing a viral coat protein. The viral coat of filamentous bacteriophages is made up of five coat proteins, encoded by a single-stranded genome. Coat protein pIII is the preferred protein for antibody fragment expression, typically at the N-terminus. If antibody fragment expression compromises the function of pIII, viral function may be restored through coexpression of a wild type pIII, although such expression will reduce the number of antibody fragments expressed on the viral coat, but may enhance access to the antibody fragment by the target antigen. Expression of viral as well as antibody fragment proteins may alternatively be encoded on multiple plasmids. This method may be used to reduce the overall size of infective plasmids and enhance the transformation efficiency.

As described above, after selection of a host expressing a high affinity antibody or antibody fragment, (e.g., glycan-interacting antibodies) the coding regions from the antibody or antibody fragment can be isolated and used to generate whole antibodies, including human antibodies, or any other desired antigen binding fragment, and expressed in any desired host, including mammalian cells, insect cells, plant cells, yeast, and bacteria, e.g., as described in detail below.

The DNA sequence encoding a high affinity antibody can be mutated for additional rounds of selection in a process known as affinity maturation. The term "affinity maturation", as used herein, refers to a method whereby antibodies are produced with increasing affinity for a given antigen through successive rounds of mutation and selection of antibody- or antibody fragment-encoding cDNA sequences. In some cases, this process is carried out in vitro. To accomplish this, amplification of CDR coding sequences may be carried out using error-prone PCR to produce millions of copies containing mutations including, but not limited to point mutations, regional mutations, insertional mutations and deletional mutations. As used herein, the term "point mutation" refers to a nucleic acid mutation in which one nucleotide within a nucleotide sequence is changed to a different nucleotide. As used herein, the term "regional mutation" refers to a nucleic acid mutation in which two or more consecutive nucleotides are changed to different nucleotides. As used herein, the term "insertional mutation" refers to a nucleic acid mutation in which one or more nucleotides are inserted into a nucleotide sequence. As used herein, the term "deletional mutation" refers to a nucleic acid mutation in which one or more nucleotides are removed from a nucleotide sequence. Insertional or deletional mutations may include the complete replacement of an entire codon or the change of one codon to another by altering one or two nucleotides of the starting codon.

Mutagenesis may be carried out on CDR-encoding cDNA sequences to create millions of mutants with singular mutations in CDR heavy and light chain regions. In another approach, random mutations are introduced only at CDR residues most likely to improve affinity. These newly generated mutagenic libraries can be used to repeat the process to screen for clones that encode antibody fragments with even higher affinity for the target antigen. Continued rounds of mutation and selection promote the synthesis of clones with greater and greater affinity (Chao, G. et al., *Isolating and engineering human antibodies using yeast surface display*. Nat Protoc. 2006; 1(2):755-68).

Examples of techniques that can be used to produce antibodies and antibody fragments, such as Fabs and scFvs, include those described in U.S. Pat. Nos. 4,946,778 and 5,258,498; Miersch et al. (Miersch, S. et al., Synthetic antibodies: Concepts, potential and practical considerations. Methods. 2012 August; 57(4):486-98), Chao et al. (Chao, G. et al., Isolating and engineering human antibodies using yeast surface display. Nat Protoc. 2006; 1(2):755-68), Huston et al. (Huston, J. S. et al., *Protein engineering of single-chain Fv analogs and fusion proteins*. Methods Enzymol. 1991; 203:46-88); Shu et al. (Shu, L. et al., Secretion of a single-gene-encoded immunoglobulin from myeloma cells. Proc Natl Acad Sci USA. 1993 Sep. 1; 90(17):7995-9); and Skerra et al. (Skerra, A. et al., *Assembly of a functional immunoglobulin Fv fragment in Escherichia coli*. Science. 1988 May 20; 240(4855):1038-41), each of which is incorporated herein by reference in its entirety.

For some uses, including the in vivo use of antibodies (e.g., glycan-interacting antibodies) in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal immunoglobulin and a human immunoglobulin constant region. Methods for producing chimeric antibodies are known in the art. (Morrison, S. L., *Transfectomas provide novel chimeric antibodies*. Science. 1985 Sep. 20; 229 (4719):1202-7; Gillies, S. D. et al., *High-level expression of chimeric antibodies using adapted cDNA variable region cassettes*. J Immunol Methods. 1989 Dec. 20; 125(1-2):191-202.; and U.S. Pat. Nos. 5,807,715; 4,816,567; and 4,816,397, which are incorporated herein by reference in their entirety).

Humanized antibodies are antibody molecules from non-human species that bind to the desired antigen and have one or more complementarity determining regions (CDRs) from the nonhuman species and framework regions from a human immunoglobulin molecule. Often, framework residues in the human framework regions are substituted with corresponding residues from the CDR and framework regions of the donor antibody to alter, preferably improve, antigen binding. These framework substitutions are identified by methods well known in the art, e.g., by modeling of the interactions of the CDR and framework residues to identify framework residues important for antigen binding, and by sequence comparison to identify unusual framework residues at particular positions. (U.S. Pat. Nos. 5,693,762 and 5,585,089; Riechmann, L. et al., Reshaping human antibodies for therapy. Nature. 1988 Mar. 24; 332(6162):323-7, which are incorporated herein by reference in their entireties). Antibodies can be humanized using a variety of techniques known in the art, including, for example, CDR-grafting (EP 239,400; PCT publication WO 91/09967; U.S. Pat. Nos. 5,225,539; 5,530,101; and 5,585,089); veneering or resurfacing (EP 592,106; EP 519,596; Padlan, E. A., *A possible procedure for reducing the immunogenicity of antibody variable domains while preserving their ligand-binding properties*. Mol Immunol. 1991 April-May; 28(4-5):489-98; Studnicka, G. M. et al., *Human-engineered monoclonal antibodies retain full specific binding activity by preserving non-CDR complementarity-modulating residues*. Protein Eng. 1994 June; 7(6):805-14; Roguska, M. A. et al., *Humanization of murine monoclonal antibodies through variable domain resurfacing*. Proc Natl Acad Sci USA. 1994 Feb. 1; 91(3):969-73); and chain shuffling (U.S. Pat. No. 5,565,332); each of which is incorporated herein by reference in their entirety. Humanized antibodies of the present invention may be developed for desired binding specificity, complement-dependent cytotoxicity, and antibody-dependent cellular-mediated cytotoxicity, etc.

In some cases, human frameworks are selected by alignment of donor antibody sequences with human framework sequences to find human framework candidates with the highest level of homology. In some cases, framework regions may be selected from more than one human framework candidate (e.g., framework regions 1-3 may be selected from one candidate and framework region 4 may be selected from an alternative candidate). In some cases, framework regions may be selected from human consensus sequences to avoid the risk of including immunogenic epitopes created by somatic mutations. Consensus sequences are sequences formed by comparing many sequences and adopting most commonly occurring residues at each position. In some cases, human frameworks may be selected from human germline sequences. These may be identified through database searching (e.g., using the NCBI protein database or other databases).

Light and heavy chain human frameworks may be selected from the same or from different clones. Light and heavy chains derived from the same clone have a greater likelihood of associating to form binding sites that are functional; however, the conserved nature of the interface between heavy and light chains typically allows light and heavy chains from different clones to associate and be functional. Frequency of pairing between human light and heavy chain frameworks can be reviewed, for example, in Tiller et al., 2013. MAbs. 5(3): 445-70, the contents of which are herein incorporated by reference in their entirety.

Residues in humanized antibody sequences may be considered for "back-mutation" to improve or restore antibody affinity lost during humanization. Back-mutation involves changing residues altered during humanization back to those present in the original non-human antibody sequence. Residues that are candidates for back-mutation may be identified, for example, by comparison to standard conformations found in canonical antibody structures (see Al-Lazikani, et al., 1997. J. Mol. Biol. 273: 927-48, the contents of which are herein incorporated by reference in their entirety). Unusual canonical residues may be identified and targeted for back-mutation. In some cases, residues that are candidates for back-mutation may be "Vernier residues", a term used to refer to residues in contact with CDRs. These residues have a higher likelihood of impacting CDR positioning and conformation, and therefor antibody affinity and/or specificity (Strohl, W. R. Therapeutic Antibody Engineering. Woodhead Publishing, Philadelphia Pa. 2012. Ch. 6, p 117). In some cases, human framework regions are kept constant and CDRs from donor antibodies are back-mutated to fit human CDR regions while maintaining binding through empirical methods.

Completely human antibodies (e.g., glycan-interacting antibodies) are particularly desirable for therapeutic treatment of human patients, so as to avoid or alleviate immune reaction to foreign protein. Human antibodies can be made by a variety of methods known in the art, including the antibody display methods described above, using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies (e.g., glycan-interacting antibodies) can also be produced using transgenic mice which are incapable of expressing functional endogenous immunoglobulins, but which can express human immunoglobulin polynucleotides. For example, the human heavy and light chain immunoglobulin polynucleotide complexes can be introduced randomly, or by homologous recombination, into mouse embryonic stem cells. Alternatively, the human variable region, constant region, and diversity region may be introduced into mouse embryonic stem cells, in addition to the human heavy and light chain polynucleotides. The mouse heavy and light chain immunoglobulin polynucleotides can be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a glycan, glycoconjugate and/or polypeptide of the invention.

Thus, using such a technique, it is possible to produce useful human IgG, IgA, IgM, IgD and IgE antibodies. For an overview of the technology for producing human antibodies, see Lonberg and Huszar (Lonberg, N. et al., *Human antibodies from transgenic mice*. Int Rev Immunol. 1995; 13(1): 65-93). For a detailed discussion of the technology for producing human antibodies and human monoclonal antibodies and protocols for producing such antibodies, see, e.g., PCT publications WO 98/24893; WO 92/01047; WO 96/34096; WO 96/33735; U.S. Pat. Nos. 5,413,923; 5,625, 126; 5,633,425; 5,569,825; 5,661,016; 5,545,806; 5,814, 318; 5,885,793; 5,916,771; 5,939,598; 6,075,181; and 6,114, 598, each of which are incorporated by reference herein in their entirety. In addition, companies such as Abgenix, Inc. (Fremont, Calif.), Protein Design Labs, Inc. (Mountain View, Calif.) and Genpharm (San Jose, Calif.) can be engaged to provide human antibodies directed against a selected antigen using technology similar to the above described technologies.

Once an antibody molecule of the present invention has been produced by an animal, a cell line, chemically synthesized, or recombinantly expressed, it can be purified (i.e., isolated) by any method known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The affinity between an antibody and a target or ligand (such as an antigen used to generate a given antibody) may be measured in terms of $K_D$ using one or more binding assays as described herein. Depending on the desired application for a given antibody, varying $K_D$ values may be desirable. High affinity antibodies typically form ligand bonds with a $K_D$ of about $10^{-5}$ M or less, e.g. about $10^{-6}$ M or less, about $10^{-7}$ M or less, about $10^{-8}$ M or less, about $10^{-9}$ M or less, about $10^{-19}$ M or less, about $10^{-11}$ M or less or about $10^{-12}$ M or less.

In some embodiments, antibodies of the invention may be characterized according to their half maximal effective or inhibitory concentration ($EC_{50}$ or $IC_{50}$, respectively). These values generally represent the concentration of antibody needed to achieve half of a desired effect. In some cases, the $EC_{50}$ represents the concentration of antibody required to reach half of the saturation level in an antibody binding assay (where the saturation level is the concentration of antibody at which additional antibody does not result in higher detection levels). Such $EC_{50}$ values may be from about 0.001 nM to about 0.01 nM, from about 0.005 nM to about 0.05 nM, from about 0.01 nM to about 1 nM, from about 0.05 nM to about 5 nM, from about 0.1 nM to about 10 nM, from about 0.5 nM to about 25 nM, from about 1 nM to about 50 nM, from about 5 nM to about 75 nM, from about 10 nM to about 100 nM, from about 25 nM to about 250 nM, from about 200 nM to about 1000 nM or more than 1000 nM. In some cases, the $IC_{50}$ represents the concentration of antibody necessary to inhibit cells expressing STn (e.g. kill, reduce proliferation and/or reduce one or more cell function) at a level equal to half of the maximum inhibition observed with the highest concentrations of antibody. Such $IC_{50}$ values may be from about 0.001 nM to about 0.01 nM, from about 0.005 nM to about 0.05 nM, from about 0.01 nM to about 1 nM, from about 0.05 nM to about 5 nM, from about 0.1 nM to about 10 nM, from about 0.5 nM to about 25 nM, from about 1 nM to about 50 nM, from about 5 nM to about 75 nM, from about 10 nM to about 100 nM, from about 25 nM to about 250 nM, from about 200 nM to about 1000 nM or more than 1000 nM.

In some embodiments, antibodies taught in the present disclosure may be tested for their ability to target patient-derived cancer cells and/or cancer stem cells (CSCs). According to such embodiments, patient-derived cancer cells may be cultured in vitro and antibodies of the present disclosure may be used to target such cells.

In other embodiments, patient-derived cells may be used to produce patient-derived xenograft (PDX) tumors. In some cases, pieces of primary or metastatic solid tumors maintained as tissue structures may be collected by surgery or biopsy procedures. In some cases, fluid drained from malignant ascites or pleural effusions may be used. Tumors may be implanted as pieces or single cell suspensions, either alone or in some studies coated with MATRIGEL® (Corning Life Sciences, Corning, N.Y.) or mixed with human fibroblasts or mesenchymal stem cells. Sites of implantation may include the dorsal region of mice (subcutaneous implantation), although implantation in the same organ as the original tumor may be an option (orthotopic implantation, i.e. pancreas, oral cavity, ovary, mammary fat pad, brain, etc.). In addition, independently of the tumor origin, some approaches may include implanting primary tumors in the renal capsule in an effort to increase engraftment success rates. A variety of mouse strains having different degrees of immunosuppression may be used in such studies. For hormone sensitive tumors, some studies may use hormone supplementation with the intent of increasing engraftment rates. In some embodiments, PDX tumors may be generated in non-obese diabetic/severe combined immunodeficiency (NOD/SCID) mice. Antibodies may be administered to mice with PDX tumors and the effect on tumor volume may be analyzed. In some cases, PDX tumors may be dissected, subjected to cellular dissociation, and the resulting cells grown in culture. The ability of antibodies of the present disclosure to target these cells may be assessed in vitro.

The preparation of antibodies, whether monoclonal or polyclonal, is known in the art. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999.

Targets

Glycan-interacting antibodies of the present invention may exert their effects via binding (reversibly or irreversibly) to one or more glycan or glycan-associated or glycan-related targets. In some embodiments, glycan-interacting antibodies can be prepared from any region of the targets taught herein. In some embodiments, targets of the present invention include glycans. Glycans used for generating antibodies may include a chain of sugars having at least 2, at least 3, at least 4, at least 5, at least 6, at least 7, at least 8, at least 9, at least 10, at least 11, at least 12, at least 13, at least 14, at least 15, at least 16, at least 17, at least 18, at least 19 or at least 20 residues. Some glycans used for generating antibodies may include from about 2 residues to about 5 residues.

In some embodiments, glycan-interacting antibody target antigens include sialic acids. N-acetylneuraminic acid (Neu5Ac) and N-glycolylneuraminic acid (Neu5Gc) are the major sialic acids on mammalian cell surfaces. Of these, Neu5Ac is naturally produced in humans. Neu5Gc is naturally produced in most mammals with the exception of humans due to a mutation in the cytidine monophosphate (CMP)-N-acetylneuraminic acid hydroxylase (CMAH) gene responsible for CMP-Neu5Gc production from CMP-Neu5Ac. Neu5Gc in humans is in fact immunogenic with nearly all humans expressing anti-Neu5Gc antibodies. Despite a lack of production, most human systems include some level of Neu5Gc due to dietary intake. These foreign products are subsequently incorporated into human glycoproteins. Such glycoproteins are contemplated as targets of the invention. Glycan target antigens of the present invention may include, but are not limited to those listed in Table 1.

TABLE 1

Glycan target antigens
Glycan

GalNAcα-R
Galα1,3Galβ1,4GlcNAcβ-R
Galβ1,3GalNAcβ-R
Galβ1,3GlcNAcα-R
Galβ1,3GlcNAcβ1,3Galβ1,4Glcβ-R
Galβ1,3GlcNAcβ-R
Galβ1,4GlcNAc6Sβ-R
Galβ1,4GlcNAcβ-R
Galβ1,4Glcβ-R
KDNα2,8Neu5Acα2,3Galβ1,4Glcβ-R
KDNα2,8Neu5Gcα2,3Galβ1,4Glcβ-R
Neu5,9Ac2α2,3Galβ1,3GalNAcα-R
Neu5,9Ac2α2,3Galβ1,3GalNAcβ-R
Neu5,9Ac2α2,3Galβ1,3GlcNAcβ-R
Neu5,9Ac2α2,3Galβ1,4GlcNAcβ-R
Neu5,9Ac2α2,3Galβ1,4Glcβ-R
Neu5,9Ac2α2,3Galβ-R
Neu5,9Ac2α2,6GalNAcα-R
Neu5,9Ac2α2,6Galβ1,4GlcNAcβ-R
Neu5,9Ac2α2,6Galβ1,4Glcβ-R
Neu5,9Ac2α2,6Galβ-R
Neu5Acα2,3Galβ1,3GalNAcα-R
Neu5Acα2,3Galβ1,3GalNAcβ-R

TABLE 1-continued

Glycan target antigens
Glycan

Neu5Acα2,3Galβ1,3GlcNAcβ1,3Galβ1,4Glcβ-R
Neu5Acα2,3Galβ1,3GlcNAcβ-R
Neu5Acα2,3Galβ1,4(Fucα1,3)GlcNAc6Sβ-R
Neu5Acα2,3Galβ1,4(Fucα1,3)GlcNAcβ-R
Neu5Acα2,3Galβ1,4GlcNAc6Sβ-R
Neu5Acα2,3Galβ1,4GlcNAcβ-R
Neu5Acα2,3Galβ1,4Glcβ-R
Neu5Acα2,3Galβ-R
Neu5Acα2,6(KDNα2,3)Galβ1,4Glcβ-R
Neu5Acα2,6(Neu5Acα2,3)Galβ1,4Glcβ-R
Neu5Acα2,6(Neu5Gcα2,3)Galβ1,4Glcβ-R
Neu5Acα2,6GalNAcα-R
Neu5Acα2,6Galβ1,4GlcNAcβ-R
Neu5Acα2,6Galβ1,4Glcβ-R
Neu5Acα2,6Galβ-R
Neu5Acα2,8KDNα2,6Galβ1,4Glcβ-R
Neu5Acα2,8Neu5Acα2,3Galβ1,4Glcβ-R
Neu5Acα2,8Neu5Acα2,3Galβ1,4Glcβ-R
Neu5Acα2,8Neu5Acα2,6Galβ1,4Glcβ-R
Neu5Acα2,8Neu5Acα2,8Neu5Acα2,3Galβ1,4Glcβ-R
Neu5Acα2,8Neu5Acα2,8Neu5Acα2,3Galβ1,4Glcβ-R
Neu5Acα2,8Neu5Gcα2,3Galβ1,4Glcβ-R
Neu5Acα2,8Neu5Gcα2,6Galβ1,4Glcβ-R
Neu5Gc9Acα2,3Galβ1,4Glcβ-R
Neu5Gc9Acα2,6Galβ1,4Glcβ-R
Neu5Gc9Acα2,3Galβ1,3GalNAcα-R
Neu5Gc9Acα2,3Galβ1,3GalNAcβ-R
Neu5Gc9Acα2,3Galβ1,3GlcNAcβ-R
Neu5Gc9Acα2,3Galβ1,4GlcNAcβ-R
Neu5Gc9Acα2,3Galβ-R
Neu5Gc9Acα2,6GalNAcα-R
Neu5Gc9Acα2,6Galβ1,4GlcNAcβ-R
Neu5Gc9Acα2,6Galβ-R
Neu5GcOMeα2,8Neu5Acα2,3Galβ1,4Glcβ-R
Neu5Gcα2,3Galβ1,3GalNAcα-R
Neu5Gcα2,3Galβ1,3GalNAcβ-R
Neu5Gcα2,3Galβ1,3GlcNAcβ1,3Galβ1,4Glcβ-R
Neu5Gcα2,3Galβ1,3GlcNAcβ-R
Neu5Gcα2,3Galβ1,4(Fucα1,3)GlcNAc6Sβ-R
Neu5Gcα2,3Galβ1,4(Fucα1,3)GlcNAcβ-R
Neu5Gcα2,3Galβ1,4GlcNAc6Sβ-R
Neu5Gcα2,3Galβ1,4GlcNAcβ-R
Neu5Gcα2,3Galβ1,4Glcβ-R
Neu5Gcα2,3Galβ-R
Neu5Gcα2,6GalNAcα-R
Neu5Gcα2,6Galβ1,4GlcNAcβ-R
Neu5Gcα2,6Galβ1,4Glcβ-R
Neu5Gcα2,6Galβ-R
Neu5Gcα2,8Neu5Acα2,3Galβ1,4Glcβ-R
Neu5Gcα2,8Neu5Gcα2,3Galβ1,4Glcβ-R

The following abbreviations are used herein: Glc—glucose, Gal—galactose, GlcNAc—N-acetylglucosamine, GalNAc—N-acetylgalactosamine, GlcNAc6S—6-Sulfo-N-acetylglucosamine, KDN—2-keto-3-deoxy-D-glycero-D-galactononoic acid, Neu5,9Ac2-N-acetyl-9-O-acetylneuraminic acid, Fuc—fucose and Neu5GcOMe—2-O-methyl-N-glycolylneuraminic acid. O-glycosidic bonds are present between each residue in the glycans listed with α and β indicating the relative stoichiometry between the two residues joined by the bond, wherein α indicates an axial orientation and β indicates an equatorial orientation. The numbers following α and/or β, in the format x,x, indicate the carbon number of each of the carbons from each of the adjoined residues that participate in bond formation. While the glycans listed in Table 1 represent individual glycan target antigens contemplated, the present invention also includes embodiments wherein the above presented glycans include different combinations of α and β-oriented O-glycosidic bonds than the ones presented. Also in Table 1, R represents an entity that the glycan may be coupled with. In some embodiments, R is a protein wherein the glycan is linked typically to a serine or threonine residue. In some embodiments, R is a linker molecule used to join the glycan to a substrate, such as in a glycan array. In some embodiments, R may be a linker with the formula of —(CH$_2$)$_2$CH$_2$NH$_2$ or —(CH$_2$)$_3$NHCOCH$_2$(OCH$_2$CH$_2$)$_6$NH$_2$. In some embodiments, R may be biotin, albumin, ProNH$_2$, —CH—, —OH, —OCH$_3$, —OCH$_2$CH$_3$, —H, hydrido, hydroxy, alkoxyl, oxygen, carbon, sulfur, nitrogen, polyacrylamide, phosphorus, NH$_2$, ProNH$_2$=O(CH$_2$)$_2$CH$_2$NH$_2$, (OCH$_2$CH$_2$)$_6$NH$_2$, O(CH$_2$)$_3$NHCOCH$_2$(OCH$_2$CH$_2$)$_6$NH$_2$, the fluorescent labels 2-aminobenzamide (AB) and/or 2-aminobenzoid acid (AA), 2-aminobenzamide analog that contains an alkyl amine (AEAB), aminooxy-groups, methylaminooxygroups, hydrazide groups, amino lipid 1,2-dihexadecyl-sn-glycero-3-phosphoethanolamine (DHPE), aminooxy (AO) functionalized DHPE and glycosylphosphatidylinositol (GPI). Without intending to limit the source or nature of R, this may include structures that affect the physical spacing of glycan residue. In some embodiments, the R group may include a combination of the R groups presented here, e.g. a biotinylated polyacrylamide. In some embodiments, the R group in combination with underlying substrates effect glycan residue spacing.

Glycan targets of the present invention may include one or more regions of antibody recognition. As used herein, the term "region of antibody recognition" refers to a segment located on any part of the molecule, an attached group or located on a region of interaction between the glycan and another molecule, including, but not limited to another glycan, protein, membrane, cell surface structure, or extracellular matrix component. In some embodiments, regions of antibody recognition are located at interchain target sites, wherein the term "interchain" means within the present polymeric chain Interchain target sites may include regions of antibody recognition having 1, 2, 3, 4, 5, 6, 7, 8, 9 or at least 10 residues, bonds between residues or combinations of residues and bonds. In some embodiments, regions of antibody recognition are located at regions of interaction between one or more glycan chains. Such regions may be between 2, 3, 4 or at least 5 glycan chains.

In some embodiments, regions of antibody recognition are located at regions of interaction between glycan branch chains connected to a common parent chain. In some embodiments, regions of antibody recognition are located at regions of interaction between a glycan branch chain and a parent chain. In some embodiments, regions of antibody recognition are located at regions of interaction between glycans and proteins. Such regions of interaction may include chemical bonds between the glycan and the protein, including, but not limited to covalent bonds, ionic bonds, hydrostatic bonds, hydrophobic bonds and hydrogen bonds. In some embodiments, regions of antibody recognition are located at regions of interaction between glycans and other biomolecules including, but not limited to lipids and nucleic acids. Such regions of interaction may include chemical bonds between the glycan and the biomolecule, including, but not limited to covalent bonds, ionic bonds, hydrostatic bonds, hydrophobic bonds and hydrogen bonds.

In some embodiments, glycan targets of the present invention are components of glycoconjugates. As used herein, the term "glycoconjugate" refers to any entity joined with a glycan moiety. In some embodiments, glycoconjugates are glycolipids. As used herein, the term "glycolipid" refers to a class of lipids wherein a carbohydrate moiety is covalently attached. In some embodiments, carbohydrate moieties present on glycolipids may be glycans. In some embodiments, lipid components of glycolipids include cer- amide moieties. Examples of glycolipids contemplated as targets of the present invention include, but are not limited to glyceroglycolipids (including, but not limited to galactolipids and sulfolipids), glycosphingolipids (including, but not limited to cerebrosides (e.g., galactocerebrosides, glucocerebrosides and sulfatides), gangliosides, globosides and glycophosphosphingolipids) and glycosylphosphatidylinositols. When located within cell membranes, glycan moieties of glycolipids are located on the extracellular side of the membrane where they may interact with other cells as well as cell signaling ligands (Maccioni, H. J. et al., *Organization of the synthesis of glycolipid oligosaccharides in the Golgi complex.* FEBS Lett. 2011 Jun. 6; 585(11):1691-8).

In some embodiments, glycoconjugate targets of the present invention are glycoprotein and/or proteoglycans. Glycoproteins refer to any proteins that are covalently bonded with glycans. Proteoglycans are a class of proteins that are heavily glycosylated with glycans that often carry a negative charge. This property makes them very hydrophilic and important components of connective tissue.

Cancer-Related Targets

In some embodiments, targets of the present invention are cancer-related antigens or epitopes. As used herein, the term "cancer-related" is used to describe entities that may be in some way associated with cancer, cancerous cells and/or cancerous tissues. Many cancer-related antigens or epitopes that include glycans have been identified that are expressed in correlation with tumor cells (Heimburg-Molinaro, J. et al., Cancer vaccines and carbohydrate epitopes. Vaccine. 2011 Nov. 8; 29(48):8802-26). These are referred to herein as "tumor-associated carbohydrate antigens" or "TACAs." TACAs include, but are not limited to mucin-related antigens [including, but not limited to Tn, Sialyl Tn (STn) and Thomsen-Friedenreich antigen], blood group Lewis related antigens [including, but not limited to Lewis$^Y$ (Le$^Y$), Lewis$^X$ (Le$^X$), Sialyl Lewis$^X$ (SLe$^X$) and Sialyl Lewis$^A$ (SLe$^A$)], glycosphingolipid-related antigens [including, but not limited to Globo H, stage-specific embryonic antigen-3 (SSEA-3) and glycosphingolipids that include sialic acid], ganglioside-related antigens [including, but not limited to gangliosides GD2, GD3, GM2, fucosyl GM1 and Neu5GcGM3] and polysialic acid-related antigens. Many of such antigens are described in International Publication No. WO2015054600, the contents of which are herein incorporated by reference in their entirety.

In some embodiments, TACA targets of the present invention include Lewis blood group antigens. Lewis blood group antigens include a fucose residue linked to GlcNAc by an α1-3 linkage or an α1-4 linkage. They may be found on both glycolipids and glycoproteins. Lewis blood group antigens may be found in the body fluid of individuals that are secretors of these antigens. Their appearance on red cells is due to absorption of Lewis antigens from the serum by the red cells.

In some embodiments, TACA targets of the present invention include Le$^Y$. Le$^Y$ (also known as CD174) is made up of Galβ1,4GlcNAC having α1,2- as well as α1,3-linked fucose residues yielding the Fucα(1,2)Galβ(1,4)Fucα(1,3)GlcNAc epitope. It is synthesized from the H antigen by α1,3 fucosyltransferases which attach the α1,3 fucose to the GlcNAc residue of the parent chain. Le$^Y$ may be expressed in a variety of cancers including, but not limited to ovarian, breast, prostate, colon, lung and epithelial. Due to its low expression level in normal tissues and elevated expression level in many cancers, the Le antigen is an attractive target for therapeutic antibodies.

In some embodiments, TACA targets of the present invention include Le$^X$. Le$^X$ includes the epitope Galβ1-4(Fucα1-3)GlcNAcβ-R. It is also known as CD15 and stage-specific embryonic antigen-1 (SSEA-1). This antigen was first recognized as being immunoreactive with sera taken from a mouse subjected to immunization with F9 teratocarcinoma cells. Le$^X$ was also found to correlate with embryonic development at specific stages. It is also expressed in a variety of tissues both in the presence and absence of cancer, but can also be found in breast and ovarian cancers where it is only expressed by cancerous cells.

In some embodiments, TACA targets of the present invention include SLe$^A$ and/or SLe$^X$. SLe$^A$ and SLe$^X$ are made up of structures Neu5Acα2-3Galβ1-3(Fucα1-4)GlcNAcβ-R and Neu5Acα2-3Galβ1-4(Fucα1-3)GlcNAcβ-R, respectively. Their expression is upregulated in cancer cells. The presence of these antigens in serum correlates with malignancy and poor prognosis. SLe$^X$ is mostly found as a mucin terminal epitope. It is expressed in a number of different cancers including breast, ovarian, melanoma, colon, liver, lung and prostate. In some embodiments of the present invention, SLe$^A$ and SLe$^X$ targets include Neu5Gc (referred to herein as GcSLe$^A$ and GcSLe$^X$, respectively).

In some cases, cancer-related targets of the invention may include mucins. Ishida et al demonstrate that interaction of MUC2 with dendritic cells (with anti-tumor activity) leads to dendritic cell apoptosis (Ishida, A. et al., 2008. Proteomics. 8: 3342-9, the contents of which are herein incorporated by reference in their entirety). In some aspects, the present invention provided anti-mucin antibodies to prevent dendritic cell apoptosis and support anti-tumor activity.

In some embodiments, TACA targets of the present invention include glycolipids and/or epitopes present on glycolipids, including, but not limited to glycosphingolipids. Glycosphingolipids include the lipid ceramide linked to a glycan by the ceramide hydroxyl group. On the cell membrane, glycosphingolipids form clusters referred to as "lipid rafts".

In some embodiments, TACA targets of the present invention include Globo H. Globo H is a cancer-related glycosphingolipid first identified in breast cancer cells. The glycan portion of Globo H includes Fucα(1-2)Galβ(1-3)GalNAcβ(1-3)Galα(1-4)Galβ(1-4)Glcβ(1). Although found in a number of normal epithelial tissues, Globo H has been identified in association with many tumor tissues including, but not limited to, small cell lung, breast, prostate, lung, pancreatic, gastric, ovarian and endometrial tumors.

In some embodiments, cancer-related glycosphingolipid targets of the present invention include gangliosides. Gangliosides are glycosphingolipids having one or more sialic acid. According to ganglioside nomenclature, G is used as an abbreviation for ganglioside. This abbreviation is followed by the letters M, D or T referring to the number of sialic acid residues attached (1, 2 or 3 respectively). Finally, the numbers 1, 2 or 3 are used to refer to the order of the distance each migrates when analyzed by thin layer chromatography (wherein 3 travels the greatest distance, followed by 2, and then 1). Gangliosides are known to be involved in cancer-related growth and metastasis and may be expressed on the cell surface of tumor cells. Gangliosides expressed on tumor cells may include, but are not limited to GD2, GD3, GM2 and fucosyl GM1 (also referred to herein as Fuc-GM1). In some embodiments of the present invention, glycan-interacting antibodies are directed toward GD3. GD3 is a regulator of cell growth. In some embodiments, GD3-directed antibodies are used to modulate cell growth and/or angiogenesis. In some embodiments, GD3-directed antibodies are used to modulate cell attachment. GD3 associated with some tumor cells may include 9-O-acetylated sialic acid residues (Mukherjee, K. et al., 2008. J Cell Biochem. 105: 724-34 and Mukherjee, K. et al., 2009. Biol Chem. 390: 325-35, the contents of each of which are herein incorporated by reference in their entirety). In some cases, antibodies of the invention are selective for 9-O-acetylated sialic acid residues. Some antibodies may be specific for 9-O-acetylated GD3s. Such antibodies may be used to target tumor cells expressing 9-O-acetylated GD3. In some embodiments of the present invention, glycan interacting antibodies are directed toward GM2. In some embodiments, GM2-directed antibodies are used to modulate cell to cell contact. In some embodiments, ganglioside targets of the present invention include Neu5Gc. In some embodiments, such targets may include a GM3 variant having Neu5Gc (referred to herein as GcGM3). The glycan component of GcGM3 is Neu5Gcα2-3Galβ1-4Glc. GcGM3 is a known component of tumor cells (Casadesus, A. V. et al., 2013. Glycoconj J. 30(7):687-99, the contents of which are herein incorporated by reference in their entirety).

In some embodiments, TACAs of the present disclosure include at least one Neu5Gc residue.

Recombinant Antibodies

Recombinant antibodies (e.g., glycan-interacting antibodies) of the invention may be generated using standard techniques known in the art. In some embodiments, recombinant antibodies may be anti-glycan antibodies. Further antibodies may be anti-STn antibodies (e.g. anti-GcSTn or anti-AcSTn antibodies). Recombinant antibodies of the invention may be produced using variable domains obtained from hybridoma cell-derived antibodies produced according to methods described herein. Heavy and light chain variable region cDNA sequences of antibodies may be determined using standard biochemical techniques. Total RNA may be extracted from antibody-producing hybridoma cells and converted to cDNA by reverse transcriptase (RT) polymerase chain reaction (PCR). PCR amplification may be carried out on resulting cDNA to amplify variable region genes. Such amplification may include the use of primers specific for amplification of heavy and light chain sequences. In other embodiments, recombinant antibodies may be produced using variable domains obtained from other sources. This includes the use of variable domains selected from one or more antibody fragment library, such as an scFv library used in antigen panning Resulting PCR products may then be subcloned into plasmids for sequence analysis. Once sequenced, antibody coding sequences may be placed into expression vectors. For humanization, coding sequences for human heavy and light chain constant domains may be used to substitute for homologous murine sequences. The resulting constructs may then be transfected into mammalian cells for large scale translation.

Anti-Tn Antibodies

In some embodiments, recombinant antibodies of the invention (e.g., glycan-interacting antibodies) may be anti-Tn antibodies. Such antibodies may bind to targets having Tn. Anti-Tn antibodies may be specific for Tn or may bind other modified forms of Tn, such as Tn linked to other moieties, including, but not limited to additional carbohydrate residues. In some cases, anti-Tn antibodies may be anti-sialyl-Tn antibodies. Such antibodies may bind to sialylated Tn that includes Neu5Ac and/or sialylated Tn that include Neu5Gc. Some anti-Tn antibodies may bind specifically to clusters of Tn antigen.

Anti-STn Antibodies

In some embodiments, antibodies of the invention (e.g., glycan-interacting antibodies) may specifically bind to STn.

Figure 1B:
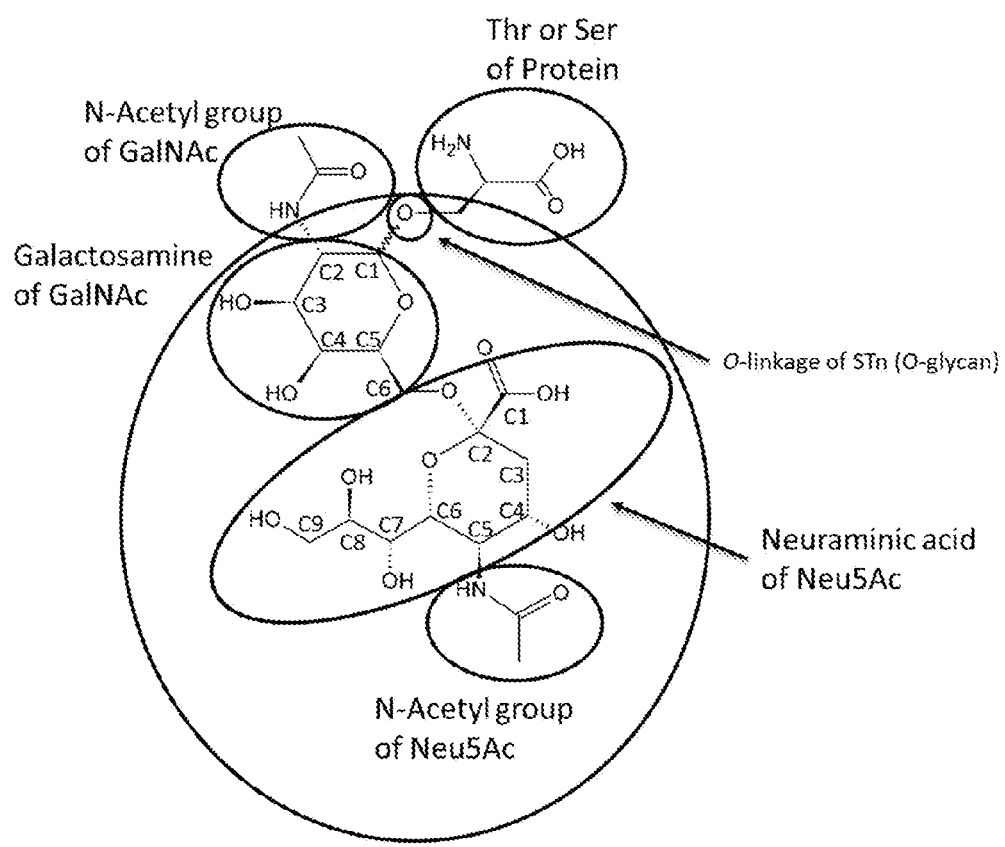
Figure 1C:
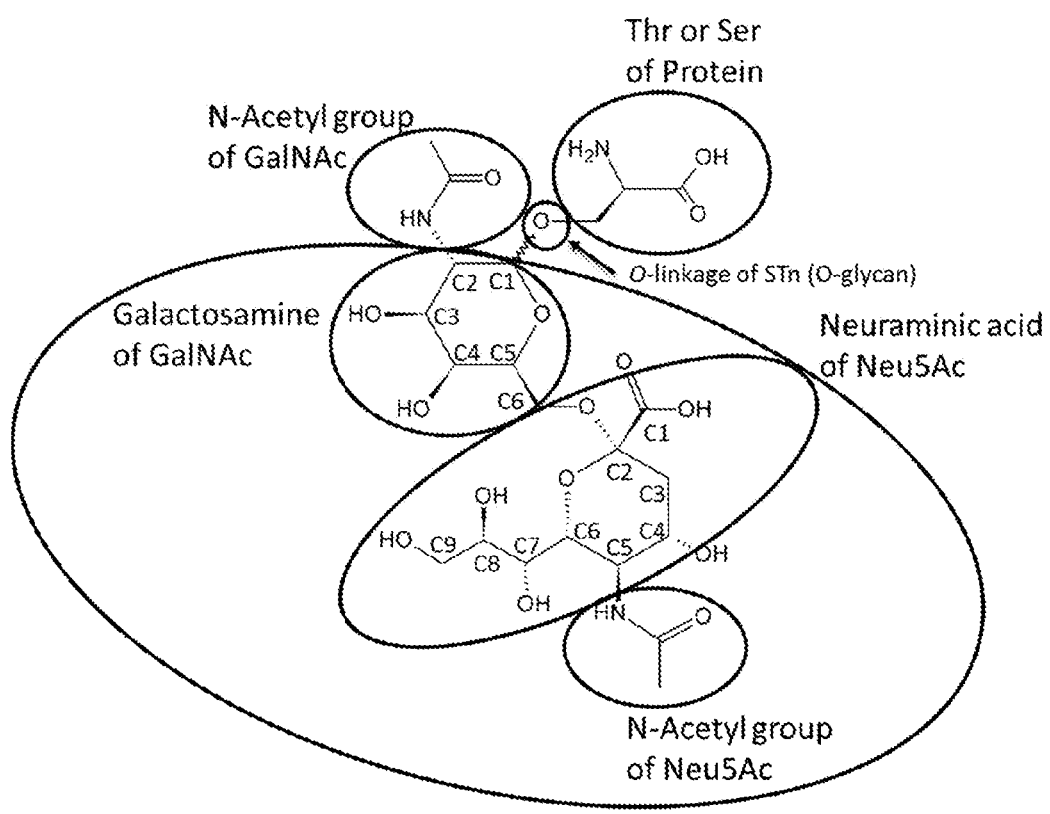
Figure 1D:
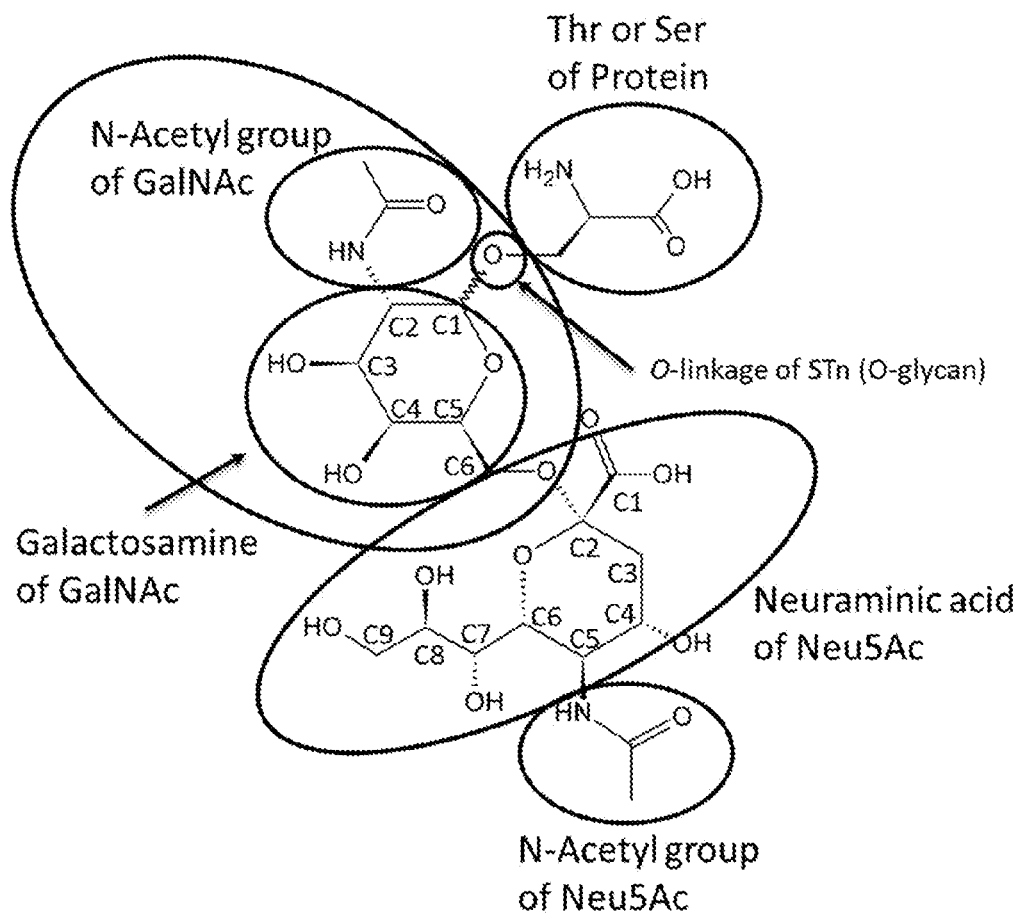

Anti-STn antibodies of the invention may be categorized by their binding to specific portions of STn antigens and/or by their specificity for AcSTn versus GcSTn. In some cases, anti-STn antibodies of the invention are Group 1 antibodies. "Group 1" antibodies according to the invention are antibodies capable of binding AcSTn and GcSTn. Such antibodies may also be referred to herein as pan-STn antibodies due to their ability to associate with a wider range of STn structures. In some embodiments, Group 1 antibodies may associate with the portion of STn indicated by the large oval in FIG. 1A. In some cases, anti-STn antibodies of the invention are Group 2 antibodies. "Group 2" antibodies, according to the invention, are antibodies capable of binding STn as well as some related structures that include an O-linkage to serine or threonine. In some embodiments, Group 2 antibodies may associate with glycans that include a sialylated galactose residue. In some cases, Group 2 antibodies may associate with the portion of STn indicated by the large oval in FIG. 1B. Some Group 2 antibodies preferably bind to structures with AcSTn over structures with GcSTn. Further anti-STn antibodies may be Group 3 antibodies. As referred to herein, "Group 3" antibodies are antibodies capable of binding STn, but may also bind a broader set of related structures. Unlike Group 2 antibodies, Group 3 antibodies do not require that such structures have an O-linkage to serine or threonine. In some embodiments, Group 3 antibodies may associate with the portion of STn indicated by the large oval in FIG. 1C. Finally, some anti-STn antibodies of the invention may be Group 4 antibodies. As referred to herein, "Group 4" antibodies are capable of binding to both AcSTn and GcSTn as well as the un-sialylated Tn antigen, and therefore have broader specificity. In some embodiments, Group 4 antibodies may associate with the portion of STn indicated by the large oval in FIG. 1D.

In some cases, anti-STn antibodies of the invention may bind specifically to clusters of STn on a particular antigen or cell surface. Some such antibodies may recognize epitopes formed by the clustering of STn, including epitopes that include areas of contact between neighboring STn structures. Such epitopes may be formed by the clustering of 2, 3, 4, 5, 6, 7, 8, 9, 10 or more STn structures.

In some embodiments, anti-STn antibodies of the present disclosure may be used bind cellular proteins carrying STn. Such antibodies may be useful for targeting cellular proteins associated with cancer cells that are distinguishable from similar proteins in non-cancerous cells by STn expression. In some cases, such proteins may include cell surface proteins. Cancer cell surface proteins carrying STn may be targeted by anti-STn antibodies during cancer treatment and/or diagnosis. Cell surface proteins carrying STn may be identified using mass spectrometry and/or using immunological methods (e.g., FACS analysis, immunoprecipitation, immunoblotting, ELISA, etc.). In some cases, cellular proteins carrying STn may include cancer cell markers, cancer stem cell markers, and/or cancer stem cell signaling proteins. In some embodiments, cellular proteins carrying STn may include, but are not limited to CD44, CD133, CD117, integrins, Notch, and Hedgehog.

Antibody Components

Antibodies of the present disclosure may include any of the amino acid or nucleotide sequence presented herein, including, but not limited to variable domain sequences, CDR sequences, framework sequences, linker sequences, and immunoglobulin sequences. In some cases, antibodies may include any of the antibody or antibody fragment sequences presented in International Publication Number WO2017083582 (the entire content of which is herein incorporated by reference), including: any of the variable domain sequences presented in Table 2 therein; any of the CDR sequences presented in Table 3 therein; any of the VH CDR sequence groups presented in Table 4 therein; any of the VL CDR sequence groups presented in Table 5 therein; any of the variable domain nucleotide sequences presented in Table 6 therein; or any of the humanized variable domain sequences presented in Table 11 therein. Some antibodies or antigen binding fragments may include different combinations of such sequences.

In some cases, antibodies or antigen binding fragments of the invention may include one or more of the variable domain sequences listed in Table 2. Residues indicated with an "X" may be absent or selected from any amino acid residues. Light chain variable domains presented may be expressed with or without a C-terminal arginine residue. This residue typically links light chain variable domains with light chain constant domains and may be expressed as part of the light chain constant domain instead of the light chain variable domain. In some cases, antibodies or antigen binding fragments thereof may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the variable domain sequences listed. In some cases, antibodies or antigen binding fragments thereof of the invention may include an amino acid sequence having one or more fragments of any of the sequences listed.

TABLE 2

Variable domain sequences

| Antibody | Variable domain | Sequence | SEQ ID NO |
|---|---|---|---|
| 2G12-2B2 | Heavy chain | QVQLQQSDXELVKPGASVKISCKASGYTFTDHA IHWVKQKPEQGLEWIGYFSPGNDDIKYNEKFRG KATLTADKSSSTAYMQLNSLSSDDSAVYFCKRS LSTPYWGQGTLXTVSA | 1 |
| 2G12-2B2 | Light chain | DIVMTQSPSSLTVTAGEKVTMSCKSSQSLLNRG NHKNYLTWYRQKPGLPPKLLIYWASTRESGVPD RFTGSGSGTDFALTISSVQAEDLAVYYCQNDYT YPYTFGGGTKLEIKR | 2 |

In some cases, antibodies or antigen binding fragments thereof of the invention may include one or more of the CDR amino acid sequences listed in Table 3. Residues indicated with an "X" may be absent or selected from any amino acid residues. In some cases, antibodies or antigen binding fragments thereof may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the CDR sequences listed. In some cases, antibodies or antigen binding fragments thereof of the invention may include an amino acid sequence having one or more fragments of any of the sequences listed.

TABLE 3

CDR sequences

| Antibody | CDR | Sequence | SEQ ID NO |
|---|---|---|---|
| 2G12-2B2 | CDR-H1 | GYTFTDHAIHWV | 3 |
| 2G12-2B2 | CDR-H2 | FSPGNDDIKY | 4 |
| 2G12-2B2 | CDR-H3 | KRSLSTPY | 5 |
| 2G12-2B2 | CDR-L1 | QSLLNRGNHKNY | 6 |
| 2G12-2B2 | CDR-L2 | WASTRES | 7 |
| 2G12-2B2 | CDR-L3 | QNDYTYPYT | 8 |

In some cases, antibodies of the present disclosure may include heavy chain variable domains having one or more CDR amino acid sequences from the CDR sequence groups listed in Table 4. Residues indicated with an "X" may be absent or selected from any amino acid residues. In some cases, antibodies or antigen binding fragments thereof may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the CDR sequences listed. In some cases, antibodies may include an amino acid sequence having one or more fragments of any of the sequences listed.

TABLE 4

VH CDR sequence groups

| Antibody | CDR-H1 | SEQ ID NO | CDR-H2 | SEQ ID NO | CDR-H3 | SEQ ID NO |
|---|---|---|---|---|---|---|
| 2G12-2B2 | GYTFTDHAIH | 9 | YFSPGNDDIKYNEKFRG | 10 | SLSTPY | 11 |

In some cases, antibodies of the present disclosure may include light chain variable domains having one or more CDR amino acid sequences from the CDR sequence groups listed in Table 5. Residues indicated with an "X" may be absent or selected from any amino acid residues. In some cases, antibodies or antigen binding fragments thereof may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the CDR sequences listed. In some cases, antibodies may include an amino acid sequence having one or more fragments of any of the sequences listed.

TABLE 5

VL CDR sequence groups

| Antibody | CDR-L1 | SEQ ID NO | CDR-L2 | SEQ ID NO | CDR-L3 | SEQ ID NO |
|---|---|---|---|---|---|---|
| 2G12-2B2 | KSSQSLLNRGNHKNYLT | 12 | WASTRES | 7 | QNDYTYPYT | 8 |

In some cases, antibodies or antigen binding fragments of the invention may include any of the IgG framework regions presented in Table 6. In some cases, antibodies or fragments thereof may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the constant domain sequences listed. In some cases, antibodies or fragments thereof of the invention may include an amino acid sequence having one or more fragments of any of the sequences listed.

TABLE 6

IgG Constant domain sequences

| Domain | Sequence | SEQ ID NO |
|---|---|---|
| Human IgG1 heavy chain constant regions | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 13 |
| Human IgG1 light chain constant regions | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 14 |
| Human IgG1 heavy chain constant regions (with N297Q mutation) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYQSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 15 |

In some embodiments, antibodies of the present invention may contain sequences that bind to the T cell receptor CD3. In some cases, the anti-CD3 sequences may include sequences from the antibody OKT3 or derivatives thereof. OKT3 is a mouse monoclonal antibody that specifically reacts with CD3 on the surface of circulating human T cells. It was approved by the U.S. Food and Drug Administration (FDA) in 1985 to be used in humans for the treatment of acute transplant rejection. OKT3 binds to a glycoprotein (the 20-kDa epsilon chain) on the CD3 complex to activate circulating T cells, leading to a transient activation of T cells, release of cytokines, and inhibition of T cell proliferation and differentiation.

In some cases, the antibodies may include one or both of the amino acid sequences in Table 7 or optimized versions thereof. In some cases, antibodies or fragments thereof may include an amino acid sequence with from about 50% to about 99.9% sequence identity (e.g., from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the amino acid sequences presented.

TABLE 7

OKT3 antibody sequences

| Anti-body | Vari-able domain | Sequence | SEQ ID NO |
|---|---|---|---|
| OKT3 | Heavy chain full length | QVQLQQSGAELARPGASVKMSCKASGYTFTRYTMHWV KQRPGQGLEWIGYINPSRGYTNYNQKFKDKATLTTDK SSSTAYMQLSSLTSEDSAVYYCARYYDDHYCLDYWGQ GTTLTVSSAKTTAPSVYPLAPVCGGTTGSSVTLGCLV KGYFPEPVLTWNSGSLSSGVHTFPAVLQSDLYTLSS SVTVTSSTWPSQSITCNVAHPASSTKVDKKIEPRPKS CDKTHTCPPCPAPELLGGPSVFLFPPKPKDTLMISRT PEVTCVVVDVSHEDPEVKFNWYVDGVEVHNAKTKPRE EQYNSTYRVVSVLTVLHQDWLNGKEYKCKVSNKALPA PIEKTISKAKGQPREPQVYTLPPSRDELTKNQVSLTC LVKGFYPSDIAVEWESNGQPENNYKTTPPVLDSDGSF FLYSKLTVDKSRWQQGNVFSCSVMHEALHNHYTQKSL SLSPGK | 16 |
| OKT3 | Light chain full length | QIVLTQSPAIMSASPGEKVTMTCSASSSVSYMNWYQQ KSGTSPKRWIYDTSKLASGVPAHFRGSGSGTSYSLTI SGMEAEDAATYYCQQWSSNPFTFGSGTKLEINRADTA PTVSIFPPSSEQLTSGGASVVCFLNNFYPKDINVKWK IDGSERQNGVLNSWTDQDSKDSTYSMSSTLTLTKDEY ERHNSYTCEATHKTSTSPIVKSFNRNEC | 17 |

In some cases, antibodies or antigen binding fragments of the invention may include one or more of the variable domain sequences listed in Table 8. Light chain variable domains presented may be expressed with or without a C-terminal arginine residue. This residue typically links light chain variable domains with light chain constant domains and may be expressed as part of the light chain constant domain instead of the light chain variable domain. In some cases, antibodies or antigen binding fragments thereof may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the variable domain sequences listed. In some cases, antibodies or anti-gen binding fragments may include an amino acid sequence having one or more fragments of any of the sequences listed.

TABLE 8

OKT3 variable domains

| Anti-body | Vari-able domain | Sequence | SEQ ID NO |
|---|---|---|---|
| OKT3 | Heavy chain | QVQLQQSGAELARPGASVKMSCKASGYTFTRYTMH WVKQRPGQGLEWIGYINPSRGYTNYNQKFKDKATL TTDKSSSTAYMQLSSLTSEDSAVYYCARYYDDHYC LDYWGQGTTLTVSS | 18 |
| OKT3 | Light chain | QIVLTQSPAIMSASPGEKVTMTCSASSSVSYMNWY QQKSGTSPKRWIYDTSKLASGVPAHFRGSGSGTSY SLTISGMEAEDAATYYCQQWSSNPFTFGSGTKLEI NR | 19 |

In some cases, antibodies or antigen binding fragments thereof of the invention may include one or more of the CDR amino acid sequences listed in Table 9. In some cases, antibodies or antigen binding fragments thereof may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the CDR sequences listed. In some cases, antibodies or antigen binding fragments thereof of the invention may include an amino acid sequence having one or more fragments of any of the sequences listed.

TABLE 9

OKT3 CDR sequences

| Antibody | CDR | Sequence | SEQ ID NO |
|---|---|---|---|
| OKT3 | CDR-H1 | GYTFTRYTMH | 20 |
| OKT3 | CDR-H2 | YINPSRGYTNYNQKFKD | 21 |
| OKT3 | CDR-H3 | YYDDHYCLDY | 22 |
| OKT3 | CDR-L1 | SASSSVSYMN | 23 |
| OKT3 | CDR-L2 | DTSKLAS | 24 |
| OKT3 | CDR-L3 | QQWSSNPFT | 25 |

In some embodiments, the antibodies or antigen binding fragments may include one or more peptide linkers to connect the antibody components or related variants described above. Exemplary peptide linker sequences are presented in Table 10. In some examples, peptide linkers comprise small flexible residues such as glycines and serines. In some cases, antibodies or antigen binding fragments thereof may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the linker sequences listed.

TABLE 10

Linker sequences

| Linker No. | Sequence | SEQ ID NO |
|---|---|---|
| Linker 1 | GGGGSGGGGSGGGGS | 26 |
| Linker 2 | ASTGGGGSGGGGSGGGGSGGGGS | 27 |
| Linker 3 | GGGGSGGGGSGGGGSGGGGS | 28 |
| Linker 4 | ASTGGGGSGGGGSGGGGS | 29 |
| Linker 5 | STGGGGSGGGGSGGGGSDI | 30 |

In some embodiments, the disclosure includes antibody fragments produced using one or more of the antibody sequences or related variants described above. Such antibody fragments may include scFvs, Fab fragments, or any other antibody fragments, including any of those described herein.

Humanized Antibodies

"Humanized" forms of non-human (e.g., murine) antibodies are chimeric antibodies that contain minimal sequences derived from non-human immunoglobulin. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and capacity.

In some embodiments, fully humanized heavy and light chains may be designed from antibody sequences and/or with CDRs presented herein. Protein models of antibody variable regions may be generated using existing antibody structures as templates. Segments of starting heavy and light chain variable region amino acid sequences may be compared with human sequences to identify human germline antibodies with similar sequences. Series of humanized heavy and light chain variable regions may be designed using human variable domain framework region sequences with the objective that T cell epitopes be avoided. Variant human sequence segments with significant incidence of potential T cell epitopes as determined by in silico technologies may then be discarded. In some cases, some of the amino acid residues in resulting variable domains may be mutated back to amino acids present in the original mouse variable domain. In some cases, some of the mouse residues in the resulting variable domains may be mutated to match residues present in human germline sequences.

Humanized heavy and light chain variable region genes may be constructed from overlapping oligonucleotides assembled into full length genes using the ligase chain reaction (LCR). LCR products may be amplified and suitable restriction sites may be added for cloning into expression vectors. PCR products may be cloned into intermediate vectors and confirmed by sequencing.

For construction of expression plasmids encoding fully humanized antibodies with human constant regions, DNA sequences encoding antibody variable region may be inserted into expression vectors (e.g., mammalian expression vectors) between an upstream promoter/enhancer, for example, cytomegalovirus immediate/early promoter/enhancer (CMV IE), plus the immunoglobulin signal sequence and a downstream immunoglobulin constant region gene. DNA samples may then be prepared for transfection into mammalian cells.

For generation of cell lines and selection of fully humanized antibodies, heavy and light chain plasmid DNA pairs may be transfected into cells for expression. In some embodiments, mammalian NS0 cells may be used. Cell lines producing humanized antibodies may be expanded for expression antibodies that may be harvested and purified from cell culture media.

In some embodiments, antibodies of the present disclosure may be prepared according to humanization methods known in the art. Such methods may include, but are not limited to CDR grafting, resurfacing, superhumanization, and human string content optimization (see, for example, Almagro, et al., 2008. Front. Biosci. 13:1619-33). In some embodiments, empirical methods are used. Such methods may include the generation of large combinatorial libraries and selecting desired variants by enrichment technologies, such as phage display, yeast display, ribosomal display, or other high throughput screening techniques. These methods may be utilized alone or in combination with framework libraries, guided selection, framework shuffling, and humaneering.

In some embodiments, humanized antibodies may be prepared by utilizing one or more of the human variable domains presented in Table 11. Such antibodies may include one or more of any of the CDR sequences presented herein or fragments or variants thereof that are substituted for the CDR sequences present in the human variable domains. In some cases, variants of the human variable domain sequences are utilized, wherein such variants have at least 50%, at least 60%, at least 70%, at least 75%, at least 80%, at least 85%, at least 90%, at least 95%, at least 96%, at least 97%, at least 98%, at least 99%, at least 99.5%, or at least 99.9% sequence identity to any of the human variable domain sequences presented.

TABLE 11

Human variable domains

| Variable domain | Kabat Germline | Sequence | SEQ ID NO |
|---|---|---|---|
| VH | IGHV1-18*01, nucleotide | CAGGTTCAGCTGGTGCAGTCTGGAGCTGAGGTG AAGAAGCCTGGGGCCTCAGTGAAGGTCTCCTGC AAGGCTTCTGGTTACACCTTTACCAGCTATGGTA TCAGCTGGGTGCGACAGGCCCCTGGACAAGGGC TTGAGTGGATGGGATGGATCAGCGCTTACAATG GTAACACAAACTATGCACAGAAGCTCCAGGGCA GAGTCACCATGACCACAGACACATCCACGAGCA | 31 |

TABLE 11-continued

Human variable domains

| Variable domain | Kabat Germline | Sequence | SEQ ID NO |
|---|---|---|---|
| | | CAGCCTACATGGAGCTGAGGAGCCTGAGATCTG ACGACACGGCCGTGTATTACTGTGCGAGAGA | |
| VH | IGHV3-11*03, nucleotide | CAGGTGCAGCTGTTGGAGTCTGGGGGAGGCTTG GTCAAGCCTGGAGGGTCCCTGAGACTCTCCTGTG CAGCCTCTGGATTCACCTTCAGTGACTACTACAT GAGCTGGATCCGCCAGGCTCCAGGGAAGGGGCT GGAGTGGGTTTCATACATTAGTAGTAGTAGTAGT TACACAAACTACGCAGACTCTGTGAAGGGCCGA TTCACCATCTCCAGAGACAACGCCAAGAACTCA CTGTATCTGCAAATGAACAGCCTGAGAGCCGAG GACACGGCCGTGTATTACTGTGCGAGA | 32 |
| VL | IGKV1-39*01, nucleotide | GACATCCAGATGACCCAGTCTCCATCCTCCCTGT CTGCATCTGTAGGAGACAGAGTCACCATCACTT GCCGGGCAAGTCAGAGCATTAGCAGCTATTTAA ATTGGTATCAGCAGAAACCAGGGAAAGCCCCTA AGCTCCTGATCTATGCTGCATCCAGTTTGCAAAG TGGGGTCCCATCAAGGTTCAGTGGCAGTGGATC TGGGACAGATTTCACTCTCACCATCAGCAGTCTG CAACCTGAAGATTTTGCAACTTACTACTGTCAAC AGAGTTACAGTACCCCTC | 33 |
| VL | IGKV4-1*01, nucleotide | GACATCGTGATGACCCAGTCTCCAGACTCCCTGG CTGTGTCTCTGGGCGAGAGGGCCACCATCAACT GCAAGTCCAGCCAGAGTGTTTTATACAGCTCCA ACAATAAGAACTACTTAGCTTGGTACCAGCAGA AACCAGGACAGCCTCCTAAGCTGCTCATTTACTG GGCATCTACCCGGGAATCCGGGGTCCCTGACCG ATTCAGTGGCAGCGGGTCTGGGACAGATTTCAC TCTCACCATCAGCAGCCTGCAGGCTGAAGATGT GGCAGTTTATTACTGTCAGCAATATTATAGTACT CCTCC | 34 |
| VH | IGHV1-18*01, amino acids | QVQLVQSGAEVKKPGASVKVSCKASGYTFTSYGIS WVRQAPGQGLEWMGWISAYNGNTNYAQKLQGR VTMTTDTSTSTAYMELRSLRSDDTAVYYCAR | 35 |
| VH | IGHV3-11*03, amino acids | QVQLLESGGGLVKPGGSLRLSCAASGFTFSDYYMS WIRQAPGKGLEWVSYISSSSSYTNYADSVKGRFTIS RDNAKNSLYLQMNSLRAEDTAVYYCAR | 36 |
| VL | IGKV1-39*01, amino acids | DIQMTQSPSSLSASVGDRVTITCRASQSISSYLNWY QQKPGKAPKLLIYAASSLQSGVPSRFSGSGSGTDFT LTISSLQPEDFATYYCQQSYSTP | 37 |
| VL | IGKV4-1*01, amino acids | DIVMTQSPDSLAVSLGERATINCKSSQSVLYSSNNK NYLAWYQQKPGQPPKLLIYWASTRESGVPDRFSG SGSGTDFTLTISSLQAEDVAVYYCQQYYSTPC | 38 |

In some embodiments, humanized antibodies of the present disclosure may include one or more of the human framework regions presented in Table 12. Some antibodies may include framework regions with at least 50%, at least 60%, at least 70%, at least 75%, at least 80%, at least 85%, at least 90%, at least 95%, or at least 98% sequence identity to any of the framework regions presented.

TABLE 12

Human framework regions

| Framework region, Variable domain | Kabat Germline | Amino Acid Sequence | SEQ ID NO |
|---|---|---|---|
| FR1, VH | IGHV1-18*01 | QVQLVQSGAEVKKPGASVKVSCKAS | 39 |
| FR1, VH | IGHV3-11*03 | QVQLLESGGGLVKPGGSLRLSCAAS | 40 |

TABLE 12-continued

Human framework regions

| Framework region, Variable domain | Kabat Germline | Amino Acid Sequence | SEQ ID NO |
|---|---|---|---|
| FR1, VL | IGKV1-39*01 | DIQMTQSPSSLSASVGDRVTITC | 41 |
| FR1, VL | IGKV4-1*01 | DIVMTQSPDSLAVSLGERATINC | 42 |
| FR2, VH | IGHV1-18*01 | WVRQAPGQGLEWMG | 43 |
| FR2, VH | IGHV3-11*03 | WIRQAPGKGLEWVS | 44 |
| FR2, VL | IGKV1-39*01 | WYQQKPGKAPKLLIY | 45 |
| FR2, VL | IGKV4-1*01 | WYQQKPGQPPKLLIY | 46 |
| FR3, VH | IGHV1-18*01 | RVTMTTDTSTSTAYMELRSLRSDDTAVYYCAR | 47 |
| FR3, VH | IGHV3-11*03 | RFTISRDNAKNSLYLQMNSLRAEDTAVYYCAR | 48 |
| FR3, VL | IGKV1-39*01 | GVPSRFSGSGSGTDFTLTISSLQPEDFATYYC | 49 |
| FR3, VL | IGKV4-1*01 | GVPDRFSGSGSGTDFTLTISSLQAEDVAVYYC | 50 |
| FR4, VH | Human consensus sequence 1 and 3 | WGQGTLVTVSS | 51 |
| FR4, VL | Human consensus sequence 1 | FGQGTKVEIK | 52 |

In some embodiments, one or more residues of humanized antibodies may be back-crossed to improve antibody binding or other properties.

In some embodiments, humanized variable domains present in antibodies of the present disclosure may include any of the anti-STn variable domains presented in Table 13. In some cases, antibodies include one or more variants of these variable domains with at least 70%, at least 75%, at least 85%, at least 90%, at least 95%, at least 96%, at least 97%, at least 98%, at least 99%, or at least 99.5% sequence identity.

TABLE 13

Humanized anti-STn variable domains

| Antibody | Chain | Sequence | SEQ ID NO |
|---|---|---|---|
| 2G12-2B2 | VL0 | DIVMTQSPDSLAVSLGERATINCKSSQSLLNRGNHKNYLTWYQQKPGQPPKLLIYWASTRESGVPDRFSGSGSGTDFTLTISSLQAEDVAVYYCQNDYTYPYTFGQGTKVEIK | 53 |
| 2G12-2B2 | VL2 | DIVMTQSPDSLAVSLGERVTMSCKSSQSLLNRGNHKNYLTWYQQKPGQPPKLLIYWASTRESGVPDRFSGSGSGTDFTLTISSLQAEDVAVYYCQNDYTYPYTFGQGTKVEIK | 54 |
| 2G12-2B2 | VL3 | DIVMTQSPDSLSVSDGERATINCKSSQSLLNRGNHKNYLTWYQQKPGQPPKLLIYWASTRESGVPDRFSGSGSGTDFTLTISSLQAEDEGVYYCQNDYTYPYTFGGGTKVEIQ | 55 |
| 2G12-2B2 | VL4 | DIVMTQSPDSLSVSDGERATINCKSSQSLLNRGNHKNYLTWYQQKPGQPPKLLIYWASTRESGVPDRFSGSGSGTDFTLTISSLQAEDEGVYYCQNDYTYPYTFGCGTKVEIQ | 56 |
| 2G12-2B2 | VH0 | QVQLVQSGAEVKKPGASVKVSCKASGYTFTDHAIHWVRQAPGQGLEWMGYFSPGNDDIKYNEKFRGRVT | 57 |

TABLE 13-continued

Humanized anti-STn variable domains

| Antibody | Chain | Sequence | SEQ ID NO |
|---|---|---|---|
|  |  | MTTDTSTSTAYMELRSLRSDDTAVYYCARSLSTPYW GQGTLVTVSS |  |
| 2G12-2B2 | VH1 | QVQLVQSGAEVKKPGASVKVSCKASGYTFTDHAIH WVRQAPGQGLEWMGYFSPGNDDIKYNEKFRGRVT MTADKSSSTAYMELRSLRSDDTAVYFCKRSLSTPYW GQGTLVTVSS | 58 |
| 2G12-2B2 | VH2 | QVQLVQSGAEVKKPGASVKISCKASGYTFTDHAIHW VRQAPGQGLEWIGYFSPGNDDIKYNEKFRGRVTLTA DKSSSTAYMELRSLRSDDTAVYFCKRSLSTPYWGQG TLVTVSS | 59 |
| 2G12-2B2 | VH3 | EVQLVQSGAEVKKPGASVKVSCKASGYTFTDHAIH WVRQAPGQGLEWMGYFSPGNDDIKYNEKFRGRVT MTADKSSSTAYMELRSLRSDDTAVYFCKRSLSTPYW GQGTLVTVSS | 60 |
| 2G12-2B2 | VH4 | EVQLVQSGAEVKKPGASVKISCKASGYTFTDHAIHW VRQAPGQGLEWIGYFSPGNDDIKYNEKFRGRVTLTA DKSSSTAYMELRSLRSDDTAVYFCKRSLSTPYWGQG TLVTVSS | 61 |
| 2G12-2B2 | VH5 | EVQLVQSGAEDKKPGASVKVSCKASGYTFTDHAIH WVRQAPGQGLEWMGYFSPGNDDIKYNEKFRGRATL TADKSSSTAYMELNSLRSDDTAVYFCKRSLSTPYWG QGTSVTVSS | 62 |
| 2G12-2B2 | VH6 | EVQLVQSGAEDKKPGASVKVSCKASGYTFTDHAIH WVRQAPGQCLEWMGYFSPGNDDIKYNEKFRGRATL TADKSSSTAYMELNSLRSDDTAVYFCKRSLSTPYWG QGTSVTVSS | 63 |

In some embodiments, humanized variable domains present in antibodies of the present disclosure may include any of the anti-CD3 variable domains presented in Table 14. In some cases, antibodies include one or more variants of these variable domains with at least 70%, at least 75%, at least 85%, at least 90%, at least 95%, at least 96%, at least 97%, at least 98%, at least 99%, or at least 99.5% sequence identity.

TABLE 14

Humanized anti-CD3 variable domains

| Antibody | Chain | Sequence | SEQ ID NO |
|---|---|---|---|
| OKT3 | VH0 | QVQLEQSGGGLVKPGGSLRLSCAASGYTFTRYTMH WIRQAPGKGLEWVSYINPSRGYTNYNQKFKDRFTIS RDNAKNSLYLQMNSLRAEDTAVYYCARYYDDHYC LDYWGQGTLVTVSS | 64 |
| OKT3 | VH1 | QVQLEQSGGGDVKPGGSLRLSCKASGYTFTRYTMH WVKQAPGKCLEWVGYINPSRGYTNYNQKFKDRAT ISRDKAKNTLYLQMNSLRAEDTAVYYCARYYDDH YSLDYWGQGTTVTVSS | 65 |
| OKT3 | VH2 | QVQLEQSGGGDVKPDGSLRLSCKASGYTFTRYTMH WVKQAPGKGLEWVGYINPSRGYTNYNQKFKDRAT ISRDKAKNTLYLQMNSLRGEDTAVYYCARYYDDH YSLDYWGQGTTVTVSS | 66 |
| OKT3 | VH3 | QVQLEQSGGGLVKPGGSLRLSCKASGYTFTRYTMH WVKQAPGKGLEWVGYINPSRGYTNYNQKFKDRAT ISRDKAKNSLYLQMNSLRAEDTAVYYCARYYDDH YSLDYWGQGTLVTVSS | 67 |
| OKT3 | VH4 | QVQLEQSGGGDVKPDGSLRLSCKASGYTFTRYTMH WVKQAPGKGLEWVGYINPSRGYTNYNQKFKDRAT ISRDKAKNTLYLQMNSLRGEDTAVYYCARYYDDH YCLDYWGQGTTVTVSS | 68 |

TABLE 14-continued

Humanized anti-CD3 variable domains

| Antibody | Chain | Sequence | SEQ ID NO |
|---|---|---|---|
| OKT3 | VL0 | DIQMTQSPSSLSASVGDRVTITCSASSSVSYMNWYQ QKPGKAPKLLIYDTSKLASGVPSRFSGSGSGTDFTLT ISSLQPEDFATYYCQQWSSNPFTFGQGTKVEIKR | 69 |
| OKT3 | VL1 | QIQLTQSPSSLSASVGDRVTITCSASSSVSYMNWYQ QKPGKAPKRWIYDTSKLASGVPSRFSGSGSGTDYTL TISSLQPEDEATYYCQQWSSNPFTFGCGTKVEVQG | 70 |
| OKT3 | VL2 | QIQLTQSPSSLEASVGDRVTITCSASSSVSYMNWYQ QKPGKAPKRWIYDTSKLASGVPSRFSGSGSGTDYTL TISSLQPEDEGTYYCQQWSSNPFTFGGGTKVEVQG | 71 |
| OKT3 | VL3 | QIQLTQSPSSLSASVGDRVTITCSASSSVSYMNWYQ QKPGKAPKRWIYDTSKLASGVPSRFSGSGSGTDYTL TISSLQPEDFATYYCQQWSSNPFTFGQGTKVEVKR | 72 |

Antibody Sequence Optimization

Variable domain sequences may be analyzed for sequence characteristics that may impact antibody function, expression, stability, and/or immunogenicity. In some cases, such characteristics may include NG residue pairs. NG residue pairs may be susceptible to asparagine deamidation, with possible conversion to glutamate and pyroglutamate in a 3:1 ratio over time. These residue pairs may be mutated, for example, to SG or QG pairs to prevent deamidation at these sites. Alternatively, these antibodies may be formulated to reduce deamidation.

In some embodiments, aspartate isomerization sites may be identified and altered. Aspartate isomerization sites include DG amino acid residue pairs. Aspartic acid at these sites can convert to glutamate and pyroglutamate in a 3:1 ratio over time. DG residue pairs may be mutated to SG or QG residue pairs to prevent isomerization at these sites. Alternatively, these antibodies may be formulated to reduce deamidation.

In some embodiments, N-terminal glutamine residues may be converted to N-terminal glutamate residues. This may prevent N-terminal pyrolization.

In some embodiments, one or more aggregation-prone patch of amino acid residues may be mutated. These may include patches having amino acids with bulky side chains, for example, histidine, phenylalanine, and tryptophan.

In some embodiments, one or more cysteine residues may be mutated to prevent the presence of unpaired cysteines. Unpaired cysteines may be reactive, for example, when accessible to solvent as part of an antibody. In some cases, unpaired cysteine residues may be mutated to serine.

In some embodiments, one or more cysteine residues may be introduced. The cysteine residues can form extra disulfide bridge(s) that allow for proper folding.

In some embodiments, one or more glycosylation sites (e.g., N-linked NXS/T sites), acid cleavage sites, and amino acid oxidation sites are mutated to improve antibody production, stability, binding, and/or activity.

In some embodiments, one or more charged residues may be altered or introduced. Such charged residues include aspartate, glutamate, arginine, histidine, and lysine. This may help maintain charge neutrality and improve overall protein stability and/or activity.

IgG Synthesis

IgG antibodies (e.g. IgG1, IgG2, IgG3 or IgG4) including one or more variable domain and/or CDR amino acid sequences presented herein (or fragment or variants thereof) may be synthesized for further testing and/or product development. Such antibodies may be produced by insertion of one or more segments of cDNA encoding desired amino acid sequences into expression vectors suited for IgG production. Expression vectors may include mammalian expression vectors suitable for IgG expression in mammalian cells. Mammalian expression of IgGs may be carried out to ensure that antibodies produced include modifications (e.g. glycosylation) characteristic of mammalian proteins and/or to ensure that antibody preparations lack endotoxin and/or other contaminants that may be present in protein preparations from bacterial expression systems.

In some embodiments, IgG antibodies may be aglycosylated IgG variants. Aglycosylated antibodies may circumvent the problem of glycan heterogeneity that can complicate process development. Further, aglycosylated antibodies may have reduced effector function which prevents non-specific activation of the immune response system. Additionally, aglycosylated antibodies may be engineered to display novel effector functions and mechanisms of action that may not be possible with their glycosylated counterparts. In one embodiment, the aglycosylated IgG variants may contain a mutation at N297 [according to the Kabat numbering system, see for example Wu, T. T. et al., 1970, JEM, 132(2):211-50 and Johnson, G. et al., 2000, Nucleic Acids Res. 28(1): 214-8, the contents of each of which are herein incorporated by reference in their entirety]. N297 is an N-glycosylation site and substitution of the asparagine residue prevents glycosylation. Such substitution includes, but is not limited to, a glutamine (N297Q), an alanine (N297A), or a glycine (N297G) residue. Aglycosylated IgG antibodies may be produced, for example, in bacteria, yeast, insect cells, plant cells, or mammalian cells. Expression vectors may include those suitable for IgG expression in desired host cells.

Immunogenic Hosts

In some embodiments, glycan-interacting antibodies of the present invention may be developed through the use of non-human animals as hosts for immunization, referred to herein as "immunogenic hosts." In some embodiments, immunogenic hosts are mammals. In some embodiments, immunogenic hosts are transgenic knockout mice. Antigens having target sites and/or epitope targets of glycan-interacting antibodies may be used to contact immunogenic hosts in order to stimulate an immune response and produce antibodies in the immunogenic host that specifically bind the target sites and/or epitope targets present on the antigens introduced.

According to some methods of the present invention, the development of anti-STn antibodies may include immunizing mice that have had the Cmah gene disrupted. Such mutations may result in more human-like physiology in that Neu5Gc, the immunogenic, non-human form of sialic acid, is no longer produced in such mice. Also provided is a Cmah$^{-/-}$ myeloma cell for producing a hybridoma that is free of Neu5Gc expression, for production of a GcSTn monoclonal antibody either by reducing the amount of recoverable anti-GcSTn or the hybridoma will begin to die due to antibody binding back to the hybridoma. Other genes can be knocked out in the background of Cmah$^{-/-}$ myeloma cells. For example, the alpha1,3-galactosyltransferase gene, which encodes an enzyme critical for the formation of an epitope highly-immunogenic to humans (Chung, C. H. et al., Cetuximab-induced anaphylaxis and IgE specific for galactose-alpha-1,3-galactose. N Engl J Med. 2008 Mar. 13; 358(11):1109-17), can be knocked out in the background of Cmah$^{-/-}$ myeloma cells.

According to other methods of the present invention, wild type mice may be used for immunization. Such methods may sometimes be favorable for the production of antibodies that interact with AcSTn or pan-STn epitopes. In some cases, immune responses in wild type mice may be more robust.

Antibodies produced through immunization may be isolated from serum of the immunogenic hosts. Antibody producing cells from the immunogenic hosts may also be used to generate cell lines that produce the desired antibody. In some embodiments, screening for antibodies and/or antibody producing cells from the immunogenic host may be carried out through the use of enzyme-linked immunosorbent assays (ELISAs) and/or glycan arrays.

Adjuvants

Immunization of immunogenic hosts with antigens described herein may include the use of one or more adjuvants. Adjuvants may be used to elicit a higher immune response in such immunogenic hosts. As such, adjuvants used according to the present invention may be selected based on their ability to affect antibody titers.

In some embodiments, water-in-oil emulsions may be useful as adjuvants. Water-in-oil emulsions may act by forming mobile antigen depots, facilitating slow antigen release and enhancing antigen presentation to immune components. Freund's adjuvant may be used as complete Freund's adjuvant (CFA), which includes mycobacterial particles that have been dried and inactivated, or as incomplete Freund's adjuvant (IFA), lacking such particles. Other water-in-oil-based adjuvants may include EMULSIGEN® (MVP Technologies, Omaha, Nebr.). EMULSIGEN® includes micron sized oil droplets that are free from animal-based components. It may be used alone or in combination with other adjuvants, including, but not limited to aluminum hydroxide and CARBIGEN™ (MVP Technologies, Omaha, Nebr.).

In some embodiments, TITERMAX® adjuvant may be used. TITERMAX® is another water-in-oil emulsion that includes squalene as well as sorbitan monooleate 80 (as an emulsifier) and other components. In some cases, TITERMAX® may provide higher immune responses, but with decreased toxicity toward immunogenic hosts.

Immunostimmulatory oligonucleotides may also be used as adjuvants. Such adjuvants may include CpG oligodeoxynucleotide (ODN). CpG ODNs are recognized by Toll-like receptor 9 (TLR9) leading to strong immunostimulatory effects. Type C CpG ODNs induce strong IFN-α production from plasmacytoid dendritic cell (pDC) and B cell stimulation as well as IFN-γ production from T-helper ($T_H$) cells. CpG ODN adjuvant has been shown to significantly enhance pneumococcal polysaccharide (19F and type 6B)-specific IgG2a and IgG3 in mice. CpG ODN also enhanced antibody responses to the protein carrier CRM197, particularly CRM197-specific IgG2a and IgG3 (Chu et al., Infection Immunity 2000, vol 68(3):1450-6). Additionally, immunization of aged mice with pneumococcal capsular polysaccharide serotype 14 (PPS14) combined with a CpG-ODN restored IgG anti-PPS14 responses to young adult levels (Sen et al., Infection Immunity, 2006, 74(3):2177-86). CpG ODNs used according to the present invention may include class A, B or C ODNs. In some embodiments, ODNs may include any of those available commercially, such as ODN-1585, ODN-1668, ODN-1826, ODN-2006, ODN-2007, ODN-2216, ODN-2336, ODN-2395 and/or ODN-M362, each of which may be purchased, for example, from InvivoGen, (San Diego, Calif.). In some cases, ODN-2395 may be used. ODN-2395 is a class C CpG ODN that specifically stimulated human as well as mouse TLR9. These ODNs include phosphorothioate backbones and CpG palindromic motifs.

In some embodiments, immune stimulating complexes (ISCOMs) may be used as adjuvants. ISCOMs are spherical open cage-like structures (typically 40 nm in diameter) that are spontaneously formed when mixing together cholesterol, phospholipids and Quillaia saponins under a specific stoichiometry. ISCOM technology is proven for a huge variety of antigens from large glycoproteins such as gp340 from Epstein-Barr virus (a 340 kDa antigen consisting of 80% carbohydrates) down to carrier-conjugated synthetic peptides and small haptens such as biotin. Some ISCOMs are capable of generating a balanced immune response with both $T_{H1}$ and $T_{H2}$ characteristics. Immune response to ISCOMs is initiated in draining lymph nodes, but is efficiently relocated to the spleen, which makes it particularly suitable for generating monoclonal antibodies as well. In some embodiments, the ISCOM adjuvant AbISCO-100 (Isconova, Uppsala, Sweden) may be used. AbISCO-100 is a saponin-based adjuvant specifically developed for use in immunogenic hosts, such as mice, that may be sensitive to other saponins.

According to embodiments of the present invention, adjuvant components of immunization solutions may be varied in order to achieve desired results. Such results may include modulating the overall level of immune response and/or level of toxicity in immunogenic hosts.

Antibody Sequence and Structural Analysis and Optimization

In some embodiments, antibodies of the present invention may be subjected to sequence analysis and/or structural analysis wherein they are analyzed for characteristics that may affect antibody chemistry, affinity, specificity, protein folding, stability, manufacturing, expression, and/or immunogenicity (i.e., immune reactions in subjects being treated with such antibodies). Such analysis may include comparisons between antibodies binding to the same or similar epitopes.

Antibodies sequences of antibodies binding to the same epitope may be analyzed for variation in light and/or heavy chain sequences. Such analysis may include germline sequences and/or CDR sequences. Information obtained from such analysis may be used to identify (and optionally to modify, delete, replace or repair) conserved amino acid residues; conserved segments of amino acids; amino acid positions with conserved side chain characteristics; conserved CDR lengths; and other features conserved among antibodies binding to the same epitope. This information may be used to design variants or to inform antibody optimization procedures to improve antibody affinity, specificity, protein folding, stability, manufacturing, expression and/or immunogenicity.

Sequence analysis may include aligning two or more antibodies that bind to the same or similar epitopes to identify similarities. Such analysis may compare the sequence and/or length of antibody regions (e.g., CDRs, variable domains, germline segments). Amino acid insertions, amino acid deletions, and substitutions may be identified and assessed. Sequence differences may be compared against antibody affinity and/or specificity.

In some cases, sequence analyses are conducted to identify (and optionally to modify, delete, replace or repair) one or more of unpaired cysteines or irregular disulfides; glycosylation sites (e.g., N-linked NXS/T sites); acid cleavage sites, amino acid oxidation sites, conformity with mouse germline sequences; asparagine deamidation sites; aspartate isomerization sites; N-terminal pyroglutamate formation sites; and aggregation-prone patches in CDRs.

In some cases, the present invention provides sequence analysis-informed variants of antibodies presented herein. As used herein, the term "sequence analysis-informed variant" refers to an antibody variant that has been modified based on one or more conclusions derived from antibody sequence analysis. In some cases, antibodies of the invention may be modified to produce antibody variants that include modifications to one or more of antibody affinity, specificity, protein folding, stability, manufacturing, expression and/or immunogenicity.

Some sequence analysis-informed variants include one or more CDR length modification. CDR length modified antibodies may include one or more added or deleted amino acids in one or more CDRs relative to an original antibody sequence. In some cases, sequence analysis-informed variants may include a substitution of one or more CDRs with one or more CDRs derived from another antibody (e.g., an antibody binding to the same or similar epitope). In some cases, sequence analysis-informed variants may include a substitution of a heavy or light chain variable domain from another antibody (e.g., an antibody binding to the same or similar epitope). Sequence analysis-informed variants may include modifications to one or more germline genes that the antibody is expressed from. Such modifications may include point mutations, regional mutations, insertional mutations or deletional mutations. In some case, germline gene modifications are carried out to move CDRs from one known germline gene to another. Sequence analysis-informed variants may include other variants described herein, including, but not limited to scFvs, monobodies, diabodies, intrabodies, CARs, antibody mimetics, etc.

In some embodiments, sequence and/or structural analysis may be used to inform the construction of antibody fragment display libraries (including, but not limited to scFv libraries, phage display libraries, and yeast display libraries). In one example, sequence alignment may be carried out to align two or more antibodies with a common antigen or epitope and amino acid residues may be identified that are conserved among the aligned antibodies or that are variable among the aligned antibodies. In such cases, antibody fragment display libraries may be constructed such that variability among library members is primarily limited to the variable amino acids identified in the sequence analysis. In some cases, such libraries may be used to identify variants with altered affinity and/or specificity for a target antigen (e.g., STn) or a specific epitope of the target antigen (e.g., the epitopes recognized by Group 1, 2, 3 and 4 antibodies as described in Example 1, hereinbelow).

In some embodiments, antibodies of the invention may be modified to remove, replace or otherwise eliminate one or more unpaired cysteine residues. In some cases, unpaired cysteine residues may be reactive and may affect antibody affinity and/or specificity. Accordingly, some antibodies of the invention have been modified to eliminate unpaired cysteine residues. In some cases, such variants may have modified epitope specificity and/or affinity. In some cases, modification of unpaired cysteine residues may alter antibody folding. In some cases, these variants include a substitution or deletion of one or more cysteine residues. In some cases, these variants include one or more additional amino acid residues (including, but not limited to, the addition of one or more cysteine residues) to prevent or reduce undesired effects from unpaired cysteine residues. In some cases, cysteine residues are replaced with an amino acid having a hydrophobic side chain (e.g., tyrosine, alanine, valine, isoleucine, leucine, methionine, phenylalanine or tryptophan). In other embodiments, the antibodies of the invention may be modified to introduce one or more cysteine residues. The addition of cysteine residues can increase the formation of disulfide bridges and as a result improve antibody folding Antibody Testing and Characterization Antibodies described herein may be tested and/or characterized using a variety of methods. Such methods may be used to determine a variety of characteristics that may include, but are not limited to, antibody affinity; specificity; and activity (e.g., activation or inhibition of cellular signaling pathways or other cellular or biological activities). Antibody testing may further include testing in vivo (e.g., in animal and/or human studies) for one or more of toxicity, therapeutic effect, pharmacodynamics, pharmacokinetics, absorption, deposition, metabolism, and excretion. Testing in animals may include, but is not limited to, testing in mice, rats, rabbits, guinea pigs, pigs, primates (e.g., Cynomolgus monkeys), sheep, goats, horses, and cattle.

Cell-Based Assays

In some embodiments, antibodies of the present invention may be tested or characterized through the use of one or more cell-based assays. Such cell-based assays may be carried out in vitro with cells in culture. In some cases, cell-based assays may be carried out in vivo. Examples of cell-based in vivo assays include tumor models in which tumor cells are injected or otherwise introduced into a host.

In some cases, cells used in cell-based assays may express one or more target glycans recognized by one or more antibodies of the invention. Such glycans may be naturally expressed by such cells or, alternatively, cells may be induced to express one or more glycans desired for purposes of a particular assay. Induced expression may be through one or more treatments that upregulate expression of glycosylated proteins or enzymes that regulate glycosylation. In other cases, induced expression may include transfection, transduction, or other form of introduction of one or more genes or transcripts for the endogenous expression of one or more glycosylated proteins or enzymes involved in regulation of glycosylation.

In some cases, cell-based assays used herein may include the use of cancer cells. Many cancer cell lines are available for experiments to test antibodies of the invention. Such cells may express target glycan or may be induced to express target glycans. Additionally, cancer cell lines may be used to test antibodies of the invention, where the cancer cell lines are representative of cancer stem cells. Cancer stem cell (CSC) cell lines may be isolated or differentiated from cancer cells grown in culture (e.g., through sorting based on markers specific for cancer stem cells). Cell lines used in cell-based assays may include, but are not limited to breast, colon, ovary, lymphocyte, bone marrow, and skin cell lines. Specific cell lines may include, but are not limited to SNU-16 cells, LS-174T cells, MC38 cells, TOV-112D cells, TOV-21G cells, Jurkat E6.1 cells, K-562 cells, B16-F0 cells, B16-F10 cells, LS180 cells, COLO205 cells, TB4 cells, HT29 cells, Panc1 cells, HPAC cells, HPAFII cells, RKO cells, SW480 cells, and SNU-C2A cells.

In some embodiments, ovarian cancer cell lines may be used. Such cell lines may include, but are not limited to SKOV3, OVCAR3, OV90 and A2870 cell lines. In some cases, CSC cells may be isolated from these cell lines by isolating cells expressing CD44 and/or CD133 cell markers.

OVCAR3 cells were first established using malignant ascites obtained from a patient suffering from progressive ovarian adenocarcinoma (Hamilton, T. C. et al., 1983. Cancer Res. 43: 5379-89). Cancer stem cell populations may be isolated from OVCAR3 cell cultures through selection based on specific cell surface markers such as CD44 (involved in cell adhesion and migration), CD133 and CD117 (Liang, D. et al., 2012. BMC Cancer. 12: 201, the contents of which are herein incorporated by reference in their entirety). OV90 cells are epithelial ovarian cancer cells that were similarly derived from human ascites (see U.S. Pat. No. 5,710,038). OV-90 cells may also express CD44 when activated (Meunier, L. et al., 2010. Transl Oncol. 3(4): 230-8).

In some embodiments, cell lines derived from gastric cancers may be used. Such cell lines may include, but are not limited to SNU-16 cells (see description in Park J. G. et al., 1990. Cancer Res. 50: 2773-80, the contents of which are herein incorporated by reference in their entirety). SNU-16 cells express STn naturally, but at low levels.

In some embodiments, methods of the present disclosure include methods of characterizing glycan-interacting antibodies by contacting colorectal cells with glycan-interacting antibodies and evaluating antibody binding to the cells, antibody internalization into the cells, and/or antibody killing of the cells. According to some such methods, the colorectal cells may be derived from a colorectal cell line grown in vitro (e.g., propagated through cell culture). In some cases, colorectal cell lines are derived from a tumor. In other embodiments, colorectal cell lines may be derived from a tumor formed using a xenograft animal model (e.g., a xenograft mouse model). Colorectal cells used for characterizing glycan-interacting antibodies may be from a patient (e.g., a patient tumor). Methods of characterizing glycan-interacting antibodies may include the use of tissue micro arrays, including those having one or more colorectal cells.

Characterizing glycan-interacting antibodies with colorectal cells may include evaluating binding between such antibodies and cells by determining the EC50 of binding of the glycan-interacting antibody to the colorectal cell. The $EC_{50}$ may be determined by using one or more of flow cytometry analysis and ELISA analysis. In some embodiments, characterizing glycan-interacting antibodies with colorectal cells may include evaluating the killing of such cells by glycan-interacting antibodies. This may be carried out by treating colorectal cells with glycan-interacting antibodies and using a cell viability assay to determine the percentage of cells killed by the treatment. In some cases, evaluating killing of colorectal cells by glycan-interacting antibodies includes determining the $IC_{50}$ for glycan-interacting antibody killing of colorectal cells. In some cases, the antibodies may be conjugated with a cytotoxic agent (e.g., MMAE or MMAF).

In some embodiments, cell-based assays used herein may include the use of T cells. T cells may be prepared using any method known in the art. For example, human T cells may be isolated from peripheral blood mononuclear cells (PBMC) by depleting non-target cells, i.e., B cells, NK cells, monocytes, platelets, dendritic cells, granulocytes and erythrocytes. The non-target cells can be magnetically labeled with antibody complexes and magnetic particles. Isolation of T cells is then achieved by depletion of magnetically labeled cells.

In some cases, the T cell-based assays may be used to evaluate binding between the bispecific antibodies and the T cell receptor CD3. The binding affinity or $EC_{50}$ values may be determined using one or more of flow cytometry analysis and ELISA analysis. In some cases, the T cell-based assays may be used to evaluate T cell activation in the presence of the bispecific antibodies. T cell activation alone, or a lack there-of, would demonstrate safety of the bispecific antibodies in a tumor-free environment. In some cases, the T cell-based assays may be used to evaluate T cell induced tumor cell killing by incubating T cells and one or more tumor cell lines described above with the bispecific antibodies. T cell-induced tumor cell killing would demonstrate the ability of the bispecific antibodies to achieve a therapeutic effect.

Glycan Arrays

In some embodiments, glycan-interacting antibodies of the present invention may be developed through the use of glycan arrays. As used herein, the term "glycan array" refers to a tool used to identify agents that interact with any of a number of different glycans linked to the array substrate. In some embodiments, glycan arrays include a number of chemically-synthesized glycans, referred to herein as "glycan probes". In some embodiments, glycan arrays include at least 2, at least 5, at least 10, at least 20, at least 30, at least 40, at least 50, at least 60, at least 70, at least 80, at least 90, at least 100, at least 150, at least 350, at least 1000 or at least 1500 glycan probes. In some embodiments, glycan arrays may be customized to present a desired set of glycan probes. In some embodiments, glycan probes may be attached to the array substrate by a linker molecule. Such linkers may include molecules including, but not limited to $-O(CH_2)_2CH_2)NH_2$ and $O(CH_2)_3NHCOCH_2(OCH_2CH_2)_6NH_2$.

In some embodiments, a glycan array has more than 70 chemically-synthesized glycans, most of which are presented as Neu5Ac and Neu5Gc-containing glycan pairs. Some examples of glycan probes may include: Neu5Ac-α-2-6-GalNAc (AcSTn); Neu5Gc-α-2-6-GalNAc (GcSTn); Neu5,9Ac2-α-2,6-GalNAc; Neu9Ac5Gc-α-2,6-GalNAc, and GalNAc (Tn). The antibody binding specificity to AcSTn vs. GcSTn can be determined using the array or other methods of determining specificity known in the art. In addition, the binding profile of antibodies to 0-acetylated STn can be determined. The loss of 0-acetylation on STn is relevant to cancer as cancer-associated expression correlates with increased STn recognition by antibodies (Ogata, S. et al., Tumor-associated sialylated antigens are constitutively expressed in normal human colonic mucosa. Cancer Res. 1995 May 1; 55(9):1869-74). In some cases, glycan arrays may be used to determine recognition of STn vs. Tn.

Antibody Fragment Display Library Screening Techniques

In some embodiments, antibodies of the present invention may be produced and/or optimized using high throughput methods of discovery. Such methods may include any of the display techniques (e.g. display library screening techniques) disclosed in International Patent Application No. WO2014074532, the contents of which are herein incorporated by reference in their entirety. In some embodiments, synthetic antibodies may be designed, selected or optimized by screening target antigens using display technologies (e.g. phage display technologies). Phage display libraries may include millions to billions of phage particles, each expressing unique antibody fragments on their viral coats. Such libraries may provide richly diverse resources that may be used to select potentially hundreds of antibody fragments with diverse levels of affinity for one or more antigens of interest (McCafferty, et al., 1990. Nature. 348:552-4; Edwards, B. M. et al., 2003. JMB. 334: 103-18; Schofield, D. et al., 2007. Genome Biol. 8, R254 and Pershad, K. et al., 2010. Protein Engineering Design and Selection. 23:279-88; the contents of each of which are herein incorporated by reference in their entirety). Often, the antibody fragments present in such libraries include scFv antibody fragments that include a fusion protein of $V_H$ and $V_L$ antibody domains joined by a flexible linker. In some cases, scFvs may contain the same sequence with the exception of unique sequences encoding variable loops of the complementarity determining regions (CDRs). In some cases, scFvs are expressed as fusion proteins, linked to viral coat proteins (e.g. the N-terminus of the viral pIII coat protein). $V_L$ chains may be expressed separately for assembly with $V_H$ chains in the periplasm prior to complex incorporation into viral coats. Precipitated library members may be sequenced from the bound phage to obtain cDNA encoding desired scFvs. Such sequences may be directly incorporated into antibody sequences for recombinant antibody production, or mutated and utilized for further optimization through in vitro affinity maturation.

Development of Cytotoxic Antibodies

In some embodiments, antibodies of the present invention may be capable of inducing antibody-dependent cell-mediated cytotoxicity (ADCC) and/or antibody-dependent cell phagocytosis (ADCP). ADCC is an immune mechanism whereby cells are lysed as a result of immune cell attack. Such immune cells may include CD56+ cells, CD3-natural killer (NK) cells, monocytes and neutrophils (Strohl, W. R. Therapeutic Antibody Engineering. Woodhead Publishing, Philadelphia Pa. 2012. Ch. 8, p 186, the contents of which are herein incorporated by reference in their entirety).

In some cases, antibodies of the present invention may be engineered to include a given isotype depending on whether or not ADCC or ADCP is desired upon antibody binding. Such antibodies, for example, may be engineered according to any of the methods disclosed by Alderson, K. L. et al., J Biomed Biotechnol. 2011. 2011:379123). In the case of mouse antibodies, different isotypes of antibodies are more effective at promoting ADCC. IgG2a, for example, is more effective at inducing ADCC than is IgG2b. Some antibodies of the present invention, including mouse IgG2b antibodies may be reengineered to be IgG2a antibodies. Such reengineered antibodies may be more effective at inducing ADCC upon binding cell-associated antigens. In some embodiments, antibodies are reengineered by modifying or introducing one or more post-translational modifications to improve ADCC and/or complement-dependent cytotoxicity (CDC) biological activity.

In some embodiments, genes encoding variable regions of antibodies developed according to methods of the present invention may be cloned into mammalian expression vectors encoding human Fc regions. Such Fc regions may be Fc regions from human IgG1κ. IgG1κ Fc regions may include amino acid mutations known to enhance Fc-receptor binding and antibody-dependent cell-mediated cytotoxicity (ADCC).

In some embodiments, antibodies of the invention may be developed for antibody-drug conjugate (ADC) therapeutic applications. ADCs are antibodies in which one or more cargo (e.g., therapeutic agents) are attached [e.g. directly or via linker (e.g. a cleavable linker or a non-cleavable linker)]. ADCs are useful for delivery of therapeutic agents (e.g., drugs or cytotoxic agents) to one or more target cells or tissues (Panowski, S. et al., 2014. mAbs 6:1, 34-45). In some cases, ADCs may be designed to bind to a surface antigen on a targeted cell. Upon binding, the entire antibody-antigen complex may be internalized and directed to a cellular lysosome. ADCs may then be degraded, releasing the bound cargo. Where the cargo is a cytotoxic agent, the target cell will be killed or otherwise disabled. Cytotoxic agents may include, but are not limited to cytoskeletal inhibitors [e.g. tubulin polymerization inhibitors such as maytansines or auristatins (e.g. monomethyl auristatin E [MMAE] and monomethyl auristatin F [MMAF])] and DNA damaging agents (e.g. DNA polymerization inhibitors such as calcheamicins and duocarmycins).

In some embodiments, antibodies of the invention may be tested for their ability to promote cell death when developed as ADCs. Cell viability assays may be performed in the presence and absence of secondary antibody-drug conjugates. Antibodies with potent cell growth inhibition may then be used to design direct antibody-drug conjugates (ADCs). The use of such secondary antibody-drug conjugates in cell-based cytotoxic assays may allow for quick pre-screening of many ADC candidates. Based on such assays, an unconjugated antibody candidate is directly added to cells in the presence of a secondary antibody that is conjugated to one or more cytotoxic agents (referred to herein as a 2° ADC). Internalization of the antibody/2° ADC complex into cells that express a high density of the targeted antigen can achieve a dose-dependent drug release within the cells, causing a cytotoxic effect to kill the cells (e.g., tumor cells), while cells expressing a low density of the targeted antigen are not affected (e.g., normal cells).

ADCs of the invention may be designed to target cancer cells. Such ADCs may include antibodies directed to one or more tumor-associated carbohydrate antigen (TACA). In some cases, ADCs of the invention are anti-STn antibodies.

Development of Chimeric Antigen Receptors

In some embodiments, antibody sequences of the invention may be used to develop a chimeric antigen receptor (CAR). CARs are transmembrane receptors expressed on immune cells that facilitate recognition and killing of target cells (e.g. tumor cells). CARs typically include three basic parts. These include an ectodomain (also known as the recognition domain), a transmembrane domain and an intracellular (signaling) domain. Ectodomains facilitate binding to cellular antigens on target cells, while intracellular domains typically include cell signaling functions to promote the killing of bound target cells. Further, they may have an extracellular domain with one or more antibody variable domains described herein or fragments thereof. CARs of the invention also include a transmembrane domain and cytoplasmic tail. CARs may be designed to include one or more segments of an antibody, antibody variable domain and/or antibody CDR, such that when such CARs are expressed on immune effector cells, the immune effector cells bind and clear any cells that are recognized by the antibody portions of the CARs.

Characteristics of CARs include their ability to redirect T cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T cells, CARs advantageously do not dimerize with endogenous T cell receptor (TCR) alpha and beta chains.

CARs engineered to target tumors may have specificity for one or more tumor associated carbohydrate antigens (TACAs). In some embodiments, ectodomains of these CARs may include one or more antibody variable domains or a fragment thereof. In some embodiments, CARs are expressed in T cells, and may be referred to as "CAR-engineered T cells" or "CAR-Ts". CAR-Ts may be engineered with CAR ectodomains having one or more antibody variable domains.

Structural Features of Chimeric Antigen Receptors

With gene-transfer technology, T cells can be engineered to stably express antibodies on their surface, conferring a desired antigen specificity. Chimeric antigen receptors (CARs) combine an antigen-recognition domain of a specific antibody with an intracellular domain of the CD3-zeta chain or FcγRI protein having T cell activating properties into a single chimeric fusion protein. CAR technology provides MHC-unrestricted recognition of target cells by T cells. Removal of the MHC restriction of T cells facilitates the use of these molecules in any patient, and also, in both $CD8^+$ and $CD4^+$ T cells, usually restricted to MHC class I or II epitopes, respectively. The use of Ab-binding regions allows T cells to respond to epitopes formed not only by protein, but also carbohydrate and lipid. This chimeric receptor approach is especially suited to immunotherapy of cancer, being able to bypass many of the mechanisms by which tumors avoid immunorecognition, such as MHC down-regulation, lack of expression of costimulatory molecules, CTL resistance, and induction of T cell suppression, and where the use of both $CD8^+$ CTL and $CD4^+$ T cells are best combined for optimum antitumor efficacy. This approach has been demonstrated to be applicable to a wide range of tumor antigens, in addition to viruses such as HIV (Finney, et al., *J. Immunology,* 2004, 172:104-113).

Although chimeric antigen receptors can trigger T cell activation in a manner similar to that of endogenous T cell receptors, in practice, the clinical application of CAR technology has been impeded by inadequate in vivo expansion of chimeric antigen receptor T cells. For example, first generation CARs included as their signaling domain the cytoplasmic region of the CD3ζ or Fc receptor γ chain. These first-generation CARs were tested in phase I clinical studies in patients with ovarian cancer, renal cancer, lymphoma, and neuroblastoma, and were found to induce modest responses, effectively redirecting T cell cytotoxicity but failing to enable T cell proliferation and survival upon repeated antigen exposure. The prototypes for second generation CARs involved receptors encompassing both CD28 and CD3ζ, and second-generation CARs have been tested for treatment of B cell malignancies and other cancers (Sadelain, et al., (2009) *Current Opinion in Immunology,* 21(2):215-223). Thus, CARs have rapidly expanded into a diverse array of receptors with different functional properties.

More recently, it was discovered that CAR-mediated T cell responses can be enhanced with the addition of a costimulatory domain. In preclinical models, the inclusion of the CD137 (4-1BB) signaling domain was found to significantly increase antitumor activity and in vivo persistence of chimeric antigen receptors as compared with inclusion of the CD3-zeta chain alone (Porter, et al., *N. Engl. J. Med.* 2011, 365:725-733).

Thus, in some embodiments of the present disclosure, antibody sequences of the invention may be used to develop a chimeric antigen receptor (CAR). In some embodiments, CARs are transmembrane receptors expressed on immune cells that facilitate recognition and killing of target cells (e.g. tumor cells).

In many cancers, tumor-specific antigens for targeting have not been defined, but in B-cell neoplasms, CD19 is an attractive target. Expression of CD19 is restricted to normal and malignant B cells and B-cell precursors. A pilot clinical trial of treatment with autologous T cells expressing an anti-CD19 chimeric antigen receptor (CART19) was performed in patients with advanced, p53-deficient chronic lymphoid leukemia (CLL). The generation of a CD19-specific immune response in bone marrow was demonstrated by temporal release of cytokines and ablation of leukemia cells that coincided with peak infiltration of chimeric antigen receptor T cells. (Porter, et al., *N. Engl. J. Med.* 2011, 365:725-733).

Further structural features of CARs may include any of those disclosed in several PCT Publications assigned to City of Hope and having the common inventor Michael Jensen. For example, PCT Publication WO 00/23573 describes genetically engineered, CD20-specific redirected T cells expressing a cell surface protein having an extracellular domain that includes a receptor specific for CD20, an intracellular signaling domain, and a transmembrane domain. Use of such cells for cellular immunotherapy of $CD20^+$ malignancies and for abrogating any untoward B cell function. In one embodiment, the cell surface protein is a single chain FvFc:ζ receptor where Fv designates the VH and VL chains of a single chain monoclonal antibody to CD20 linked by peptide, Fc represents a hinge-$CH_2$—$CH_3$ region of a human IgG1, and ζ represents the intracellular signaling domain of the zeta chain of human CD3. A method of making a redirected T cell expressing a chimeric T cell receptor by electroporation using naked DNA encoding the receptor. Similarly, PCT Publication WO 02/077029 describes genetically engineered, CD19-specific redirected immune cells expressing a cell surface protein having an extracellular domain that includes a receptor which is specific for CD19, an intracellular signaling domain, and a transmembrane domain. Use of such cells for cellular immunotherapy of $CD19^+$ malignancies and for abrogating any untoward B cell function. In one embodiment, the immune cell is a T cell and the cell surface protein is a single chain scFvFc:ζ receptor where scFv designates the $V_H$ and $V_L$ chains of a single chain monoclonal antibody to CD19, Fc represents at least part of a constant region of an IgG1, and zeta represents the intracellular signaling domain of the T cell antigen receptor complex zeta chain (zeta chain of human CD3). The extracellular domain scFvFc and the intracellular domain zeta are linked by a transmembrane domain such as the transmembrane domain of CD4. A method of making a redirected T cell expressing a chimeric T cell receptor by electroporation using naked DNA encoding the receptor. These chimeric antigen receptors have the ability, when expressed in T cells, to redirect antigen recognition based on the monoclonal antibody's specificity.

The design of scFvFc:ζ receptors with target specificities for tumor cell-surface epitopes is a conceptually attractive strategy to generate antitumor immune effector cells for adoptive therapy as it does not rely on pre-existing anti-tumor immunity. These receptors are "universal" in that they bind antigen in a MHC independent fashion, thus, one receptor construct can be used to treat a population of patients with antigen positive tumors. City of Hope PCT Publications WO 02/088334, WO 2007/059298 and WO 2010/065818 describe "zetakines" made up of an extracellular domain that includes a soluble receptor ligand linked to a support region capable of tethering the extracellular domain to a cell surface, a transmembrane region and an intracellular signaling domain. Zetakines, when expressed on the surface of T lymphocytes, direct T cell activity to those specific cells expressing a receptor for which the soluble receptor ligand is specific.

Additional features of CARs may include any of those disclosed in two PCT Publications assigned to University of Texas and having a common inventor Lawrence Cooper. PCT Publication No. WO 2009/091826 describes compositions that include a human CD19-specific chimeric T cell receptor (or chimeric antigen receptor, CAR) polypeptide (designated hCD19CAR) that includes an intracellular signaling domain, a transmembrane domain and an extracellular domain, the extracellular domain including a human CD 19 binding region. In another aspect, the CD 19 binding region is an F(ab')2, Fab', Fab, Fv or scFv. The intracellular domain may include an intracellular signaling domain of human CD3 and may further include human CD28 intracellular segment. In certain aspects, the transmembrane domain is a CD28 transmembrane domain. PCT Publication No. WO 2013/074916 describes methods and compositions for immunotherapy employing CAR$^+$ T cells genetically modified to eliminate expression of T cell receptor and/or HLA. In particular embodiments, the T cell receptor-negative and/or HLA-negative T cells are generated using zinc finger nucleases, for example. The CAR$^+$ T cells from allogeneic healthy donors can be administered to any patient without causing graft versus host disease (GVHD), acting as universal reagents for off-the-shelf treatment of medical conditions such as cancer, autoimmunity, and infection.

PCT Publication WO 2011/041093 assigned to the U.S. Department of Health and Human Services describes antivascular endothelial growth factor receptor-2 chimeric antigen receptors that include an antigen binding domain of a KDR-1121 or DC101 antibody, an extracellular hinge domain, a T cell receptor transmembrane domain, and an intracellular T cell receptor signaling domain, and their use in the treatment of cancer.

PCT Publications WO 2012/079000 and WO 2013/040557, the contents of each of which are herein incorporated by reference in their entirety, are assigned to University of Pennsylvania and share the common inventor Carl H. June; these publications describe CARs comprising an antigen binding domain, a transmembrane domain, a costimulatory signaling region, and a CD3 zeta signaling domain, and methods for generating RNA Chimeric Antigen Receptor (CAR) transfected T cells, respectively.

PCT Publication WO2013/126712, also assigned to University of Pennsylvania and sharing the common inventor Carl H. June, describes compositions and methods for generating a persisting population of T cells exhibiting prolonged exponential expansion in culture that is ligand independent and independent of the addition of exogenous cytokines or feeder cells, which are useful for the treatment of cancer. In some embodiments, the antigen binding domain is an anti-cMet binding domain. In some embodiments, the antigen binding domain is an anti-mesothelin binding domain. In some embodiments, the antigen binding domain is an anti-CD 19 binding domain. The hinge domain is IgG4, the transmembrane domain is a CD28 transmembrane domain. In some embodiments, the costimulatory signaling region is a CD28 signaling region. Also provided is a vector comprising a nucleic acid sequence encoding a chimeric antigen receptor (CAR), and the CAR comprising an antigen binding domain, a hinge domain, a transmembrane domain, a costimulatory signaling region, and a CD3 zeta signaling domain.

PCT Publication WO 2014/039513 assigned to University of Pennsylvania describes compositions and methods for inhibiting one or more diacylglycerol kinase (DGK) isoform in a cell in order to enhance the cytolytic activity of the cell. The cells may be used in adoptive T cell transfer in which, the cell is modified to express a chimeric antigen receptor (CAR). Inhibition of DGK in T cells used in adoptive T cell transfer increases cytolytic activity of the T cells and thus may be used in the treatment of a variety of conditions, including cancer, infection, and immune disorders.

PCT Publication WO 2014/055771 assigned to University of Pennsylvania describes compositions and methods for treating ovarian cancer. Specifically, the invention relates to administering a genetically modified T cell having alpha-folate receptor (FR-alpha) binding domain and CD27 costimulatory domain to treat ovarian cancer. In one embodiment, the FR-alpha binding domain is said to be fully human, thereby preventing a host immune response.

In some embodiments, CARs of the invention may be engineered to target tumors. Such CARs may have specificity for one or more TACAs. In some case, ectodomains of these CARs may comprise one or more antibody variable domain presented herein or a fragment thereof. In some embodiments, CARs of the invention are expressed in T cells, referred to herein as "CAR-engineered T cells" or "CAR-Ts". CAR-Ts may be engineered with CAR ectodomains having one or more antibody variable domain presented herein.

Multispecific Antibodies

In some embodiments, antibodies of the present invention may bind more than one epitope. As used herein, the terms "multibody" or "multispecific antibody" refer to an antibody wherein two or more variable regions bind to different epitopes. The epitopes may be on the same or different targets. In certain embodiments, a multi-specific antibody is a "bispecific antibody," which recognizes two different epitopes on the same or different antigens.

Bispecific Antibodies

A bispecific antibody (also referred to herein as "BsAb") is an antibody that is capable of binding two different antigens. Such antibodies typically comprise antigen-binding regions from at least two different antibodies. For example, a bispecific monoclonal antibody (BsMAb) is an artificial protein composed of fragments of two different monoclonal antibodies, thus allowing the BsAb to bind to two different types of antigen. One common application for this technology is in cancer immunotherapy, where BsMAbs are engineered to simultaneously bind to a cytotoxic cell (using a receptor like CD3) and a target like a tumor cell to be destroyed.

Bispecific antibodies may include any of those described in Riethmuller, G., 2012. *Cancer Immunity.* 12:12-18; Marvin, J. S. et al., 2005. *Acta Pharmacologica Sinica.* 26(6): 649-58; Schaefer, W. et al., 2011. PNAS. 108(27):11187-92; and Kontermann, R. E. and Brinkmann, U., 2015. *Drug*

*Discov Today.* 20(7):838-47, the contents of each of which are herein incorporated by reference in their entirety.

Tumor-associated carbohydrate antigens (TACAs) historically have been challenging targets for antibody therapeutics. In some embodiments, the present disclosure provides bispecific antibodies that include both a glycan-interacting region and a T cell-interacting region. Such antibodies may be capable of binding both to glycans (e.g., TACAs) and CD3, a T cell receptor that also facilitates T cell activation. Such antibodies, referred to herein as glycan-CD3 bispecific antibodies, may be used for T cell recruitment and/or activation. In some embodiments glycan-CD3 bispecific antibodies include STn-CD3 bispecific antibodies, wherein the glycan-interacting region binds to STn.

T cells are a type of white blood cells that are of key importance to the immune system. T cells are part of the cell-mediated immunity that recognizes and directly kills foreign substances or abnormal cells such as bacteria, viruses, or cancer cells. Broadly speaking, T cells can be divided into two different types, helper T cells and cytotoxic T cells. Once stimulated by a foreign antigen, helper T cells release various cytokines, such as IFN-γ, IL-4, IL-5, IL-9, IL-10 and IL-13. These cytokines stimulate antibody production by B cells and activate other immune cells such as macrophages and cytotoxic T cells. Cytotoxic T cells, which are activated by the cytokines, bind to and kill infected cells or cancer cells. Cytotoxic T cells recognize the antigens on the surface of the target cells through their T cell receptors, and destroy the target cells through degranulation and cell-mediated apoptosis.

STn-CD3 bispecific antibodies may be used to recruit and/or activate T cells for the reduction and/or elimination of cells expressing STn. Such STn expressing cells may include cancer cells, including those present or derived from tumors. STn expression may be cancer specific. In some cases, STn may be expressed on the surface of tumor cells that include, but are not limited to, ovarian, colon, prostate, breast, and pancreatic tumor cells. In some situations, STn expression may be limited or absent in non-cancerous or non-tumor cells.

In some embodiments, STn-CD3 bispecific antibodies may be used to stimulate anti-tumor immune activity. In some embodiments, STn-CD3 bispecific antibodies may be used to reduce or prevent innate immune suppression. Some STn-CD3 bispecific antibodies may be used to target one or more tumor cells that are resistant to chemotherapy. STn-CD3 bispecific antibodies may be used, according to some implementations, to reduce or prevent tumor cells metastasis.

In some embodiments, STn-CD3 bispecific antibodies may demonstrate low half-maximal effective concentrations for binding to T cells and/or STn. In some embodiments, STn-CD3 bispecific antibodies may demonstrate T cell activation and/or T cell-induced tumor killing in vitro.

New generations of BsMAb, called "trifunctional bispecific" antibodies, have been developed. These consist of two heavy and two light chains, one each from two different antibodies, where the two Fab regions (the arms) are directed against two antigens, and the Fc region (the foot) comprises the two heavy chains and forms the third binding site.

Of the two paratopes that form the tops of the variable domains of a bispecific antibody, one can be directed against a target antigen and the other against a T-lymphocyte antigen like CD3. In the case of trifunctional antibodies, the Fc region may additionally bind to a cell that expresses Fc receptors, like a macrophage, a natural killer (NK) cell or a dendritic cell. In sum, the targeted cell is connected to one or two cells of the immune system, which subsequently destroy it.

Other types of bispecific antibodies have been designed to overcome certain problems, such as short half-life, immunogenicity and side-effects caused by cytokine liberation. They include chemically linked Fabs, consisting only of the Fab regions, and various types of bivalent and trivalent single-chain variable fragments (scFvs), fusion proteins mimicking the variable domains of two antibodies. The furthest developed of these newer formats are the bi-specific T cell engagers (BiTEs) and mAb2's, antibodies engineered to contain an Fcab antigen-binding fragment instead of the Fc constant region.

A bispecific, single-chain antibody Fv fragment (Bs-scFv) was successfully used to kill cancer cells. Some human cancers are caused by functional defects in p53 that are restored by gene therapy with wild-type p53. Weisbart, et al., describe the construction and expression of a bispecific single-chain antibody that penetrates living colon cancer cells, binds intracellular p53, and targets and restores its wild type function (Weisbart, et al., *Int. J. Oncol.* 2004 October; 25(4):1113-8; and Weisbart, et al., *Int. J. Oncol.* 2004 December; 25(6):1867-73). In these studies, a bispecific, single-chain antibody Fv fragment (Bs-scFv) was constructed from (i) a single-chain Fv fragment of mAb 3E10 that penetrates living cells and localizes in the nucleus, and (ii) a single-chain Fv fragment of a non-penetrating antibody, mAb PAb421 that binds the C-terminal of p53. PAb421 binding restores wild-type functions of some p53 mutants, including those of SW480 human colon cancer cells. The Bs-scFv penetrated SW480 cells and was cytotoxic, suggesting an ability to restore activity to mutant p53. COS-7 cells (monkey kidney cells with wild-type p53) served as a control since they are unresponsive to PAb421 due to the presence of SV40 large T antigen that inhibits binding of PAb421 to p53. Bs-scFv penetrated COS-7 cells but was not cytotoxic, thereby eliminating non-specific toxicity of Bs-scFv unrelated to binding p53. Fv fragments alone were not cytotoxic, indicating that killing was due to transduction of p53. A single mutation in CDR1 of PAb421 VH eliminated binding of the Bs-scFv to p53 and abrogated cytotoxicity for SW480 cells without altering cellular penetration, further supporting the requirement of PAb421 binding to p53 for cytotoxicity (Weisbart, et al., *Int. J. Oncol.* 2004 October; 25(4):1113-8; and Weisbart, et al., *Int. J. Oncol.* 2004 December; 25(6):1867-73).

In some embodiments, antibodies of the present invention may be diabodies. Diabodies are functional bispecific single-chain antibodies (bscAb). These bivalent antigen-binding molecules are composed of non-covalent dimers of scFvs, and can be produced in mammalian cells using recombinant methods. (See, e.g., Mack et al, *Proc. Natl. Acad. Sci.*, 92: 7021-7025, 1995). Few diabodies have entered clinical development. An iodine-123-labeled diabody version of the anti-CEA chimeric antibody cT84.66 has been evaluated for pre-surgical immunoscintigraphic detection of colorectal cancer in a study sponsored by the Beckman Research Institute of the City of Hope (Clinicaltrials.gov NCT00647153) (Nelson, A. L., *MAbs.* 2010. January-February; 2(1):77-83).

Using molecular genetics, two scFvs can be engineered in tandem into a single polypeptide, separated by a linker domain, called a "tandem scFv" (tascFv). TascFvs have been found to be poorly soluble and require refolding when produced in bacteria, or they may be manufactured in mammalian cell culture systems, which avoids refolding requirements but may result in poor yields. Construction of a tascFv with genes for two different scFvs yields a "bispecific single-chain variable fragments" (bis-scFvs). Only two tascFvs have been developed clinically by commercial firms; both are bispecific agents in active early phase development by Micromet for oncologic indications, and are described as bispecific T cell engagers. Blinatumomab is an anti-CD19/anti-CD3 bispecific tascFv that potentiates T cell responses to B-cell non-Hodgkin lymphoma in Phase 2. MT110 is an anti-EP-CAM/anti-CD3 bispecific tascFv that potentiates T cell responses to solid tumors in Phase 1. Bispecific, tetravalent "TandAbs" are also being researched by Affimed (Nelson, A. L., MAbs. 0.2010. January-February; 2(1):77-83).

Also included are maxibodies (bivalent scFv fused to the amino terminus of the Fc (CH2-CH3 domains) of IgG.

Bispecific T cell-engager (BiTE) antibodies refer to antibodies designed to transiently engage cytotoxic T cells for lysis of selected target cells. These typically include at least two functional regions, one interacting with T cells (referred to herein as a "T cell-interacting region") and one interacting with a target antigen. The target antigen may be an antigen on the surface of a cell being targeted for destruction. By binding both a T cell and a target antigen, BiTEs may bring T cells into to contact with the target cell and facilitate cell destruction. In some embodiments, the functional regions include scFvs. Some BiTE antibodies include two scFvs joined by a linker. In some antibodies, the two functional regions are located at different regions of an antibody (e.g., one in the Fab region and one at the Fc region).

The clinical activity of BiTE antibodies corroborates findings that ex vivo expanded, autologous T cells derived from tumor tissue, or transfected with specific T cell receptors, have shown therapeutic potential in the treatment of solid tumors. While these personalized approaches prove that T cells alone can have considerable therapeutic activity, even in late-stage cancer, they are cumbersome to perform on a broad basis. This is different for cytotoxic T-lymphocyte antigen 4 (CTLA-4) antibodies, which facilitate generation of tumor-specific T cell clones, and also for bi- and tri-specific antibodies that directly engage a large proportion of patients' T cells for cancer cell lysis. The potential of global T cell engagement for human cancer therapy by T cell-engaging antibodies is under active investigation (Baeuerle P A, et al., Current Opinion in Molecular Therapeutics. 2009, 11(1):22-30 and Baeuerle P A and Reinhardt C, Cancer Res. 2009, 69(12): 4941-4, the contents of each of which are herein incorporated by reference in their entirety).

Third generation molecules include "miniaturized" antibodies. Among the best examples of mAb miniaturization are the small modular immunopharmaceuticals (SMIPs) from Trubion Pharmaceuticals. These molecules, which can be monovalent or bivalent, are recombinant single-chain molecules containing one $V_L$, one $V_H$ antigen-binding domain, and one or two constant "effector" domains, all connected by linker domains. Presumably, such a molecule might offer the advantages of increased tissue or tumor penetration claimed by fragments while retaining the immune effector functions conferred by constant domains. At least three "miniaturized" SMIPs have entered clinical development. TRU-015, an anti-CD20 SMIP developed in collaboration with Wyeth, is the most advanced project, having progressed to Phase 2 for rheumatoid arthritis (RA). Earlier attempts in systemic lupus erythematosus (SLE) and B cell lymphomas were ultimately discontinued. Trubion and Facet Biotechnology are collaborating in the development of TRU-016, an anti-CD37 SMIP, for the treatment of CLL and other lymphoid neoplasias, a project that has reached Phase 2. Wyeth has licensed the anti-CD20 SMIP SBI-087 for the treatment of autoimmune diseases, including RA, SLE and possibly multiple sclerosis, although these projects remain in the earliest stages of clinical testing. (Nelson, A. L., MAbs. 2010. January-February; 2(1):77-83).

Genmab is researching application of their "Unibody" technology, in which the hinge region has been removed from IgG4 molecules. While IgG4 molecules are unstable and can exchange light-heavy chain heterodimers with one another, deletion of the hinge region prevents heavy chain-heavy chain pairing entirely, leaving highly specific monovalent light/heavy heterodimers, while retaining the Fc region to ensure stability and extended half-life in vivo. This configuration may minimize the risk of immune activation or oncogenic growth, as IgG4 interacts poorly with FcRs and monovalent unibodies fail to promote intracellular signaling complex formation. These contentions are, however, largely supported by laboratory, rather than clinical, evidence. Biotecnol is also developing a "miniaturized" mAb, CAB051, which is a "compacted" 100 kDa anti-HER2 antibody in preclinical research (Nelson, A. L., MAbs. 2010. January-February; 2(1):77-83).

Recombinant therapeutics composed of single antigen-binding domains have also been developed, although they currently account for only 4% of the clinical pipeline. These molecules are extremely small, with molecular weights approximately one-tenth of those observed for full-sized mAbs. Arana and Domantis engineer molecules composed of antigen-binding domains of human immunoglobulin light or heavy chains, although only Arana has a candidate in clinical testing, ART-621, an anti-TNFα molecule in Phase 2 study for the treatment of psoriasis and rheumatoid arthritis. Ablynx produces "nanobodies" derived from the antigen-binding variable heavy chain regions ($V_{HHS}$) of heavy chain antibodies found in camels and llamas, which lack light chains. Two Ablynx anti-von Willebrand Factor nanobodies have advanced to clinical development, including ALX-0081, in Phase 2 development as an intravenous therapy to prevent thrombosis in patients undergoing percutaneous coronary intervention for acute coronary syndrome, and ALX-0681, a Phase 1 molecule for subcutaneous administration intended for both patients with acute coronary syndrome and thrombotic thrombocytopenic purpura (Nelson, A. L., MAbs. 2010. January-February; 2(1):77-83).

In some embodiments, the bispecific antibody of the present invention may adopt an "IgG-scFv" format. IgG-scFvs are bispecific antibodies that include an IgG antibody with one or more scFv domains fused to one or more of the IgG polypeptide chains (see Strohl, W. R. et al, 2012. Woodhead Publishing Series in Biomedicine, Therapeutic Antibody Engineering. p 316-19). In some cases, IgG-scFvs include an scFv fused to the C-terminus of each antibody heavy chain Examples of bispecific antibodies using this format include, but are not limited to, BsAb by ZymoGenetics (now Bristol-Myers Squibb), HERCULES by Biogen Idec (U.S. Pat. No. 7,951,918), and TvAb by Roche (WO2012025525 and WO2012025530). One of ZymoGenetics' BsAbs, anti-IL17A/anti-IL23 BsAb, is currently in a Phase 1 trial in patients with inflammatory and autoimmune diseases. Their engineering process also involves a step for shuffling the anti-IL-17A and anti-CD23 variable regions between the Fab and scFv regions and rearranging the scFv molecules in both the VH-VL and the VL-VH orientations (Mabry, R., Protein Eng Des Sel. 2010, 23(3):115-27). Biogen Idec's HERCULES approach is slightly different from the standard IgG-scFv format in that the scFvs are fused to either the N- or C-termini of the heavy chains of an IgG1 antibody. Preclinical studies of their lead antibody targeting TRAIL-R2 and LTβR demonstrated that both the N- and the C-terminally fused forms have good pharmacokinetics, stability and pre-clinical efficacy (Michaelson et al., MAbs. 2009 March-April; 1(2): 128-141). Roche also adopted this format, which is referred to as "TvAb" for tetravalent bispecific antibody. The most advanced candidate, Ang-2-VEGF-TAvi6, consists of disulfide bond-stabilized scFvs specific for Ang-2 fused to the C-termini of the heavy chains of anti-VEGF mAb bevacizumab (Avastin®). Ang-2-VEGF-TAvi6 is currently in preclinical studies.

In some embodiments, antibodies of the present disclosure include IgG-scFv antibodies that are bispecific T cell engager antibodies.

In some embodiments, multispecific antibodies may include one or more of the scFv sequences listed in Table 15. In some cases, such scFvs may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the sequences listed. In some cases, scFvs may include an amino acid sequence having one or more fragments of any of the sequences listed.

TABLE 15 scFv sequences

| ScFv No. | Sequence | SEQ ID NO |
|---|---|---|
| scFv1 | QVQLEQSGGGLVKPGGSLRLSCAASGYTFTRYTMHWIRQAPGKG LEWVSYINPSRGYTNYNQKFKDRFTISRDNAKNSLYLQMNSLRAE DTAVYYCARYYDDHYCLDYWGQGTLVTVSSASTGGGGSGGGGS GGGGSGGGGSDIQMTQSPSSLSASVGDRVTITCSASSSVSYMNWY QQKPGKAPKLLIYDTSKLASGVPSRFSGSGSGTDFTLTISSLQPEDF ATYYCQQWSSNPFTFGQGTKVEIKR | 73 |
| scFv2 | QVQLEQSGGGLVKPGGSLRLSCKASGYTFTRYTMHWVKQAPGK GLEWVGYINPSRGYTNYNQKFKDRATISRDKAKNSLYLQMNSLR AEDTAVYYCARYYDDHYSLDYWGQGTLVTVSSASTGGGGSGGG GSGGGGSGGGGSQIQLTQSPSSLSASVGDRVTITCSASSSVSYMN WYQQKPGKAPKRWIYDTSKLASGVPSRFSGSGSGTDYTLTISSLQ PEDFATYYCQQWSSNPFTFGQGTKVEVKR | 74 |
| scFv3 v1 | QVQLEQSGGGDVKPDGSLRLSCKASGYTFTRYTMHWVKQAPGK GLEWVGYINPSRGYTNYNQKFKDRATISRDKAKNTLYLQMNSLR GEDTAVYYCARYYDDHYSLDYWGQGTTVTVSSASTGGGGSGGG GSGGGGSGGGGSQIQLTQSPSSLEASVGDRVTITCSASSSVSYMN WYQQKPGKAPKRWIYDTSKLASGVPSRFSGSGSGTDYTLTISSLQ PEDEGTYYCQQWSSNPFTFGGGTKVEVQG | 75 |
| scFv3 v2 | QVQLEQSGGGDVKPDGSLRLSCKASGYTFTRYTMHWVKQAPGK GLEWIGYINPSRGYTNYNQKFKDRATISRDKAKNTAYLQMNSLR GEDTAVYYCARYYDDHYSLDYWGQGTTVTVSSASTGGGGSGGG GSGGGGSQIQLTQSPSSLEASVGDRVTITCSASSSVSYMNWYQQK PGKAPKRWIYDTSKLASGVPSRFSGSGSGTDYTLTISSLQPEDEGT YYCQQWSSNPFTFGGGTKVEVQG | 76 |
| scFv4 | QIQLTQSPSSLEASVGDRVTITCSASSSVSYMNWYQQKPGKAPKR WIYDTSKLASGVPSRFSGSGSGTDYTLTISSLQPEDEGTYYCQQWS SNPFTFGGGTKVEVQGGGGGSGGGGSGGGGSGGGGSQVQLEQS GGGDVKPDGSLRLSCKASGYTFTRYTMHWVKQAPGKGLEWVG YINPSRGYTNYNQKFKDRATISRDKAKNTLYLQMNSLRGEDTAV YYCARYYDDHYSLDYWGQGTTVTVSSAST | 77 |
| scFv5 | QVQLEQSGGGDVKPDGSLRLSCKASGYTFTRYTMHWVKQAPGK CLEWVGYINPSRGYTNYNQKFKDRATISRDKAKNTLYLQMNSLR AEDTAVYYCARYYDDHYSLDYWGQGTTVTVSSASTGGGGSGGG GSGGGGSGGGGSQIQLTQSPSSLSASVGDRVTITCSASSSVSYMN WYQQKPGKAPKRWIYDTSKLASGVPSRFSGSGSGTDYTLTISSLQ PEDEATYYCQQWSSNPFTFGCGTKVEVQG | 78 |
| scFv6 | QIQLTQSPSSLSASVGDRVTITCSASSSVSYMNWYQQKPGKAPKR WIYDTSKLASGVPSRFSGSGSGTDYTLTISSLQPEDEATYYCQQWS SNPFTFGCGTKVEVQGGGGGSGGGGSGGGGSGGGGSQVQLEQSG GGDVKPGGSLRLSCKASGYTFTRYTMHWVKQAPGKCLEWVGYI NPSRGYTNYNQKFKDRATISRDKAKNTLYLQMNSLRAEDTAVYY CARYYDDHYSLDYWGQGTTVTVSSAST | 79 |
| scFv7 | QVQLEQSGGGDVKPDGSLRLSCKASGYTFTRYTMHWVKQAPGK GLEWVGYINPSRGYTNYNQKFKDRATISRDKAKNTLYLQMNSLR GEDTAVYYCARYYDDHYCLDYWGQGTTVTVSSASTGGGGSGGG GSGGGGSGGGGSQIQLTQSPSSLEASVGDRVTITCSASSSVSYMN WYQQKPGKAPKRWIYDTSKLASGVPSRFSGSGSGTDYTLTISSLQ PEDEGTYYCQQWSSNPFTFGGGTKVEVQG | 80 |

TABLE 15-continued scFv sequences

| ScFv No. | Sequence | SEQ ID NO |
|---|---|---|
| scFv8 | DIKLQQSGAELARPGASVKMSCKTSGYTFTRYTMHWVKQRPGQ GLEWIGYINPSRGYTNYNQKFKDKATLTTDKSSSTAYMQLSSLTS EDSAVYYCARYYDDHYCLDYWGQGTTLTVSSASTGGGGSGGGG SGGGGSGGGGSDIQLTQSPAIMSASPGEKVTMTCRASSSVSYMN WYQQKSGTSPKRWIYDTSKVASGVPYRFSGSGSGTSYSLTISSME AEDAATYYCQQWSSNPLTFGAGTKLELQG | 81 |
| scFv9 v1 | QVQLQQSGAELARPGASVKMSCKASGYTFTRYTMHWVKQRPGQ GLEWIGYINPSRGYTNYNQKFKDKATLTTDKSSSTAYMQLSSLTS EDSAVYYCARYYDDHYCLDYWGQGTTLTVSSASTGGGGSGGGG SGGGGSGGGGSQIVLTQSPAIMSASPGEKVTMTCSASSSVSYMNW YQQKSGTSPKRWIYDTSKLASGVPAHFRGSGSGTSYSLTISGMEA EDAATYYCQQWSSNPFTFGSGTKLEINR | 82 |
| scFv9 v2 | QVQLQQSGAELARPGASVKMSCKASGYTFTRYTMHWVKQRPGQ GLEWIGYINPSRGYTNYNQKFKDKATLTTDKSSSTAYMQLSSLTS EDSAVYYCARYYDDHYCLDYWGQGTTLTVSSASTGGGGSGGGG SGGGGSQIVLTQSPAIMSASPGEKVTMTCSASSSVSYMNWYQQKS GTSPKRWIYDTSKLASGVPAHFRGSGSGTSYSLTISGMEAEDAAT YYCQQWSSNPFTFGSGTKLEINR | 83 |
| scFv9 v3 | QVQLQQSGAELARPGASVKMSCKASGYTFTRYTMHWVKQRPGQ GLEWIGYINPSRGYTNYNQKFKDKATLTTDKSSSTAYMQLSSLTS EDSAVYYCARYYDDHYCLDYWGQGTTLTVSSSTGGGGSGGGGS GGGGSDIQIVLTQSPAIMSASPGEKVTMTCSASSSVSYMNWYQQK SGTSPKRWIYDTSKLASGVPAHFRGSGSGTSYSLTISGMEAEDAA TYYCQQWSSNPFTFGSGTKLEINR | 84 |
| scFv10 | EVQLVQSGAEDKKPGASVKVSCKASGYTFTDHAIHWVRQAPGQ GLEWMGYFSPGNDDIKYNEKFRGRATLTADKSSSTAYMELNSLR SDDTAVYFCKRSLSTPYWGQGTSVTVSSASTGGGGSGGGGSGGG GSGGGGSDIVMTQSPDSLSVSDGERATINCKSSQSLLNRGNHKNY LTWYQQKPGQPPKLLIYWASTRESGVPDRFSGSGSGTDFTLTISSL QAEDEGVYYCQNDYTYPYTFGGGTKVEIQ | 85 |
| scFv11 | EVQLVQSGAEDKKPGASVKVSCKASGYTFTDHAIHWVRQAPGQ CLEWMGYFSPGNDDIKYNEKFRGRATLTADKSSSTAYMELNSLR SDDTAVYFCKRSLSTPYWGQGTSVTVSSASTGGGGSGGGGSGGG GSGGGGSDIVMTQSPDSLSVSDGERATINCKSSQSLLNRGNHKNY LTWYQQKPGQPPKLLIYWASTRESGVPDRFSGSGSGTDFTLTISSL QAEDEGVYYCQNDYTYPYTFGCGTKVEIQ | 86 |
| scFv12 | DIVMTQSPDSLSVSDGERATINCKSSQSLLNRGNHKNYLTWYQQ KPGQPPKLLIYWASTRESGVPDRFSGSGSGTDFTLTISSLQAEDEG VYYCQNDYTYPYTFGGGTKVEIKRTGGGGSGGGGSGGGGSEVQL VQSGAEDKKPGASVKVSCKASGYTFTDHAIHWVRQAPGQGLEW MGYFSPGNDDIKYNEKFRGRATLTADKSSSTAYMELNSLRSDDT AVYFCKRSLSTPYWGQGTSVTVSS | 87 |

In some embodiments, bispecific antibodies may include one or more of the antibody heavy and light chains presented in Table 16. In some cases, such antibody heavy and/or light chains may include an amino acid sequence with from about 50% to about 99.9% sequence identity (e.g. from about 50% to about 60%, from about 55% to about 65%, from about 60% to about 70%, from about 65% to about 75%, from about 70% to about 80%, from about 75% to about 85%, from about 80% to about 90%, from about 85% to about 95%, from about 90% to about 99.9%, from about 95% to about 99.9%, about 97%, about 97.5%, about 98%, about 98.5%, about 99%, about 99.5%, about 99.6%, about 99.7% or about 99.8%) with one or more of the sequences listed. In some cases, antibody heavy and/or light chains may include an amino acid sequence having one or more fragments of any of the sequences listed.

TABLE 16

Bispecific antibody heavy and light chain sequences

| BsAb ID | Variable domain | Sequence | SEQ ID NO |
|---|---|---|---|
| FV1 | Heavy chain full length | EVQLVQSGAEVKKPGASVKVSCKASGYTFTDHAIHWV RQAPGQGLEWMGYFSPGNDDIKYNEKFRGRVTMTAD KSSSTAYMELRSLSDDTAVYFCKRSLSTPYWGQGTLV TVSSASTKGPSVFPLAPSSKSTSGGTAALGCLVKDYFPE | 88 |

TABLE 16-continued

Bispecific antibody heavy and light chain sequences

| BsAb ID | Variable domain | Sequence | SEQ ID NO |
|---|---|---|---|
| | | PVTVSWNSGALTSGVHTFPAVLQSSGLYSLSSVVTVPSS SLGTQTYICNVNHKPSNTKVDKKVEPKSCDKTHTCPPC PAPELLGGPSVFLFPPKPKDTLMISRTPEVTCVVVDVSH EDPEVKFNWYVDGVEVHNAKTKPREEQYQSTYRVVS VLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPGGGGSGGG GSGGGGSQVQLEQSGGGLVKPGGSLRLSCAASGYTFTR YTMHWIRQAPGKGLEWVSYINPSRGYTNYNQKFKDRF TISRDNAKNSLYLQMNSLRAEDTAVYYCARYYDDHYC LDYWGQGTLVTVSSASTGGGGSGGGGSGGGGSGGGG SDIQMTQSPSSLSASVGDRVTITCSASSSVSYMNWYQQ KPGKAPKLLIYDTSKLASGVPSRFSGSGSGTDFTLTISSL QPEDFATYYCQQWSSNPFTFGQGTKVEIKR | |
| FV1 | Light chain full length | DIVMTQSPDSLAVSLGERATINCKSSQSLLNRGNHKNY LTWYQQKPGQPPKLLIYWASTRESGVPDRFSGSGSGTD FTLTISSLQAEDVAVYYCQNDYTYPYTFGQGTKVEIKR TVAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC | 89 |
| FV2 | Heavy chain full length | EVQLVQSGAEVKKPGASVKVSCKASGYTFTDHAIHWV RQAPGQGLEWMGYFSPGNDDIKYNEKFRGRVTMTAD KSSSTAYMELRSLRSDDTAVYFCKRSLSTPYWGQGTLV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKKVEPKSCDKTHTCPPC PAPELLGGPSVFLFPPKPKDTLMISRTPEVTCVVVDVSH EDPEVKFNWYVDGVEVHNAKTKPREEQYQSTYRVVS VLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPGGGGSGGG GSGGGGSQVQLEQSGGGLVKPGGSLRLSCKASGYTFTR YTMHWVKQAPGKGLEWVGYINPSRGYTNYNQKFKDR ATISRDKAKNSLYLQMNSLRAEDTAVYYCARYYDDHY SLDYWGQGTLVTVSSASTGGGGSGGGGSGGGGSGGGG GSQIQLTQSPSSLSASVGDRVTITCSASSSVSYMNWYQQ KPGKAPKRWIYDTSKLASGVPSRFSGSGSGTDYTLTISS LQPEDFATYYCQQWSSNPFTFGQGTKVEVKR | 90 |
| FV2 | Light chain full length | DIVMTQSPDSLAVSLGERATINCKSSQSLLNRGNHKNY LTWYQQKPGQPPKLLIYWASTRESGVPDRFSGSGSGTD FTLTISSLQAEDVAVYYCQNDYTYPYTFGQGTKVEIKR TVAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC | 89 |
| FV3 | Heavy chain full length | EVQLVQSGAEVKKPGASVKVSCKASGYTFTDHAIHWV RQAPGQGLEWMGYFSPGNDDIKYNEKFRGRVTMTAD KSSSTAYMELRSLRSDDTAVYFCKRSLSTPYWGQGTLV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKKVEPKSCDKTHTCPPC PAPELLGGPSVFLFPPKPKDTLMISRTPEVTCVVVDVSH EDPEVKFNWYVDGVEVHNAKTKPREEQYQSTYRVVS VLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPGGGGSGGG GSGGGGSQVQLEQSGGGDVKPDGSLRLSCKASGYTFT RYTMHWVKQAPGKGLEWVGYINPSRGYTNYNQKFKD RATISRDKAKNTLYLQMNSLRGEDTAVYYCARYYDDH YSLDYWGQGTTVTVSSASTGGGGSGGGGSGGGGSGGG GGSQIQLTQSPSSLEASVGDRVTITCSASSSVSYMNWYQ QKPGKAPKRWIYDTSKLASGVPSRFSGSGSGTDYTLTIS SLQPEDEGTYYCQQWSSNPFTFGGGTKVEVQG | 91 |

TABLE 16-continued

Bispecific antibody heavy and light chain sequences

| BsAb ID | Variable domain | Sequence | SEQ ID NO |
|---|---|---|---|
| FV3 | Light chain full length | DIVMTQSPDSLAVSLGERATINCKSSQSLLNRGNHKNYLTWYQQKPGQPPKLLIYWASTRESGVPDRFSGSGSGTDFTLTISSLQAEDVAVYYCQNDYTYPYTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 89 |
| FV4 | Heavy chain full length | EVQLVQSGAEVKKPGASVKVSCKASGYTFTDHAIHWVRQAPGQGLEWMGYFSPGNDDIKYNEKFRGRVTMTADKSSSTAYMELRSLRSDDTAVYFCKRSLSTPYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYQSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGGGGGSGGGGSGGGGSQIQLTQSPSSLEASVGDRVTITCSASSSVSYMNWYQQKPGKAPKRWIYDTSKLASGVPSRFSGSGSGTDYTLTISSLQPEDEGTYYCQQWSSNPFTFGGGTKVEVQGGGGGSGGGGSGGGGSGGGGSQVQLEQSGGGDVKPDGSLRLSCKASGYTFTRYTMHWVKQAPGKGLEWVGYINPSRGYTNYNQKFKDRATISRDKAKNTLYLQMNSLRGEDTAVYYCARYYDDHYSLDYWGQGTTVTVSSAST | 92 |
| FV4 | Light chain full length | DIVMTQSPDSLAVSLGERATINCKSSQSLLNRGNHKNYLTWYQQKPGQPPKLLIYWASTRESGVPDRFSGSGSGTDFTLTISSLQAEDVAVYYCQNDYTYPYTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 89 |
| FV5 | Heavy chain full length | EVQLVQSGAEVKKPGASVKVSCKASGYTFTDHAIHWVRQAPGQGLEWMGYFSPGNDDIKYNEKFRGRVTMTADKSSSTAYMELRSLRSDDTAVYFCKRSLSTPYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYQSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGGGGSGGGGSGGGSQVQLEQSGGGDVKPGGSLRLSCKASGYTFTRYTMHWVKQAPGKCLEWVGYINPSRGYTNYNQKFKDRATISRDKAKNTLYLQMNSLRAEDTAVYYCARYYDDHYSLDYWGQGTTVTVSSASTGGGGSGGGGSGGGGSGGGGSQIQLTQSPSSLSASVGDRVTITCSASSSVSYMNWYQQKPGKAPKRWIYDTSKLASGVPSRFSGSGSGTDYTLTISSLQPEDEATYYCQQWSSNPFTFGCGTKVEVQG | 93 |
| FV5 | Light chain full length | DIVMTQSPDSLAVSLGERATINCKSSQSLLNRGNHKNYLTWYQQKPGQPPKLLIYWASTRESGVPDRFSGSGSGTDFTLTISSLQAEDVAVYYCQNDYTYPYTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 89 |
| FV6 | Heavy chain full length | EVQLVQSGAEVKKPGASVKVSCKASGYTFTDHAIHWVRQAPGQGLEWMGYFSPGNDDIKYNEKFRGRVTMTADKSSSTAYMELRSLRSDDTAVYFCKRSLSTPYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYQSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGGGGSGGGGGGSQIQLTQSPSSLSASVGDRVTITCSASSSVSYM | 94 |

TABLE 16-continued

Bispecific antibody heavy and light chain sequences

| BsAb ID | Variable domain | Sequence | SEQ ID NO |
|---|---|---|---|
| | | NWYQQKPGKAPKRWIYDTSKLASGVPSRFSGSGSGTD YTLTISSLQPEDEATYYCQQWSSNPFTFGCGTKVEVQG GGGGSGGGGSGGGGSGGGGSQVQLEQSGGGDVKPGG SLRLSCKASGYTFTRYTMHWVKQAPGKCLEWVGYINP SRGYTNYNQKFKDRATISRDKAKNTLYLQMNSLRAED TAVYYCARYYDDHYSLDYWGQGTTVTVSSAST | |
| FV6 | Light chain full length | DIVMTQSPDSLAVSLGERATINCKSSQSLLNRGNHKNY LTWYQQKPGQPPKLLIYWASTRESGVPDRFSGSGSGTD FTLTISSLQAEDVAVYYCQNDYTYPYTFGQGTKVEIKR TVAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC | 89 |
| FV7 | Heavy chain full length | EVQLVQSGAEVKKPGASVKVSCKASGYTFTDHAIHWV RQAPGQGLEWMGYFSPGNDDIKYNEKFRGRVTMTAD KSSSTAYMELRSLRSDDTAVYFCKRSLSTPYWGQGTLV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKKVEPKSCDKTHTCPPC PAPELLGGPSVFLFPPKPKDTLMISRTPEVTCVVVDVSH EDPEVKFNWYVDGVEVHNAKTKPREEQYQSTYRVVS VLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPGGGGSGGG GSGGGGSQVQLEQSGGGDVKPDGSLRLSCKASGYTFT RYTMHWVKQAPGKGLEWVGYINPSRGYTNYNQKFKD RATISRDKAKNTLYLQMNSLRGEDTAVYYCARYYDDH YCLDYWGQGTTVTVSSASTGGGGSGGGGSGGGGSGG GGSQIQLTQSPSSLEASVGDRVTITCSASSSVSYMNWYQ QKPGKAPKRWIYDTSKLASGVPSRFSGSGSGTDYTLTIS SLQPEDEGTYYCQQWSSNPFTFGGGTKVEVQG | 95 |
| FV7 | Light chain full length | DIVMTQSPDSLAVSLGERATINCKSSQSLLNRGNHKNY LTWYQQKPGQPPKLLIYWASTRESGVPDRFSGSGSGTD FTLTISSLQAEDVAVYYCQNDYTYPYTFGQGTKVEIKR TVAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC | 89 |
| FV8 | Heavy chain full length | EVQLVQSGAEVKKPGASVKVSCKASGYTFTDHAIHWV RQAPGQGLEWMGYFSPGNDDIKYNEKFRGRVTMTAD KSSSTAYMELRSLRSDDTAVYFCKRSLSTPYWGQGTLV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKKVEPKSCDKTHTCPPC PAPELLGGPSVFLFPPKPKDTLMISRTPEVTCVVVDVSH EDPEVKFNWYVDGVEVHNAKTKPREEQYQSTYRVVS VLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPGGGGSGGG GSGGGGSDIKLQQSGAELARPGASVKMSCKTSGYTFTR YTMHWVKQRPGQGLEWIGYINPSRGYTNYNQKFKDK ATLTTDKSSSTAYMQLSSLTSEDSAVYYCARYYDDHY CLDYWGQGTTLTVSSASTGGGGSGGGGSGGGGSGGG GSDIQLTQSPAIMSASPGEKVTMTCRASSSVSYMNWYQ QKSGTSPKRWIYDTSKVASGVPYRFSGSGSGTSYSLTIS SMEAEDAATYYCQQWSSNPLTFGAGTKLELQG | 96 |
| FV8 | Light chain full length | DIVMTQSPDSLAVSLGERATINCKSSQSLLNRGNHKNY LTWYQQKPGQPPKLLIYWASTRESGVPDRFSGSGSGTD FTLTISSLQAEDVAVYYCQNDYTYPYTFGQGTKVEIKR TVAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC | 89 |
| FV9 | Heavy chain full length | EVQLVQSGAEVKKPGASVKVSCKASGYTFTDHAIHWV RQAPGQGLEWMGYFSPGNDDIKYNEKFRGRVTMTAD KSSSTAYMELRSLRSDDTAVYFCKRSLSTPYWGQGTLV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKKVEPKSCDKTHTCPPC PAPELLGGPSVFLFPPKPKDTLMISRTPEVTCVVVDVSH | 97 |

TABLE 16-continued

Bispecific antibody heavy and light chain sequences

| BsAb ID | Variable domain | Sequence | SEQ ID NO |
|---|---|---|---|
| | | EDPEVKFNWYVDGVEVHNAKTKPREEQYQSTYRVVS<br>VLTVLHQDWLNGKEYKCKVSNKALPAPIEKTISKAKG<br>QPREPQVYTLPPSREEMTKNQVSLTCLVKGFYPSDIAVE<br>WESNGQPENNYKTTPPVLDSDGSFFLYSKLTVDKSRW<br>QQGNVFSCSVMHEALHNHYTQKSLSLSPGGGGSGGG<br>GSGGGGSQVQLQQSGAELARPGASVKMSCKASGYTFT<br>RYTMHWVKQRPGQGLEWIGYINPSRGYTNYNQKFKD<br>KATLTTDKSSSTAYMQLSSLTSEDSAVYYCARYYDDH<br>YCLDYWGQGTTLTVSSASTGGGGSGGGGSGGGGSGG<br>GGSQIVLTQSPAIMSASPGEKVTMTCSASSSVSYMNWY<br>QQKSGTSPKRWIYDTSKLASGVPAHFRGSGSGTSYSLTI<br>SGMEAEDAATYYCQQWSSNPFTFGSGTKLEINR | |
| FV9 | Light chain full length | DIVMTQSPDSLAVSLGERATINCKSSQSLLNRGNHKNY<br>LTWYQQKPGQPPKLLIYWASTRESGVPDRFSGSGSGTD<br>FTLTISSLQAEDVAVYYCQNDYTYPYTFGQGTKVEIKR<br>TVAAPSVFIFPPSDEQLKSGTASVVCLLNNFYPREAKVQ<br>WKVDNALQSGNSQESVTEQDSKDSTYSLSSTLTLSKAD<br>YEKHKVYACEVTHQGLSSPVTKSFNRGEC | 89 |
| C1 | Heavy chain full length | EVQLVQSGAEVKKPGASVKVSCKASGYTFTDHAIHWV<br>RQAPGQGLEWMGYFSPGNDDIKYNEKFRGRVTMTAD<br>KSSSTAYMELRSLRSDDTAVYFCKRSLSTPYWGQGTLV<br>TVSSASTKGPSVFPLAPSSKSTSGGTAALGCLVKDYFPE<br>PVTVSWNSGALTSGVHTFPAVLQSSGLYSLSSVVTVPSS<br>SLGTQTYICNVNHKPSNTKVDKKVEPKSCDKTHTCPPC<br>PAPELLGGPSVFLFPPKPKDTLMISRTPEVTCVVVDVSH<br>EDPEVKFNWYVDGVEVHNAKTKPREEQYQSTYRVVS<br>VLTVLHQDWLNGKEYKCKVSNKALPAPIEKTISKAKG<br>QPREPQVYTLPPSREEMTKNQVSLTCLVKGFYPSDIAVE<br>WESNGQPENNYKTTPPVLDSDGSFFLYSKLTVDKSRW<br>QQGNVFSCSVMHEALHNHYTQKSLSLSPGGGGSGGG<br>GSGGGGSQVQLQQSGAELARPGASVKMSCKASGYTFT<br>RYTMHWVKQRPGQGLEWIGYINPSRGYTNYNQKFKD<br>KATLTTDKSSSTAYMQLSSLTSEDSAVYYCARYYDDH<br>YCLDYWGQGTTLTVSSASTGGGGSGGGGSGGGGSQIV<br>LTQSPAIMSASPGEKVTMTCSASSSVSYMNWYQQKSG<br>TSPKRWIYDTSKLASGVPAHFRGSGSGTSYSLTISGMEA<br>EDAATYYCQQWSSNPFTFGSGTKLEINR | 98 |
| C1 | Light chain full length | DIVMTQSPDSLAVSLGERATINCKSSQSLLNRGNHKNY<br>LTWYQQKPGQPPKLLIYWASTRESGVPDRFSGSGSGTD<br>FTLTISSLQAEDVAVYYCQNDYTYPYTFGQGTKVEIKR<br>TVAAPSVFIFPPSDEQLKSGTASVVCLLNNFYPREAKVQ<br>WKVDNALQSGNSQESVTEQDSKDSTYSLSSTLTLSKAD<br>YEKHKVYACEVTHQGLSSPVTKSFNRGEC | 89 |
| C2 | Heavy chain full length | EVQLVQSGAEVKKPGASVKVSCKASGYTFTDHAIHWV<br>RQAPGQGLEWMGYFSPGNDDIKYNEKFRGRVTMTAD<br>KSSSTAYMELRSLRSDDTAVYFCKRSLSTPYWGQGTLV<br>TVSSASTKGPSVFPLAPSSKSTSGGTAALGCLVKDYFPE<br>PVTVSWNSGALTSGVHTFPAVLQSSGLYSLSSVVTVPSS<br>SLGTQTYICNVNHKPSNTKVDKKVEPKSCDKTHTCPPC<br>PAPELLGGPSVFLFPPKPKDTLMISRTPEVTCVVVDVSH<br>EDPEVKFNWYVDGVEVHNAKTKPREEQYQSTYRVVS<br>VLTVLHQDWLNGKEYKCKVSNKALPAPIEKTISKAKG<br>QPREPQVYTLPPSREEMTKNQVSLTCLVKGFYPSDIAVE<br>WESNGQPENNYKTTPPVLDSDGSFFLYSKLTVDKSRW<br>QQGNVFSCSVMHEALHNHYTQKSLSLSPGGGGSGGG<br>GSGGGGSQVQLEQSGGGDVKPDGSLRLSCKASGYTFT<br>RYTMHWVKQAPGKGLEWIGYINPSRGYTNYNQKFKD<br>RATISRDKAKNTAYLQMNSLRGEDTAVYYCARYYDD<br>HYSLDYWGQGTTVTVSSASTGGGGSGGGGSGGGGSQI<br>QLTQSPSSLEASVGDRVTITCSASSSVSYMNWYQQKPG<br>KAPKRWIYDTSKLASGVPSRFSGSGSGTDYTLTISSLQP<br>EDEGTYYCQQWSSNPFTFGGGTKVEVQG | 99 |
| C2 | Light chain full length | DIVMTQSPDSLAVSLGERATINCKSSQSLLNRGNHKNY<br>LTWYQQKPGQPPKLLIYWASTRESGVPDRFSGSGSGTD<br>FTLTISSLQAEDVAVYYCQNDYTYPYTFGQGTKVEIKR<br>TVAAPSVFIFPPSDEQLKSGTASVVCLLNNFYPREAKVQ<br>WKVDNALQSGNSQESVTEQDSKDSTYSLSSTLTLSKAD<br>YEKHKVYACEVTHQGLSSPVTKSFNRGEC | 89 |

TABLE 16-continued

Bispecific antibody heavy and light chain sequences

| BsAb ID | Variable domain | Sequence | SEQ ID NO |
|---|---|---|---|
| C3 | Heavy chain full length | EVQLVQSGAEVKKPGASVKVSCKASGYTFTDHAIHWV RQAPGQGLEWMGYFSPGNDDIKYNEKFRGRVTMTAD KSSSTAYMELRSLRSDDTAVYFCKRSLSTPYWGQGTLV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKKVEPKSCDKTHTCPPC PAPELLGGPSVFLFPPKPKDTLMISRTPEVTCVVVDVSH EDPEVKFNWYVDGVEVHNAKTKPREEQYQSTYRVVS VLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRW QQGNVFSCSVMHEALHNHYTQKSLSLSPGGGGSGGG GSGGGGSQVQLQQSGAELARPGASVKMSCKASGYTFT RYTMHWVKQRPGQGLEWIGYINPSRGYTNYNQKFKD KATLTTDKSSSTAYMQLSSLTSEDSAVYYCARYYDDH YCLDYWGQGTTLTVSSSTGGGGSGGGGSGGGGSDIQIV LTQSPAIMSASPGEKVTMTCSASSSVSYMNWYQQKSG TSPKRWIYDTSKLASGVPAHFRGSGSGTSYSLTISGMEA EDAATYYCQQWSSNPFTFGSGTKLEINR | 100 |
| C3 | Light chain full length | DIVMTQSPDSLAVSLGERATINCKSSQSLLNRGNHKNY LTWYQQKPGQPPKLLIYWASTRESGVPDRFSGSGSGTD FTLTISSLQAEDVAVYYCQNDYTYPYTFGQGTKVEIKR TVAAPSVFIFPPSDEQLKSGTASVVCLLNNFYPREAKVQ WKVDNALQSGNSQESVTEQDSKDSTYSLSSTLTLSKAD YEKHKVYACEVTHQGLSSPVTKSFNRGEC | 89 |
| C4 | Heavy chain full length | QVQLQQSGAELARPGASVKMSCKASGYTFTRYTMHW VKQRPGQGLEWIGYINPSRGYTNYNQKFKDKATLTTD KSSSTAYMQLSSLTSEDSAVYYCARYYDDHYCLDYWG QGTTLTVSSASTKGPSVFPLAPSSKSTSGGTAALGCLVK DYFPEPVTVSWNSGALTSGVHTFPAVLQSSGLYSLSSV VTVPSSSLGTQTYICNVNHKPSNTKVDKKVEPKSCDKT HTCPPCPAPELLGGPSVFLFPPKPKDTLMISRTPEVTCVV VDVSHEDPEVKFNWYVDGVEVHNAKTKPREEQYQST YRVVSVLTVLHQDWLNGKEYKCKVSNKALPAPIEKTIS KAKGQPREPQVYTLPPSREEMTKNQVSLTCLVKGFYPS DIAVEWESNGQPENNYKTTPPVLDSDGSFFLYSKLTVD KSRWQQGNVFSCSVMHEALHNHYTQKSLSLSPGGGGG SGGGGSGGGGSEVQLVQSGAEDKKPGASVKVSCKASG YTFTDHAIHWVRQAPGQGLEWMGYFSPGNDDIKYNEK FRGRATLTADKSSSTAYMELNSLRSDDTAVYFCKRSLS TPYWGQGTSVTVSSASTGGGGSGGGGSGGGGSGGGGS DIVMTQSPDSLSVSDGERATINCKSSQSLLNRGNHKNY LTWYQQKPGQPPKLLIYWASTRESGVPDRFSGSGSGTD FTLTISSLQAEDEGVYYCQNDYTYPYTFGGGTKVEIQ | 101 |
| C4 | Light chain full length | QIVLTQSPAIMSASPGEKVTMTCSASSSVSYMNWYQQK SGTSPKRWIYDTSKLASGVPAHFRGSGSGTSYSLTISGM EAEDAATYYCQQWSSNPFTFGSGTKLEINRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC | 102 |
| C5 | Heavy chain full length | QVQLQQSGAELARPGASVKMSCKASGYTFTRYTMHW VKQRPGQGLEWIGYINPSRGYTNYNQKFKDKATLTTD KSSSTAYMQLSSLTSEDSAVYYCARYYDDHYCLDYWG QGTTLTVSSASTKGPSVFPLAPSSKSTSGGTAALGCLVK DYFPEPVTVSWNSGALTSGVHTFPAVLQSSGLYSLSSV VTVPSSSLGTQTYICNVNHKPSNTKVDKKVEPKSCDKT HTCPPCPAPELLGGPSVFLFPPKPKDTLMISRTPEVTCVV VDVSHEDPEVKFNWYVDGVEVHNAKTKPREEQYQST YRVVSVLTVLHQDWLNGKEYKCKVSNKALPAPIEKTIS KAKGQPREPQVYTLPPSREEMTKNQVSLTCLVKGFYPS DIAVEWESNGQPENNYKTTPPVLDSDGSFFLYSKLTVD KSRWQQGNVFSCSVMHEALHNHYTQKSLSLSPGGGGG SGGGGSGGGGSEVQLVQSGAEDKKPGASVKVSCKASG YTFTDHAIHWVRQAPGQCLEWMGYFSPGNDDIKYNEK FRGRATLTADKSSSTAYMELNSLRSDDTAVYFCKRSLS TPYWGQGTSVTVSSASTGGGGSGGGGSGGGGSGGGGS DIVMTQSPDSLSVSDGERATINCKSSQSLLNRGNHKNY LTWYQQKPGQPPKLLIYWASTRESGVPDRFSGSGSGTD FTLTISSLQAEDEGVYYCQNDYTYPYTFGCGTKVEIQ | 103 |

TABLE 16-continued

Bispecific antibody heavy and light chain sequences

| BsAb ID | Variable domain | Sequence | SEQ ID NO |
|---|---|---|---|
| C5 | Light chain full length | QIVLTQSPAIMSASPGEKVTMTCSASSSVSYMNWYQQK SGTSPKRWIYDTSKLASGVPAHFRGSGSGTSYSLTISGM EAEDAATYYCQQWSSNPFTFGSGTKLEINRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC | 102 |
| C6 | Heavy chain full length | QVQLQQSGAELARPGASVKMSCKASGYTFTRYTMHW VKQRPGQGLEWIGYINPSRGYTNYNQKFKDKATLTTD KSSSTAYMQLSSLTSEDSAVYYCARYYDDHYCLDYWG QGTTLTVSSASTKGPSVFPLAPSSKSTSGGTAALGCLVK DYFPEPVTVSWNSGALTSGVHTFPAVLQSSGLYSLSSV VTVPSSSLGTQTYICNVNHKPSNTKVDKKVEPKSCDKT HTCPPCPAPELLGGPSVFLFPPKPKDTLMISRTPEVTCVV VDVSHEDPEVKFNWYVDGVEVHNAKTKPREEQYQST YRVVSVLTVLHQDWLNGKEYKCKVSNKALPAPIEKTIS KAKGQPREPQVYTLPPSREEMTKNQVSLTCLVKGFYPS DIAVEWESNGQPENNYKTTPPVLDSDGSFFLYSKLTVD KSRWQQGNVFSCSVMHEALHNHYTQKSLSLSPGGGGG SGGGGSGGGGSDIVMTQSPDSLSVSDGERATINCKSSQS LLNRGNHKNYLTWYQQKPGQPPKLLIYWASTRESGVP DRFSGSGSGTDFTLTISSLQAEDEGVYYCQNDYTYPYTF GGGTKVEIKRTGGGGSGGGGSGGGGSEVQLVQSGAED KKPGASVKVSCKASGYTFTDHAIHWVRQAPGQGLEW MGYFSPGNDDIKYNEKFRGRATLTADKSSSTAYMELNS LRSDDTAVYFCKRSLSTPYWGQGTSVTVSS | 104 |
| C6 | Light chain full length | QIVLTQSPAIMSASPGEKVTMTCSASSSVSYMNWYQQK SGTSPKRWIYDTSKLASGVPAHFRGSGSGTSYSLTISGM EAEDAATYYCQQWSSNPFTFGSGTKLEINRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC | 102 |

Development of Multispecific Antibodies

In some embodiments, antibody sequences of the invention may be used to develop multispecific antibodies (e.g., bispecific, trispecific, or of greater multispecificity). Multispecific antibodies can be specific for different epitopes of a target antigen of the present invention, or can be specific for both a target antigen of the present invention, and a heterologous epitope, such as a heterologous glycan, peptide or solid support material. (See, e.g., WO 93/17715; WO 92/08802; WO 91/00360; WO 92/05793; Tutt, A. et al., *Trispecific F(ab')3 derivatives that use cooperative signaling via the TCR/CD3 complex and CD2 to activate and redirect resting cytotoxic T cells. J. Immunol.* 1991 Jul. 1; 147(1):60-9; U.S. Pat. Nos. 4,474,893; 4,714,681; 4,925,648; 5,573,920; 5,601,819; and Kostelny, S. A. et al., *Formation of a bispecific antibody by the use of leucine zippers. J. Immunol.* 1992 Mar. 1; 148(5):1547-53); U.S. Pat. No. 5,932,448.

Disclosed and claimed in PCT Publication WO2014144573 to Memorial Sloan-Kettering Cancer Center are multimerization technologies for making dimeric multispecific binding agents (e.g., fusion proteins comprising antibody components) with improved properties over multispecific binding agents without the capability of dimerization.

Disclosed and claimed in PCT Publication WO2014144357 to Merck Patent GMBH are tetravalent bispecific antibodies (TetBiAbs), and methods of making and methods of using TetBiAbs for diagnostics and for the treatment of cancer or immune disorders. TetBiAbs feature a second pair of Fab fragments with a second antigen specificity attached to the C-terminus of an antibody, thus providing a molecule that is bivalent for each of the two antigen specificities. The tetravalent antibody is produced by genetic engineering methods, by linking an antibody heavy chain covalently to a Fab light chain, which associates with its cognate, co-expressed Fab heavy chain.

Disclosed and claimed in PCT Publication WO2014028560 to IBC Pharmaceuticals, Inc. are T cell redirecting bispecific antibodies (bsAb), with at least one binding site for a T cell antigen and at least one binding site for an antigen on a diseased cell or pathogen, for treatment of disease. Preferably, this bsAb is an anti-CD3×anti-CD19 bispecific antibody, although antibodies against other T cell antigens and/or disease-associated antigens may be used. The complex is capable of targeting effector T cells to induce T cell-mediated cytotoxicity of cells associated with a disease, such as cancer, autoimmune disease or infectious disease. The cytotoxic immune response is enhanced by co-administration of interferon-based agents that comprise interferon-α, interferon-bgr; interferon-λ1, interferon-λ2 or interferon-λ3.

Disclosed and claimed in PCT Publication WO2013092001 to Synimmune GMBH is a bispecific antibody molecule, as well as a method for producing the same, its use and a nucleic acid molecule encoding the bispecific antibody molecule. In particular is provided an antibody molecule that is capable of mediating target cell restricted activation of immune cells.

Disclosed and claimed in PCT Publication WO2012007167 is a multispecific modular antibody specifically binding to at least a glycoepitope and a receptor of the erbB class on the surface of a tumor cell, thereby crosslinking the glycoepitope and the receptor, which antibody has apoptotic activity effecting cytolysis independent of NK cells.

Disclosed and claimed in PCT Publications WO2012048332 and WO2013055404 are meditopes, meditope-binding antibodies, meditope delivery systems, as well as a monoclonal antibody framework binding interface for meditopes, and methods for their use. Specifically, two antibody binding peptides, C-QFDLSTRRLK-C ("cQFD"; sequence identification number 1 therein; SEQ ID NO: 105 herein) and C-QYNLSSRALK-C ("cQYN"; sequence identification number 2 therein; SEQ ID NO: 106 herein) were shown to have novel mAb binding properties. Also called "meditopes," cQFD and cQYN were shown to bind to a region of the Fab framework of the anti-EGFR mAb cetuximab and not to bind the complementarity determining regions (CDRs) that bind antigen. The binding region on the Fab framework is distinct from other framework-binding antigens, such as the superantigens Staphylococcal protein A (SpA) (Graille et al., 2000) and *Peptostreptococcus magnus* protein L (PpL) (Graille et al., 2001). Accordingly, one embodiment disclosed is a framework binding interface comprising a framework region of a unique murine-human antibody or functional fragment thereof that binds a cyclic meditope.

Exemplary patents and patent publications of interest are: U.S. Pat. Nos. 5,585,089; 5,693,761; and 5,693,762, all filed Jun. 7, 1995 and U.S. Pat. No. 6,180,370, all assigned to Protein Design Labs, Inc., describe methods for producing, and compositions of, humanized immunoglobulins having one or more complementarily determining regions (CDR's) and possible additional amino acids from a donor immunoglobulin and a framework region from an accepting human immunoglobulin. Each humanized immunoglobulin chain is said to usually comprise, in addition to the CDR's, amino acids from the donor immunoglobulin framework that are, e.g., capable of interacting with the CDRs to effect binding affinity, such as one or more amino acids which are immediately adjacent to a CDR in the donor immunoglobulin or those within about 3 Å as predicted by molecular modeling. The heavy and light chains may each be designed by using any one or all of various position criteria. When combined into an intact antibody, the humanized immunoglobulins of the present invention are said to be substantially nonimmunogenic in humans and retain substantially the same affinity as the donor immunoglobulin to the antigen, such as a protein or other compound containing an epitope.

U.S. Pat. No. 5,951,983, assigned to Universite Catholique De Louvain and Bio Transplant, Inc., describes a humanized antibody against T-lymphocytes. Framework regions from a human V kappa gene designated as HUM5400 (EMBL accession X55400) and from the human antibody clone Amu 5-3 (GenBank accession number U00562) are set forth therein.

U.S. Pat. No. 5,091,513, to Creative Biomolecules, Inc., describes a family of synthetic proteins having affinity for a preselected antigen. The proteins are characterized by one or more sequences of amino acids constituting a region which behaves as a biosynthetic antibody binding site (BABS). The sites comprise 1) non-covalently associated or disulfide bonded synthetic $V_H$ and $V_L$ dimers, 2) $V_H$-$V_L$ or $V_L$-$V_H$ single chains wherein the $V_H$ and $V_L$ are attached by a polypeptide linker, or 3) individuals $V_H$ or $V_L$ domains. The binding domains comprise linked CDR and FR regions, which may be derived from separate immunoglobulins. The proteins may also include other polypeptide sequences which function, e.g., as an enzyme, toxin, binding site, or site of attachment to an immobilization media or radioactive atom. Methods are disclosed for producing the proteins, for designing BABS having any specificity that can be elicited by in vivo generation of antibody, and for producing analogs thereof.

U.S. Pat. No. 8,399,625, to ESBATech, an Alcon Biomedical Research Unit, LLC, describes antibody acceptor frameworks and methods for grafting non-human antibodies, e.g., rabbit antibodies, using a particularly well-suited antibody acceptor framework.

Antibody-Coated Agents

In some embodiments, antibodies or antibody fragments described herein may be used to prepare a composition that includes an antibody-coated agent. As used herein, the term "antibody-coated agent" refers to any particle, nanoparticle, molecule, protein, fusion-protein, lipid, liposome, cell membrane, cell, or other structure that includes one or more surface-associated antibodies or antibody fragments. Antibody-coated agents may target one or more glycans, proteins, cells, tissues, and/or organs based on the specificity of the antibody or antibody fragments used for coating.

Antibody-coated agents may include associated, enclosed, or embedded cargo. The cargo may be a detectable label. Some cargo may include one or more therapeutic agent. Such therapeutic agents may include, but are not limited to drugs, chemotherapeutic agents, and cytotoxic agents. Cytotoxic agents may be used to kill or otherwise disable a cell. Cytotoxic agents may include, but are not limited to cytoskeletal inhibitors [e.g. tubulin polymerization inhibitors such as maytansines or auristatins (e.g. monomethyl auristatin E [MMAE] and monomethyl auristatin F [MMAF])] and DNA damaging agents (e.g. DNA polymerization inhibitors such as calcheamicins and duocarmycins).

In some embodiments, antibody-coated agents may include nanoparticles coated with one or more antibodies or antibody fragments described herein. Such antibody-coated agents may target one or more glycan, including, but not limited to cell-associated glycans. Some such antibody-coated agents include one or more cytotoxic agents.

Proteins and Variants

Glycan-interacting antibodies of the present invention may exist as a whole polypeptide, a plurality of polypeptides or fragments of polypeptides, which independently may be encoded by one or more nucleic acids, a plurality of nucleic acids, fragments of nucleic acids or variants of any of the aforementioned. As used herein, "polypeptide" means a polymer of amino acid residues (natural or unnatural) linked together most often by peptide bonds. The term, as used herein, refers to proteins, polypeptides, and peptides of any size, structure, or function. In some instances, the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also include single chain or multichain polypeptides and may be associated or linked. The term polypeptide may also apply to amino acid polymers in which one or more amino acid residues are an artificial chemical analogue of a corresponding naturally occurring amino acid.

The term "polypeptide variant" refers to molecules which differ in their amino acid sequence from a native or reference sequence. The polypeptide variants may possess substitutions, deletions, and/or insertions at certain positions within the amino acid sequence, as compared to a native or reference sequence. Ordinarily, polypeptide variants will possess at least about 50% identity (homology) to a native or reference sequence.

In some embodiments "variant mimics" are provided. As used herein, the term "variant mimic" is one which contains one or more amino acids which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine. The amino acid sequences of the glycan-interacting antibodies of the invention may include naturally occurring amino acids and as such may be considered to be proteins, peptides, polypeptides, or fragments thereof. Alternatively, the glycan-interacting antibodies may include both naturally and non-naturally occurring amino acids.

The term "amino acid sequence variant" refers to molecules with some differences in their amino acid sequences as compared to a native or starting sequence. The amino acid sequence variants may possess substitutions, deletions, and/or insertions at certain positions within the amino acid sequence. "Native" or "starting" sequence should not be confused with a wild type sequence. As used herein, a native or starting sequence is a relative term referring to an original molecule against which a comparison may be made. "Native" or "starting" sequences or molecules may represent the wild-type (that sequence found in nature) but do not have to be the wild-type sequence.

Ordinarily, variants will possess at least 50%, at least 70%, at least 75%, at least 80%, at least 85%, at least 90%, at least 95%, at least 96%, at least 97%, at least 98%, at least 99%, at least 99.5% at least 99.8%, or at least 99.9% sequence identity as compared to a native sequence. "Sequence identity" as it applies to amino acid sequences or nucleotide sequences is defined as the percentage of residues in the candidate sequence that are identical with the residues in the second sequence after aligning the sequences and taking gaps and fragments into consideration, if necessary, to achieve the maximum percent sequence identity. Calculation of the percent identity of two polymeric sequences, for example, can be performed by aligning the two sequences for optimal comparison purposes (e.g., gaps can be introduced in one or both of a first and a second polymeric sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The residues at corresponding positions are then compared. When a position in the first sequence is occupied by the same residue as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, N.J., 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

By "homologs" as it applies to amino acid sequences is meant the corresponding sequence of other species having substantial identity to a second sequence of a second species. "Analogs" is meant to include polypeptide variants which differ by one or more amino acid alterations, e.g., substitutions, additions or deletions of amino acid residues that still maintain the properties of the parent polypeptide.

The present invention contemplates several types of glycan-interacting antibodies which are amino acid based including variants and derivatives. These include substitutional, insertional, deletion and covalent variants and derivatives. As such, included within the scope of this invention are glycan-interacting antibody molecules containing substitutions, insertions and/or additions, deletions and covalently modifications. For example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to proteins are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to proteins are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to proteins, are those with one or more amino acids in the native or starting amino acid sequence removed. Ordinarily, deletional variants will have one or more amino acids deleted in a particular region of the molecule.

As used herein, the term "derivative" is used synonymously with the term "variant" and refers to a molecule that has been modified or changed in any way relative to a reference molecule or starting molecule. In some embodiments, derivatives include native or starting proteins that have been modified with an organic proteinaceous or non-proteinaceous derivatizing agent, and post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the proteins used in accordance with the present invention.

Other post-translational modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W. H. Freeman & Co., San Francisco, pp. 79-86 (1983)).

Covalent derivatives specifically include fusion molecules in which proteins of the invention are covalently bonded to a non-proteinaceous polymer. The non-proteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol. The proteins may be linked to various non-proteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

"Features" when referring to proteins are defined as distinct amino acid sequence-based components of a molecule. Features of the proteins of the present invention include surface manifestations, local conformational shape, folds, loops, half-loops, domains, half-domains, sites, termini or any combination thereof.

As used herein when referring to proteins the term "surface manifestation" refers to a polypeptide based component of a protein appearing on an outermost surface.

As used herein when referring to proteins the term "local conformational shape" means a polypeptide based structural manifestation of a protein which is located within a definable space of the protein.

As used herein when referring to proteins the term "fold" means the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein the term "turn" as it relates to protein conformation means a bend which alters the direction of the backbone of a peptide or polypeptide and may involve one, two, three or more amino acid residues.

As used herein when referring to proteins the term "loop" refers to a structural feature of a peptide or polypeptide which reverses the direction of the backbone of a peptide or polypeptide and includes four or more amino acid residues. Oliva et al. have identified at least 5 classes of protein loops (J. Mol Biol 266 (4): 814-830; 1997).

As used herein when referring to proteins the term "half-loop" refers to a portion of an identified loop having at least half the number of amino acid resides as the loop from which it is derived. It is understood that loops may not always contain an even number of amino acid residues. Therefore, in those cases where a loop contains or is identified to include an odd number of amino acids, a half-loop of the odd-numbered loop will include the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein when referring to proteins the term "domain" refers to a motif of a polypeptide having one or more identifiable structural or functional characteristics or properties (e.g., binding capacity, serving as a site for protein-protein interactions.

As used herein when referring to proteins the term "half-domain" means portion of an identified domain having at least half the number of amino acid resides as the domain from which it is derived. It is understood that domains may not always contain an even number of amino acid residues. Therefore, in those cases where a domain contains or is identified to include an odd number of amino acids, a half-domain of the odd-numbered domain will include the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the amino acids of any of the domain types herein need not be contiguous along the backbone of the polypeptide (i.e., nonadjacent amino acids may fold structurally to produce a domain, half-domain or subdomain).

As used herein when referring to proteins the terms "site" as it pertains to amino acid based embodiments is used synonymous with "amino acid residue" and "amino acid side chain". A site represents a position within a peptide or polypeptide that may be modified, manipulated, altered, derivatized or varied within the polypeptide based molecules of the present invention.

As used herein the terms "termini or terminus" when referring to proteins refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus (terminated by an amino acid with a free amino group ($NH_2$)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Once any of the features have been identified or defined as a component of a molecule of the invention, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full-length molecule would.

Modifications and manipulations can be accomplished by methods known in the art such as site directed mutagenesis. The resulting modified molecules may then be tested for activity using in vitro or in vivo assays such as those described herein or any other suitable screening assay known in the art.

Isotopic Variations

The glycan-interacting antibodies of the present invention may contain one or more atoms that are isotopes. As used herein, the term "isotope" refers to a chemical element that has one or more additional neutron. In one embodiment, compounds of the present invention may be deuterated. As used herein, the term "deuterated" refers to a substance that has had one or more hydrogen atoms replaced by deuterium isotopes. Deuterium isotopes are isotopes of hydrogen. The nucleus of hydrogen contains one proton while deuterium nuclei contain both a proton and a neutron. The glycan-interacting antibodies may be deuterated in order to change a physical property of the compound, such as stability, or to allow the compounds to be used in diagnostic and experimental applications.

Conjugates and Combinations

It is contemplated by the present invention that the glycan-interacting antibodies of the present invention may be complexed, conjugated or combined with one or more homologous or heterologous molecules. As used herein, "homologous molecule" means a molecule which is similar in at least one of structure or function relative to a starting molecule while a "heterologous molecule" is one that differs in at least one of structure or function relative to a starting molecule. Structural homologs are therefore molecules which are substantially structurally similar. They can be identical. Functional homologs are molecules which are substantially functionally similar. They can be identical.

Glycan-interacting antibodies of the invention may include conjugates. Such conjugates of the invention may include a naturally occurring substance or ligand, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethyleneimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

The conjugates can also include targeting groups, e.g., a cell or tissue targeting agent or group, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Targeting groups may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent fucose, or aptamers.

The targeting group can be any ligand that is capable of targeting a specific receptor. Examples include, without limitation, folate, GalNAc, galactose, mannose, mannose-6P, aptamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein.

In still other embodiments, glycan-interacting antibodies are covalently conjugated to a cell penetrating polypeptide. The cell-penetrating peptide may also include a signal sequence. The conjugates of the invention can be designed to have increased stability; increased cell transfection; and/or altered biodistribution (e.g., targeted to specific tissues or cell types).

Conjugating moieties may be added to glycan-interacting antibodies such that they allow labeling or flagging targets for clearance. Such tagging/flagging molecules include, but are not limited to ubiquitin, fluorescent molecules, human influenza hemaglutinin (HA), c-myc [a 10 amino acid segment of the human protooncogene myc with sequence EQKLISEEDL (SEQ ID NO: 107)], histidine (His), flag [a short peptide of sequence DYKDDDDK (SEQ ID NO: 108)], glutathione S-transferase (GST), V5 (a paramyxovirus of simian virus 5 epitope), biotin, avidin, streptavidin, horse radish peroxidase (HRP) and digoxigenin.

In some embodiments, glycan-interacting antibodies may be combined with one another or other molecule in the treatment of a disease or condition.

Nucleic Acids

The present invention embraces nucleic acid molecules. In some embodiments, nucleic acids encode antibodies of the invention (including, but not limited to antibodies, antibody fragments, intrabodies and chimeric receptor antigens). Such nucleic acid molecules include, without limitation, DNA molecules, RNA molecules, polynucleotides, oligonucleotides, mRNA molecules, vectors, plasmids and other constructs. As used herein, the term "construct" refers to any recombinant nucleic acid molecule including, but not limited to plasmids, cosmids, autonomously replicating polynucleotide molecules or linear or circular single-stranded or double-stranded DNA or RNA polynucleotide molecules. The present invention also embraces cells programmed or generated to express nucleic acid molecules encoding glycan-interacting antibodies. Such cells may be generated through the use of transfection, electroporation, viral delivery and the like. Viruses engineered with constructs of the invention may include, but are not limited to lentiviruses, adenoviruses, adeno-associated viruses and phages. In some cases, nucleic acids of the invention include codon-optimized nucleic acids. Methods of generating codon-optimized nucleic acids are known in the art and may include, but are not limited to those described in U.S. Pat. Nos. 5,786,464 and 6,114,148, the contents of each of which are herein incorporated by reference in their entirety. In some embodiments, nucleic acid sequences are codon optimized to improve protein expression or to remove cryptic splice sites.

In some embodiments, the present disclosure provides cells that include at least once nucleic acid and/or vector for expression of antibodies described herein. Further provided are antibodies that are produced by such cells.

II. Methods and Uses

Methods of the present disclosure include, but are not limited to, methods of preparing one or more glycan-CD3 bispecific antibodies, and methods of utilizing one or more glycan-interacting antibodies, such as glycan-CD3 bispecific antibodies, as therapeutics. In some embodiments, glycan-CD3 bispecific antibodies include STn-CD3 bispecific antibodies.

Antibody Preparation

In some embodiments, the present disclosure provides methods for preparing bispecific antibodies that can be used to recruit and/or activate T cells to target cells expressing STn. Such STn expressing cells may include cancer cells, including those present or derived from tumors. In some aspects, the bispecific antibodies bind to CD3 on T cells.

In some embodiments, bispecific antibodies of the present invention may be engineered by fusing single-chain variable fragments (scFvs) having affinity for one antigen to an IgG antibody having affinity for the other antigen. The scFvs may be fused to either the C- or N-termini of the heavy chains of the IgG antibody. As one example, glycan-CD3 bispecific antibodies may be engineered by fusing an anti-CD3 scFv to the C-termini of the heavy chains of an anti-STn IgG antibody. As another example, glycan-CD3 bispecific antibodies may be engineered by fusing an anti-STn scFv to the C-termini of the heavy chains of an anti-CD3 IgG antibody.

The scFvs may be constructed by connecting the VH and the VL domains with a peptide linker. The domains can be arranged in either the VH-(linker)-VL or the VL-(linker)-VH orientation. The scFv may be connected to the IgG heavy chain by a peptide linker as well. The peptide linkers may be between 1 to 50 amino acids long. In some embodiments, the peptide linker may be at least about 5 amino acids, about 15 amino acids, about 18 amino acids, about 20 amino acids, about 25 amino acids, about 30 amino acids, or about 40 amino acids long. In some embodiments, the peptide linker may comprise stretches of glycine and serine residues. In some embodiments, the linker may include any of the peptide linker sequences presented herein.

The IgG heavy chain constant regions may be selected from IgG1, IgG2, IgG3, IgG4, or related variants and chimeric fusions thereof. The IgG light chain constant regions may be selected from a human lambda and a human kappa light chain. For example, glycan-CD3 bispecific antibodies may comprise IgG1 heavy chain constant regions and kappa light chain constant regions. In some embodiments, the IgG heavy chain constant regions may be mutated to remove glycosylation sites.

In some embodiments, heavy chain and light chain variable domains for binding to STn and/or CD3 may be humanized to reduce immunogenicity. In some cases, the humanized antibodies may be further optimized via introducing mutations to stabilize the antibodies and/or enhance antibody binding and activity. In some cases, humanized anti-STn VH and VL used in glycan-CD3 bispecific antibodies may be selected from any of those presented herein. Some humanized anti-CD3 VH and VL used in glycan-CD3 bispecific antibodies may be selected from any of those presented herein.

Besides the scFv-IgG fusion format, bispecific antibodies of the present invention may be engineered using many other formats. For example, the glycan-CD3 bispecific antibodies may be engineered by fusing an STn targeting scFv to a CD3 targeting scFv. The two scFv may be connected via a flexible peptide linker that allows for free rotation of the two targeting arms. Alternatively, the glycan-CD3 bispecific antibodies may be engineered by creating a "diabody" through crossover pairing of two single chain $V_H$ and $V_L$ fragments. As another alternative, the glycan-CD3 bispecific antibodies may be engineered by chemically linking STn targeting Fab fragments to CD3 targeting Fab fragments. The chemical linking means may include, but are not limited to, a thioether bond and/or a disulfide bond.

Therapeutics

Compounds described herein may be used as therapeutics to treat one or more therapeutic indications. In some embodiments, the compounds include antibodies capable of binding T cells. The antibodies may bind CD3 on T cells and activate them to promote cytotoxic destruction of a target cell. Some methods of the present disclosure include methods of killing a cell (e.g., a target cell) using antibodies capable of binding and/or activating T cells or compositions thereof. The antibodies may be bispecific antibodies, capable of binding to T cells and a target cell. The antibodies may bind glycans on the target (e.g., STn). Some methods of the present disclosure include methods of treating a subject using antibodies capable of binding and or activating T cells or compositions thereof. In some embodiments, the present disclosure provides medicaments for carrying out these and other methods applicable to treating subjects as described herein.

Cancer-Related Applications

Aberrant glycosylation is a hallmark of cancer cell transformation. Multiple aberrant glycosylation forms have been described in human cancers, identifying specific tumor-associated carbohydrate antigens (TACAs) as a class of cell surface molecules suitable for specific tumor targeting (Cheever, M. A. et al., Clin Cancer Res. 2009 Sep. 1; 15(17):5323-37). TACA antigen expression has been found in epithelial cancers including, but not limited to, breast, colon, lung, bladder, cervical, ovarian, stomach, prostate, and liver. TACA antigen expression has been found in embryonal cancers including, but not limited to, yolk sac tumors and seminomas. In addition, TACA antigen expression has been found in many melanomas, carcinomas, and leukemias of various tissues (Heimburg-Molinaro et al., Vaccine. 2011 Nov. 8: 29(48):8802-8826). Antibodies of the present invention that target one or more TACA are referred to herein as "anti-TACA antibodies."

MUC1 is a key cell surface glycoprotein that is normally extensively glycosylated but is underglycosylated in tumor cells. Sparse glycosylation of MUC1 leads to exposure of immunogenic antigens. These may be along the MUC1 core peptide sequence or along core carbohydrate residues. These TACAs include, but are not limited to, N-acetylgalactosamine (Tn), sialyl($\alpha$2,6)N-acetylgalactosamine (STn) and galactose($\beta$1-3)N-acetylgalactosamine (also known as Thomsen-Friedenreich antigen or TF). It has been estimated that about 80% of all carcinomas express Tn among the core carbohydrates of MUC1 with STn being strongly expressed on human carcinoma cells and linked to cancer progression and metastasis. With few exceptions, Tn and STn are not expressed in normal healthy tissues. Sialic acid forms a prominent epitope on STn. The invention takes advantage of the fact that aberrant Neu5Gc-STn (GcSTn) glycan expression appears to be highly specific to various carcinomas.

In the case of MUC1, Neu5Gc incorporation into STn yields a tumor-specific target, a site that is an attractive target for antibody-based therapies to treat tumor tissue. In some embodiments of the present invention, glycan-interacting antibodies target MUC1 expressing cancer cells that include Neu5Gc. To date, Neu5Gc has been detected in glycoconjugates from a number of human cancer tissues including, but not limited to colon cancer, retinoblastoma tissue, melanoma, breast cancer and yolk sac tumor tissue. In some embodiments of the present invention, methods are contemplated for glycan-interacting antibody treatment of these forms of cancer as well as other forms of cancer, not specifically listed here, characterized by the presence of cancer cells that include Neu5Gc.

Additional antigens that include glycans have been identified that are expressed in correlation with cancer (Heimburg-Molinaro, J. et al., Cancer vaccines and carbohydrate epitopes. Vaccine. 2011 Nov. 8; 29(48):8802-26). These tumor-associated carbohydrate antigens include, but are not limited to blood group Lewis related antigens [including, but not limited to Lewis$^Y$ (Le$^Y$), Lewis$^X$ (Le$^X$), Sialyl Lewis$^X$ (SLe$^X$) and Sialyl Lewis$^A$ (SLe$^A$)], glycosphingolipid-related antigens [including, but not limited to Globo H, stage-specific embryonic antigen-3 (SSEA-3) and glycosphingolipids that include sialic acid], ganglioside-related antigens [including, but not limited to gangliosides GD2, GD3, GM2, fucosyl GM1 and Neu5GcGM3] and polysialic acid-related antigens.

In some embodiments, therapeutics of the present invention may be directed toward Lewis blood group antigens. Lewis blood group antigens include a fucose residue linked to GlcNAc by an $\alpha$1-3 linkage or an $\alpha$1-4 linkage. They may be found on both glycolipids and glycoproteins. Lewis blood group antigens may be found in the body fluid of individuals that are secretors of these antigens. Their appearance on red cells is due to absorption of Lewis antigens from the serum by the red cells.

In some embodiments, therapeutics of the present invention may be directed toward Le$^Y$. Le$^Y$ (also known as CD174) is made up of Gal$\beta$1,4GlcNAC and includes $\alpha$1,2- as well as $\alpha$1,3-linked fucose residues yielding the Fuc$\alpha$(1,2)Gal$\beta$(1,4)Fuc$\alpha$(1,3)GlcNAc epitope. It is synthesized from the H antigen by $\alpha$1,3 fucosyltransferases which attach the $\alpha$1,3 fucose to the GlcNAc residue of the parent chain. Le$^Y$ may be expressed in a variety of cancers including, but not limited to ovarian, breast, prostate, colon, lung and epithelial. Due to its low expression level in normal tissues and elevated expression level in many cancers, the Le$^Y$ antigen is an attractive target for therapeutic antibodies.

In some embodiments, therapeutics of the present invention may be directed toward Le$^X$. Le$^X$ includes the epitope Gal$\beta$1-4(Fuc$\alpha$1-3)GlcNAc$\beta$-R. It is also known as CD15 and stage-specific embryonic antigen-1 (SSEA-1). This antigen was first recognized as being immunoreactive with sera taken from a mouse subjected to immunization with F9 teratocarcinoma cells. Le$^X$ was also found to correlate with embryonic development at specific stages. It is also expressed in a variety of tissues both in the presence and absence of cancer, but can also be found in breast and ovarian cancers where it is only expressed by cancerous cells.

In some embodiments, therapeutics of the present invention may be directed toward SLe$^A$ and/or SLe$^X$. SLe$^A$ and SLe$^X$ include the structures Neu5Ac$\alpha$2-3Gal$\beta$1-3(Fuc$\alpha$1-4)GlcNAc$\beta$-R and Neu5Ac$\alpha$2-3Gal$\beta$1-4(Fuc$\alpha$1-3)GlcNAc$\beta$-R respectively. Their expression is upregulated in cancer cells. The presence of these antigens in serum correlates with malignancy and poor prognosis. SLe$^X$ is mostly found as a mucin terminal epitope. It is expressed in a number of different cancers including breast, ovarian, melanoma, colon, liver, lung and prostate. In some embodiments of the present invention, SLe$^A$ and SLe$^X$ targets include Neu5Gc (referred to herein as GcSLe$^A$ and GcSLe$^X$, respectively).

In some embodiments, therapeutics of the present invention may be directed toward glycolipids and/or epitopes present on glycolipids, including, but not limited to glycosphingolipids. Glycosphingolipids include the lipid ceramide linked to a glycan by the ceramide hydroxyl group. On the cell membrane, glycosphingolipids form clusters referred to as "lipid rafts".

In some embodiments, therapeutics of the present invention may be directed toward Globo H. Globo H is a cancer-related glycosphingolipid first identified in breast cancer cells. The glycan portion of Globo H includes Fucα(1-2)Galβ(1-3)GalNAcβ(1-3)Galα(1-4)Galβ(1-4)Glcβ(1). Although found in a number of normal epithelial tissues, Globo H has been identified in association with many tumor tissues including, but not limited to, small cell lung, breast, prostate, lung, pancreatic, gastric, ovarian and endometrial tumors.

In some embodiments, therapeutics of the present invention may be directed toward gangliosides. Gangliosides are glycosphingolipids that include one or more sialic acid. According to ganglioside nomenclature, G is used as an abbreviation for ganglioside. This abbreviation is followed by the letters M, D, or T referring to the number of sialic acid residues attached (1, 2 or 3 respectively). Finally, the numbers 1, 2 or 3 are used to refer to the order of the distance each migrates when analyzed by thin layer chromatography (wherein 3 travels the greatest distance, followed by 2, and then 1). Gangliosides are known to be involved in cancer-related growth and metastasis and may be expressed on the cell surface of tumor cells. Gangliosides expressed on tumor cells may include, but are not limited to GD2, GD3, GM2 and fucosyl GM1 (also referred to herein as Fuc-GM1). In some embodiments of the present invention, glycan-interacting antibodies are directed toward GD3. GD3 is a regulator of cell growth. In some embodiments, GD3-directed antibodies are used to modulate cell growth and/or angiogenesis. In some embodiments, GD3-directed antibodies are used to modulate cell attachment. In some embodiments of the present invention, glycan interacting antibodies are directed toward GM2. In some embodiments, GM2-directed antibodies are used to modulate cell to cell contact. In some embodiments, ganglioside targets of the present invention include one or more Neu5Gc residue. In some embodiments, such targets may include a GM3 variant having Neu5Gc (referred to herein as GcGM3). The glycan component of GcGM3 is Neu5Gcα2-3Galβ1-4Glc. GcGM3 is a known component of tumor cells.

In some embodiments, TACAs targeted by anti-TACA antibodies of the present invention may include, but are not limited to any of those listed in US Publication Nos. US2013/0236486A1, US2013/0108624A1, US2010/0178292A1, US2010/0104572A1, US2012/0039984A1, US2009/0196916A1, and US2009/0041836A1, the contents of each of which are herein incorporated by reference in their entirety.

In some embodiments, the present invention provides methods of treating cancer that include the administration of anti-glycan antibodies taught herein or the administration of compositions of such antibodies (e.g., compositions of anti-glycan antibodies having at least one excipient).

In some embodiments, methods of the disclosure include completely eradicating tumor cells to induce durable initial remission through administration of one or more glycan-interacting antibodies. Other methods include inhibition of tumor resurgence for a period of time, in some cases without excessive toxicity. Such periods of time may be from about 1 month to about 18 months, from about 1 year to about 5 years, from about 2 years to about 10 years, or greater than 10 years.

STn in Cancer

The immune system has multiple mechanisms for promoting anti-tumor cell immune activity including both innate and adaptive immune activity. As used herein, the term "anti-tumor cell immune activity" refers to any activity of the immune system that kills or prevents growth and/or proliferation of tumor cells. In some cases, anti-tumor immune activity includes recognition and tumor cell killing by natural killer (NK) cells and phagocytosis by macrophages. Adaptive anti-tumor immune responses include tumor antigen uptake and presentation by antigen presenting cells (APCs) such as dendritic cells (DCs) leading to modulation of T cell anti-tumor activity and/or expansion of B cells with secretion of tumor-specific antibodies. The binding of tumor-specific antibodies to tumors can lead to antibody-dependent cellular cytotoxicity (ADCC) and complement-dependent cytotoxicity (CDC) mechanisms of tumor cell death.

As used herein, the term "immune-resistant tumor cell" refers to a tumor cell that reduces or evades anti-tumor cell immune activity. Some studies indicate that the expression of STn (a known TACA) on tumor cell surfaces or secreted into the tumor cell microenvironment can promote tumor cell evasion of anti-tumor immune activity. As used herein, the term "tumor cell microenvironment" refers to any area adjacent to or surrounding a tumor cell. Such areas include, but are not limited to areas between tumor cells, between tumor and non-tumor cells, surrounding fluids and surrounding components of the extracellular matrix.

Sialylated mucins having STn were demonstrated by Ogata et al to reduce NK cell targeting of tumor cells (Ogata, S. et al., 1992. Canc. Res. 52:4741-6, the contents of which are herein incorporated by reference in their entirety). This study found that the presence of ovine, bovine and porcine submaxillary mucin (OSM, BSM and PSM, respectively) led to nearly one hundred percent inhibition of cytotoxicity (see Table 2 of Ogata et al). Further studies by Jandus et al, demonstrate that some tumor cells can evade NK destruction due to the expression of sialoglycan ligands that can interact with NK cell siglec receptors, leading to NK inhibition (Jandus, C. et al., 2014, JCI. pii: 65899, the contents of which are herein incorporated by reference in their entirety).

Studies by Toda et al., demonstrate that STn may bind CD22 receptors on B cells, leading to decreased signal transduction and reduced B cell activation (Toda, M. et al., 2008. Biochem Biophys Res Commun. 372(1):45-50, the contents of which are herein incorporated by reference in their entirety). Dendritic cells (DCs) can affect adaptive immune activity by modulating T cell activity. Studies by Carrascal et al found that STn expression by bladder cancer cells induced tolerance in DCs, reducing their ability to induce anti-tumor cell immune activity in T cells (Carrascal, M A et al., 2014. Mol Oncol. pii: S1574-7891(14)00047-7, the contents of which are herein incorporated by reference in their entirety). These studies revealed that DCs coming into contact with STn-positive bladder cancer cells displayed a tolerogenic expression profile with low expression of CD80, CD86, IL-12 and TNF-α. Further, DCs were found to modulate regulatory T cells such that the T cells had low expression of IFN-γ and high expression of FoxP3. Other studies by van Vliet and others, indicate that DC surface expression of macrophage galactose-type lectin (MGL) can lead to targeting of those cells to tumor tissues (van Vliet, S J., 2007. Amsterdam: Vrije Universiteit. p 1-232 and van Vliet, S J. et al., 2008. J Immunol. 181(5):3148-55, Nollau, P. et al., 2013. J Histochem Cytochem. 61(3):199-205, the contents of each of which are herein incorporated by reference in their entirety). DCs arriving at tissues due to MGL interactions may influence T helper (Th) cells in one of three ways. DCs can induce T cell tolerance, T cell immune activity or downregulation of effector T cells. MGL has been shown to bind to both AcSTn and GcSTn and the affinity has been analyzed in depth (Mortezai, N. et al., 2013. Glycobiology. 23(7):844-52, the contents of which are herein incorporated by reference in their entirety). Interestingly, MUC1 expression on tumors has been shown to lead to T cell tolerance, protecting tumor cells from immune eradication.

In some embodiments, glycan-interacting antibodies (including, but not limited to anti-STn antibodies) of the present invention may be used to treat subjects having one or more tumor cells expressing one or more TACAs. In some cases, glycan-interacting antibodies (including, but not limited to anti-STn antibodies) of the invention may be used to increase anti-tumor cell immune activity toward tumor cells expressing STn. Such antibodies may increase the adaptive immune response and/or the innate immune response toward immune-resistant tumor cells. Some glycan-interacting antibodies may be used to increase NK anti-tumor cell activity. Such glycan-interacting antibodies may, in some cases, block the interaction between glycan receptors expressed on NK cells and STn glycans on cancer cells or in surrounding tissues.

In some embodiments, glycan-interacting antibodies (including, but not limited to anti-STn antibodies) of the invention may be used to increase B cell anti-tumor cell activity. Such antibodies may reduce the interaction between CD22 receptors on B cells and STn glycans on cancer cells or in surrounding tissues. A study by Sjoberg et al. demonstrates that 9-O-acetylation of α2,6-linked sialic acids on glycoproteins also reduced interaction between B cell CD22 receptors and such glycoproteins (Sjoberg, E. R. et al. 1994. JCB. 126(2): 549-562). Another study by Shi et al. reveals that higher levels of 9-O-acetylated sialic acid residues on murine erythroleukemia cells makes these cells more susceptible to complement-mediated lysis (Shi, W-X. et al., 1996. J of Biol Chem. 271(49): 31526-32, the contents of which are herein incorporated by reference in their entirety). In some embodiments, anti-STn antibodies of the invention are capable of selectively binding non-9-O-acetylated STn, reducing overall STn binding, but reducing tumor cell growth and/or proliferation. (e.g. through increased B cell anti-tumor activity and increased complement-mediated tumor cell destruction). In some embodiments, glycan-interacting antibodies (including, but not limited to anti-STn antibodies) of the invention may be used to increase DC anti-tumor activity. Such antibodies may be used to reduce DC tolerance to tumor cells. Reduced DC tolerance may include increasing DC expression of CD80, CD86, IL-12 and/or TNF-α. In some cases, DC anti-tumor cell activity may include promotion of T cell anti-tumor cell activity. Such antibodies may prevent binding between DC MGL and glycans expressed on or around cancer cells.

A study by Ibrahim et al. suggests that high levels of anti-STn antibodies along with endocrine therapy may increase overall survival and time to progression (TTP) in women with metastatic breast cancer (Ibrahim, N. K. et al., 2013. 4(7): 577-584, the contents of which are herein incorporated by reference in their entirety). In this study, anti-STn antibody levels were elevated after vaccination with STn linked to keyhole-limpet Hemocyanin (KLH). In some embodiments, anti-STn antibodies of the invention may be used in combination with endocrine therapy (e.g. tamoxifen and/or an aromatase inhibitor).

In some embodiments, glycan-interacting antibodies of the invention may be used to reduce or eliminate cancerous cells and/or cells expressing STn. Such cells include cells that may be part of a tumor.

In some cases, the present invention provides methods of reducing tumor volumes by administering anti-glycan antibodies of the invention to subjects with one or more tumors. Reduction in tumor volumes may be determined by comparing tumor volumes in a subject before and after treatment, or by comparing tumor volumes between anti-glycan antibody-treated and control treated subjects.

In some cases, anti-glycan antibodies of the invention may be administered to achieve a desired percent reduction in tumor volume in a subject. This may be assessed by determining the volume of one or more tumors (e.g., through the use of calipers or imaging techniques like CT scan) in a subject before and after treatment with an anti-glycan antibody and then calculating the percent reduction in tumor volume from the two values. In some embodiments, tumor volume in subjects treated with anti-glycan antibodies may be reduced by from about 0.1% to about 2%, from about 1% to about 5%, from about 3% to about 12%, from about 10% to about 30%, from about 20% to about 50%, from about 40% to about 60%, from about 50% to about 75%, from about 60% to about 85%, or from about 80% to about 99%. In some cases, tumor volume in subjects treated with anti-glycan antibodies may be reduced by at least 1%, by at least 5%, by at least 10%, by at least 20%, by at least 40%, by at least 50%, by at least 60%, by at least 80%, by at least 85%, by at least 90%, by at least 95%, by at least 98%, by at least 99%, or by 100%.

In some cases, anti-glycan antibodies of the invention may be administered to achieve a desired percent tumor growth inhibition (% T/C). % T/C is calculated by determining tumor volumes in treated subjects and comparing them to tumor volumes in non-treated or placebo-treated subjects. In some embodiments, the present invention provides methods of reducing tumor volume in a subject by administering an anti-glycan antibody, wherein the % T/C is from about 0.1% to about 1%, from about 0.5% to about 5%, from about 2% to about 20%, from about 3% to about 16%, from about 10% to about 30%, from about 20% to about 60%, or from about 40% to about 80%. In some cases, the % T/C is at least 80%. In some cases, the % T/C is less than 0.1%.

In some embodiments, antibodies used to reduce tumor volumes in subjects may be selected based on their ability to bind cell surface glycans (e.g., STn) and/or their ability to kill cancerous cells. In some instances, antibodies may be selected based on their half-maximal effective concentration ($EC_{50}$) for binding cells having cell surface STn. $EC_{50}$ values for such antibodies may be determined, e.g., through flow cytometry analysis with cells having cell surface STn. Such antibodies may have $EC_{50}$ values of from about 0.1 nM to about 2 nM, from about 0.5 nM to about 5 nM, from about 1 nM to about 10 nM, from about 5 nM to about 20 nM, or from about 10 nM to about 30 nM.

In some embodiments, the present invention provides methods of killing cancer cells, such as tumor cells, by administering one or more antibodies presented herein.

In some embodiments, the present disclosure provides a method of identifying a subject in need of anti-STn antibody treatment by isolating cancer cells (including, but not limited to cancer stem cells) and/or obtaining biopsy material from a subject and screening the cancer cells and/or biopsy material for STn expression. According to such methods, subjects with cancer cells and/or biopsy material expressing STn are deemed to likely benefit from anti-STn antibody treatment or to be in need of anti-STn antibody treatment (e.g., treatment with one or more antibody described herein). In some cases, antibodies described herein may be used for screening of cancer cells and/or biopsy material. Cancer cells may be screened in vitro by culturing the cancer cells and detecting STn expression using standard immunological assays (e.g., ELISA, Western blot, or other standard immunological assays). In some cases, cancer cells may be screened for STn expression using flow cytometry techniques. In other embodiments, cancer cells may be grown in culture and tested for viability after treatment with anti-STn antibodies that are antibody-drug conjugates (ADCs). Such ADCs may include a cytotoxic agent, including, but not limited to those described herein. Cytotoxic agents may include MMAE. Anti-STn antibodies may include humanized antibodies, including, but not limited to, those described herein. In other embodiments, cancer cells may be screened by using the cancer cells to form tumors in mice (e.g., NOD/SCID mice). The tumors developed in mice may be screened by preparing tissue sections from such tumors and subjecting the tissue sections to immunohistochemical analysis using anti-STn antibodies, including, but not limited to anti-STn antibodies described herein. In some cases, the tumors formed in mice may be assessed for changes in tumor volume after treatment of the mice with anti-STn antibodies, including, but not limited to anti-STn antibodies described herein. Such anti-STn antibodies may include ADCs. ADCs may include one or more cytotoxic agent, including, but not limited to any of those described herein (e.g., MMAE). Subjects with cancer cells that demonstrate STn expression after screening may be determined to be in need of anti-STn antibody treatment.

In some embodiments, the present disclosure provides a method of identifying an antibody suitable for treating cancer by isolating cancer cells (including, but not limited to cancer stem cells) from a subject, screening the cancer cells for STn expression, and contacting STn-expressing cancer cells with one or more candidate antibodies specific for STn to determine whether any of the one or more candidate antibodies are able to bind the cancer cells. As used herein, the term "candidate antibody" refers to an antibody or one of a group of antibodies that are being evaluated for one or more purposes. Subject cancer cells may be screened in vitro by culturing the cancer cells and detecting STn expression using STn-detecting antibodies with standard immunological assays (e.g., ELISA, Western blot, or other standard immunological assays) or using flow cytometry techniques. As used herein, the term "STn-detecting antibody" refers to an antibody that binds STn and that allows for observation of such binding either through the presence of an incorporated detectable label or through the use of a secondary antibody having a detectable label. In other embodiments, screening the cancer cells may involve using them to form tumors in mice (e.g., NOD/SCID mice). Screening may be carried out by assessing the mouse tumors for expression of STn or for reduction in volume after administration of anti-STn antibodies, including, but not limited to ADCs.

In some embodiments, the present invention includes methods of evaluating the suitability of an antibody for treating cancer in a subject by obtaining cancer cells from a subject, using the cancer cells to form tumors in mice (e.g., NOD/SCID mice), administering an anti-STn antibody to the mice, and measuring changes in tumor volume in the mice, wherein if the tumor volume in the mice is decreased, the anti-STn antibody is determined to be suitable for treating cancer in the subject. In some cases, the anti-STn antibodies are administered multiple times. According to such methods, antibodies may be administered hourly, daily, weekly, monthly, and/or yearly. In some cases, antibodies are administered weekly for a period of from about 2 to about 12 weeks. In some cases, antibodies are administered weekly for a period of at least 12 weeks.

STn expression has been implicated in contributing to the metastatic potential of cancer cells. According to some methods of the disclosure, glycan-interacting antibodies may be used to reduce metastasis. Such methods may include the reduction of metastasis by from about 1% to about 15%, from about 5% to about 25%, from about 10% to about 50%, from about 20% to about 60%, from about 30% to about 70%, from about 40% to about 80%, from about 50% to about 90%, from about 75% to about 95%, or at least 95%.

Bispecific Antibody Therapeutics

In some embodiments, methods of the present disclosure include methods of targeting cancer and/or tumor cells with glycan-interacting antibodies that are bispecific antibodies. Such methods may include the use of glycan-interacting antibodies that include glycan-CD3 bispecific antibodies, for example, through administration to a subject having one or more cancer and/or tumor cells. Glycan-CD3 bispecific antibodies may be used to recruit and/or activate T cells to target cells expressing one or more glycans. In some embodiments, STn-CD3 bispecific antibodies are utilized to recruit and/or activate T cells to target cells expressing STn. Such methods may be used to reduce and/or eliminate such STn expressing target cells. STn expressing target cells may include cancer and/or tumor cells. As a non-limiting example, such cancer and/or tumor cells may be part of or derived from ovarian, colon, prostate, breast, and/or pancreatic tumors.

In some embodiments, glycan-CD3 bispecific antibodies may be used to target cancer and/or tumor cells, while having less or no effect on non-cancerous and/or non-tumor cells. Methods of the disclosure may include the use of glycan-CD3 bispecific antibodies to stimulate anti-tumor immune functions. In some embodiments, methods include reducing or preventing innate immune suppression through the use of glyan-CD3 bispecific antibodies. Methods may include targeting one or more tumor cells that are resistant to chemotherapy with glycan-CD3 bispecific antibodies. Some methods may include reducing or preventing cancer and/or tumor cell metastasis using glycan-CD3 bispecific antibodies. In some embodiments, methods of the present disclosure may include inducing T cells activation and/or T cell-induced cancer and/or tumor cell killing with glycan-CD3 bispecific antibodies. Such methods may be carried out in vitro or in vivo (e.g., through administration of glycan-CD3 bispecific antibodies to a subject having one or more cancer and/or tumor cells).

In some embodiments, methods of the present disclosure may include an ex vivo approach for targeting cancer and/or tumor cells in a patient. For example, glycan-CD3 bispecific antibodies may be used to incubate with a patient's T cells that have been isolated, expanded and activated ex vivo. The antibody-associated activated T cells may be transplanted back into a patient via systemic infusion, local injection and/or combinations thereof. This approach (also referred to as an "arming" approach) may reduce the dose requirement of BsAb and avoid overt systemic cytokine release reaction that may be associated with direct administration.

Cancer Stem Cells as Therapy Targets

Cancer stem cells or CSCs (also called tumor initiating cells) are a subset of cancer cells within a heterogeneous tumor population that drive the initiation, growth, dissemination, and recurrence of primary and metastatic tumors (Karsten and Goletz, SpringerPlus, 2013, 2, 301), which can occur in varying proportions of the total population depending on tumor type. CSCs are distinguished from terminally differentiated cells by their capacity to self-renew and give rise to non-CSC, differentiated progeny (Gupta et al., Nature medicine, 2009, 15, 1010-1012). These properties are akin to those of normal stem cells. Such distinctions between normal stem cells and CSCs have important implications for therapy.

An increasing number of cell-surface biomarkers have been identified that purport to differentiate CSCs from their non-CSC counterparts (Medema et al., Nature cell biology, 2013, 15, 338-344; Zoller, Cancer, 2011, 11, 254-267). These may include, but are not limited to CD44, CD133, CD117, and aldehyde dehydrogenase isoform 1 (ALDH1). Although some of these derive from studies of mouse tumors and human cell lines, others have been validated using primary human tumor samples. One of these, the membrane-spanning CD44 glycoprotein, or hyaluronan receptor, which is a well-known constituent of a variety of tumor types, has also more recently found acceptance as a bona fide CSC marker in human cancers, and in fact is the one most frequently observed (Lobo et al., 2007, 23, 675-699).

CD44 exists in several variant isoforms generated by alternative splicing events occurring among the 20 exons and 19 introns of the full-length CD44 gene (Williams et al, Experimental biology and medicine, 2013, 238, 324-338). Growing experimental evidence points to the supporting role of CD44 and its variants in contributing to the innate metastatic and drug resistant phenotype of CSCs (Negi et al., Journal of drug targeting, 2012, 20, 561-573), in part due to modulation of intracellular signal transduction pathways (Williams et al, Experimental biology and medicine, 2013, 238, 324-338). Additionally, patients with triple negative breast cancer, along with several other cancer types, that display high levels of CD44 cells are known to have a poor prognosis and higher mortality (Negi et al., Journal of drug targeting, 2012, 20, 561-573). These observations support the notion that targeting CD44 offers a means of treating cancer through inhibition or elimination of CSCs, in addition to mature cancer cells. Indeed, numerous approaches to targeting CD44 have been attempted experimentally with varying degrees of success. These include a wide range of technologies that include the use of conjugated and unconjugated antibodies, nano-carrier drug systems, and hyaluronan-conjugated drugs (Negi et al., Journal of drug targeting, 2012, 20, 561-573). In several instances, however, toxic effects were observed in in vivo studies; these untoward side effects may be attributable to the widespread occurrence of CD44 and variants on the membranes of most vertebrate cells (Naor et al., Seminars in cancer biology, 2008, 18, 260-267), in addition to its presence on the surface of the targeted CSCs and mature tumor cells. Targeting CD44 protein, which is a constituent of normal human stem cells (Williams et al, Experimental biology and medicine, 2013, 238, 324-338), can also harm normal stem cell function (Leth-Larsen et al., Molecular medicine, 2012, 18, 1109-1121). Although a large body of research points to the desirability of targeting CD44 protein on CSCs, as well as on mature tumor cells, the intrinsic problem with this approach remains the present difficulty in designing inhibitors that will spare normal tissue as well as normal stem cells.

Another well-known tumor antigen with implications to CSC biology is the epithelial mucin MUC1, a membrane tethered glycoprotein that is differentially expressed at high levels on the majority of adenocarcinomas but at low levels or not at all on normal epithelial cells. MUC1 has recently been identified as a CSC biomarker on a variety of neoplasias including breast (Engelmann et al., Cancer research, 2008, 68, 2419-2426), and pancreatic cancers, where its expression is correlated with high metastasis and poor prognosis. As a constituent of CSCs, MUC1 has been shown to function in cell adhesion, proliferation, survival, and signaling (Engelmann et al., Cancer research, 2008, 68, 2419-2426) and may also be co-expressed with CD44 (Leth-Larsen et al., Molecular medicine, 2012, 18, 1109-1121). Immunotherapeutic approaches for targeting MUC1 in cancer are being pursued using vaccines as well as other approaches, but primarily in the context of mature cancer cell therapy (Julien et al., Biomolecules, 2012, 2, 435-466; Acres et al., Expert review of vaccines, 2005, 4, 493-502).

Cancer stem cells have been hypothesized to be generated through the epithelial-to-mesenchymal (EMT) transition (Gupta et al., Nature medicine, 2009, 15, 1010-1012), and/or reversely the mesenchymal-to-epithelial (MET) transition that occurs at the site of metastasis (Leth-Larsen et al., Molecular medicine, 2012, 18, 1109-1121) (also called CSCs plasticity where non-CSCs can give rise to CSCs). This discovery further underscores the need to eliminate both CSCs and non-CSCs in a tumor population.

Recent studies with enriched CSC populations has revealed that these cells, unlike the bulk of the tumor, are relatively quiescent and are preferentially resistant to many types of current therapies, including chemotherapy and radiation (Leth-Larsen et al., Molecular medicine, 2012, 18, 1109-1121). Thus, current therapeutic strategies target non-CSC components of the tumor, leaving CSCs largely unaffected only to re-emerge after appropriate cues to reform recurrent primary tumors at the initial site or to disseminate to distant sites, colonize, and create metastatic disease, the major cause of cancer mortality.

Current understanding of the properties of cancer stem cells clearly emphasized the need not only to target the bulk of cells present in tumors, as is current practice, but also the CSC compartment in order to potentially effect complete cures.

As discussed above, strategies that have been developed based on tumor (including CSCs) associated biomarkers face a challenge that most cancer biomarkers are also present in normal cells including normal stem cells. A therapy that targets a protein biomarker to eliminate CSCs, may also target normal stem cells, causing elimination of normal cells.

Tumor-Specific Glycans in CSCs

Aberrant forms of glycosylation, including appearance of the Thomsen-nouveau (Tn) antigen (GalNAc-O-Ser/Thr), have been described in numerous human cancers, identifying glycans as an entirely novel class of tumor-associated carbohydrate antigens suitable for specific tumor targeting (Rabu et al., Future oncology, 2012, 8, 943-960). The formation of the sialyl derivative of Tn (STn) is mediated by the sialyl transferase ST6GalNAc-I which adds sialic acid in an α2,6 linkage to the Tn antigen. The sialylation of Tn prevents further sugar additions, thus truncating further glycan extensions (Schultz et al., Cancer metastasis reviews, 2012, 31, 501-518).

While the presence of STn in normal adult human tissues is rare, STn occurs in various human cancers, including ovarian, bladder, breast, cervical, colon, and lung cancer, among others (Ferreira et al., Molecular oncology, 2013, 7, 719-731; Kinney et al., Cancer, 1997, 80, 2240-2249).

Further, the presence of STn in tumors is associated with metastatic disease, poor prognosis, and reduced overall survival (Ferreira et al., Molecular oncology, 2013, 7, 719-731; Kinney et al., Cancer, 1997, 80, 2240-2249); therefore, STn is considered a highly attractive target for cancer detection and therapy. There are two distinct forms of sialic acid—Neu5Ac and Neu5Gc—located at the terminal position of STn. The Neu5Ac-sialylated form is predominant in humans since humans cannot synthesize Neu5Gc due to an inactive CMP-Neu5Ac hydroxylase (CMAH) gene. However, consumption of Neu5Gc-rich foods leads to foreign Neu5Gc incorporation into human cells, especially in carcinomas. Previous studies have shown that solid tumors take up and express the Neu5Gc form of sialic acid (Inoue et al., Glycobiology, 2010, 20, 752-762; Malykh et al., Biochimie, 2001, 83, 623-634; Padler-Karavani et al., Cancer research, 2011, 71, 3352-3363). mAbs that bind to both glyco-isoforms of STn that are potential cancer targets: Neu5Ac-STn (AcSTn) and Neu5Gc-STn (GcSTn) (i.e., designated as pan-STn antibodies).

STn accumulation is associated with specific somatic mutations observed repeatedly in solid tumors and with the inactivation of the gene that encodes the molecular chaperone Core 1 Beta3-Galactosyltransferase-Specific Molecular Chaperone (COSMC), which is required for the formation of active T-synthase (Ju et al., Nature, 2005, 437, 125). T-synthase competes with ST6GalNAc-I for the GalNAc substrate and therefore when inactivated by mutation results in elevated STn synthesis. Additionally, STn accumulation can also result from increased expression of ST6GalNAc-I, which is often observed (Brockhausen et al., Biological chemistry, 2001, 382, 219-232; Ikehara et al., Glycobiology, 1999, 9, 1213-1224). De novo expression of STn can modulate carcinoma cells, change the malignant phenotype, and lead to more aggressive cell behaviors (Pinho et al., Cancer letters, 2007, 249, 157-170). As such, STn is not only an interesting cancer biomarker and therapeutic target, but interfering with STn function offers the intriguing potential to have significant functional, anti-metastatic therapeutic benefits.

Although it is well-known that glycosylation of cellular glycoproteins is altered in cancer, it appears that aberrant glycosylation is selective with respect to both the glycoprotein and glycan in question. In fact, in human tumor CSCs only CD44 and MUC1 are major carriers of the STn antigen (Cazet et al., Breast cancer research: BCR, 2010, 12,204; Julien et al., Glycobiology, 2006, 16, 54-64), immediately suggesting a selective approach for targeting not only mature tumor cells but also CSCs. Whereas MUC1 is a normal surface constituent of some epithelial cells where it serves a barrier function, tumor-associated MUC1 is characterized by hypoglycosylation and increased sialylation on CSCs in the same fashion as observed in mature cancer cells, with STn appearing as a specific marker for both CSCs and mature tumor cells (Curry et al., Journal of surgical oncology, 2013, 107, 713-722). The aberrant oligosaccharide profile of MUC1 gives rise to the expression of neomarkers such as sialyl-Le$^a$ (used in the CA19-9 test), sialyl-Le$^x$, and sialyl-Tn (TAG-72), as well as the cryptic epitopes such as Tn in cancer cells (e.g., CSCs). In addition, because of underglycosylation, the peptide core of the mucin becomes exposed such that epitopes within the core (not accessible within normal tissue-derived MUC1) may serve as potential antigens.

Clinical approaches targeting STn have thus far consisted solely of STn vaccines. The most advanced clinical candidate is Theratope, a therapeutic vaccine consisting of STn coupled to keyhole limpet hemocyanin. In in vivo mouse studies Theratope immunization induced a potent antibody response that was shown to mediate a delay in the growth of injected STn-expressing mammary carcinoma cells (Julien et al., British journal of cancer, 2009, 100, 1746-1751). However, Theratope failed to meet its primary endpoint in a phase III clinical trial in metastatic breast cancer. A leading hypothesis for why the Theratope trial missed its primary endpoint is that the patient population was not evaluated for STn expression prior to enrollment. Since STn expression in breast cancer is highly heterogeneous between patients, ranging from 25%-80% depending on the study and detection method, lack of ability to correlate STn expression with response may have masked any benefit from Theratope. Importantly, a subset of patients receiving hormonal therapy showed a significant 7.5 month increase in median overall survival when treated with Theratope compared to hormone therapy alone (Ibrahim et al., Journal of clinical oncology: official journal of the American Society of Clinical Oncology, 2004, 22, 2547; and Miles et al., The oncologist, 2011, 16, 1092-1100), validating the therapeutic potential of targeting STn in particular patient populations. Additionally, since the immune response often varies considerably between vaccinated patients, vaccine approaches lack the ability to control or modulate antibody titer, resulting in wide ranges of therapeutic antibody exposure among patients. Nonetheless, Theratope was well tolerated with minimal toxicity, demonstrating the safety of targeting STn for cancer therapy.

The growing understanding of the molecular basis of STn expression in cancer cells strongly suggests that cells that express STn on any cell surface protein will also express STn on many (if not all) other O-glycosylated cell surface proteins, rendering it an excellent widely-distributed cancer-associated therapeutic target. Thus, STn positive cancer cell populations may be enriched for CSCs. In addition, recent data demonstrate that abrogation of STn expression renders cancers less aggressive with significant reductions in metastatic behavior (Gill et al., Proceedings of the National Academy of Sciences of the United States of America 2013, 110, E3152-3161).

Anti-STn Antibodies Targeting CSCs as Cancer Treatment

Several anti-STn antibodies have been described in the field, but some demonstrate low specificity towards the STn antigen or sialylated isoforms. For example, the commercial B72.3 anti-STn antibody has been shown to bind not only to STn but also to the Tn antigen (Bapat, S. A. (2010) Human ovarian cancer stem cells. Reproduction 140, 33-41). The availability of monoclonal antibodies (mAbs) targeting STn, engineered to induce antibody-dependent cellular cytotoxicity (ADCC) and/or complement-dependent cytotoxicity (CDC), or conjugated with a cytotoxic payload [e.g. antibody drug conjugate (ADC)], offers the potential of a significant therapeutic benefit for cancer patients with STn-expressing tumors. In addition, such antibodies would also allow for the development of a companion diagnostic to pre-select patients most likely to respond to therapy.

STn is often present on one or more of CSC surface antigens, and together they serve to promote the stemness and chemoresistance properties associated with CSCs. Thus, anti-STn antibodies offer a CSC-associated cancer targeting agent with the potential not only to directly kill CSCs via direct engagement and/or ADCC, but also offer a unique opportunity to bind to a wide array of cell-surface proteins and interfere with their associated functions essential for CSC viability, self-renewal, and replication.

As discuss herein, the rationale and advantages of targeting STn on CSCs may include: (1) many tumor-specific truncated glycoproteins carry STn in cancer; (2) STn is a unique glycan target expressed preferentially on CD44, MUC1, and potentially other important cell-surface markers, on both CSCs and mature tumor cells, irrespective of proliferation status, allowing for targeting of both of these tumor components by a single therapeutic agent; (3) STn is also a component of CA-125, a biomarker of ovarian cancer and others; (4) STn is a component of the ovarian CSC marker CD44. Therefore, the use of pan-STn murine mAbs, targeting an epitope that encompasses both the Neu5Ac and Neu5Gc forms of sialic acid linked to Tn, will bind to and kill or impair the function of CSCs and, by virtue of the common epitope, non-CSC tumor cells.

In some embodiments, the present invention provides new anti-pan STn mAb(s) for specific elimination of human CSCs as well as mature tumor cells. In one aspect of the present invention, the anti-STn antibody will target the validated STn glycan itself—not a particular glycopeptide or carrier protein, which should offer the broad potential of binding to CD44, MUC1, or other STn-glycosylated markers on both CSC and non-CSC tumor populations. In some embodiments, glycan-interacting antibodies of the present disclosure may be used to target stem cell-related proteins that have one or more associated glycans. As used herein, the term "stem cell-related protein" refers to any protein that is associated with one or more stem cells. Such proteins may include, but are not limited to, cell surface proteins, markers, intracellular proteins, transcription factors, and proteins involved in cellular signaling that affect stem cell survival, growth, replication, and/or maintenance. In some cases, such glycans include STn. Stem cell-related proteins may include, but are not limited to, Notch, Hedgehog, CD44, CD117, CD133, and integrin.

Given the exceptional specificity in targeting tumor-associated STn, the present invention may spare normal tissues, including normal adult stem cells, thereby allowing for an excellent therapeutic window.

In accordance with the present invention, provided herein is a unique immunotherapeutic solution aimed at eradicating human neoplasias by eliminating both CSCs and mature cancer cells contained within the tumor compartment. The present invention provides therapies and methods specifically targeting tumors, which now include targeting CSCs, and hence expanding the therapeutic window by targeting associated tumor-specific carbohydrate moieties of these potential targets. The elimination is specifically conferred through targeting tumor associated cell-surface sialylated Tn antigen (STn) structures that are uniquely present in cancer tissue, including cancer stem cells Ovarian CSCs Ovarian cancer is the leading gynecological cancer effecting women in the U.S. During 2013. It is estimated that 22,240 women will be diagnosed with and 14,030 will die of this disease, making it the fifth leading cause of female-related cancer deaths and the most lethal gynecologic malignancy in the U.S. (Siegel et al., Cancer statistics, 2013. CA: a cancer journal for clinicians 63, 11-30). This high mortality can be ascribed to non-symptomatic onset, late-stage initial diagnosis, aggressiveness of this type of cancer, and a general lack of therapeutically targetable genetic changes. The current standard of care is tumor debulking followed by taxane and platinum based chemotherapy. While this initial treatment results in ~70% of patients achieving an initial complete clinical response, a majority of these patients will unfortunately relapse with chemoresistant disease (Foster et al., Cancer letters, 2013, 338, 147-157; and McCann et al., PloS one, 2011, 6, e28077). In part, recurrent disease has been attributable, as with other cancer types, to the presence of CSCs within the total tumor population. Indeed, ovarian CSCs have been identified and shown to be resistant to chemo- and radiotherapy (Burgos-Ojeda et al., Cancer letters, 2012, 322, 1-7). Thus, again as the case with other forms of cancer, eliminating CSCs along with mature cells in the tumor population offers the best hope to manage recurrent disease and ideally effect cures.

In some embodiments of the present invention, ovarian CSCs may be targeted for ovarian cancer treatment. Although CD133 is the most widely studied of putative ovarian CSC markers, it is recognized that CD44, a known carrier of STn as discussed above, is associated with ovarian cancer and is included in the set of markers that identify ovarian CSCs (Zhang et al., Cancer research, 2008, 68, 4311-4320; Foster et al., Cancer letters, 2013, 338, 147-157; and Zoller, Cancer, 2011, 11, 254-267). Further, STn is expressed on the well-known ovarian cancer biomarker CA-125 (MUC16), as well as on MUC1, where the levels of these STn-associated mucins in serum have been used recently as further differentiators of cancerous versus benign ovarian disease. Elevated serum levels of STn occur in ~50% of ovarian cancer patients and correlate with a lower 5-year survival rate (Kobayashi et al., Journal of clinical oncology: official journal of the American Society of Clinical Oncology, 1991, 9, 983-987; Kobayashi et al., Journal of clinical oncology: official journal of the American Society of Clinical Oncology, 1992, 10, 95-101; and Chen et al., Journal of proteome research, 2013, 12, 1408-1418). Finally, Vathipadiekal et al. in a study of differential gene expression between human primary ovarian carcinoma CSCs and non-CSC populations found that the expression of STn-generating sialyl transferase ST6GalNAc-I did not differ among cells from the two compartments.

In some embodiments, the present invention provides antibodies for targeting CSCs to prevent control or cure cancer related to CSCs. Such antibodies may include anti-STn antibodies, including, but not limited to any of those described (or derived from any of those described) in international application number PCT/US14/60079, the contents of which are herein incorporated by reference in their entirety. Further anti-STn antibodies may include antibody 3F1 (SBH Sciences, Natick, Mass.) or derivatives thereof, including recombinant antibodies with CDRs from 3F1 and/or humanized derivatives.

In some embodiments, antibodies of the invention may be used to target ovarian cancer stem cells that are resistant to other forms of treatment. Such treatments may include chemotherapy. Chemotherapy treatments may include any of those described herein and may include, but are not limited to treatment with carboplatin and/or paclitaxel. Methods of targeting chemotherapy-resistant ovarian cancer stem cells may take advantage of changes in cell surface glycan expression in ovarian cancer stem cells occurring after chemotherapy treatment. In some cases, chemotherapy-resistant ovarian cancer stem cells express STn before and/or after chemotherapy treatment. After chemotherapy treatments, some chemotherapy-resistant ovarian cancer stem cells may proliferate resulting in a population of tumor cells that express one or more cell surface glycans (e.g., STn) that distinguish these cells from surrounding cells. Anti-glycan antibodies, including, but not limited to those presented herein, may be used to kill such populations of ovarian cancer stem cells by targeting these distinguishing glycans. In some cases, anti-STn antibodies may be provided. Such antibodies may include, but are not limited to any of the antibodies described herein. In some cases, such antibodies may have at least one variable domain that is human or humanized. In some embodiments, subjects having one or more chemotherapy-resistant ovarian cancer stems cells may be treated with anti-STn antibodies of the invention after treatment with carboplatin and/or paclitaxel.

Colorectal Cancer

Colorectal cancer (CRC) has the 4$^{th}$ largest incidence, and is currently the third leading cause of cancer-related death in the US. Currently, 20% of patients are diagnosed with metastatic disease and roughly 50% of patients with CRC will eventually develop metastases. For those diagnosed with metastatic disease, the 5-year survival rate is 13.1%. In patients with metastatic colon cancer (mCRC), there is precedence for use of therapeutic antibodies (e.g., monoclonal antibodies), such as anti-epidermal growth factor receptor (EGFR) monoclonal antibodies and anti-VEGF monoclonal antibodies.

In some embodiments, glycan-interacting antibodies of the present disclosure may be used to treat CRC and/or mCRC. In some cases, such glycan-interacting antibodies are anti-STn antibodies, including, but not limited to any of those described herein. Glycan-interacting antibodies used to treat CRC and/or mCRC may be conjugated with a cytotoxic agent (e.g., MMAE and MMAF). Glycan-interacting antibodies may be used in combination with other therapies such as therapies with a chemotherapeutic agent (e.g., fluoropyrimidine, oxaliplatin, and/or irinotecan) and/or with a therapeutic antibody (e.g., bevacizumab and/or anti-EGFR).

According to some embodiments, glycan-interacting antibodies used to treat colorectal cancer may be administered at a dose of from about 0.5 mg/kg to about 20 mg/kg. For example, antibodies may be administered at doses of from about 0.5 mg/kg to about 2 mg/kg, from about 1 mg/kg to about 5 mg/kg, from about 2.5 mg/kg to about 10 mg/kg, or from about 5 mg/kg to about 20 mg/kg.

Combined Cancer Therapies

In some embodiments, compounds and compositions of the invention may be combined with one or more additional forms of cancer treatment. In some cases, such additional forms may include chemotherapeutic treatments. Accordingly, some methods of the invention include methods of treating cancer by administering at least one chemotherapeutic agent to a subject having cancer and administering a glycan-interacting antibody. Such antibodies may include anti-STn antibodies described herein.

As used herein, the term, "chemotherapy" refers to a form of treatment using chemical substances. Such chemical substances are referred to herein as "chemotherapeutic agents." In the treatment of cancer, chemotherapeutic agents are agents that slow or prohibit the proliferation of cancer cells.

In some embodiments, chemotherapeutic agents of the invention may be nucleic acid antagonistic agents. Such agents primarily affect proliferating cells, such as cancer cells, and typically function by disrupting DNA repair and/or synthesis. In some cases, nucleic acid antagonistic agents are alkylating agents (e.g., bifunctional alkylators or monofunctional alkylators). Alkylating agents are reactive compounds that may be used to disrupt DNA synthesis in dividing cells. Alkylating agents of the invention may include, but are not limited to, cyclophosphamide, mechlorethamine, chlorambucil, melphalan, dacarbazine, nitrosoureas, and temozolomide.

In other embodiments, nucleic acid antagonistic agents of the invention may include anthracyclines. Anthracyclines are bacterial derived compounds that disrupt nucleic acid synthesis. Anthracyclines of the invention may include, but are not limited to daunorubicin, doxorubicin, epirubicin, idarubicin, mitoxantrone, and valrubicin. In some embodiments, anthracyclines may be liposomally encapsulated.

In further embodiments, nucleic acid antagonistic agents may be histone deacetylase inhibitors and/or topoisomerase inhibitors. These inhibitors prevent changes in DNA supercoiling that are necessary for DNA synthesis and repair. Inhibitors of topoisomerase I may include, but are not limited to irinotecan and topotecan. Inhibitors of topoisomerase II may include, but are not limited to etoposide, teniposide, and tafluposide. Histone deacetylase inhibitors may include, but are not limited to vorinostat and romidepsin.

In some embodiments, nucleic acid antagonistic agents of the invention may include nucleotide analogs and/or nucleotide precursor analogs. Proliferating cells require nucleotides for incorporation into nucleic acids in resulting daughter cells. Nucleotide analogs may disrupt the formation of such nucleic acids or render them non-functional. Nucleotide analogs of the invention may include, but are not limited to azacitidine, azathioprine, capecitabine, doxifluridine, fluorouracil, gemcitabine, hydroxyurea, mercaptopurine, methotrexate, and tioguanine. In some embodiments, leucovorin as administered along with nucleotide analogs to enhance their effects and/or reduce harmful side effects.

In some embodiments, nucleic acid antagonistic agents of the invention are platinum-based agents. These agents disrupt nucleic acids by cross-linking them. Platinum-based agents of the invention may include, but are not limited to oxaliplatin, cisplatin, and carboplatin.

In some cases, chemotherapeutic agents of the invention include cytoskeletal disrupting agents. Actively dividing cells undergo major cytoskeletal changes that may be disrupted by these compounds. Cytoskeletal disrupting agents of the invention may include, but are not limited to vinca alkaloids, epothilones, paclitaxel, ABRAXANE® (paclitaxel protein-bound particles for injectable suspension), and docetaxel.

Although effective at targeting proliferating cancer cells, chemotherapeutic agents often affect some non-cancerous cells as well. Because of this, their administration is typically limited by dose, length of treatment, or area of treatment. Further, because chemotherapeutic agents primarily affect proliferating cells, non-proliferating cancer stem cells may remain viable after treatment and capable of reforming cancerous cells. Accordingly, in some embodiments, methods of the invention include methods of treating cancer in which at least one chemotherapeutic agent is first administered to a subject having cancer, followed by administration of a glycan-interacting antibody. In some cases, the glycan-interacting antibody is selected to target a specific cell surface glycan associated with chemotherapy-resistant cells. As used herein, the term "chemotherapy-resistant" is used to refer to cells that are unaffected by or that have limited susceptibility to chemotherapy treatment.

Methods of targeting chemotherapy-resistant cells (e.g., chemotherapy-resistant cancer stem cells) may take advantage of changes in STn expression in these cells occurring after chemotherapy treatment. In some cases, chemotherapy-resistant cells express STn before and/or after chemotherapy treatment. In some cases, cell surface STn expression in chemoresistant cells may be increased following chemotherapy treatment [e.g., due to altered expression of factors involved in STn synthesis (e.g., STnGalNAc I, T-synthase, or Cosmc), decreased degradation, or other mechanisms leading to increased cell surface STn expression]. After chemotherapy treatments, some chemotherapy-resistant cells expressing cell surface STn may proliferate resulting in a population of STn-expressing tumor cells that are chemotherapy-resistant. In some embodiments, anti-STn antibodies may be used to target chemotherapy-resistant cells. In some cases, these cells are cancer stem cells. Accordingly, methods of the invention may include methods of administering an anti-STn antibody to target STn-expressing chemotherapy-resistant cells present after administration of one or more chemotherapeutic agent.

The identification of cell surface glycans on chemotherapy-resistant cells may be carried out by analyzing chemotherapy-resistant cells after chemotherapy treatment for the identity of cell surface glycans that distinguish these cells from surrounding cells. In some embodiments, such cell surface glycans may include, but are not limited to mucin-related antigens (including, but not limited to Tn, STn and Thomsen-Friedenreich antigen), blood group Lewis related antigens [including, but not limited to Lewis$^Y$ (Le$^Y$), Lewis$^X$ (Le$^X$), Sialyl Lewis$^X$ (SLe$^X$) and Sialyl Lewis$^A$ (SLe$^A$)], glycosphingolipid-related antigens [including, but not limited to Globo H, stage-specific embryonic antigen-3 (SSEA-3) and glycosphingolipids having sialic acid], ganglioside-related antigens [including, but not limited to gangliosides GD2, GD3, GM2, fucosyl GM1 and Neu5GcGM3] and polysialic acid-related antigens. Many of such antigens are described in International Publication No. WO2015054600, the contents of which are herein incorporated by reference in their entirety. Analyses carried out to identify cell surface glycans expressed on cancer stem cells remaining after chemotherapy may be carried out according to any methods known in the art. In some cases, such analyses are carried out by obtaining a tissue sample and assessing the expression of cell surface glycans in the tissue sample using one or more immunological assay (e.g., immunohistochemical analysis, ELISA analysis, flow cytometric analysis, antibody array, or mass spectrometry).

In some embodiments, chemotherapy-resistant cells are analyzed to assess the expression level of cell surface STn. This may be carried out by obtaining a tissue sample and analyzing the sample for expression of cell surface STn [for example, using one or more immunological assay (e.g., immunohistochemical analysis, ELISA analysis, flow cytometric analysis, antibody array, or mass spectrometry)]. Where chemotherapy-resistant cells express STn, anti-STn antibodies may be administered to a subject after administration of chemotherapeutic agents.

In some embodiments, one or more tumors are primed for treatment with one or more glycan-interacting antibodies by contacting the tumors with at least one chemotherapeutic agent. According to such embodiments, priming a tumor for glycan-interacting antibody treatment refers to reducing proliferating cells in a tumor, leaving one or more chemotherapy-resistant tumor cells behind. According to such methods, glycan-interacting antibodies may be used to further reduce tumor volumes by eliminating chemotherapy-resistant cells that remain after treatment with one or more chemotherapeutic agents.

Administration of glycan-interacting antibodies after administration of one or more chemotherapeutic agent may be carried out from about 1 day to about one year after treatment with one or more chemotherapeutic agents (e.g., from about 1 day to about 10 days, from 1 week to about 4 weeks, from about 2 weeks to about 10 weeks, from about 1 month to about 3 months, from about 2 months to about 6 months, or from about 3 months to about 12 months). In some cases, administration of glycan-interacting antibodies may be carried out at least 1 year after treatment with one or more chemotherapeutic agents.

In some embodiments, multiple rounds of administration with one or more chemotherapeutic agents may be followed by administration of glycan-interacting antibodies (e.g., 2 rounds, 3 rounds, 4 rounds, 5 rounds, 6 rounds, 7 rounds, 8 rounds, 9 rounds, 10 rounds, or at least 10 rounds). In some cases, rounds of treatment are repeated until tissue analyses reveal that cancerous cells and/or chemotherapy-resistant cells are reduced or eliminated.

The dose of chemotherapeutic agents may be adjusted based on the size of the subject receiving treatment. In some embodiments, doses include those described by Calvo et al. 2014 (Calvo, E. et al., 2014. Chemotherapeutic agents and their uses, dosages, and toxicities. Cancer Network. p 1-12). In some cases, doses are adjusted based on the surface area of the subject being treated [typically measured in square meters (m$^2$)]. Chemotherapeutic agents of the invention may be administered at doses of from about 0.01 mg/m$^2$ to about 1 mg/m$^2$, from about 0.1 mg/m$^2$ to about 5 mg/m$^2$, from about 1 mg/m$^2$ to about 20 mg/m$^2$, from about 10 mg/m$^2$ to about 100 mg/m$^2$, from about 50 mg/m$^2$ to about 500 mg/m$^2$, from about 200 mg/m$^2$ to about 2000 mg/m$^2$, or from about 1000 mg/m$^2$ to about 10000 mg/m$^2$. In some cases, chemotherapeutic agents of the invention are administered at a dose of at least 10000 mg/m$^2$. According to some methods, chemotherapeutic agents are administered intravenously.

In some embodiments, administration of chemotherapeutic agents includes administration of carboplatin. According to some methods, carboplatin is administered at a dose of from about 200 mg/m$^2$ to about 400 mg/m$^2$. In some embodiments, administration of chemotherapeutic agents includes administration of paclitaxel. According to some methods, paclitaxel is administered at a dose of from about 20 mg/m$^2$ to about 300 mg/m$^2$.

In some embodiments, glycan-interacting antibodies of the present disclosure are administered in combination with anti-angiogenic therapies (e.g., bevacizumab). According to some embodiments, methods of treating cancer are provided that include identifying a subject in need of cancer treatment, wherein the subject has cancer that is not fully responsive to treatment with at least one poly-ADP-ribose polymerase inhibitor, and administering an anti-STn antibody to the subject. Such anti-STn antibodies may include any of those known in the art or described herein.

Immune-Related Targets

In some embodiments, glycan-interacting antibodies of the invention may be immunomodulatory antibodies. As used herein, an immunomodulatory antibody is an antibody that enhances or suppresses one or more immune function or pathway.

Many bacterial glycans are known to include sialic acid. In some cases, such glycans allow bacteria to evade the innate immune system of hosts, including, but not limited to humans. In one example, bacterial glycans inhibit alternate complement pathway activation through factor H recognition. In another example, bacterial glycans mask underlying residues that may be antigenic. Some bacterial glycans participate in cell signaling events through activation of inhibitory sialic acid binding Ig-like lectins (Siglecs) that dampen the immune response to entities including certain sialylated moieties (Chen, X. et al., Advances in the biology and chemistry of sialic acids. ACS Chem Biol. 2010 Feb. 19;

5(2):163-76). In some embodiments, glycan-interacting antibodies of the present invention may be used to treat immune complications related to bacterial glycans.

Due to the foreign nature of Neu5Gc as described herein, some Neu5Gc glycans are immunogenic resulting in immune related destruction of cells and other entities where these glycans may be expressed. Such autoimmune destruction may be pathogenic. In some embodiments, glycan-interacting antibodies may be used to treat patients suffering from autoimmune disorders related to Neu5Gc glycans.

In some embodiments, immunomodulatory antibodies of the invention may be used to promote or suppress T cell-mediated immunity. Such antibodies may interact with one or more glycans present on T cells, T cell-related proteins and/or on one or more other cell types that interact with T cells. Immunomodulatory antibodies that enhance T cell mediated immunity may be used to stimulate T cell mediated targeting of cancer cells.

In some tumors, infiltration by tumor-associated macrophages (TAMs) may lead to immunosuppression promoting tumor cell viability and growth. This is thought to be due to immunosuppressive cell signaling that occurs through interactions between myeloid C-type lectin receptors (CLRs) present on TAMs and tumor-associated mucins (Allavena, P. et al., Clin Dev Immunol. 2010; 2010:547179). In some embodiments, binding of immunomodulatory antibodies of the invention to one or more tumor-associated mucin or TACA prevents immunosuppressive cell signaling in TAMs.

III. Pharmaceutical Compositions

In some embodiments, the present disclosure includes pharmaceutical compositions. Pharmaceutical compositions are any composition that includes at least one substance used for medical treatment or "medicament" along with one or more pharmaceutically acceptable excipients. Such pharmaceutical compositions may include antibodies of the present disclosure and/or fragments, peptides, or proteins derived from such antibodies. Pharmaceutical compositions may be characterized by one or more of bioavailability, therapeutic window and/or volume of distribution.

IV. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc). can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1. Glycan Array Analysis

Optimized glycan arrays are utilized to test antibody affinity and specificity for multiple glycans in a single experiment. Glycan arrays include 71 chemically synthesized and well-defined glycans, most of which are Neu5Ac and Neu5Gc glycan pairs. Array slides are obtained commercially (Arraylt Corp, Sunnyvale, Calif.) and include the glycans listed in Table 17.

TABLE 17

Array glycans

| Glycan ID No. | Glycan |
| --- | --- |
| 1 | Neu5,9Ac2α2,3Galβ1,4GlcNAcβO(CH2)2CH2NH2 |
| 2 | Neu5Gc9Acα2,3Galβ1,4GlcNAcβO(CH2)2CH2NH2 |
| 3 | Neu5,9Ac2α2,6Galβ1,4GlcNAcβO(CH2)2CH2NH2 |
| 4 | Neu5Gc9Acα2,6Galβ1,4GlcNAcβO(CH2)2CH2NH2 |
| 5 | Neu5Acα2,6GalNAcαO(CH2)2CH2NH2 |
| 6 | Neu5Gcα2,6GalNAcαO(CH2)2CH2NH2 |
| 7 | Neu5,9Ac2α2,3Galβ1,3GlcNAcβO(CH2)2CH2NH2 |

TABLE 17-continued

Array glycans

| Glycan ID No. | Glycan |
|---|---|
| 8 | Neu5Gc9Acα2,3Galβ1,3GlcNAcβO(CH2)2CH2NH2 |
| 9 | Neu5,9Ac2α2,3Galβ1,3GalNAcαO(CH2)2CH2NH2 |
| 10 | Neu5Gc9Acα2,3Galβ1,3GalNAcαO(CH2)2CH2NH2 |
| 11 | Neu5Acα2,3Galβ1,4GlcNAcβO(CH2)2CH2NH2 |
| 12 | Neu5Gcα2,3Galβ1,4GlcNAcβO(CH2)2CH2NH2 |
| 13 | Neu5Acα2,3Galβ1,3GlcNAcβO(CH2)2CH2NH2 |
| 14 | Neu5Gcα2,3Galβ1,3GlcNAcβO(CH2)2CH2NH2 |
| 15 | Neu5Acα2,3Galβ1,3GalNAcαO(CH2)2CH2NH2 |
| 16 | Neu5Gcα2,3Galβ1,3GalNAcαO(CH2)2CH2NH2 |
| 17 | Neu5Acα2,6Galβ1,4GlcNAcβO(CH2)2CH2NH2 |
| 18 | Neu5Gcα2,6Galβ1,4GlcNAcβO(CH2)2CH2NH2 |
| 19 | Neu5Acα2,6Galβ1,4GlcβO(CH2)2CH2NH2 |
| 20 | Neu5Gcα2,6Galβ1,4GlcβO(CH2)2CH2NH2 |
| 21 | Neu5Acα2,3Galβ1,4GlcβO(CH2)2CH2NH2 |
| 22 | Neu5Gcα2,3Galβ1,4GlcβO(CH2)2CH2NH2 |
| 23 | Neu5,9Ac2α2,6GalNAcαO(CH2)2CH2NH2 |
| 24 | Neu5Gc9Acα2,6GalNAcαO(CH2)2CH2NH2 |
| 25 | Neu5Acα2,3GalβO(CH2)2CH2NH2 |
| 26 | Neu5Gcα2,3GalβO(CH2)2CH2NH2 |
| 27 | Neu5Acα2,6GalβO(CH2)2CH2NH2 |
| 28 | Neu5Gcα2,6GalβO(CH2)2CH2NH2 |
| 29 | Neu5,9Ac2α2,3GalβO(CH2)2CH2NH2 |
| 30 | Neu5Gc9Acα2,3GalβO(CH2)2CH2NH2 |
| 31 | Neu5,9Ac2α2,6GalβO(CH2)2CH2NH2 |
| 32 | Neu5Gc9Acα2,6GalβO(CH2)2CH2NH2 |
| 33 | Neu5Acα2,3Galβ1,3GalNAcβO(CH2)2CH2NH2 |
| 34 | Neu5Gcα2,3Galβ1,3GalNAcβO(CH2)2CH2NH2 |
| 35 | Neu5,9Ac2α2,3Galβ1,3GalNAcβO(CH2)2CH2NH2 |
| 36 | Neu5Gc9Acα2,3Galβ1,3GalNAcβO(CH2)2CH2NH2 |
| 37 | Neu5,9Ac2α2,6Galβ1,4GlcβO(CH2)2CH2NH2 |
| 38 | Neu5Gc9Acα2,6Galβ1,4GlcβO(CH2)2CH2NH2 |
| 39 | Neu5,9Ac2α2,3Galβ1,4GlcβO(CH2)2CH2NH2 |
| 40 | Neu5Gc9Acα2,3Galβ1,4GlcβO(CH2)2CH2NH2 |
| 41 | Neu5Acα2,8Neu5Acα2,3Galβ1,4GlcβO(CH2)2CH2NH2 |
| 42 | Neu5Acα2,8Neu5Acα2,8Neu5Acα2,3Galβ1,4GlcβO(CH2)2CH2NH2 |
| 43 | Galβ1,4GlcβO(CH2)2CH2NH2 |
| 45 | Galβ1,4GlcNAcβO(CH2)2CH2NH2 |
| 47 | GalNAcαO(CH2)2CH2NH2 |
| 51 | Galβ1,3GalNAcβO(CH2)2CH2NH2 |
| 52 | Galβ1,3GlcNAcαO(CH2)2CH2NH2 |
| 53 | Galβ1,3GlcNAcβO(CH2)2CH2NH2 |
| 54 | Galβ1,4GlcNAc6SβO(CH2)2CH2NH2 |
| 55 | Neu5Acα2,3Galβ1,4(Fucα1,3)GlcNAcβO(CH2)2CH2NH2 |
| 56 | Neu5Gcα2,3Galβ1,4(Fucα1,3)GlcNAcβO(CH2)2CH2NH2 |
| 57 | Neu5Acα2,3Galβ1,4(Fucα1,3)GlcNAc6SβO(CH2)2CH2NH2 |
| 58 | Neu5Gcα2,3Galβ1,4(Fucα1,3)GlcNAc6SβO(CH2)2CH2NH2 |
| 59 | Galβ1,3GlcNAcβ1,3Galβ1,4GlcβO(CH2)2CH2NH2 |
| 60 | Neu5Acα2,3Galβ1,3GlcNAcβ1,3Galβ1,4GlcβO(CH2)2CH2NH2 |
| 61 | Neu5Gcα2,3Galβ1,3GlcNAcβ1,3Galβ1,4GlcβO(CH2)2CH2NH2 |
| 62 | Neu5Acα2,3Galβ1,4GlcNAc6SβO(CH2)2CH2NH2 |
| 63 | Neu5Gcα2,3Galβ1,4GlcNAc6SβO(CH2)2CH2NH2 |
| 64 | Neu5Acα2,8Neu5Acα2,3Galβ1,4GlcβO(CH2)3NHCOCH2(OCH2CH2)6NH2 |
| 65 | Neu5Acα2,8Neu5Acα2,8Neu5Acα2,3Galβ1,4GlcβO(CH2)3NHCOCH2(OCH2CH2)6NH2 |
| 66 | Neu5Acα2,6(Neu5Acα2,3)Galβ1,4GlcβO(CH2)2CH2NH2 |
| 67 | Neu5Acα2,6(Neu5Gcα2,3)Galβ1,4GlcβO(CH2)2CH2NH2 |
| 68 | Neu5Acα2,6(KDNα2,3)Galβ1,4GlcβO(CH2)2CH2NH2 |
| 69 | Neu5Gcα2,8Neu5Acα2,3Galβ1,4GlcβO(CH2)2CH2NH2 |
| 70 | KDNα2,8Neu5Acα2,3Galβ1,4GlcβO(CH2)2CH2NH2 |
| 71 | Neu5Acα2,8Kdnα2,6Galβ1,4GlcβO(CH2)2CH2NH2 |
| 72 | Neu5Acα2,8Neu5Gcα2,3Galβ1,4GlcβO(CH2)2CH2NH2 |
| 73 | Neu5Acα2,8Neu5Gcα2,6Galβ1,4GlcβO(CH2)2CH2NH2 |
| 74 | KDNα2,8Neu5Gcα2,3Galβ1,4GlcβO(CH2)2CH2NH2 |
| 75 | Neu5Gcα2,8Neu5Gcα2,3Galβ1,4GlcβO(CH2)2CH2NH2 |
| 76 | Neu5Acα2,8Neu5Acα2,6Galβ1,4GlcβO(CH2)2CH2NH2 |

300 ml of epoxy blocking buffer is prepared by combining 15 ml of 2 M Tris buffer (pH 8) with 0.9 ml of 16.6 M ethanolamine and 284.1 ml of distilled water. The solution is brought to a final pH of 9.0 with HCl. The solution is filtered using a 0.2 µM nitrocellulose membrane. The epoxy buffer solution as well as 1 L of distilled water are pre-warmed to 50° C. Glass slides are arranged in a slide holder and quickly submerged in a staining tub with the warmed epoxy blocking buffer. Slides are incubated in the epoxy blocking buffer (0.1 M Tris, 0.05 M ethanolamine, pH 9.0) for 1 hour at 50° C. with periodic shaking to deactivate epoxy binding sites. Next, slides are rinsed with distilled water and blocked with PBS with 1% OVA at 25° C. for one hour. Serum samples with polyclonal antibodies (1:1000) or purified monoclonal antibodies (1 µg/mL), are diluted in PBS with 1% OVA and added to the glycan array for one hour at 25° C. Slides are washed twice with PBS with 0.1% (v/v) Tween, then once with PBS alone. Binding of antibodies are detected by incubating glycan microarray slides with 1.5 µg/mL Cy3-conjugated anti-mouse IgG (Jackson Immunoresearch, West Grove, Pa.) in PBS for one hour. Slides are then washed extensively, dried and scanned with a Genepix 4000B scanner (Molecular Devices, Sunnyvale, Calif.). The parameters are set as laser at 100%, gain at 350, and 10 µm pixels. Raw data from scanned images are extracted using the Genepix software and analysis of raw data is carried out. Antibodies are considered to be highly specific for AcSTn and GcSTn if they demonstrate binding to both molecules, but not to Tn or any other glycans on the array. Binding is compared to mouse monoclonal anti-STn antibody 3F1, B72.3 and CC49.

Based on array analysis, antibodies are classified according to array glycan binding profile. Antibodies are classified as "Group 1" antibodies, capable of binding AcSTn and GcSTn, if they bind to glycans 5, 6, 23 and 24. Such antibodies are referred to as Pan-STn antibodies due to their ability to associate with a wider range of STn structures and the portion of STn indicated by the large oval in FIG. 1A. Antibodies are classified as "Group 2" antibodies, capable of binding STn as well as some related structures that include an O-linkage to serine or threonine, if they bind to glycans 5, 6, 23, 24, 27 and 31. These antibodies are thought to associate with the portion of STn indicated by the large oval in FIG. 1B. Some Group 2 antibodies preferably bind to structures with AcSTn over structures with GcSTn. Antibodies are classified as "Group 3" antibodies (capable of binding STn, but may also bind a broader set of related structures) if they bind glycans 5, 6, 23, 24, 17, 3, 19, 37, 27 and 31. Unlike Group 2 antibodies, Group 3 antibodies do not require that such structures have an O-linkage to serine or threonine. Group 3 antibodies are thought to associate with the portion of STn indicated by the large oval in FIG. 1C. Finally, antibodies are "Group 4" antibodies, capable of binding to both AcSTn and GcSTn as well as the unsialylated Tn antigen (therefore having broader specificity) if they bind to glycans 5, 6, 23, 24 and 47. Group 4 antibodies are thought to associate with the portion of STn indicated by the large oval in FIG. 1D.

Example 2. Isolation of PBMCs from Whole Blood

Whole blood is obtained from Research Blood Components (Boston, Mass.) in heparin treated tubes (10 mL/tube). Blood is spun at 1,200 rpm for 10 min to separate plasma from cells. The buffy coat containing lymphocytes is collected and transferred to a fresh tube for FICOLL extraction (10 mL FICOLL/40 mL RPMI). Tubes are spun for 30 min at 2,000 rpm and the PBMC layer is collected into a fresh tube. Tubes containing PBMCs are spun for 7 min at 1,200 rpm and supernatant is removed. Pellets are washed with RPMI+10% (v/v) FBS before further processing.

Example 3. Flow Cytometry-Based Analysis of Antibody Binding

Flow cytometry-based analysis is carried out to elucidate the dose-response curve for binding of antibodies to cell surface antigens.

MDA-MB-231 cells are human breast cancer cells. They are grown in Earle's Minimum Essential Medium supplemented with 10% fetal calf serum (FCS), 100 µg/ml penicillin, 100 UI/ml streptomycin and 45 µs/ml gentamycin. Stably transfected versions of MDA-MB-231 (MDA-MB-231-STn, clone TAH3.P10) are also cultured under the same conditions with the exception of an added 1 mg/ml of G418 to support cells expressing the transgene. As a result of over expression, transfected cells express high levels of Neu5Ac-STn (see Julien, S. et al., Glycoconjugate journal. 2001. 18, 883-93; the contents of which are herein incorporated by reference in their entirety).

OV90 and OVCAR3 cells are also used. These are human ovarian cancer cell lines, described previously.

For analysis, tumor cells are harvested using StemPro Accutase (Life Technologies, Carlsbad, Calif.) and washed with PBS including 5% heat-inactivated FBS before pelleting by light centrifugation. Cell numbers and viability are determined by trypan blue dye exclusion analysis and cell concentrations are adjusted to $5 \times 10^6$ cells/ml in PBS with 5% (v/v) heat-inactivated FBS. 50 µl of cells are added to each well of an assay plate. Cells are combined with 50 µl solutions of antibody being analyzed or control antibodies and incubated for 1 hour at 4° C. Cells are washed and pelleted twice with PBS with 5% FBS before being treated with 100 µl of PBS with 5% FBS including a 1:1,500 dilution of anti-mouse IgG (Southern Biotech, Birmingham, Ala.) conjugated to allophycocyanin (APC). Cells are incubated for 30 min at 4° C. before washing and resuspending in 200 µl of propidium iodide (PI) diluted 1:1000 in PBS with 5% FBS. Treated cells are then subjected to flow cytometry analysis.

T cells are used to assess binding of antibodies to CD3. For T cell binding assay, PBMCs are isolated from 100 ml of human blood sample using the protocol described previously. PBMCs are suspended in RPMI 1640 medium supplemented with 10% FCS and adjusted to a concentration of 500,000 cells per 50 µl. 50 µl of cells are added to each well of an assay plate. Serial dilutions of bispecific antibodies are prepared in a polypropylene plate. Equal volumes of PBMCs and bispecific antibody dilutions are mixed to produce a binding curve. Anti-CD2-FITC (BD Biosciences, San Jose, Calif.) is added to each well to selectively stain T cells. The plate is incubated for 1 hour at 4° C. Cells are washed and pelleted three times with FACS buffer consisting of PBS, 5% FBS and 0.05% sodium azide. Cells are incubated with a 1:500 dilution of anti-Fc secondary antibody conjugated to Alexa 647 for 20 minutes at 4° C. Cells are washed and pelleted three times again with FACS buffer. Cells are then resuspended in 200 µL FACS buffer and analyzed on a BD ACCURI™ C6 flow cytometer (BD Biosciences, San Jose, Calif.).

For data analysis, a total of 5,000 events are acquired per sample. Data is analyzed using FLOWJO® software (BD Biosciences, San Jose, Calif.). Mean APC or Alexa 647 fluorescence and % APC or % Alexa 647 positive cells are calculated. Data is log transformed and then fit to a nonlinear regression model to obtain a dose-response curve and half maximal effective concentration ($EC_{50}$) calculations using Prism software.

Example 4. Humanization of Anti-CD3 Variable Domains

Humanized anti-CD3 variable domains were developed based on an existing anti-CD3 antibody, OKT3. First, the variable domain sequences of OKT3 were analyzed to identify complementarity determining region (CDR) boundaries. The respective CDRs on heavy chain variable domain (CDR-H1, CDR-H2, CDR-H3) and light chain variable domain (CDR-L1, CDR-L2, CDR-L3) are presented in Table 18.

TABLE 18

OKT3 CDR sequences

| Chain | CDR-1 | SEQ ID NO | CDR-2 | SEQ ID NO | CDR-3 | SEQ ID NO |
|---|---|---|---|---|---|---|
| VH | GYTFTRYTMH | 20 | YINPSRGYTNYNQKFKD | 21 | YYDDHYCLDY | 22 |
| VL | SASSSVSYMN | 23 | DTSKLAS | 24 | QQWSSNPFT | 25 |

Mouse germline antibody sequences for OKT3 were then identified. The mouse germline sequences corresponding to VH and VL were determined to be muJ558.44 and muIGKV4-59, respectively.

Next, OKT3 variable domain sequences were compared to human framework sequences and human framework sequences suitable for CDR grafting were selected based on sequence similarity and other characteristics, such as framework stability and pairing capacity. Table 19 indicates the human framework or human consensus sequence selected to replace the corresponding framework region of OKT3 in humanized variable domains. FR4 of human consensus 3 heavy chain (identical to human consensus 1 sequence) corresponds to the amino acid sequence WGQGTLVTVSS (SEQ ID NO: 51) and FR4 of human consensus 1 light chain corresponds to the amino acid sequence FGQGTKVEIK (SEQ ID NO: 52)

TABLE 19

Structure of humanized OKT3 variable domains

| Chain | FR1 | CDR1 | FR2 | CDR2 | FR3 | CDR3 | FR4 |
|---|---|---|---|---|---|---|---|
| VH | IGHV3-11*03 | OKT3 CDR-H1 | IGHV3-11*03 | OKT3 CDR-H2 | IGHV3-11*03 | OKT3 CDR-H3 | Human consensus 3, heavy chain (identical to human consensus 1 sequence) |
| VL | IGKV1-39*01 | OKT3 CDR-L1 | IGKV1-39*01 | OKT3 CDR-L2 | IGKV1-39*01 | OKT3 CDR-L3 | Human consensus 1, light chain |

Finally, structural analysis was conducted to identify residues that may be back-crossed to improve antibody binding, stability or other properties. For example, humanized OKT3 VH domain was assessed for the presence of unpaired cysteine residues. Residue 100 located in VH CDR3 was identified as an unpaired cysteine. It is partially buried on VL/VH interface and could be susceptible to oxidation. Based on structural analysis, a serine residue was selected to substitute this cysteine Additional mutations were identified using a similar approach. Based on this analysis, several humanized VL and VH sequences were designed for synthesis and testing. These include the variable domain sequences presented in Table 20. VH or VL domains are indicated, followed by a digit to show the variant number. Domains with the digit "0" represent the humanized sequence without any back-mutation.

TABLE 20

Humanized variable domains

| mAb | Chain | Sequence | SEQ ID NO |
|---|---|---|---|
| OKT3 | VH0 | QVQLEQSGGGLVKPGGSLRLSCAASGYTFTRYTMHWIRQAPG KGLEWVSYINPSRGYTNYNQKFKDRFTISRDNAKNSLYLQMN SLRAEDTAVYYCARYYDDHYCLDYWGQGTLVTVSS | 64 |
| OKT3 | VH1 | QVQLEQSGGGDVKPGGSLRLSCKASGYTFTRYTMHWVKQAP GKCLEWVGYINPSRGYTNYNQKFKDRATISRDKAKNTLYLQ MNSLRAEDTAVYYCARYYDDHYSLDYWGQGTTVTVSS | 65 |
| OKT3 | VH2 | QVQLEQSGGGDVKPDGSLRLSCKASGYTFTRYTMHWVKQAP GKGLEWVGYINPSRGYTNYNQKFKDRATISRDKAKNTLYLQ MNSLRGEDTAVYYCARYYDDHYSLDYWGQGTTVTVSS | 66 |
| OKT3 | VH3 | QVQLEQSGGGLVKPGGSLRLSCKASGYTFTRYTMHWVKQAP GKGLEWVGYINPSRGYTNYNQKFKDRATISRDKAKNSLYLQ MNSLRAEDTAVYYCARYYDDHYSLDYWGQGTLVTVSS | 67 |
| OKT3 | VH4 | QVQLEQSGGGDVKPDGSLRLSCKASGYTFTRYTMHWVKQAP GKGLEWVGYINPSRGYTNYNQKFKDRATISRDKAKNTLYLQ MNSLRGEDTAVYYCARYYDDHYCLDYWGQGTTVTVSS | 68 |
| OKT3 | VL0 | DIQMTQSPSSLSASVGDRVTITCSASSSVSYMNWYQQKPGKA PKLLIYDTSKLASGVPSRFSGSGSGTDFTLTISSLQPEDFATYYC QQWSSNPFTFGQGTKVEIKR | 69 |
| OKT3 | VL1 | QIQLTQSPSSLSASVGDRVTITCSASSSVSYMNWYQQKPGKAP KRWIYDTSKLASGVPSRFSGSGSGTDYTLTISSLQPEDEATYY CQQWSSNPFTFGCGTKVEVQG | 70 |
| OKT3 | VL2 | QIQLTQSPSSLEASVGDRVTITCSASSSVSYMNWYQQKPGKAP KRWIYDTSKLASGVPSRFSGSGSGTDYTLTISSLQPEDEGTYY CQQWSSNPFTFGGGTKVEVQG | 71 |
| OKT3 | VL3 | QIQLTQSPSSLSASVGDRVTITCSASSSVSYMNWYQQKPGKAP KRWIYDTSKLASGVPSRFSGSGSGTDYTLTISSLQPEDFATYYC QQWSSNPFTFGQGTKVEVKR | 72 |

Example 5. Generation of Anti-CD3 scFvs

Single-chain variable fragments (scFvs) were constructed using the humanized variable domains in either the VH-VL or the VL-VH orientation. Variable domain pairs were selected for initial expression of full antibodies and testing. Selected pairs include VL0 and VH0 (no back-mutation); VL3 and VH3; VL1 and VH1; VL2 and VH2; and VL2 and VH4.

In the scFv, VH and VL are connected via a peptide linker. These were selected from the linker sequences presented in Table 21.

TABLE 21

| Linker No. | Sequence | SEQ ID NO |
|---|---|---|
| Linker 1 | GGGGSGGGGSGGGGS | 26 |
| Linker 2 | ASTGGGGSGGGGSGGGGSGGGGS | 27 |
| Linker 3 | GGGGSGGGGSGGGGSGGGGS | 28 |
| Linker 4 | ASTGGGGSGGGGSGGGGS | 29 |
| Linker 5 | STGGGGSGGGGSGGGGSDI | 30 |

A number of anti-CD3 scFvs were generated that contain different combinations of the selected variable domains and linker sequences. Representative scFv candidates and test controls are presented in Table 22. Additional labels (e.g., v1, v2) following the same scFv number indicate linker engineered variants. ScFv8 and scFv9 v1-v3 are positive controls. ScFv8 includes anti-CD3 VH and VL sequences from the anti-CD19/anti-CD3 bispecific antibody Blinatumomab (Amgen, Thousand Oaks, Calif.), and ScFv9 v1-v3 includes the mouse VH and VL sequences from OKT3.

TABLE 22

Anti-CD3 scFv sequences

| ScFv No. | VH | VL | Orientation | Linker No. | SEQ ID NO |
|---|---|---|---|---|---|
| scFv1 | OKT3 VH0 | OKT3 VL0 | VH-VL | Linker 2 | 73 |
| scFv2 | OKT3 VH3 | OKT3 VL3 | VH-VL | Linker 2 | 74 |
| scFv3 v1 | OKT3 VH2 | OKT3 VL2 | VH-VL | Linker 2 | 75 |
| scFv3 v2 | OKT3 VH2 | OKT3 VL2 | VH-VL | Linker 4 | 76 |
| scFv4 | OKT3 VH2 | OKT3 VL2 | VL-VH | Linker 3 | 77 |
| scFv5 | OKT3 VH1 | OKT3 VL1 | VH-VL | Linker 2 | 78 |
| scFv6 | OKT3 VH1 | OKT3 VL1 | VL-VH | Linker 3 | 79 |
| scFv7 | OKT3 VH4 | OKT3 VL2 | VH-VL | Linker 2 | 80 |
| scFv8 | Blinatumomab VH | Blinatumomab VL | VH-VL | Linker 2 | 81 |
| scFv9 v1 | OKT3 VH | OKT3 VL | VH-VL | Linker 2 | 82 |
| scFv9 v2 | OKT3 VH | OKT3 VL | VH-VL | Linker 4 | 83 |
| scFv9 v3 | OKT3 VH | OKT3 VL | VH-VL | Linker 5 | 84 |

Example 6. Generation of Anti-STn scFvs

In an alternative design, anti-STn variable domains were engineered in an scFv. Suitable anti-STn variable domains were selected from previously humanized anti-STn variable domains. The pair of VL0 (SEQ ID NO: 53) and VH3 (SEQ ID NO: 60) from 2G12-2B2 was used in the initial testing. These two sequences were further modified to improve the stability of the scFv. The modified sequences are presented in Table 23.

TABLE 23

Stabilized anti-STn variable domains

| mAb | Chain | Sequence | SEQ ID NO |
|---|---|---|---|
| 2G12-2B2 | VL3 | DIVMTQSPDSLSVSDGERATINCKSSQSLLNRGNHKN YLTWYQQKPGQPPKLLIYWASTRESGVPDRFSGSGS GTDFTLTISSLQAEDEGVYYCQNDYTYPYTFGGGTK VEIQ | 55 |
| 2G12-2B2 | VL4 | DIVMTQSPDSLSVSDGERATINCKSSQSLLNRGNHKN YLTWYQQKPGQPPKLLIYWASTRESGVPDRFSGSGS GTDFTLTISSLQAEDEGVYYCQNDYTYPYTFGCGTK VEIQ | 56 |
| 2G12-2B2 | VH5 | EVQLVQSGAEDKKPGASVKVSCKASGYTFTDHAIH WVRQAPGQGLEWMGYFSPGNDDIKYNEKFRGRATL TADKSSSTAYMELNSLRSDDTAVYFCKRSLSTPYWG QGTSVTVSS | 62 |
| 2G12-2B2 | VH6 | EVQLVQSGAEDKKPGASVKVSCKASGYTFTDHAIH WVRQAPGQCLEWMGYFSPGNDDIKYNEKFRGRATL TADKSSSTAYMELNSLRSDDTAVYFCKRSLSTPYWG QGTSVTVSS | 63 |

Anti-STn scFvs constructed using the modified 2G12-2B2 variable domains and selected linker sequences are presented in Table 24.

TABLE 24

Anti-STn scFv sequences

| ScFv No. | VH | VL | Orientation | Linker No. | SEQ ID NO |
|---|---|---|---|---|---|
| scFv10 | 2G12-2B2 VH5 | 2G12-2B2 VL3 | VH-VL | Linker 2 | 85 |
| scFv11 | 2G12-2B2 VH6 | 2G12-2B2 VL4 | VH-VL | Linker 2 | 86 |
| scFv12 | 2G12-2B2 VH5 | 2G12-2B2 VL3 | VL-VH | Linker 1 | 87 |

Example 7. Generation of STn-CD3 Bispecific Antibodies

STn-CD3 bispecific antibodies were constructed by fusing an scFv to the C-terminus of the heavy chain of an IgG1 antibody. Two different designs were tested. In one design, an anti-CD3 scFv was fused to an anti-STn antibody containing a pair of anti-STn variable domains in its Fab region. In an alternative design, an anti-STn scFv was fused to an anti-CD3 antibody containing a pair of anti-CD3 variable domains in its Fab region.

The IgG backbone used to generate the bispecific antibodies consists of IgG1 heavy chain constant regions with an N297Q mutation (SEQ ID NO: 15) and immunoglobulin kappa light chain constant regions (SEQ ID NO: 14). The N297Q mutation removes an N-glycosylation site, leading to an aglycosylated antibody, which can simplify bioprocessing and enhance the effector functions of the antibody. The Fab region of the IgG antibody comprises a pair of either anti-STn variable domains or anti-CD3 variable domains described above.

The scFv was attached to the C-terminus of an IgG heavy chain via a peptide linker. The linker sequence corresponds to the sequence of Linker 1 (SEQ ID NO: 26). The C-terminal lysine residue of the Fc CH$_3$ domain was removed.

A number of bispecific antibodies were designed. These include the antibodies presented in Table 25. In this table, the "BsAb ID" refers to a unique identifier assigned to each bispecific antibody prepared, and corresponding Fab fragment and scFv are indicated for each bispecific antibody. The scFv Nos correspond to those described above.

TABLE 25

Bispecific antibodies

| BsAb ID | Fab | scFv No. |
|---|---|---|
| FV1 | 2G12-2B2 VL0, VH3 | scFv1 |
| FV2 | 2G12-2B2 VL0, VH3 | scFv2 |
| FV3 | 2G12-2B2 VL0, VH3 | scFv3 v1 |
| FV4 | 2G12-2B2 VL0, VH3 | scFv4 |
| FV5 | 2G12-2B2 VL0, VH3 | scFv5 |
| FV6 | 2G12-2B2 VL0, VH3 | scFv6 |
| FV7 | 2G12-2B2 VL0, VH3 | scFv7 |
| FV8 | 2G12-2B2 VL0, VH3 | scFv8 |
| FV9 | 2G12-2B2 VL0, VH3 | scFv9 v1 |
| C1 | 2G12-2B2 VL0, VH3 | scFv9 v2 |
| C2 | 2G12-2B2 VL0, VH3 | scFv3 v2 |
| C3 | 2G12-2B2 VL0, VH3 | scFv9 v3 |
| C4 | OKT3 VL, VH | scFv10 |
| C5 | OKT3 VL, VH | scFv11 |
| C6 | OKT3 VL, VH | scFv12 |

The full length amino acid sequences of the bispecific antibodies are presented in Table 26.

TABLE 26

Bispecific antibody sequences

| BsAb ID | Variable domain | SEQ ID NO |
|---|---|---|
| FV1 | Heavy chain full length | 88 |
| FV1 | Light chain full length | 89 |
| FV2 | Heavy chain full length | 90 |
| FV2 | Light chain full length | 89 |
| FV3 | Heavy chain full length | 91 |
| FV3 | Light chain full length | 89 |
| FV4 | Heavy chain full length | 92 |
| FV4 | Light chain full length | 89 |

TABLE 26-continued

Bispecific antibody sequences

| BsAb ID | Variable domain | SEQ ID NO |
|---|---|---|
| FV5 | Heavy chain full length | 93 |
| FV5 | Light chain full length | 89 |
| FV6 | Heavy chain full length | 94 |
| FV6 | Light chain full length | 89 |
| FV7 | Heavy chain full length | 95 |
| FV7 | Light chain full length | 89 |
| FV8 | Heavy chain full length | 96 |
| FV8 | Light chain full length | 89 |
| FV9 | Heavy chain full length | 97 |
| FV9 | Light chain full length | 89 |
| C1 | Heavy chain full length | 98 |
| C1 | Light chain full length | 89 |
| C2 | Heavy chain full length | 99 |
| C2 | Light chain full length | 89 |
| C3 | Heavy chain full length | 100 |
| C3 | Light chain full length | 89 |
| C4 | Heavy chain full length | 101 |
| C4 | Light chain full length | 102 |
| C5 | Heavy chain full length | 103 |
| C5 | Light chain full length | 102 |
| C6 | Heavy chain full length | 104 |
| C6 | Light chain full length | 102 |

Example 8. Production of Bispecific Antibodies

Antibody expression vectors were transfected into suspension human embryonic kidney 298 cells (HEK293) by DNA 2.0 (Newark, Calif.) on a 10 mL scale. HEK293 were grown for 7 days and harvested. Supernatant pH was adjusted to 7.4 with 1 M HEPES and KanCap A resin was used to capture antibodies/Fc fusion proteins. Resin washes were repeated as follows: PBS, PBS plus 1 M NaCl, PBS plus 4% ethanol, and PBS. Antibodies were eluted with 100 mM citrate pH 3.5 into $\frac{1}{10}^{th}$ volume of 1 M HEPES pH 7.4. Antibodies were desalted using PD-10 columns into PBS. Protein was quantified by OD280, and quantity and concentration was determined using calculated extinction coefficients. Reduced and non-reduced SDS-PAGE analysis (Bio-Rad criterion Tris/Glycine/SDS, 4-20%) were used to determine purity and approximate molecular mass. An additional SDS-Page (4-12% Tris-BIS) was run under reducing and non-reducing conditions followed by Coomassie staining using SimplyBlue SafeStain (Thermo Fisher Scientific, Waltham, Mass.) to further evaluate sample purity. Charles River (Wilmington, Mass.) Endotoxin Quantitation kit was used to determine endotoxin levels. Aggregation status was determined by HPLC, with detection at 280 nm using a Sepax Zenix-C SEC-300, 3 m, 300 A, 4.6*150 mm size exclusion column and PBS running buffer. Proteins were stored and shipped as 1 mL aliquots after filter sterilization and snap frozen in liquid nitrogen.

Seven stabilized versions of the bispecific antibody were produced for testing: FV2, FV3, FV4, FV5, FV6, FV7, C2, and C6. These included mutations to humanize the murine OKT3 variable domains and additional mutations to retain proper folding, including mutations to balance charges as well as mutations to increase the formation of disulfide bridges. Reduced and non-reduced SDS-PAGE analysis confirmed that these bispecific antibodies had the expected molecular mass and high purity. Therefore, these antibodies were subjected to the characterization described below. Additional bispecific antibodies that were designed included the control engineered versions of anti-CD3 scFvs that incorporated the murine OKT3 anti-CD3 module (FV1, FV8, FV9, C1, C3, C4, and C5).

Example 9. Characterization of Bispecific Antibodies

The bispecific antibodies were assessed for binding affinity to STn and CD3 in live tumor cells and T cells, respectively. Binding specificity to STn was further determined through glycan array analysis.

Figure 2A:
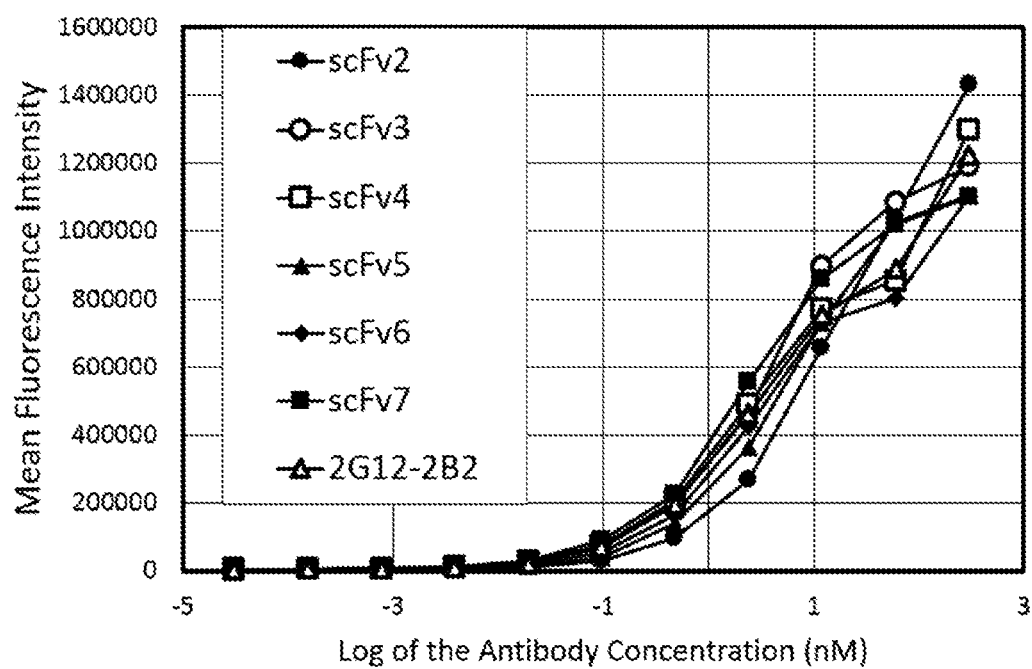
FIG. 2A is a graph showing antibody binding to STn-expressing MDA-MB-231 cells (as indicated by mean fluorescence intensity) with increasing antibody concentrations.

For live tumor cell STn binding, bispecific antibodies were screened over a concentration range of 0 to 300 nM, comparing binding to MDA-MB-231 cells with or without transfection-induced STn expression. Binding was determined using an anti-human APC conjugated secondary antibody and only live cells were considered (based on propidium iodide negative gating). Human isotype IgG1 antibody was used as an isotype negative control. 2G12-2B2 comprising VL0 and VH3 was used as a positive control. Each of the antibodies bound tightly to MDA-MB-231 STn+ cells with binding affinities nearly identical to the 2G12-2B2 control [half maximal effective concentration ($EC_{50}$) for binding of from about 1 to about 50 nM, see FIG. 2A].

Figure 2B:
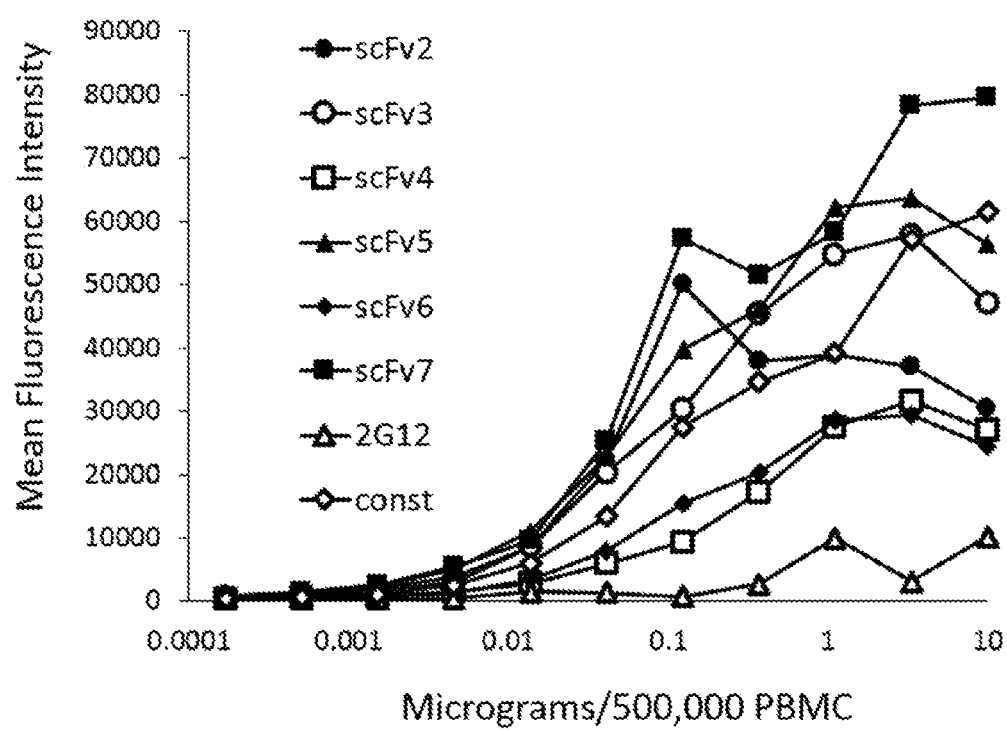
FIG. 2B is a graph showing antibody binding to T cells (as indicated by mean fluorescence intensity) with increasing antibody concentrations.

For T cell binding assay, bispecific antibodies were screened over a concentration range of 0 to 10 μg per 500,000 cells. The geometric mean of cell fluorescence was obtained for each sample. These data were log transformed then fit to a nonlinear regression model to obtain a dose response curve. 2G12-2B2 having VL0 and $V_H3$ variable domains was used as a negative control. The result is presented in FIG. 2B. While the control showed no binding to T cells, all of the other antibodies demonstrated strong binding to T cells [half maximal effective concentrations ($EC_{50}$) for binding of from about 0.01 to 0.5 μg/500,000 PBMC, see FIG. 2B]. Of these, scFvs 3, 5, and 7 demonstrated the strongest affinity. This data, together with the tumor cell STn binding data, confirmed bispecific binding affinity of the tested antibodies.

To determine glycan specificities of each of the bispecific antibodies, glycan array analysis was carried out according to Example 1 and antibodies were assigned array glycan binding profiles according to the parameters described therein. Among the seven antibodies, FV3 and FV7 showed the highest selectivity for STn associated with "Group 1" glycans (glycans 5, 6, 23, and 24). FV4 and FV5 demonstrated some glycan promiscuity while retaining binding to STn glycans. FV2 and FV6, while still binding STn glycans, had the most promiscuous binding to other glycans on the array.

Example 10. T Cell Proliferation

T cell activation by the bispecific antibodies, in the absence of tumor cells, was tested. T cell activation alone, or a lack there-of, indicates safety of the bispecific antibodies in a tumor-free environment. For T cell preparation, PBMCs were isolated as described previously. To label with carboxyfluorescein succinimidyl ester (CFSE), a fluorescent staining dye, cells were washed into PBS+1% (w/v) BSA at $10^6$ cells/ml. One 500 μg vial of CFDA-SE and DMSO was warmed to room temperature. 45 μl of DMSO was added to the vial to dissolve the powder and prepare a 5 μM stock. Immediately before addition to the cell suspension, this stock was diluted by adding 10 μl of 5 mM stock in 1 ml PBS+BSA. 10 μl of diluted stock was added to 1 ml of cell suspension and mixed by swirling. The mixture was incubated in a 37° C. water bath for 10 min. Uptake was quenched by adding equal volumes of complete medium (RPMI+10% (v/v) FBS) followed by centrifugation for 7 min at 1200 rpm. Cells were washed once more in complete media and adjusted to $2 \times 10^6$ cells/ml in RPMI 1640+10% (v/v) FBS. Cells were plated in 500 μl media per well of a 48 well plate. All antibodies were adjusted to 10 μg/ml in RPMI+FBS to make 100-200 μl each. Antibodies were added to wells at 1 (50 μl), 0.3 (33 μl) and 0.1 (5 μl) μg/ml final concentration in the well. Plates were incubated at 37° C., 5% $CO_2$ for 4 days. Staining cocktail was prepared with anti-CD25 and anti-CD69 antibodies in stain buffer (BD Biosciences, San Jose, Calif.). FACS tubes were prepared by adding 100 μl staining cocktail to each staining tube. Cells were resuspended in each well and transferred to their staining tubes. Samples were incubated 20 min and washed twice in wash buffer before detection by flow cytometry using a BD Accuri C6 flow cytometer (Becton Dickinson, Franklin Lakes, N.J.). Viable lymphocyte cluster provided primary gating to determine percent additional cells over control with the following fluorescent markers: CFSE (FITC); CD25 (APC); and CD69 (PE). Proliferation was quantified after 96 hours stimulation of T cells alone with a bispecific antibody or a control antibody. OKT3 was used as a positive control and 2G12-2B2 antibody was used as a negative control in the assay.

The result showed that while the control CD3-binding antibody OKT3 induced robust T cell proliferation, no versions of the bispecific antibody did so, likely due to reduced effector functions. This result indicates that the presence of tumor cells is required for T cell activity and supporting bispecific antibody safety.

Example 11. In Vitro Cytotoxicity Assay

An in vitro cytotoxicity assay was employed to assess the effect of the bispecific antibodies on T cell induced tumor cell killing. For T cell preparation, PBMCs were isolated as described previously and T cells were isolated by magnetic separation using the Pan T Cell Isolation Kit II (Miltenyi Biotec, Bergisch Gladbach, Germany). T cells were resuspended in RPMI 1640 medium with 10% (v/v) FCS at a concentration of $3 \times 10^6$ cells/ml. A total of $1 \times 10^7$ T cells were used in one experiment. For tumor cell preparation, tumor cell lines were removed from culture using StemPro Accutase buffer as described above. Cells were washed into serum free medium and adjusted to $1 \times 10^7$ cells/ml in a polypropylene tube. Cell membranes were labeled with PKH26 Labeling Kit (Sigma-Aldrich, St. Louis, Mo.). Cells were spun down and all supernatant was aspirated (volume remaining less than 25-50 μl). Cells were resuspended in Diluent C in half the original volume immediately before adding the dye. 4 μl of dye solution was mixed with 1 ml of Diluent C in a polypropylene tube. An equal volume of the diluted dye was added to the cell suspension and immediately mixed by pipetting up and down a few times. The cell suspension was incubated for 5 min at RT. An equivalent volume of FBS was added to stop the dye uptake. Cells were spun down and the supernatant was removed. Tumor cells were washed two times with RPMI 1640+10% (v/v) FCS and resuspended at $3 \times 10^5$ cells/ml. A total of $1 \times 10^6$ tumor cells were used in one experiment.

The cytotoxicity assay was performed by incubating serial dilutions of a bispecific antibody with a suspension of T cells and tumor cells. Antibody serial dilutions were prepared in a polypropylene plate. T cells and tumor cells were mixed in equal volumes to produce a cell suspension with an effector to target cell (E:T) ratio of 10:1. 100 μl of cell suspension was aliquoted to wells of a 96-well plate. 50 µl of antibody dilutions from the dilution plate were added to produce final concentrations in the well from 3 µg/ml to 0.004 µg/ml. The plate was incubated at 37° C., 5% $CO_2$ for 24 hours. 10 µl propidium iodide (PI) per well was added to all wells and read on the flow cytometer. Green cells (tumor cells) were gated and the % tumor cells PI negative and PI positive for live and dead, respectively, was quantified to assess cell killing.

Three tumor cell lines were tested with varying degrees of STn expression: MDA-MB-231 STn+ (high), OV90 (moderate-high), and OVCAR3 (low-moderate). The STn+ population in OV90 and OVCAR3 cells were determined to be 90% and 30%, respectively. Wild-type (wt) MDA-MB-231 STn-cells were used for comparison. The effect of bispecific antibodies on inducing tumor cytotoxicity are compared at an antibody concentration of 15 nM. Results from the cytotoxicity assay are presented in Table 27.

TABLE 27

Cytotoxicity assay results

| BsAb ID | MDA-MB-231 wt % cell death | MDA-MB-231 STn+ % cell death | OV90 STn+ % cell death | OVCAR3 STn+ % cell death |
|---|---|---|---|---|
| FV2 | 25.8 | 70.6 | 37.9 | 23.6 |
| FV3 | 13.4 | 71.0 | 36.9 | 21.8 |
| FV4 | 30.3 | 66.5 | 42.6 | 24.2 |
| FV5 | 14.3 | 73.2 | 39.6 | 20.5 |
| FV6 | 30.2 | 74.9 | 39.9 | 19.5 |
| FV7 | 19.1 | 75.7 | 42.1 | 21.3 |
| C2 | 10.3 | 68.9 | 38.6 | 21.6 |
| C6 | 8.9 | 64.7 | 35.3 | 18.1 |
| IgG control | 10.0 | 9.5 | 20.5 | 21.3 |
| No mAb control | 10.2 | 8.3 | 22.5 | 17.8 |

All bispecific antibodies demonstrated efficient promotion of tumor cell death in high STn expressing MDA-MB-231 cells (~70% cell death). Partial cell death was observed in OV90 cells (~40% cell death) and under the current culture conditions utilized. No measurable cell death, above background, was quantified in OVCAR3 cells.

The specificity of T cell-induced tumor cell killing was evident by the percent of cell death in MDA-MB-231 wild-type (STn−) cells. Antibodies inducing less than 15% cell death in STn-cells are considered specific, between 15 and 25% moderately specific, and above 25% non-specific. Accordingly, FV3, FV5, C2 and C6 are considered specific, FV7 moderately specific, and FV2, FV4 and FV5 non-specific. This correlated well with the binding affinity to MDA-MB-231 wild-type cells measured by flow cytometry. At 10 nM antibody concentration, FV3 and FV5 had low binding affinity (less than 25,000 unit in mean APC fluorescence), FV2 and FV7 modest (between 25,000 and 100,000), and FV4 and FV6 high (above 100,000). This in turn correlated with their binding selectivity from the glycan array analysis described above (with FV3 and FV7 demonstrating Group 1 binding, FV5 binding to <10 additional glycans, and FV2, FV4 and FV6 binding to >10 additional glycans. This strong correlation points to using glycan selectivity to identify lead bispecific antibodies for further development. Bispecific antibody FV3 was identified as a candidate with optimal targeting properties in the orientation where anti-CD3 is used as an scFV and lacks the presence of any free cysteines that could be reactive. C6, the reverse orientation of the IgG and scFv modules, also demonstrated favorable targeting properties.

Figure 3A:
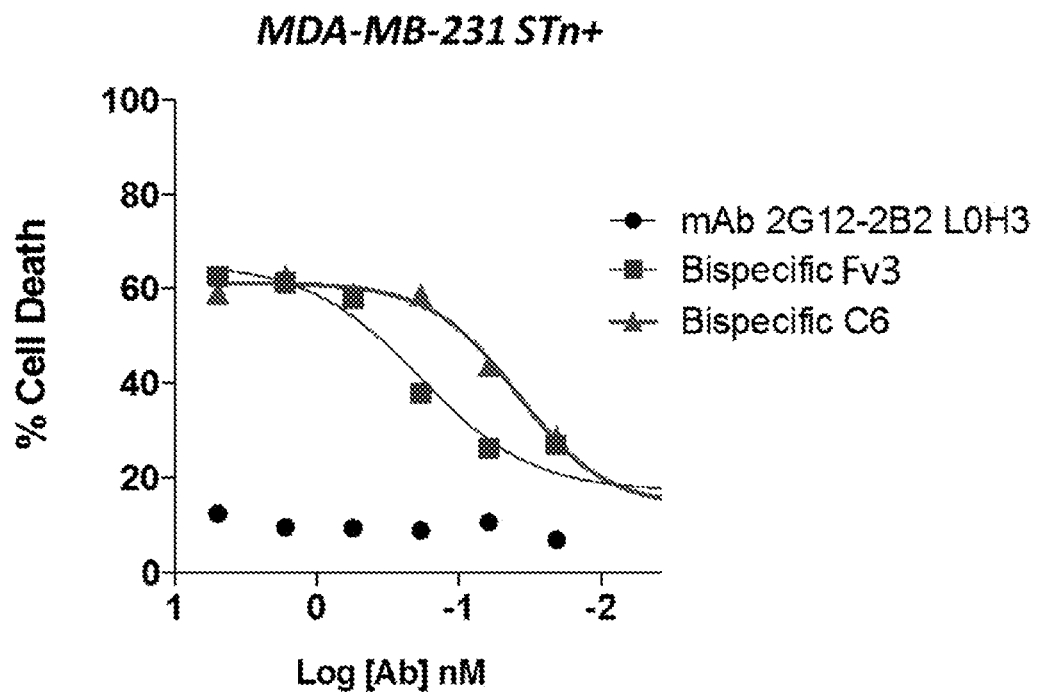
FIG. 3A is a graph showing percent cell death in MDA-MB-231 cells expressing STn with increasing antibody concentrations.
Figure 3B:
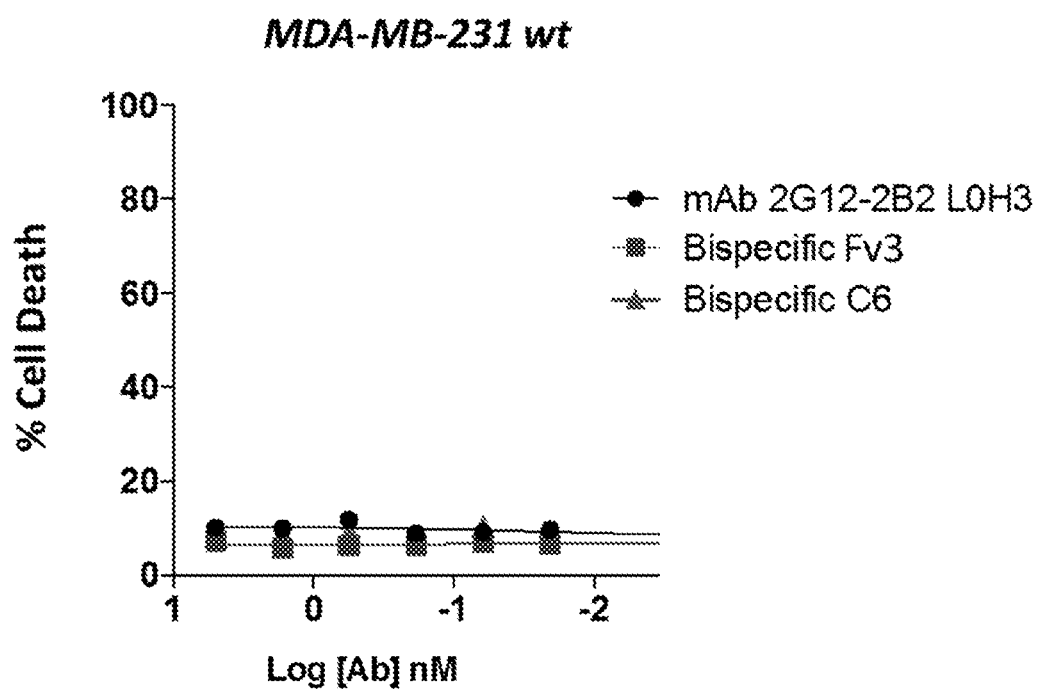
FIG. 3B is a graph showing percent cell death in MDA-MB-231 wild type cells with increasing antibody concentrations.

To further characterize the T cell-mediated killing of STn-expressing cells, half maximal inhibitory concentration ($IC_{50}$) for STn+ MDA-MB-231 cell killing were determined through a titration curve of FV3 and C6. Resulting dose response curves are presented in FIG. 3A for MDA-MB-231 STn+ cells and in FIG. 3B for wild-type cells. These studies demonstrated a dose-dependent killing of STn+ MDA-MB-231 cells with an IC50<1 nM (FIG. 3A). This was well below the threshold for binding to STn-cells and suggests a therapeutic window for specific binding and efficacy in vitro.

Example 12. T Cell Cytokine Production

T cells are isolated from fresh whole blood as described in the previous examples. T cell activation by the bispecific antibodies, in the absence or presence of tumor cells, is assessed by the production of cytokines IL-2, IL-4, IL-5, IL-13, IFN-γ, TNF-α, and IL-17. Cell culture supernatants are assayed for cytokine production using appropriate ELISA kits. The results are compared to a positive control such as OKT3 or Blinatumomab. Bispecific antibodies that elicit robust T cell activation only in the presence of tumor cells are selected for further analysis.

Example 13. In Vivo Mouse Studies

The bispecific antibody candidates are assessed for in vivo anti-tumor efficacy in a humanized mouse model. First, the growth conditions of select patient-derived xenograft (PDX) tumor models are established in humanized mice. In vivo tumor STn expression is characterized and a single model is selected for testing the bispecific antibodies. Next, the bispecific antibodies are administered into the mice and the anti-tumor response is assessed through tumor size, T cell infiltration and other markers of growth such as Ki67 (proliferation) and H&E (necrosis). The in vivo anti-tumor efficacy is used as a basis for the further clinical development of these bispecific antibody candidates.

What is claimed is:

1. A bispecific antibody, comprising a sialyl Tn (STn)-binding region and a CD3-binding region, wherein the STn-binding region comprises a complementarity determining region (CDR)-H1, a CDR-H2, a CDR-H3, a CDR-L1, a CDR-L2, and a CDR-L3 respectively comprising the sequences of SEQ ID NOs: 3, 4, 5, 6, 7, and 8; or SEQ ID NOs: 9, 10, 11, 12, 7, and 8, and wherein the CD3-binding region comprises a heavy chain variable domain (VH) comprising the sequence of SEQ ID NO: 66 and a light chain variable domain (VL) comprising the sequence of SEQ ID NO: 71.

2. The bispecific antibody of claim 1, wherein the STn-binding region comprises a heavy chain variable domain (VH) comprising the sequence of SEQ ID NO: 60 and a light chain variable domain (VL) comprising the sequence of SEQ ID NO: 53.

3. The bispecific antibody of claim 1, wherein the CD3-binding region comprises a single-chain variable fragment (scFv) comprising the sequence of SEQ ID NO: 75 or 77.

4. The bispecific antibody of claim 1, wherein the antibody comprises a heavy chain comprising the sequence of SEQ ID NO: 91 or 92, and a light chain comprising the sequence of SEQ ID NO: 89.

5. The bispecific antibody of claim 1, wherein the antibody simultaneously binds a T cell and a cancer cell.

6. The bispecific antibody of claim 1, wherein the antibody binds the cancer cell with a half maximal effective concentration ($EC_{50}$) of from about 1 nM to about 50 nM.

7. A composition comprising the bispecific antibody of claim 1 and at least one pharmaceutically acceptable excipient.

8. The bispecific antibody of claim 4, wherein the antibody simultaneously binds a T cell and a cancer cell.

9. The bispecific antibody of claim 4, wherein the antibody binds the cancer cell with a half maximal effective concentration ($EC_{50}$) of from about 1 nM to about 50 nM.

10. A composition comprising the bispecific antibody of claim 4 and at least one pharmaceutically acceptable excipient.

* * * * *

UNITED STATES PATENT AND TRADEMARK OFFICE
CERTIFICATE OF CORRECTION

PATENT NO. : 11,401,330 B2
APPLICATION NO. : 16/462075
DATED : August 2, 2022
INVENTOR(S) : David A. Eavarone, Jeffrey Behrens and Alexey Alexandrovich Lugovskoy It is certified that error appears in the above-identified patent and that said Letters Patent is hereby corrected as shown below:

On the Title Page

Item (71) Applicant, "Seattle Genetics, Inc." should be changed to --Seagen Inc.--.

Signed and Sealed this
Eighteenth Day of October, 2022

Katherine Kelly Vidal
*Director of the United States Patent and Trademark Office*